United States Patent
Engel et al.

[11] Patent Number: 6,114,390
[45] Date of Patent: Sep. 5, 2000

[54] AMINO ACID DERIVATIVES, PHARMACEUTICAL COMPOSITIONS CONTAINING THESE COMPOUNDS AND PROCESSES FOR PREPARING THEM

[75] Inventors: Wolfhard Engel; Wolfgang Eberlein; Klaus Rudolf, all of Biberach; Henri Doods, Warthausen; Heike-Andrea Wieland, Biberach; Klaus-Dieter Willim, Hochdorf/Schweinhausen; Michael Entzeroth, Warthausen; Wolfgang Wienen, Biberach/Rissegg, all of Germany

[73] Assignee: Karl Thomae GmbH, Biberach, Germany

[21] Appl. No.: 08/950,113

[22] Filed: Oct. 14, 1997

Related U.S. Application Data

[63] Continuation of application No. 08/945,048, filed as application No. PCT/EP96/05222, Oct. 14, 1996, abandoned.

[51] Int. Cl.[7] .......................... A61K 31/17; C07C 275/14
[52] U.S. Cl. ........................... 514/595; 514/616; 564/56; 564/157
[58] Field of Search ................ 564/56; 514/595

[56] References Cited

U.S. PATENT DOCUMENTS 5,616,620  4/1997  Rudolf et al. .................... 514/620

FOREIGN PATENT DOCUMENTS 4301452   7/1994  Germany .
WO 94 17035  8/1994  WIPO .

*Primary Examiner*—Richard L. Raymond
*Attorney, Agent, or Firm*—Robert P. Raymond; Alan R. Stempel; Mary-Ellen M. Devlin

[57] ABSTRACT

NPY-antagonistic compounds of the formula

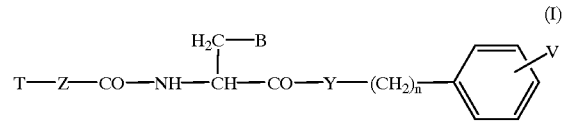

Exemplary are:
(A) (R)-N-[[4-(Aminocarbonylaminomethyl)phenyl] methyl]-$N^2$-bis(4-hydroxyphenyl)acetyl]-argininamide-trifluoracetate;
(B) (R)-N-[[4-(Aminocarbonylaminomethyl)phenyl] methyl]-$N^2$-[bis(4-chlorphenyl)acetyl]-argininamide-trifluoracetate;
(C) (R)-N-[[4-Aminocarbonylaminomethyl)phenyl] methyl]-$N^2$-(diphenylacetyl)-argininamide-trifluoracetate;
(D) (R)-$N^2$-(Diphenylacetyl)-N-[[4-(ethoxycarbonylmethylamino-carbonylaminomethyl) phenyl]methyl]-argininamide-trifluoroacetate;
(E) (R,S)-$N^5$-(Aminoiminomethyl)-$N^2$-(diphenylacetyl)-N-[(4-hy-droxyphenyl)methyl]-$N^5$-methyl-ornithinamide-hydrochloride;
(F) (R)-N-[[4-(Aminocarbonylmethyl)phenyl]methyl]-$N^2$-(diphenyl-acetyl)-argininamide-diacetate;
(G) (R)-$N^2$-(Diphenylacetyl)-N-[[4-(ethylaminocarbonylamino-methyl)-phenyl]methyl]-argininamide-bis-(trifluoroacetate); and,
(H) (R)-$N^2$-(Diphenylacetyl)-N-[[4-(ethoxycarbonylamino-carbonylaminomethyl)phenyl] methyl]-argininamide-trifluoroacetate.

10 Claims, No Drawings

AMINO ACID DERIVATIVES, PHARMACEUTICAL COMPOSITIONS CONTAINING THESE COMPOUNDS AND PROCESSES FOR PREPARING THEM

RELATED APPLICATIONS

This application is a continuation-in-part of Ser. No. 08/945,048, filed Feb. 10, 1998, now abandoned, which is a International Application Number PCT/EP96/05222 filed Oct. 14, 1996.

FIELD OF THE INVENTION

The invention relates to novel compounds (amino acid derivatives), pharmaceutical compositions comprising these compounds, their use in the treatment of various disease conditions, their use as adjuvant in the production of antibodies, and their use in RIA and ELISA assays.

DETAILED DESCRIPTION OF THE INVENTION

The present invention provides new amino acid derivatives of the general formula

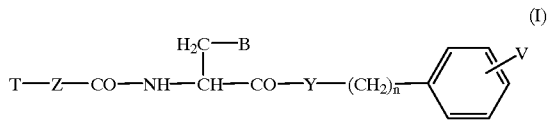

(I)

the tautomers, diastereomers and enantiomers thereof, mixtures thereof and the salts thereof, particularly the physiologically acceptable salts thereof with inorganic or organic acids or bases, pharmaceutical compositions containing these compounds, the use thereof and processes for preparing them.

In the above general formula I:

T denotes a phenyl, 1-naphthyl or 2-naphthyl group, a carbon-attached 5-membered heteroaromatic ring which contains a nitrogen, oxygen or sulphur atom or a nitrogen and an oxygen, sulphur or additional nitrogen atom, whilst a nitrogen atom of an imino group may be substituted by an alkyl, alkoxycarbonylalkyl, carboxyalkyl, dialkylaminoalkyl, aminocarbonyl, alkylaminocarbonyl, dialkylaminocarbonyl or alkoxycarbonyl group, or T denotes a carbon-attached six-membered heteroaromatic ring which contains 1, 2 or 3 nitrogenatoms, whilst both the 5-membered and the 6-membered heteroaromatic rings may each be attached via two adjacent carbon atoms to a 1,4-butadienylene group and the bicyclic heteroaromatic rings thus formed may also be attached via a carbon atom of the 1,4-butadienylene group and the groups given for T hereinbefore and the heteroaromatic rings in the carbon skeleton may additionally be mono-, di- or at most trisubstituted by fluorine, chlorine or bromine atoms, by alkyl groups, $C_{3-8}$-cycloalkyl groups, alkoxy, phenyl, phenylalkoxy, trifluoromethyl, alkoxycarbonylalkyl, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, alkanoyl, cyano, trifluoromethoxy, trifluoromethylthio, trifluoromethylsulphinyl or trifluoromethylsulphonyl groups, wherein the substituents may be identical or different and the above-mentioned benzoyl, benzoylamino and benzoylmethylamino group may in turn additionally be substituted in the phenyl moiety by a fluorine, chlorine or bromine atom or by an alkyl, trifluoromethyl, amino or acetylamino group, or T may denote a group $T^1T^2U$, wherein $T^1$ and $T^2$ denote phenyl groups which may independently be mono- or disubstituted by fluorine, chlorine or bromine atoms, by methyl, methoxy, hydroxycarbonylmethoxy, alkoxycarbonylmethoxy, hydroxy or trifluoromethyl groups, wherein the substituents may be identical or different and wherein the phenyl groups may be connected to one another in the 2,2'-position via a bond, an oxygen or sulphur atom, or via a —$CH_2$—, —$C(CH_3)_2$—, —$CH_2CH_2$—, —CH=CH— or —NH—CO— bridge, and U denotes a CH group in which the hydrogen atom may be replaced by an alkoxy or phenoxy group;

Z denotes a single bond, an oxygen atom, a —NH— group, or a methylene or ethylene group, whilst in the ethylene group the methylene group attached to the carbonyl group may be replaced by an oxygen atom or an —NH— group;

B denotes a phenyl group substituted by an aminoiminomethyl group, a 1H-benzimidazol-5-yl or 1H-benzimidazol-6-yl group optionally substituted in the 2-position by an amino group, or a group —$CH_2CH_2AB^1$, wherein A denotes a methylene group or an amino group optionally substituted by a $C_{1-4}$-alkyl group and $B^1$ denotes an aminoiminomethyl, 1H-imidazol-2-yl or 4,5-dihydro-1H-imidazol-2-yl group;

Y denotes an oxygen atom or an $NR^1$ group wherein $R^1$ denotes a hydrogen atom or a branched or unbranched $C_{1-6}$-alkyl group optionally substituted by a carboxy or alkoxycarbonyl group, or $R^1$ denotes a phenylmethyl group;

n denotes the number 1, 2 or 3;

V denotes a group —$(CH_2)_m$—$Y^1$—W—$Y^2$ or, if B denotes a group —$CH_2CH_2AB^1$, wherein A represents an amino group substituted by a $C_{1-4}$-alkyl group, V may also denote a hydroxy group, whilst in a group —$(CH_2)_m$—$Y^1$—W—$Y^2$ m denotes the number 1, 2, 3 or 4, W denotes a —$SO_2$— group or a group >C=X, wherein X is an oxygen atom or one of the divalent groups =N—$CONH_2$ or =N—CN, $Y^1$ denotes a single bond, an oxygen atom or a group —$NR^2$—, wherein $R^2$ denotes a hydrogen atom or a straight-chain or branched $C_{1-6}$-alkyl group or $R^2$ represents a methylene group or bond connected to the o-position of the benzene ring attached to the group V, with the proviso that $R^2$ represents a methylene group if m is the number 1, or $R^2$ together with the group $Y^2$ denotes a $C_{3-5}$-n-alkylene group, $Y^2$ denotes a straight-chain or branched $C_{1-10}$-alkyl group optionally substituted by a hydroxy, alkoxycarbonyl or aminocarbonyl group, a $C_{4-10}$-cycloalkyl group, a straight-chain or branched $C_{1-5}$-alkoxy group, an aminoalkyl, alkylaminoalkyl, dialkylaminoalkyl, phenylmethoxy or 2-phenylethoxy group, a phenyl or phenyl($C_{1-3}$alkyl) group optionally mono-, di- or tri-substituted in the phenyl moiety by fluorine, chlorine or bromine atoms or by methyl, trifluoromethyl, cyano, amino, hydroxy, methoxy, acetyl, acetylamino, aminocarbonyl, methylaminocarbonyl or dimethylaminocarbonyl groups, or $Y^2$ denotes a —$NR^3R^4$ group, wherein $R^3$ denotes a hydrogen atom, a straight-chain or branched $C_{1-6}$-alkyl group optionally substituted by a hydroxy, carboxy, alkoxycarbonyl or dialkylamino group, with the proviso that the hydroxy group is not bound in the 1-position of the alkyl group, a $C_{4-8}$-cycloalkyl group or a phenyl, phenylmethyl, 2-phenylethyl or 3-phenylpropyl group optionally mono-, di- or tri-substituted in the phenyl moiety by fluorine, chlorine or bromine atoms or by methyl, trifluoromethyl, hydroxy, methoxy, amino, acetylamino, aminocarbonyl, methylaminocarbonyl, dimethylaminocarbonyl or cyano groups, wherein the substituents may be the same or different, or an alkanoyl, benzoyl, phenylalkanoyl, alkoxycarbonyl or aminocarbonyl group and $R^4$ has the meanings given for $R^3$ with the exception of phenyl, alkanoyl, benzoyl, phenylalkanoyl, alkoxycarbonyl and aminocarbonyl group or $R^3$ and $R^4$ together denote a $C_{4-6}$-n-alkylene group or $R^4$ together with the group $R^2$ of the group —$NR^2$— given for $Y^1$ hereinbefore denotes an unbranched alkylene group or oxoalkylene group having 2 to 4 carbon atoms, or $Y^2$ together with the group $R^2$ of the group —$NR^2$— given for $Y^1$ hereinbefore denotes a $C_{2-4}$-alkylenoxy group, in which the alkyleneoxy group is linked to the group W via the oxygen atom, or W—$Y^2$ together may also represent a 5-amino-1H-1,2,4-triazol-3-yl, 1H-2-imidazolyl, 3-methyl-1,2,4-oxadiazol-5-yl, 6-methyl-4-(3H)-oxopyrimidin-2-yl or 5-methyl-4-(3H)-oxopyrimidin-2-yl group;

whilst all the above-mentioned alkyl, alkoxy, phenylalkoxy, alkoxycarbonylalkyl, carboxyalkyl, dialkylaminoalkyl, alkylaminocarbonyl, dialkylaminocarbonyl, alkanoyl and alkoxycarbonyl groups, unless otherwise specified, may each contain 1 to 4 carbon atoms in the alkyl and alkoxy moieties.

As examples of the definitions given hereinbefore for the groups:

T may denote, for example, a phenyl, 2-pyridinyl, 3-pyridinyl, 4-pyridinyl, 2-thienyl, 3-thienyl, 2-furyl, 3-furyl, 1H-pyrrol-2-yl, 1H-pyrrol-3-yl, 1-methyl-1H-pyrrol-2-yl, 1-methyl-1H-pyrrol-3-yl, 1-naphthyl, 2-naphthyl, 1H-indol-2-yl, 1H-indol-3-yl, 1H-indol-4-yl, 1H-indol-5-yl, 1H-indol-6-yl, 1H-indol-7-yl, benzo[b]furan-2-yl, benzo[b]furan-3-yl, benzo[b]thiophen-2-yl, benzo[b]thiophen-3-yl, 2-quinolinyl, 3-quinolinyl, 4-quinolinyl, benzo[c]thiophen-1-yl, 1-isoquinolinyl, 3-isoquinolinyl, 4-isoquinolinyl, pyrazinyl, 2-pyrimidinyl, 4-pyrimidinyl, 5-pyrimidinyl, 3-pyridazinyl, 4-pyridazinyl, 2-imidazolyl, 4-imidazolyl, 1-H-benzimidazolyl-5-yl, 3-pyrazolyl, 4-pyrazolyl, 1,3-oxazol-2-yl, 1,3-oxazol-4-yl, 1,3-oxazol-5-yl, 3-isoxazolyl, 4-isoxazolyl, 5-isoxazolyl, 2-quinazolinyl, 4-quinazolinyl or 2-quinoxalinyl group, whilst these may additionally be substituted by the groups mentioned hereinbefore, the ($T^1T^2U$) group may denote a diphenylmethyl, 9H-fluoren-9-yl, 5,11-dihydro-6(6H)-oxodibenz[b,e]azepin-11-yl, 5H-dibenzo[a,d]-cyclohepten-5-yl, 9H-xanthen-9-yl or 9H-thioxanthen-9-yl group, B may denote a [(aminoiminomethyl)amino]ethyl, [(aminoiminomethyl)methylamino]ethyl, 3-(aminoiminomethyl)phenyl, [(1H-imidazol-2-yl)amino]ethyl, (4,5-dihydro-1H-imidazol-2-yl)propyl or 4-(aminoiminomethyl)phenyl group, V may denote an acetylaminomethyl, ethoxycarbonylaminomethyl, aminosulphonylaminomethyl, aminocarbonylaminomethyl, aminocarbonylmethyl, methylaminosulphonylmethyl, methoxycarbonylaminomethyl, methylaminocarbonylaminomethyl, benzoylaminomethyl, phenylaminocarbonylaminomethyl, aminosulphonylmethyl, [(5-amino-1H-1,2,4-triazol-3-yl)amino]methyl, [(1H-2-imidazolyl)amino]methyl], ethylaminocarbonylaminomethyl, 1-methylethylaminocarbonylaminomethyl, [[amino(aminocarbonylimino)methyl]-amino]methyl, ethoxycarbonylaminocarbonylaminomethyl, dimethylaminocarbonylaminomethyl, aminocarbonyloxymethyl, tert.butoxycarbonylaminomethyl, aminocarbonylaminocarbonylaminomethyl, [(amino(cyanoimino)methyl]amino]methyl, methoxycarbonylmethyl, methylaminocarbonylmethyl, [[(dimethylamino)carbonyl]methylamino]methyl, [(aminocarbonyl)methylamino]methyl, [[(methylamino)carbonyl]methylamino]methyl, [(methoxycarbonyl)methylamino]methyl, [[(carboxymethyl)amino]carbonyl]methyl, [[[bis(carboxymethyl)]amino]carbonyl]methyl, [[[bis(methoxycarbonyl-methyl)]amino]carbonyl]methyl, [(ethoxycarbonylaminocarbonyl)methylamino]methyl, ethoxycarbonylmethylaminocarbonylaminomethyl, carboxymethylaminocarbonylaminomethyl, dimethylaminocarbonylmethyl, 2-(aminocarbonyl)ethyl, (2-oxo-1-imidazolidinyl)methyl, 2-(3-methyl-1,2,4-oxadiazol-5-yl)ethyl, 5-methyl-4(3H)-oxopyrimidin-2-ylaminomethyl, 6-methyl-4(3H)-oxopyrimidin-2-ylaminomethyl, 2-(methoxycarbonyl)ethyl, [(4-amino-1,4-dioxobutyl)amino]methyl or 2-(aminocarbonylamino)ethyl group.

The present invention relates to the racemates, in so far as the asymmetric carbon atom of the central amino acid is the only chiral element in the compounds of general formula I. However, the application also includes the individual diastereomers or the mixtures thereof which are present when a compound falling within general formula I contains two or more than two chiral elements. Particularly preferred compounds of general formula I are those which are in the (D) or (R) configuration in terms of the partial amino acid structure

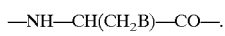

—NH—CH(CH$_2$B)—CO—.

The compounds of general formula I have valuable pharmacological properties based on their selective NPY-antagonistic properties. The invention also relates to pharmaceutical compositions containing these compounds, and the use thereof and the preparation thereof.

Preferred compounds of the above general formula I are those wherein:

T denotes a phenyl, 1-naphthyl or 2-naphthyl group, a carbon-attached 5-membered heteroaromatic ring which contains one nitrogen, one oxygen or two nitrogen atoms, whilst one nitrogen atom of an imino group may be substituted by an alkyl, alkoxycarbonylalkyl, carboxyalkyl, dialkylaminoalkyl, aminocarbonyl alkylaminocarbonyl, dialkylaminocarbonyl or alkoxycarbonyl group and wherein a 1,4-butadienylene group may be attached to the 5-membered heteroaromatic ring via two adjacent carbon atoms, whilst the bicyclic heteroaromatic rings thus formed may also be connected via a carbon atom of the 1,4-butadienylene group and wherein the groups given for T hereinbefore and the heteroaromatic rings in the carbon skeleton may additionally be mono-, di- or at most tri-substituted by fluorine, chlorine or bromine atoms or by methyl, ethyl, n-propyl, n-butyl, cyclopropyl, methoxy, phenyl, 2-phenylethoxy, trifluoromethyl, hydroxy, amino, acetylamino, benzoylamino, benzoyl, aminocarbonyl, methylaminocarbonyl, dimethylaminocarbonyl, acetyl, cyano, trifluoromethoxy or trifluoromethylthio groups, and the substituents may be the same or different, or T denotes a group $T^1T^2U$, wherein $T^1$ and $T^2$ denote phenyl groups, which independently of one another, may each be mono- or disubstituted by fluorine, chlorine or bromine atoms or by methyl, methoxy, hydroxycarbonylmethoxy, alkoxycarbonylmethoxy, hydroxy or trifluoromethyl groups, wherein the substituents may be identical or different and wherein the phenyl groups may be connected to one another in the 2,2'-position via an —NH—CO-bridge, and U denotes a CH group in which the hydrogen atom may be replaced by a phenoxy group;

Z denotes a single bond, an oxygen atom or a —NH— group, a methylene group or a methyleneoxy or methyleneamino group bound to the carbonyl group via the heteroatom;

B denotes a phenyl group substituted by an aminoiminomethyl group, or B denotes a 1H-benzimidazol-5-yl or 1H-benzimidazol-6-yl optionally substituted in the 2-position by an amino group, or B denotes a group $CH_2CH_2AB^1$, wherein A denotes a methylene group or an amino group optionally substituted by a methyl group and $B^1$ denotes an aminoiminomethyl or 1H-imidazol-2-yl group;

Y denotes an oxygen atom or a —$NR^1$— group, wherein $R^1$ denotes a hydrogen atom or a methyl or ethyl group optionally substituted by a carboxy, methoxycarbonyl or ethoxycarbonyl group;

n denotes the number 1;

V denotes a group —$(CH_2)_m$—$Y^1$—W—$Y^2$ or, if B denotes a group —$CH_2CH_2AB^1$ wherein A represents a methyl-substituted amino group, V may also represent a hydroxy group, whilst in a group —$(CH_2)_m$—$Y^1$—W—$Y^2$ m denotes the number 1 or 2, W denotes an —$SO_2$— group or a group >C=X, wherein X denotes an oxygen atom or one of the divalent groups =N—$CONH_2$ or =N—CN, $Y^1$ denotes a single bond, an oxygen atom or a group —$NR^2$—, wherein $R^2$ denotes an oxygen atom or a $C_{1-3}$-alkyl group or $R^2$ denotes a methylene group linked to the o-position of the benzene ring connected to the group V, or $R^2$ together with the group $Y^2$ represents an n-propylene or n-butylene group, $Y^2$ denotes a straight-chain or branched $C_{1-5}$-alkyl group optionally substituted by a hydroxy, methoxycarbonyl, ethoxycarbonyl or aminocarbonyl group, a $C_{4-8}$-cycloalkyl group, a straight-chain or branched $C_{1-4}$-alkoxy group, a phenyl group optionally substituted by a fluorine, chlorine or bromine atom or a methyl, trifluoromethyl, methoxy or aminocarbonyl group, or $Y^2$ denotes an —$NR^3R^4$ group, wherein $R^3$ denotes a hydrogen atom, a straight-chain or branched $C_{1-4}$-alkyl group optionally substituted by a carboxy, methoxycarbonyl, ethoxycarbonyl or dialkylamino group, a $C_{4-8}$-cycloalkyl group, a phenyl group optionally mono-, di- or tri-substituted by fluorine, chlorine or bromine atoms or by methyl, trifluoromethyl, hydroxy, methoxy, amino, acetylamino, aminocarbonyl or cyano groups, wherein the substituents may be identical or different, or $R^3$ denotes an alkanoyl, benzoyl, alkoxycarbonyl or aminocarbonyl group and $R^4$ has the meanings given for $R^3$ with the exception of phenyl, alkanoyl, benzoyl, alkoxycarbonyl and aminocarbonyl group or $R^3$ and $R^4$ together denote a $C_{4-6}$-n-alkylene group or $R^4$ together with the group $R^2$ of the group —$NR^2$— mentioned for $Y^1$ hereinbefore denotes an unbranched alkylene group or oxoalkylene group having 2 to 4 carbon atoms, or $Y^2$ together with the group $R^2$ of the group —$NR^2$— specified for $Y^1$ hereinbefore denotes a $C_{2-4}$-alkyleneoxy group, wherein the alkyleneoxy group is linked to the group W via the oxygen atom, or W—$Y^2$ together may also represent a 5-amino-1H-1,2,4-triazol-3-yl, 1H-2-imidazolyl, 3-methyl-1,2,4-oxadiazol-5-yl, 6-methyl-4-(3H)-oxopyrimidin-2-yl or 5-methyl-4-(3H)-oxopyrimidin-2-yl group;

wherein the above-mentioned alkyl, alkanoyl, alkoxycarbonyl, alkoxycarbonylalkyl, carboxyalkyl and dialkylaminoalkyl groups, unless other specified, may each contain 1 to 4 carbon atoms in the alkyl and alkoxy moieties, the tautomers, diastereomers, enantiomers and salts thereof.

Particularly preferred compounds of the above general formula I are those wherein:

T denotes a phenyl, 1-naphthyl, 2-naphthyl, 1H-indol-2-yl, 1H-indol-3-yl, 1H-indol-4-yl, 1H-indol-5-yl, benzo[b]furan-2-yl or 1H-benzimidazol-5-yl group optionally mono-, di- or tri-substituted in the carbon skeleton by fluorine, chlorine or bromine atoms or by methyl, ethyl, n-propyl, n-butyl, cyclopropyl, methoxy, phenyl, 2-phenylethoxy, trifluoromethyl, hydroxy, amino, acetylamino, benzoylamino, benzoyl, aminocarbonyl, methylaminocarbonyl, dimethylaminocarbonyl, acetyl, cyano, trifluoromethoxy or trifluoromethylthio groups, wherein the substituents may be identical or different and the nitrogen atom of the imino group of the 1H-indol-2-yl, 1H-indol-3-yl, 1H-indol-4-yl, 1H-indol-5-yl and 1H-benzimidazol-5-yl group may additionally be substituted by a methyl, methoxycarbonylmethyl, ethoxycarbonylmethyl, carboxymethyl, 3-dimethylaminopropyl, 3-diethylaminopropyl, aminocarbonyl, methylaminocarbonyl, ethylaminocarbonyl, dimethylaminocarbonyl, diethylaminocarbonyl, methoxycarbonyl or ethoxycarbonyl group, or T denotes a group $T^1T^2U$, wherein $T^1$ and $T^2$ denote phenyl groups which may independently be substituted by a fluorine, chlorine or bromine atom or by a methyl, methoxy, hydroxycarbonylmethoxy, methoxycarbonylmethoxy, hydroxy or trifluoromethyl group, wherein the substituents may be identical or different, and U denotes a >CH— group;

Z denotes a single bond, an oxygen atom, an —NH— group, a methylene group or a methyleneamino group bound to the carbonyl group via the nitrogen atom;

B denotes a phenyl group substituted by an aminoiminomethyl group, or B denotes a group —$CH_2CH_2AB^1$, wherein A denotes a methylene group or an optionally methyl-substituted amino group and B¹ denotes an aminoiminomethyl or 1H-imidazol-2-yl group;

Y denotes an oxygen atom or a —NR¹— group, wherein

R¹ denotes a hydrogen atom, a methyl, ethyl, carboxymethyl, methoxycarbonylmethyl or ethoxycarbonylmethyl group;

n denotes the number 1;

V denotes a group —(CH₂)ₘ—Y¹—W—Y², or, if B denotes a group —CH₂CH₂AB¹, wherein A represents a methyl-substituted amino group, V may also represent a hydroxy group, whilst in the group —(CH₂)ₘ—Y—W—Y² m denotes the number 1 or 2,

W denotes an —SO₂— group or a group >C=X, wherein X denotes an oxygen atom or one of the divalent groups =N—CONH₂ or =N—CN, Y¹ denotes a single bond, an oxygen atom or a group —NR²—, wherein R² denotes a hydrogen atom or a methyl or ethyl group, Y² denotes a straight-chain or branched C₁₋₅-alkyl group optionally substituted by a hydroxy, methoxycarbonyl, ethoxycarbonyl or aminocarbonyl group, or Y² denotes a methoxy, ethoxy, n-propoxy, isopropoxy, n-butoxy, 2-methylpropoxy, tert.butoxy, or 2-butyloxy group, a phenyl group optionally substituted by a fluorine, chlorine or bromine atom or by a methyl, trifluoromethyl, methoxy or aminocarbonyl group, or Y² denotes a —NR³R⁴— group, wherein R³ denotes a hydrogen atom, a methyl or ethyl group optionally substituted by a carboxy, methoxycarbonyl, ethoxycarbonyl, dimethylamino, diethylamino or dipropylamino group, a C₄₋₈-cycloalkyl group, a phenyl group optionally mono-, di- or tri-substituted by fluorine, chlorine or bromine atoms or by methyl, trifluoromethyl, hydroxy, methoxy, amino, acetylamino, aminocarbonyl or cyano groups, wherein the substituents may be identical or different, or R³ denotes an alkanoyl, benzoyl, alkoxycarbonyl or aminocarbonyl group and R⁴ has the meanings given for R³ with the exception of phenyl, alkanoyl, benzoyl, alkoxycarbonyl and aminocarbonyl groups, or W—Y² may together also represent a 5-amino-1H-1,2,4-triazol-3-yl, 1H-2-imidazolyl, 3-methyl-1,2,4-oxadiazol-5-yl, or 6-methyl-4-(3H)-oxopyrimidin-2-yl group;

whilst the above-mentioned alkanoyl and alkoxycarbonyl groups, unless otherwise specified, may each contain 1 to 4 carbon atoms in the alkyl and alkoxy moieties;

the tautomers, diastereomers, enantiomers and salts thereof.

Most particularly preferred compounds of the above general formula I are those wherein T denotes a 4-hydroxyphenyl, 2,4-dichlorophenyl, 3,4-dichlorophenyl, 4-amino-3, 5-dichlorophenyl, 4-amino-3, 5-dibromophenyl, 4-(benzoylamino)phenyl, 1-naphthyl, 2-naphthyl, 6-methoxy-2-naphthyl, 1H-indol-2-yl, 1H-indol-3-yl, 1-methyl-1H-indol-3-yl, 5-bromo-1H-indol-3-yl, 1-(ethoxycarbonylmethyl)-1H-indol-3-yl, 1-[3-(diethylamino)propyl]-1H-indol-3-yl, 5-(2-phenylethoxy)-1H-indol-2-yl or 5-bromo-3-methyl-1H-indol-2-yl group, or T denotes a group T¹T²U, wherein T¹ and T² denote phenyl groups which may independently be substituted in the 4-position by a fluorine, chlorine or bromine atom or by a methyl, methoxy, hydroxycarbonylmethoxy, methoxycarbonylmethoxy, hydroxy or trifluoromethyl group, wherein the substituents may be identical or different, and U denotes a >CH— group;

Z denotes a single bond, an oxygen atom, an —NH— group, a methylene group or a methyleneamino group bound to the carbonyl group via the nitrogen atom;

B denotes a phenyl group substituted in the 3-position by an aminoiminomethyl group, or B denotes a group —CH₂CH₂AB¹, wherein A denotes a methylene group or an amino group optionally substituted by a methyl group and B¹ denotes an aminoiminomethyl or 1H-imidazol-2-yl group;

Y denotes an oxygen atom or an —NR¹— group, wherein

R¹ denotes a hydrogen atom, a methyl, ethyl, carboxymethyl, methoxycarbonylmethyl or ethoxycarbonylmethyl group;

n denotes the number 1; and

V denotes an acetylaminomethyl, ethoxycarbonylaminomethyl, aminosulphonylaminomethyl, aminocarbonylaminomethyl, aminocarbonylmethyl, methoxycarbonylaminomethyl, methylaminocarbonylaminomethyl, benzoylaminomethyl, phenylaminocarbonylaminomethyl, ethylaminocarbonylaminomethyl, 1-methylethylaminocarbonylaminomethyl, ethoxycarbonylaminocarbonylaminomethyl, dimethylaminocarbonylaminomethyl, aminocarbonyloxymethyl, aminocarbonylaminocarbonylaminomethyl, [[amino (cyanoimino)methyl]amino]methyl, methylaminocarbonylmethyl, [[[bis (methoxycarbonylmethyl)amino]carbonyl]methyl, [(ethoxycarbonylaminocarbonyl)methylamino]methyl, ethoxycarbonylmethylaminocarbonylaminomethyl, carboxymethylaminocarbonylaminomethyl, dimethylaminocarbonylmethyl or 2-(aminocarbonylamino)ethyl group bound in the 3- or 4-position of the benzene nucleus, the tautomers, diastereomers, enantiomers and salts thereof.

The following may be mentioned as examples of particularly preferred compounds:

(1) (R)-N-[[4-(acetylaminomethyl)phenyl]methyl]-N²-(diphenylacetyl)-argininamide, (2) (R)-N²-(diphenylacetyl)-N-[[4-ethoxycarbonylaminomethyl)-phenyl]methyl]-argininamide, (3) (R)-N-[[4-(aminosulphonylaminomethyl)phenyl] methyl]-N²-(diphenylacetyl)-argininamide, (4) (R)-N-[[4-(aminocarbonylaminomethyl)phenyl] methyl]-N²-(diphenylacetyl)-argininamide, (5) (R,S)-N⁵-(aminoiminomethyl)-N²-(diphenylacetyl)-N-[(4-hydroxyphenyl)methyl]-N⁵-methyl-ornithinamide, (6) (R)-N-[[4-(aminocarbonylmethyl)phenyl]methyl]-N²-(diphenylacetyl)-argininamide, (7) (R)-N²-(diphenylacetyl)-N-[[4-(methylaminosulphonylmethyl)-phenyl]methyl]-argininamide, (8) (R)-N-[[3-(aminocarbonylaminomethyl)phenyl] methyl]-N²-(diphenylacetyl)-argininamide, (9) (R,S)-N-[[4-(aminocarbonylaminomethyl)phenyl] methyl]-N⁵-(aminoiminomethyl-N²-(diphenylacetyl)-N⁵-methyl-ornithinamide,

(10) (R)-N²-(diphenylacetyl)-N-[[4-(methoxycarbonylaminomethyl)phenyl]methyl]-argininamide,

(11) (R)-N²-(diphenylacetyl)-N-[[4-(methylaminocarbonylaminomethyl)phenyl]methyl]-argininamide,
(12) (R)-N-[[4-(benzoylaminomethyl)phenyl]methyl]-N²-(diphenylacetyl)-argininamide,
(13) (R)-N²-(diphenylacetyl)-N-[[4-(phenylaminocarbonylaminomethyl)phenyl]methyl]-argininamide,
(14) (R,S)-N-[[4-(aminocarbonylaminomethyl)phenyl]methyl]-3-[3-(aminoiminomethyl)phenyl]-N²-(diphenylacetyl)-alaninamide,
(15) (R)-N-[[4-(aminocarbonylaminomethyl)phenyl]methyl]-N²-(diphenylacetyl)-N⁵-(1H-imidazol-2-yl)-ornithinamide,
(16) (R)-N-[[4-(aminosulphonylmethyl)phenyl]methyl]-N²-(diphenylacetyl)-argininamide,
(17) (R)-N-[[4-[[(5-amino-1H-1,2,4-triazol-3-yl)amino]methyl]-phenyl]methyl]-N²-(diphenylacetyl)-argininamide,
(18) (R)-N²-(diphenylacetyl)-N-[[4-[[(1H-imidazol-2-yl)amino]-methyl]phenyl]methyl]-argininamide,
(19) (R)-N-[[4-(aminocarbonylaminomethyl)phenyl]methyl]-N²-[(3,4-dichlorophenyl)acetyl]-argininamide,
(20) (R)-N-[[4-(aminocarbonylaminomethyl)phenyl]methyl]-N²-[(2-naphthyl)acetyl]-argininamide,
(21) (R)-N-[[4-(aminocarbonylaminomethyl)phenyl]methyl]-N²-[(5-bromo-1H-indol-3-yl)acetyl]-argininamide,
(22) (R)-N-[[4-(aminocarbonylaminomethyl)phenyl]methyl]-N²-(3,3-diphenyl-1-oxopropyl)-argininamide,
(23) (R)-N²-(diphenylacetyl)-N- [[4-(ethylaminocarbonylaminomethyl)phenyl]methyl]-argininamide,
(24) (R)-N²-(diphenylacetyl)-N- [[4-[(1-methylethyl)-aminocarbonylaminomethyl]phenyl]methyl]-argininamide,
(25) (R)-N-[[4-[[[amino(aminocarbonylimino)methyl]amino]-methyl]phenyl]methyl]-N²-(diphenylacetyl)-argininamide,
(26) (R)-N-[[4-(aminocarbonylaminomethyl)phenyl]methyl]-N²-[(4-amino-3,5-dichlorophenyl)acetyl]-argininamide,
(27) (R)-N-[[4-(aminocarbonylaminomethyl)phenyl]methyl]-N²-[(3-methyl-5-phenyl-1H-indol-2-yl)carbonyl]-argininamide,
(28) (R)-N-[[4-(aminocarbonylaminomethyl)phenyl]methyl]-N²-[4-(benzoylamino)phenyl]acetyl]-argininamide,
(29) (R)-N-[[4-(aminocarbonylaminomethyl)phenyl]methyl]-N²-[[5-(2-phenylethoxy)-1H-indol-2-yl]carbonyl]-argininamide,
(30) (R)-N- [[4-(aminocarbonylaminomethyl)phenyl]methyl]-N²-[(4-amino-3,5-dibromophenyl)acetyl]-argininamide,
(31) (R)-N-[[4-(aminocarbonylaminomethyl)phenyl]methyl]-N²-[(5-bromo-3-methyl-1H-indol-2-yl)carbonyl]-argininamide,
(32) (R)-N-[[4-(aminocarbonylmethyl)phenyl]methyl]-N²-[(2-naphthyl)-carbonyl]-argininamide,
(33) (R)-N-[[4-(aminocarbonylmethyl)phenyl]methyl]-N²-(diphenylacetyl)-N⁵-(1H-imidazol-2-yl)-ornithinamide,
(34) (R)-N²-(diphenylacetyl)-N-[[4-(ethoxycarbonylaminocarbonylaminomethyl)phenyl]methyl]-argininamide,
(35) (R)-N-[[4-(dimethylaminocarbonylaminomethyl)phenyl]-methyl]-N²-(diphenylacetyl)-argininamide,
(36) (R,S)-N-[[4-(aminocarbonylmethyl)phenyl]methyl]-N⁵-(aminoiminomethyl)-N²-(diphenylacetyl)-N⁵-methyl-ornithinamide,
(37) (R)-N-[[4-(aminocarbonylaminomethyl)phenyl]methyl]-N²-(2,2-diphenyl-1-oxo-2-phenoxyethyl)-argininamide,
(38) (R)-N-[[4-(aminocarbonyloxymethyl)phenyl]methyl]-N²-(diphenylacetyl)-argininamide,
(39) (R)-N-[[4-[[[(1,1-dimethylethoxy)carbonyl]amino]-methyl]phenyl]-methyl]-N²-(diphenylacetyl)-argininamide,
(40) (R,S)-N-[[4-(aminocarbonylmethyl)phenyl]methyl]-3-[3-(aminoiminomethyl)phenyl]-N²-(diphenylacetyl)-alaninamide,
(41) (R)-N-[[4-(aminocarbonylaminocarbonylaminomethyl)-phenyl]-methyl]-N²-(diphenylacetyl)-argininamide,
(42) (R)-N-[[4-[[[amino(cyanoimino)methyl]amino]methyl]-phenyl]methyl]-N²-(diphenylacetyl)-argininamide,
(43) (R)-N²-(diphenylacetyl)-N-[[4-(methoxycarbonylmethyl)-phenyl]methyl]-argininamide,
(44) (R)-N²-(diphenylacetyl)-N-[[4-(methylaminocarbonylmethyl)phenyl]methyl]-argininamide,
(45) (R)-N-[[4-[[[(dimethylamino)carbonyl]methylamino]methyl]-phenyl]methyl]-N²-(diphenylacetyl)-argininamide,
(46) (R)-N-[[4-[[[(amino)carbonyl]methylamino]methyl]phenyl]-methyl]-N²-(diphenylacetyl)-argininamide,
(47) (R)-N²-(diphenylacetyl)-N-[[4-[[[(methylamino)-carbonyl)methylamino]methyl]phenyl]methyl]-argininamide,
(48) (R)-N²-(diphenylacetyl)-N-[[4-[[(methoxycarbonyl)-methylamino]methyl]phenyl]methyl]-argininamide,
(49) (R)-N-[[4-[[[(carboxymethyl)amino]carbonyl]methyl]-phenyl]methyl]-N²-(diphenylacetyl)-argininamide,
(50) (R)-N-[[4-[[[bis-(carboxymethyl)amino]carbonyl]-methyl]phenyl]methyl]-N²-(diphenylacetyl)-argininamide,
(51) (R)-N-[[4-[[[bis-(methoxycarbonylmethyl)amino]carbonyl]-methyl]phenyl]methyl]-N²-(diphenylacetyl)-argininamide,
(52) (R)-N²-(diphenylacetyl)-N-[[4-[[[[(ethoxycarbonyl)amino]-carbonyl]methylamino]methyl]phenyl]methyl]-argininamide,
(53) (R)-N²-(diphenylacetyl)-arginine-[4-(aminocarbonylaminomethyl)phenyl]methylester,
(54) (R)-N-[[4-(aminocarbonylaminomethyl)phenyl]methyl]-N²-[(2,4-dichlorophenyl)acetyl]argininamide,
(55) (R)-N-[[4-(aminocarbonylaminomethyl)phenyl]methyl]-N²-[(2,6-dichlorophenyl)acetyl]-argininamide,
(56) (R)-N-[[4-(aminocarbonylaminomethyl)phenyl]methyl]-N²-[bis-(4-methoxyphenyl)acetyl]-argininamide,
(57) (R)-N-[[4-(aminocarbonylaminomethyl)phenyl]methyl]-N²-[(4-nydroxyphenyl)acetyl]-argininamide,
(58) (R)-N²-(diphenylacetyl)-N-[[4-(ethoxycarbonylmethylaminocarbonylaminomethyl)phenyl]methyl]-argininamide,
(59) (R)-N-[[4-(carboxymethylaminocarbonylaminomethyl)phenyl]methyl]-N²-(diphenylacetyl)-argininamide,
(60) (R)-N-[[4-(dimethylaminocarbonylmethyl)phenyl]methyl]-N²-(diphenylacetyl)-argininamide,
(61) (R)-N-[[4-(aminocarbonylaminomethyl)phenyl]methyl]-N²-(diphenylacetyl)-N-(ethoxycarbonylmethyl)-argininamide,
(62) (R)-N-[[4-(aminocarbonylaminomethyl)phenyl]methyl]-N-(carboxymethyl)-N²-(diphenylacetyl)-argininamide,

(63) (R)-N-[[4-[2-(aminocarbonyl)ethyl)phenyl]methyl]-N²-(diphenylacetyl)-argininamide,
(64) (R)-N-[[4-(aminocarbonylaminomethyl)phenyl]methyl]-N²-[(2-naphthyl)carbonyl]-argininamide,
(65) (R)-N-[[2-(aminocarbonyl)-2,3-dihydro-1H-isoindol-5-yl]methyl]-N²-(diphenylacetyl)-argininamide,
(66) (R,S)-N-[[4-(aminocarbonylaminomethyl)phenyl]methyl]-N²-[[[(2-naphthyl)methyl]amino]carbonyl]-argininamide,
(67) (R)-N²-(diphenylacetyl)-N-[[4-[(2-oxo-1-imidazolidinyl)-methyl]-phenyl]methyl]-argininamide,
(68) (R,S)-N-[[4-(aminocarbonylaminomethyl)phenyl]methyl]-3-[3-(aminoiminomethyl)phenyl]-N²-[[(2-butyl-1H-benzimidazol-5-yl)-amino]carbonyl]-alaninamide,
(69) (R)-N-[[4-(aminocarbonylaminomethyl)phenyl]methyl]-N²-[[(l-naphthyl)amino]carbonyl]-argininamide,
(70) (R,S)-N²-(diphenylacetyl)-N-[[4-(2-(3-methyl-1,2,4-oxadiazol-5-yl)ethyl]phenyl]methyl]-argininamide,
(71) (R)-N-[[4-(aminocarbonylaminomethyl)phenyl]methyl]-N²-[(1H-indol-2-yl)carbonyl]-argininamide,
(72) (R)-N-[[4-(aminocarbonylaminomethyl)phenyl]methyl]-N²-[(1H-indol-3-yl)acetyl]-argininamide,
(73) (R)-N-[[4-(aminocarbonylaminomethyl)phenyl]methyl]-N²-[[(3,4-dichlorophenyl)amino]carbonyl]-argininamide,
(74) (R)-N-[[4-(aminocarbonylaminomethyl)phenyl]methyl]-N²-[(1H-indol-4-yl)carbonyl]-argininamide,
(75) (R)-N-[[4-(aminocarbonylaminomethyl)phenyl]methyl]-N²-[(1H-indol-3-yl)carbonyl]-argininamide,
(76) (R)-N-[[4-(aminocarbonylaminomethyl)phenyl]methyl]-N²-[(1H-indol-5-yl)carbonyl]-argininamide,
(77) (R)-N-[[4-(aminocarbonylaminomethyl)phenyl]methyl]-N²-[3,5-bis-(trifluoromethyl)benzoyl]-argininamide,
(78) (R)-N-[[4-(aminocarbonylaminomethyl)phenyl]methyl]-N²-(4-butylbenzoyl)-argininamide,
(79) (R)-N-[[4-(aminocarbonylaminomethyl)phenyl]methyl]-N²-(3,5-dimethylbenzoyl)-argininamide,
(80) (R)-N-[[4-(aminocarbonylaminomethyl)phenyl]methyl]-N²-[(benzo[b]furan-2-yl)carbonyl]-argininamide,
(81) (R)-N-[[4-(aminocarbonylaminomethyl)phenyl]methyl]-N²-(6-methoxy-2-naphthoyl)-argininamide,
(82) (R)-N-[[4-(aminocarbonylaminomethyl)phenyl]methyl]-N²-[(7-methyl-2-propyl-1H-benzimidazol-5-yl)carbonyl]-argininamide,
(83) (R)-N-[[4-(aminocarbonylaminomethyl)phenyl]methyl]-N²-[(2-cyclopropyl-1,4-dimethyl-1H-benzimidazol-6-yl)carbonyl]-argininamide,
(84) (R)-N²-(diphenylacetyl)-N-[[4-[[(5-methyl-4(3H)-oxopyrimidin-2-yl)amino]methyl]phenyl]methyl]-argininamide,
(85) (R)-N²-(diphenylacetyl)-N-[[4-[[(6-methyl-4(3H)-oxopyrimidin-2-yl)amino]methyl]phenyl]methyl]-argininamide,
(86) (R,S)-N-[[4-(aminocarbonylaminomethyl)phenyl]methyl]-3-(1H-benzimidazol-5-yl)-N²-(diphenylacetyl)-alaninamide,
(87) (R)-N²-(diphenylacetyl)-N-[[4-(3-methyl-1,2,4-oxodiazol-5-yl-methyl)phenyl]methyl]-argininamide,
(88) (R,S)-N-[[4-(aminocarbonylmethyl)phenyl]methyl]-N²-[[(3,4-dichlorophenyl)amino]carbonyl]-N⁵-(1H-imidazol-2-yl)-ornithinamide,
(89) (R)-N-[[4-(aminocarbonylaminomethyl)phenyl]methyl]-N²-[[1-(ethoxycarbonylmethyl)-1H-indol-3-yl]acetyl]-argininamide,
(90) (R)-N-[[4-(aminocarbonylaminomethyl)phenyl]methyl]-N²-[[1-(carboxymethyl)-1H-indol-3-yl]acetyl]-argininamide,
(91) (R)-N-[[4-(aminocarbonylaminomethyl)phenyl]methyl]-N²-[[1-[3-(diethylamino)propyl]-1H-indol-3-yl]acetyl]-argininamide,
(92) (R)-N-[[4-(aminocarbonylmethyl)phenyl]methyl]-N²-[[(2,4-dichlorophenyl)amino]carbonyl]-N⁵-(1H-imidazol-2-yl)-ornithinamide,
(93) (R)-N-[[4-(aminocarbonylaminomethyl)phenyl]methyl]-N²-[(2-naphthyl)methoxycarbonyl]-argininamide,
(94) (R)-N-[[4-(aminocarbonylaminomethyl)phenyl]methyl]-N²-[(1-methyl-1H-indol-3-yl)acetyl]-argininamide,
(95) (R)-N²-(diphenylacetyl)-N-[[4-[2-(methoxycarbonyl)ethyl]-phenyl]methyl]-argininamide,
(96) (R)-N-[[3-[[(4-amino-1,4-dioxobutyl)amino]methyl]phenyl]-methyl]-N²-(diphenylacetyl)-argininamide,
(97) (R)-N-[[4-[2-(aminocarbonylamino)ethyl]phenyl]methyl]-N²-(diphenylacetyl)-argininamide,
(98) (R,S)-N-[[4-(aminocarbonylaminomethyl)phenyl]methyl]-6-(4,5-dihydro-1H-imidazol-2-yl)-N²-(diphenylacetyl)-norleucinamide,
(99) (R)-N-[[4-(aminocarbonylaminomethyl)phenyl]methyl]-N²-(diphenylacetyl)-N-methyl-argininamide,
(100) (R,S)-N-[[4-(aminocarbonylaminomethyl)phenyl]methyl]-6-(aminoiminomethyl)-N²-(diphenylacetyl)-norleucinamide,
(101) N-[[4-(aminocarbonylaminomethyl)phenyl]methyl]-N²-[(D,L-5,11-dihydro-6(6H)-oxodibenz[b,e]azepin-11-yl)carbonyl]-D-argininamide (Isomer A),
(102) N-[[4-(aminocarbonylaminomethyl)phenyl]methyl]-N²-[(D,L-5,11-dihydro-6(6H)-oxodibenz[b,e]azepin-11-yl)carbonyl]-D-argininamide (Isomer B),
(103) (R)-N-[[4-(aminocarbonylaminomethyl)phenyl]methyl]-N²-[bis-(4-fluorophenyl)acetyl]-argininamide,
(104) (R)-N-[[4-(aminocarbonylaminomethyl)phenyl]methyl]-N²-[bis-(4-chlorophenyl)acetyl]-argininamide,
(105) (R,S)-N-[[4-(aminocarbonylmethyl)phenyl]methyl]-3-[4-aminoiminomethyl)phenyl]-N²-(diphenylacetyl)-alaninamide,
(106) (R)-N-[[4-[[[3-(dimethylamino)propyl]amino]carbonyl]-methyl]phenyl]methyl]-N²-(diphenylacetyl)-argininamide,
(107) (R)-N-[[4-[[[2-(dimethylamino)ethyl]amino]carbonyl]-methyl]phenyl]methyl]-N²-(diphenylacetyl)-argininamide,
(108) (R)-N-[[4-(aminocarbonylaminomethyl)phenyl]methyl]-N²-[bis-(4-hydroxyphenyl)acetyl]-argininamide,
(109) (R,S)-3-[3-(aminoiminomethyl)phenyl]-N²-(diphenylacetyl)-N-[[4-(ethoxycarbonylmethylaminocarbonylaminomethyl)-phenyl]methyl]-alaninamide,
(110) (R,S)-N-[[4-(aminocarbonylaminomethyl)phenyl]methyl]-3-[3-(aminoiminomethyl)phenyl]-N²-[bis-(4-methoxyphenyl)acetyl]-alaninamide,
(111) (R,S)-3-[3-(aminoiminomethyl)phenyl]-N-[[4-[[[3-(di-methylamino)propyl]amino]carbonyl]methyl]-N²-(diphenylacetyl)-alaninamide,
(112) (R,S)-3-[3-(aminoiminomethyl)phenyl]-N-[[4-[(2,5-dioxo-1-imidazolidinyl)methyl]phenyl]methyl]-N²-(diphenylacetyl)-alaninamide,
(113) (R)-N-[[4-(aminocarbonylaminomethyl)phenyl]methyl]-N²-[bis-[4-(methoxycarbonylmethoxy)phenyl]acetyl]-argininamide,
(114) (R)-N-[[4-(aminocarbonylaminomethyl)phenyl]methyl]-N²-[α-(4-hydroxyphenyl)-α-[4-(methoxycarbonylmethoxy)phenyl]-acetyl]-argininamide, (115) (R)-N-[[4-(aminocarbonylaminomethyl)phenyl]
methyl]-$N^2$-[bis-[4-(hydroxycarbonylmethoxy)phenyl]
acetyl]-argininamide
and the salts thereof.

The compounds of general formula I are prepared by methods known in principle, whereby in particular the methods derived from peptide chemistry (see for example Houben-Weyl, "Methoden der Organischen Chemie", Vol. 15/2) may be used. The amino protecting groups used may be those described in Houben-Weyl, "Methoden der Organischen Chemie", Vol. 15/1, preferably urethane protecting groups such as fluorenylmethoxycarbonyl, phenylmethoxycarbonyl and tert.-butyloxycarbonyl groups. Any functional groups present in group B of the compounds of general formula I or in the precursors thereof are additionally protected by suitable protecting groups in order to prevent any secondary reactions (see for example G. B. Fields et al., Int. J. Peptide Protein Res. 35: 161 (1990); T. W. Greene, "Protective Groups in Organic Synthesis"). Examples of side chain-protected amino acids of this kind include, in particular, Arg($NO_2$), Arg(Mtr), Arg(di-Z), Arg(Pmc), Lys (Boc), Lys(Z), Orn(Boc), Orn(Z), Lys(Cl-Z) which are commercially obtainable, possibly in the form of derivatives. Particular care should be taken to ensure that so-called orthogonal combinations of protecting groups are used in order to protect the α-amino and side-chain amino group, e.g.:

| Protection of the N (side chain) | $N^\alpha$-protection |
|---|---|
| p-toluenesulphonyl | phenylmethoxycarbonyl |
|  | tert.butyloxycarbonyl |
| phenylmethoxycarbonyl | (4-methoxyphenyl)methoxycarbonyl |
|  | tert.butoxycarbonyl |
|  | adamantyloxycarbonyl |
|  | biphenylylisopropyloxycarbonyl |
|  | isonicotinoyloxycarbonyl |
|  | o-nitrophenylsulphenyl |
|  | formyl |
| tert.butoxycarbonyl | phenylmethoxycarbonyl |
|  | p-toluenesulphonyl |
|  | o-nitrophenylsulphenyl |
|  | biphenylylisopropyloxycarbonyl |
|  | 9-fluorenylmethoxycarbonyl |
| acetyl, trifluoroacetyl, formyl, (2-chlorophenyl)-methoxycarbonyl, (4-chloro-phenyl)methoxycarbonyl, 4-(nitrophenyl)methoxycarbonyl, phthaloyl | tert.butyloxycarbonyl |

Instead of protecting amino groups in the side chains, amino acids or derivatives thereof which carry precursor functions and are substituted in the side chain particularly by nitro or cyano may also be used, for example 5-cyano-norvaline or 3-(3-cyanophenyl)-alanine.

The basic functions in the side chain of non-commercial α-amino acids, which are characterised for example by (aminoiminomethyl) groups, may be protected in the same way as is already known for the protection of the side chains of arginine and the derivatives thereof (see also M. Bodanszky, "Peptide Chemistry", Springer-Verlag, 1988, p. 94–97); groups which are particularly suitable as protecting groups for the (aminoiminomethyl) group are the p-toluenesulphonyl, mesitylenesulphonyl(Mts), methoxytrimethylphenylsulphonyl(Mtr), 2,2,5,7,8-pentamethylchroman-6-sulphonyl(Pmc), pentachlorophenoxycarbonyl and nitro protecting groups.

The methods known from peptide chemistry (see for example Houben-Weyl, "Methoden der Organischen Chemie", Vol. 15/2) are used for the actual coupling. Preferably, carbodiimides are used, such as dicyclohexylcarbodiimide (DCC), diisopropylcarbodiimide (DIC) or ethyl-(3-dimethylaminopropyl)-carbodiimide, O-(1H-benzotriazol-1-yl)-N,N,N',N'-tetra-methyluronium-hexafluorophosphate (HBTU) or -tetrafluoroborate (TBTU) or 1H-benzotriazol-1-yl-oxy-tris-(dimethylamino)-phosphoniumhexafluorophosphate (BOP). By the addition of 1-hydroxybenzotriazole (HOBt) or 3-hydroxy-4-oxo-3,4-dihydro-1,2,3-benzotriazine (HOObt) the racemisation may, if desired, additionally be suppressed or the speed of the reaction may be increased. The couplings are normally carried out with equimolar amounts of the coupling components and the coupling reagent in solvents such as dichloromethane, tetrahydrofuran, acetonitrile, dimethylformamide (DMF), dimethylacetamide (DMA), N-methylpyrrolidone (NMP) or mixtures thereof and at temperatures between –30 and ±30° C., preferably between –20 and +20° C. If necessary, N-ethyl-diisopropylamine (DIEA) (Hünig-Base) is preferred as an additional auxiliary base.

Another coupling method used to synthesise compounds of general formula I was the so-called "anhydride method" (see also: M. Bodanszky, "Peptide Chemistry", Springer-Verlag 1988, p. 58–59; M. Bodanszky, "Principles of Peptide Synthesis", Springer-Verlag 1984, p. 21–27). The "mixed anhydride method" is preferred, in the Vaughan variant (J. R. Vaughan Jr., J. Amer. Chem.Soc. 73: 3547 (1951)), in which the mixed anhydride is obtained from the optionally $N^2$-protected α-amino acid which is to be coupled and the monoisobutylcarbonate, using isobutylchlorocarbonate in the presence of bases such as 4-methylmorpholine or 4-ethylmorpholine. The preparation of this mixed anhydride and the coupling with amines are carried out in a one-pot process using the above-mentioned solvents, at temperatures between –20 and +20° C., preferably 0 and +20° C.

Any protective groups present in the α-amino acid side chain are cleaved with suitable reagents known in principle from the literature, after the synthesis of the N- and C-terminally substituted amino acid derivative, and arylsulphonyl and heteroarylsulphonyl protecting groups are preferably cleaved by acidolysis, i.e. by the action of strong acids, preferably trifluoroacetic acid, whilst nitro and arylmethoxycarbonyl protecting groups are cleaved by hydrogenolysis, e.g. using hydrogen in the presence of palladium black and using glacial acetic acid as solvent. If the substrate contains functions which are sensitive to hydrogenolysis, e.g. halogen atoms such as chlorine, bromine or iodine, a phenylmethanol or heteroarylmethanol function or another benzylheteroatom bond, particularly a benzyl-oxygen bond, the nitro group may also be cleaved in a non-hydrogenolytic manner, e.g. with zinc/2N trifluoroacetic acid (see also: A. Turan, A. Patthy and S. Bajusz, Acta Chim. Acad. Sci. Hung, Tom. 85 (3): 327–332 [1975]; C. A. 83: 206526y [1975]), with tin(II)-chloride in 60% aqueous formic acid (see also: SUNSTAR KK, JA-A-3271-299), with zinc in the presence of acetic acid (see also: A. Malabarba, P. Ferrari, G. Cietto, R. Pallanza and M. Berti, J. Antibiot. 42(12): 1800–1816 (1989)) or excess aqueous 20% titanium(III)-chloride in aqueous methanol and in the presence of aqueous ammonium acetate buffer at 24° C. (see also: R. M. Freidinger, R. Hirschmann and D. F. Veber, J. Org. Chem. 43(25): 4800–4803 [1978]).

Any precursor functions present in the side chain of α-amino acid may also be subsequently converted into the desired amino functions by hydrogenolysis; nitroalkyl groups yield aminoalkyl groups under conditions familiar to chemists whilst the cyano group changes into the aminomethyl group.

Instead, nitrile functions may also be reduced with complex hydrides which are selective with respect to other critical functions contained in the molecule, particularly amide groups (see also: J. Seyden-Penne, "Reductions by the Alumino- and Borohydrides in Organic Synthesis", VCH Publishers Inc., 1991, p. 132ff.), e.g. with sodium borohydride in methanol and in the presence of cobalt(II)-chloride, with sodium borohydride in tetrahydrofuran in the presence of trifluoroacetic acid or with tetrakis-(n-butyl)-ammonium borohydride in dichloromethane; it is also possible to reduce aliphatic nitro functions to the primary amino function using sodium borohydride in the presence of tin(II)-chloride or copper(II)-acetylacetonate, without attacking the carboxamide groups present in compounds of type I (see also: J. Seyden-Penne, ibid. p. 137ff.).

The following methods are particularly suitable for preparing the compounds of general formula I according to the invention:

a) Coupling of compounds of general formula II,

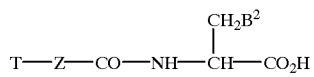

(II)

wherein

T and Z are as hereinbefore defined, $B^2$ has the meanings given for B hereinbefore or represents a group B substituted by the above-mentioned protecting groups, or denotes a precursor group for the group B, e.g. a cyanophenyl- or cyanopropyl-group with compounds of general formula III,

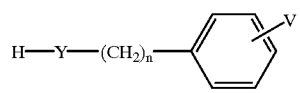

(III)

wherein n, V and Y are as hereinbefore defined, and, if necessary, subsequently cleaving protecting groups or converting precursor functions as described hereinbefore.

The coupling is carried out using the methods known from peptide chemistry described hereinbefore, particularly using DCC, DIC, HBTU, TBTU or BOP as reagents or using the mixed anhydride method.

If the starting compound II used is enantiomerically pure, and provided that Z is not an oxygen atom or an NH—group, partial racemisation must be expected during the coupling step if triethylamine is used as the auxiliary base whilst quantitative racemisation is to be expected if dimethylformamide, dimethylacetamide or N-methyl-pyrrolidone is used as solvent.

The alternative method recommended by A. Hassner and V. Alexonian, Tetrahedron Letters 1978, 4475–4478, i.e reaction at ambient temperature and in the presence of DCC and 4-(1-pyrrolidinyl)pyridine as base, has proved particularly useful for preparing compounds of general formula I wherein Y denotes an oxygen atom.

b) In order to prepare compounds of general formula I wherein Z has the meanings given hereinbefore, with the exception of an oxygen atom, a NH group and an ethylene group, wherein the methylene group connected to the carbonyl group is replaced by an oxygen atom or an NH group:

Coupling compounds of general formula IV,

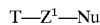

(IV)

wherein

T is as hereinbefore defined, $Z^1$ denotes a single bond, a methylene or ethylene group and Nu denotes a leaving group, e.g. a hydroxy group, a halogen atom such as a chlorine, bromine or iodine atom, a $C_{1-10}$-alkylsulphonyloxy group, a phenylsulphonyloxy or naphthylsulphonyloxy group optionally mono-, di- or tri-substituted by chlorine or bromine atoms or by methyl or nitro groups, wherein the substituents may be identical or different, with α-amino acid derivatives of general formula V,

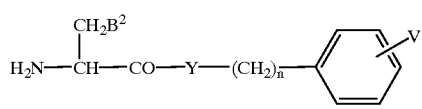

(V)

wherein n, V and Y are as hereinbefore defined, $B^2$ has the meanings given for B hereinbefore or denotes a group B substituted by the above-mentioned protecting groups, or it denotes a precursor group for the group B, e.g. a cyanophenyl- or cyanopropyl group, and, if necessary, subsequently cleaving any protecting groups or converting precursor functions according to the methods described above.

If in general formula IV Nu denotes a hydroxy group, the coupling methods known from peptide chemistry and discussed in detail hereinbefore are used, particularly using the above-mentioned coupling reagents DCC, DIC, HBTU, TBTU or BOP, or the mixed anhydride method may be used.

If in general formula IV Nu denotes a halogen atom or an alkyl- or arylsulphonyloxy group, the reaction is carried out under Schotten-Baumann or Einhorn conditions, i.e. the components are reacted in the presence of at least one equivalent of an auxiliary base at temperatures between −50° C. and +120° C., preferably between −10° C. and +30° C., optionally in the presence of solvents. Preferred auxiliary bases include alkali and alkaline earth metal hydroxides, such as sodium hydroxide, potassium hydroxide or barium hydroxide, alkali metal carbonates, e.g. sodium carbonate, potassium carbonate or caesium carbonate, alkali metal acetates, e.g. sodium or potassium acetate, and tertiary amines, e.g. pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, and preferred solvents include dichloromethane, tetrahydrofuran, 1,4-dioxane, acetonitrile, dimethylformamide, dimethylacetamide, N-methyl-pyrrolidone or mixtures thereof. If alkali or alkaline earth metal hydroxides, alkali metal carbonate or acetates are used as auxiliary bases, water may also be added to the reaction mixture as a cosolvent.

c) In order to prepare compounds of general formula I, wherein Y denotes an oxygen atom:

Transesterification of amino acid esters of general formula VI,

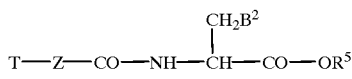

(VI)

wherein

T and Z are as hereinbefore defined, $B^2$ has the meanings given for B hereinbefore or denotes a group B substituted by the above-mentioned protecting groups or denotes a precursor group for the group B, e.g. a cyanophenyl or cyanopropyl group, and $R^5$ denotes a $C_{1-4}$-alkyl group, with an alcohol of general formula VII,

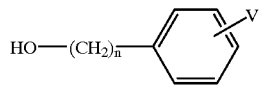

(VII)

wherein n and V are as hereinbefore defined and, if necessary, subsequently cleaving the protecting groups or modifying precursor functions according to the methods described hereinbefore.

The transesterification may be catalysed by acids or alkalis (see also: J. March, "Advanced Organic Chemistry", John Wiley & Sons, Third Edition, 1985 pages 351–352). Examples of preferred alkaline catalysts include the alkali metal alkoxides which are readily obtainable from the alcohols of general formula VII or $R^4OH$, e.g. lithium, sodium or potassium alkoxides; examples of preferred acid catalysts include, in addition to anhydrous hydrogen chloride, especially sulphuric acid, p-toluenesulphonic acid, naphthalin-1- or -2-sulphonic acid or acid ion exchanger freshly charged with hydrogen ions, e.g. Wofatit KPS z.A. The balance between the two esters which are present in equilibrium is shifted in the desired direction in this process by distilling off the more volatile alcohol $R^5OH$.

In the case of alkaline catalysis, the end product of general formula I is obtained as a racemate, even if the starting compound VI has been used in enantiomerically pure form.

d) In order to prepare compounds of general formula I, wherein Y denotes an oxygen atom:

Reaction of salts, preferably alkali metal salts, of the carboxylic acids of general formula II,

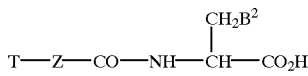

(II)

wherein

T and Z are as hereinbefore defined, $B^2$ has the meanings given for B hereinbefore or denotes a group B substituted by the above-mentioned protecting groups, or denotes a precursor group for the group B, e.g. a cyanophenyl or cyanopropyl group, with compounds of general formula VIII,

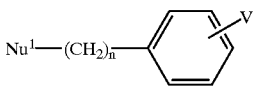

(VIII)

wherein n and V are as hereinbefore defined and $Nu^1$ denotes a leaving —group, e.g. a halogen atom such as a chlorine, bromine or iodine atom, a $C_{1-10}$-alkylsulphonyloxy group, a phenylsulphonyloxy or naphthylsulphonyloxy group optionally mono-, di- or trisubstituted by chlorine or bromine atoms or by methyl or nitro groups, wherein the substituents may be identical or different.

The reaction is carried out in a suitable solvent, preferably in the presence of dipolar aprotic solvents such as dimethylsulphoxide, hexamethylphosphoric acid triamide, 1,3-dimethyl-2-imidazolidinone, dimethylacetamide, dimethylformamide or N-methyl-2-pyrrolidinone at temperatures between $-10°$ C. and $+50°$ C., but preferably at ambient temperature. The alkali metal salts of the carboxylic acids of general formula II are preferably produced in situ by the action of alkali metal carbonates, e.g. potassium or caesium carbonate, alkali metal hydroxides, e.g. sodium hydroxide, or alkali metal hydrides, e.g. sodium hydride, on the compounds of general formula II, before the halides of general formula VIII are added (see also: J. E. Schaer, D. C. Kunarth and J. J. Scherry, Tetrahedron Letters 1973, 689–692; A. M. Mac Leod, K. J. Merchant, M. A. Cascieri, S. Sadowski, E. Ber., C. J. Serain and R. Baker, J. Med. Chem. 36: 2044–2045 (1993); A. Rosowsky, R. A. Forsch. Ci—S. Su, H. Lazarus and G. P. Beardsley, J. Med. Chem. 27: 605–609 (1984)).

e) In order to prepare compounds of general formula I, wherein B denotes the group $—CH_2CH_2AB^1$, wherein A denotes an amino group optionally substituted by a $C_{1-4}$-alkyl group and $B^1$ denotes an aminoiminomethyl or 4,5-dihydro-1H-imidazol-2-yl group:

Reacting compounds of general formula IX,

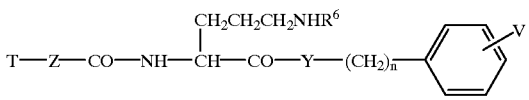

(IX)

wherein n, T, V, Y and Z are as hereinbefore defined and $R^6$ denotes a hydrogen atom or a $C_{1-4}$-alkyl group, with carbonic acid derivatives of general formula X,

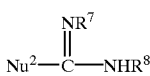

(X)

wherein $R^7$ and $R^8$ each denote hydrogen atoms or together denote a 1,2-ethylene bridge and $Nu^2$ is a leaving group, e.g. an alkoxy-, alkylthio-, alkylsulphinyl- or alkylsulphonyl group each having 1 to 10 carbon atoms in the alkyl moiety, e.g. a methoxy, ethoxy, methylthio, ethylthio, methylsulphinyl, ethylsulphinyl, propylsulphinyl, isopropylsulphinyl, methylsulphonyl or ethylsulphonyl group, a chlorine atom, an SO$_2$H, SO$_3$H or OPOCl$_2$ group or a group of general formula XI,

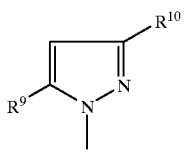

(XI)

wherein

R$^9$ and R$^{10}$, which may be identical or different, denote hydrogen atoms or C$_{1-3}$-alkyl groups.

Occasionally it is advantageous, e.g. when Nu$^2$ is an alkoxy group, to use the mineral acid salts, e.g. the neutral sulphates or hydrochlorides, of the compounds of general formula X instead of the compounds themselves.

The reactions are carried out analogously to methods known from the literature (see G. B. L. Smith, J. Amer. Chem. Soc. 51: 476 [1929]; B. Rathke, Chem. Ber. 17, 297 [1884]; R. Phillips and H. T. Clarke, J. Amer. Chem. Soc. 45: 1755 [1923]; S. J. Angyal and W. K. Warburton, J. Amer. Chem. Soc. 73: 2492 [1951]; H. Lecher and F. Graf, Chem. Ber. 56: 1326 [1923]; J. Wityak, S. J. Gould, S. J. Hein and D. A. Keszler, J. Org. Chem. 52: 2179 [1987]; T. Teraji, Y. Nakai, G. J. Durant, WO-A-81/00109, Chem. Abstr. 94: 192336z [1981]; C. A. Maryanoff, R. C. Stanzione, J. N. Plampin and J. E. Mills, J. Org. Chem. 51: 1882–1884 [1986]; A. E. Miller and J. J. Bischoff, Synthesis 1986, 777; R. A. B. Bannard, A. A. Casselman, W. F. Cockburn and G. M. Brown, Can. J. Chem. 36: 1541 [1958]; Aktieselskabet Grea, Kopenhagen, DE 28 26 452-C2; K. Kim. Y- T. Lin and H. S. Mosher, Tetrah. Letters, 29: 3183–3186 [1988]; H. B. Arzeno et al., Synth. Commun. 20: 3433–3437 [1990]; H. Bredereck and K. Bredereck, Chem. Ber. 94: 2278 [1961]; H. Eilingsfeld, G. Neubauer, M. Seefelder and H. Weidinger, Chem. Ber. 97: 1232 [1964]; P. Pruszynski, Can. J. Chem. 65: 626 [1987]; D. F. Gavin, W. J. Schnabel, E. Kober and M. A. Robinson, J. Org. Chem. 32: 2511 [1967]; N. K. Hart, S. R. Johns, J. A. Lamberton and R. I. Willing, Aust. J. Chem. 23: 1679 [1970]; CIBA Ltd., Belgian Patent 655403; Chem. Abstr. 64: 17481 [1966]; R. A. B. Bannard, A. A. Casselman, W. F. Cockburn and G. M. Brown, Can. J. Chem. 36: 1541 [1958]; J. P. Greenstein, J. Org. Chem. 2: 480 [1937]; F. L. Scott und J. Reilly, J. Amer. Chem. Soc. 74: 4562 [1952]; W. R. Roush and A. E. Walts, J. Amer. Chem. Soc. 106: 721 [1984], M. S. Bernatowicz, Y. Wu and G. R. Matsueda, J. Org. Chem. 57: 2497–2502 [1992]; H. Tsunematsu, T. Imamura and S. Makisumi, J. Biochem. 94: 123–128 [1983]) at temperatures between 0° C. and +100° C., preferably +40° C. and +80° C., using inert solvents, such as dichloromethane, tetrahydrofuran, 1,4-dioxane, acetonitrile, dimethylformamide, dimethylacetamide, N-methyl-pyrrolidone or mixtures thereof and, depending on the nature of the Nu$^2$ group, frequently in the presence of auxiliary bases, particularly alkali metal carbonates such as sodium or potassium carbonate, or tertiary amines, preferably N-ethyl-diisopropylamine or triethylamine.

f) In order to prepare compounds of formula I, wherein B denotes the group —CH$_2$CH$_2$AB$^1$, wherein A denotes an amino group optionally substituted by a C$_{1-4}$-alkyl group and B$^1$ denotes an aminoiminomethyl group:

Reacting compounds of general formula IX,

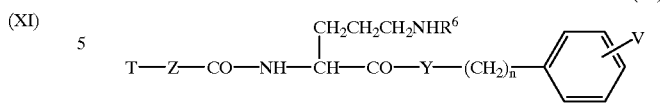

(IX)

wherein n, T, V, Y and Z are as hereinbefore defined and R$^6$ denotes a hydrogen atom or a C$_{1-4}$-alkyl group, with cyanamide.

The reactions are carried out at temperatures of between 20° C. and 150° C., optionally in an autoclave. The preferred solvents are alcohols such as methanol, ethanol or n-propanol, ethers such as dioxane or esters such as ethyl acetate. Water may be used as a further cosolvent. Although the reaction will succeed without the addition of acids, it is preferable to carry out the reaction in the presence of organic acids, e.g. acetic acid, and particularly strong acids, e.g. methanesulphonic acid, sulphuric acid, hydrogen bromide, hydrogen chloride or hydrochloric acid. If, for example, the salts of the amines of general formula IX are used, then the compounds of general formula I are obtained in the form of the corresponding salts (see also: Houben-Weyl, "Methoden der Organischen Chemie", 4th Edition, Georg-Thieme-Verlag, Stuttgart, from 1952, Volume VIII, p. 98, p. 180; Ullmanns "Encyclopadie der Technischen Chemie", Verlag Chemie, Weinheim, 1972–1977, Volume VIII, p. 328; E. H. Sheers, Kirk-othmer Encycl. Chem. Technol., 2nd ed., 10: 734 [1966]; A. Kämpf, Chem. Ber. 37: 1681 [1904]; R. A. Corral, O. O. Orazi and M. F. de Petruccelli, Chem. Commun. 1970, 556).

g) In order to prepare compounds of general formula I, wherein B denotes a phenyl group substituted by an aminoiminomethyl group or the group —CH$_2$CH$_2$AB$^1$, wherein A is an methylene group and B$^1$ denotes an aminoiminomethyl or 4,5-dihydro-1H-imidazol-2-yl group:

Reacting compounds of general formula XII,

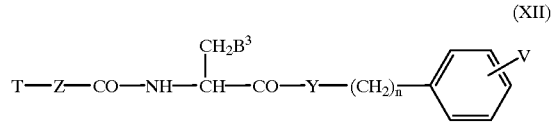

(XII)

wherein n, T, V, Y and Z are as hereinbefore defined and B$^3$ denotes a cyanophenyl or 2-cyanoethyl group, with alcohols of general formula XIII,

R$^5$—OH (XIII)

(wherein

R$^5$ denotes a C$_{1-4}$-alkyl group) followed by treatment with ammonia or 1,2-diaminoethane.

The first stage of the reaction is preferably carried out in an alcohol of general formula XIII as solvent, e.g. in methanol or ethanol, in the presence of dry hydrogen chloride and in the absence of water, at temperatures between −30° C. and +40° C., preferably at 0° C. to +20° C., whilst the iminoesters, which are obtained in the form of their hydrochlorides in this acid variant are generally not purified but converted directly, in the second step, into the desired compounds of general formula I by treatment with ammonia or 1,2-diaminoethane and at temperatures between −20° C. and the boiling temperature of the solvent (see also: A. Pinner and F. Klein, Chem. Ber. 10: 1889 [1877]; A. Pinner, "The Iminoethers and the Derivatives thereof", Oppenheim, Berlin, 1892; R. Roger and D. G. Neilson, Chem. Rev. 61: 179 [1961]; G. Wagner and J. Wunderlich, Pharmazie 31: 766 [1976]; G. Wagner, B. Voigt, D. Danicke and T. Liebermann, Pharmazie 31: 528 [1976]; R. R. Tidwell, L. L. Fox and J. D. Geratz, Biochim. Biophys. Acta 445: 729 [1976]; T. Pantev and R. Georgieva, Farmatsiya (Sofia) 29: 1 [1979]). The iminoesters are also obtained in the form of their free bases in the base-catalysed addition of alcohols of general formula XIII to the nitrites of formula XII. The preferred basic catalysts are the alkali metal alkoxides which correspond to the alcohols used; the combination of sodium methoxide and methanol is particularly preferred (see also: C. Soula, A. Marsura and C. Luu-Duc, J. Pharm. Belg. 42: 293 [1987]; W. J. Haggerty and W. J. Rost, J. Pharm. Sci. 58: 50 [1969]).

In the acid variant of the synthesis of amidines of general formula I, instead of using dry hydrogen chloride in the first stage it is also possible to use other anhydrous acid agents, e.g. hydrogen bromide, p-toluenesulphonic acid or sulphuric acid. In the second stage, the reaction of the resulting iminoesters with ammonia or 1,2-diaminoethane, instead of using the free ammonia or 1,2-diaminoethane, the salts thereof with weak inorganic acids are frequently used, such as the corresponding ammonium carbonates or ammonium acetates.

In the alkaline variant, ammonia or 1,2-diaminoethane is generally used in the second stage in the form of the salts thereof with inorganic acids, e.g. in the form of the hydrochlorides; glacial acetic acid may also advantageously be used as solvent in the second step.

h) In order to prepare compounds of general formula I, wherein B denotes a phenyl group substituted by an aminoiminomethyl group, or the group —CH$_2$CH$_2$AB$^1$ wherein A is a methylene group and B$^1$ is an aminoiminomethyl group:

Addition of hydroxylamine to nitrites of general formula XII,

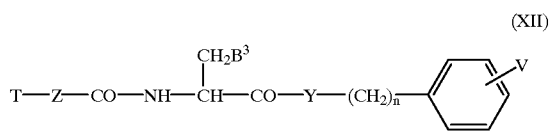

wherein n, T, V, Y and Z are as hereinbefore defined and B$^3$ denotes a cyanophenyl or 2-cyanoethyl group, and subsequent hydrogenolysis of the resulting amidoximes of general formula XIV,

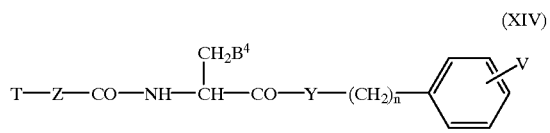

wherein n, T, V, Y and Z are as hereinbefore defined and B$^4$ denotes a group —C$_6$H$_4$—C(=NOH)NH$_2$ or —CH$_2$CH$_2$C(=NOH)NH$_2$.

The first step, the reaction to form the amidoximes of general formula XIV, is carried out in suitable solvents, e.g.

in dioxane, dimethylformamide, dimethylacetamide, N-methyl-pyrrolidone, 1,3-dimethyl-2-imidazolidinone, methanol, n-propanol, but preferably in ethanol, using small amounts of water as cosolvent and at temperatures between +30 and +100° C., preferably between +60° C. and +80° C. However, it is particularly advantageous in the reaction to release the hydroxylamine in situ from its salts, e.g. the hydrochloride or sulphate thereof, by means of weak bases, preferably alkali metal carbonates and most preferably sodium carbonate.

The second step, the hydrogenolysis of the amidoxime, is carried out using palladium or nickel catalysts, e.g. palladium/animal charcoal, palladium black, palladium/barium sulphate or Raney nickel, in suitable solvents such as ethanol, methanol, glacial acetic acid, 1,4-dioxane or ethyl acetate, at temperatures between 0 and +100° C., preferably between +50° C. and +70° C., under a hydrogen pressure of 0.5 to 200 bar, preferably 1 to 5 bar.

i) In order to prepare compounds of general formula I, wherein B denotes a phenyl group substituted by an aminoiminomethyl group or the group —CH$_2$CH$_2$AB$^1$, wherein A is a methylene group and B$^1$ is an aminoiminomethyl group:

Converting nitrites of general formula XII

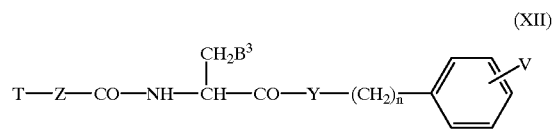

wherein n, T, V, Y and Z are as hereinbefore defined and B$^3$ denotes a cyanophenyl or 2-cyanoethyl group, into thioamides of general formula XV,

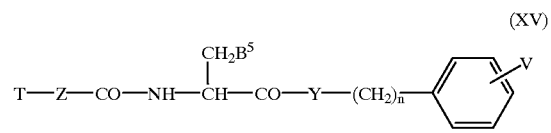

wherein n, T, V, Y and Z are as hereinbefore defined and B$^5$ denotes a phenyl group substituted by an aminothiocarbonyl group, or a 2-(aminothiocarbonyl)ethyl group, subsequent alkylation with compounds of general formula XVI,

wherein

R$^5$ denotes a C$_{1-4}$-alkyl group and Nu$^3$ denotes a leaving group such as a halogen atom, e.g. a chlorine, bromine or iodine atom or an alkylsulphonyloxy, alkoxysulphonyloxy, arylsulphonyloxy group, methanesulphonyloxy, methoxysulphonyloxy or toluenesulphonyloxy group, or with a trialkyloxonium tetrafluoroborate of general formula XVII,

wherein

R$^5$ is as hereinbefore defined, and subsequent aminolysis.

The reactions are carried out according to methods known from the literature (see also: P. Chabrier and S. H. Renard, C. R. Acad. Sci. Paris 230: 1673 [1950]; Y. Nii, K. Okano, S. Kobayashi and M. Ohto, Tetrah. Lett. 1979, 2517; Hoffmann-La Roche, EP-A-381033).

In order to prepare the thiocarboxylic acid amides of general formula XV from the nitriles of general formula XII, it is preferable to carry out the reaction with hydrogen sulphide in pyridine and in the presence of gaseous ammonia or triethylamine, possibly in a pressurised autoclave. Suitable reaction temperatures are between 0° C. and +100° C., preferably between +50 and +60° C. (see also: Houben-Weyl, "Methoden der Organischen Chemie", 4th Edition, Georg-Thieme Verlag, Stuttgart, from 1952, Volume IX, p. 762). It is also suitable to carry out the reaction with thioacetamide in dimethylformamide saturated with dry hydrogen chloride at temperatures between 80 and 100° C. (see also: E. C. Taylor and J. A. Zoltewicz, J. Amer. Chem. Soc. 82: 2656 [1960]).

In order to prepare the thioimide acid esters or the salts thereof from the thioamides of general formula XV, reaction with methyliodide is preferred. Suitable solvents include ketones such as acetone or cyclohexanone, and dipolar aprotic solvents of the dimethylformamide, dimethylacetamide, N-methyl-pyrrolidone or 1,3-dimethyl-2-imidazolidinone type or mixtures thereof. Suitable reaction temperatures are between −20° C. and +100° C., preferably ambient temperature.

The aminolysis is carried out at temperatures between 0° C. and +100° C., preferably +40° C. and +80° C., using inert solvents, e.g. dichloromethane, tetrahydrofuran, 1,4-dioxane, acetonitrile, dimethylformamide, dimethylacetamide, N-methyl-pyrrolidone or mixtures thereof, and optionally in the presence of auxiliary bases, particularly alkali metal carbonates such as sodium or potassium carbonate, or tertiary amines, preferably N-ethyldiisopropylamine or triethylamine.

j) In order to prepare compounds of general formula I wherein B denotes the group —$CH_2CH_2AB^1$, where A denotes an amino group optionally substituted by a $C_{1-4}$-alkyl group and $B^1$ denotes a 1H-imidazol-2-yl group:
Reacting compounds of general formula IX,

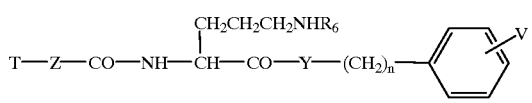

(IX)

wherein n, T, V, Y and Z are as hereinbefore defined and $R^6$ denotes a hydrogen atom or a $C_{1-4}$-alkyl group, with thiuronium salts of general formula XVIII,

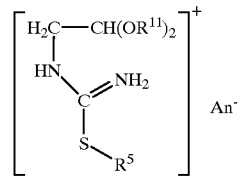

(XVIII)

wherein $R^5$ and $R^{11}$, which may be identical or different, denote $C_{1-4}$-alkyl groups and An- is a monovalent anion, such as a chloride, bromide, iodide, methylsulphate, methanesulphonate or toluenesulphonate anion or ½ $SO_4^{2-}$—, and subsequent cyclisation of the intermediate products of general formula XIX,

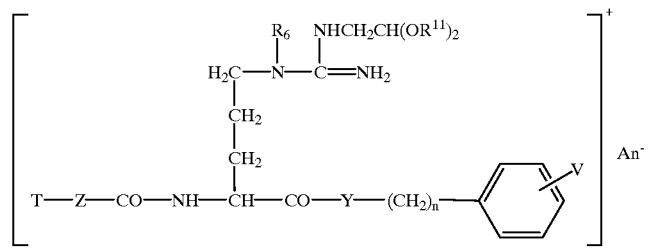

(XIX)

which are generally not isolated,
wherein
n, $R^6$, $R^{11}$, T, V, Y and Z are as hereinbefore defined.

The reaction of the amines of general formula IX with the thiuronium salts of general formula XVIII is carried out in lower alcohols such as methanol or ethanol as solvent at reaction temperatures of between 50 and 100° C., but preferably at the boiling point of the solvent used, whilst auxiliary bases such as triethylamine, diisopropylethylamine or 4-(dimethylamino)pyridine, may be added to the reaction mixture.

Cyclisation is carried out, for example, by heating with dilute aqueous inorganic acid, e.g. dilute sulphuric acid, hydrochloric acid or phosphoric acid (see also: B. T. Storey, W. W. Sullivan and C. L. Moyer, J. Org. Chem. 29, 3118–3120 (1964)).

k) In order to prepare compounds of general formula I wherein B denotes the group —$CH_2CH_2AB^1$, where A is an amino group optionally substituted by a $C_{1-4}$-alkyl group and $B^1$ denotes a 1H-imidazol-2-yl group:
Reacting uronium salts of general formula XX,

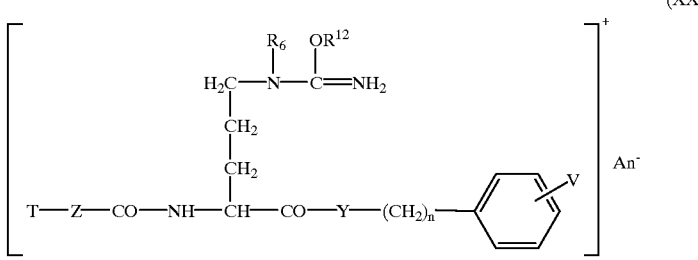

(XX)

wherein n, T, V, Y and Z are as hereinbefore defined, $R^6$ denotes a hydrogen atom or a $C_{1-4}$-alkyl group, $R^{12}$ denotes a $C_{1-4}$-alkyl group and $An^-$ denotes a monovalent anion, for example a chloride, bromide, iodide, methylsulphate, methanesulphonate or toluenesulphonate anion or ½ $SO_4^{2-}$, with aminoacetaldehyde acetals of general formula XXI,

(XXI)

wherein
$R^{11}$ denotes a $C_{1-4}$-alkyl group,
and subsequent cyclisation of the intermediate products of general formula XIX,

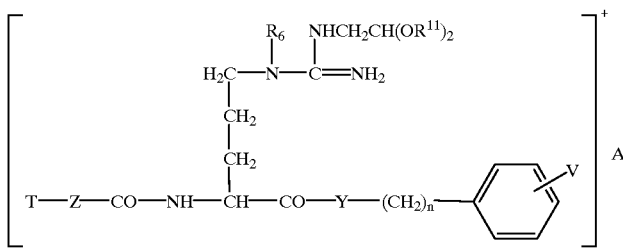

(XIX)

which are not generally isolated,
wherein n, T, V, Y and Z are as hereinbefore defined, $R^6$ denotes a hydrogen atom or a $C_{1-4}$-alkyl group and $R^{11}$ denotes a $C_{1-4}$-alkyl group.

The conditions of the reaction largely correspond to the instructions given in process j) in both reaction steps. The reaction of the aminoacetaldehyde acetals of general formula XXI with the uronium salts of general formula XX is carried out in lower alcohols such as methanol or ethanol as solvent, at reaction temperatures of between 50 and 100° C., but preferably at the boiling point of the solvent used, whilst auxiliary bases such as triethylamine, diisopropylethylamine or 4-(dimethylamino)pyridine, may be added to the reaction mixture.

Instead of the salts of general formula XX, the underlying bases may be used in the first step if the equivalent amount of acetic acid is added to the reaction mixture.

The cyclisation is carried out, for example, by heating with dilute aqueous inorganic acid, e.g. dilute sulphuric acid, hydrochloric acid or phosphoric acid (see also: B. T. Storey, W. W. Sullivan and C. L. Moyer, J. Org. Chem. 29, 3118–3120 (1964)).

l) In order to prepare compounds of general formula I, wherein B denotes a phenyl group substituted by an aminoiminomethyl group or a group —$CH_2CH_2AB^1$, wherein A is a methylene group or an amino group optionally substituted by a $C_{1-4}$-alkyl group and $B^1$ denotes an aminoiminomethyl or 4,5-dihydro-1H-imidazol-2-yl group:
Reacting compounds of general formula XXII,

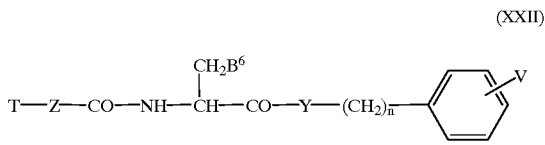

(XXII)

wherein
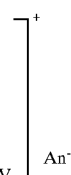

(n, T, V, Y and Z are as hereinbefore defined and $B^6$ denotes a cyanophenyl group or the group —$CH_2CH_2A$—CN, wherein A is as hereinbefore defined) with inorganic acid salts of ammonia or 1,2-diaminoethane.

The reaction is carried out using suitable solvents, for example lower alcohols such as methanol and ethanol or mixtures thereof, at temperatures between +10 and +190° C., preferably between 90 and 160° C. Examples of acids for salt formation include hydrochloric acid, hydrobromic acid, hydriodic acid, sulphuric acid, phosphoric acid, methanesulphonic acid or p-toluenesulphonic acid. The reaction is preferably carried out using equivalent quantities of the ammonium salt or 1,2-diaminoethane salt and in the presence of additional free ammonia or 1,2-diaminoethane, but will also succeed in the absence of these free bases.

m) In order to prepare compounds of general formula I, wherein B denotes the group —$CH_2CH_2AB^1$, where A is an amino group optionally substituted by a $C_{1-4}$-alkyl group and $B^1$ denotes an aminoiminomethyl group:
Reaction of uronium salts of general formula XX,

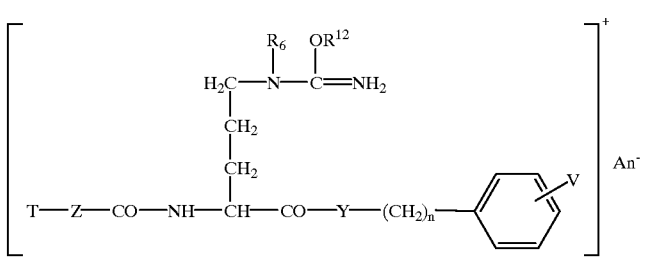

(XX)

wherein n, T, V, Y and Z are as hereinbefore defined, $R^6$ denotes a hydrogen atom or a $C_{1-4}$-alkyl group, $R_{12}$ denotes a $C_{1-4}$-alkyl group and An- denotes a monovalent anion, for example a chloride, bromide, iodide, methylsulphate, methanesulphonate or toluenesulphonate anion or ½ $SO_4^{2-}$, or the corresponding free isoureas, with ammonia.

The reaction is carried out at temperatures between 0 and 110° C., preferably between +15 and +60° C., with aqueous or gaseous ammonia, optionally in a suitable solvent, such as water, dimethylformamide, dimethylacetamide, dimethylsulphoxide, N-methylpyrrolidone, tetrahydrofuran, dioxane, an alcohol such as methanol or ethanol or in a mixture thereof, the compounds of general formula I occurring directly as salts with the acid HAn. If the underlying bases, the corresponding free isoureas, are used in the reaction instead of the uronium salts XX, one equivalent of a weak acid, preferably acetic acid, must be added to the mixture.

n) In order to prepare compounds of general formula I, wherein B denotes a 1H-benzimidazol-5-yl or 1H-benzimidazol-6-yl group:

Cyclising a compound of general formula XXIII optionally formed in the reaction mixture by reduction,

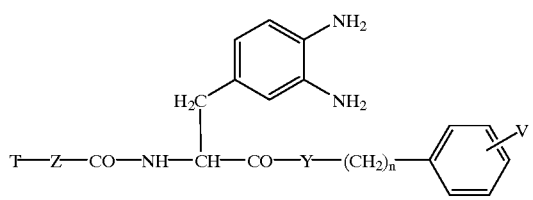

(XXIII)

wherein n, T, V, Y and Z are as hereinbefore defined, with formic acid optionally followed by cleaving of a formyl group bound in the 1-position of the benzimidazole.

The cyclisation is carried out by stirring the compounds of general formula XXIII in formic acid as solvent, optionally with the addition of other suitable solvents such as water or dimethylformamide, at temperatures between +15 and 100° C.

Any formyl group bound in the 1-position of the benzimidazole is cleaved by treating with dilute aqueous acids or bases, preferably with a mixture of methanol and concentrated aqueous hydrochloric acid.

The cyclisation may also be carried out by preparing a compound of general formula XXIII in the reaction mixture by reducing a compound of general formula XXIV

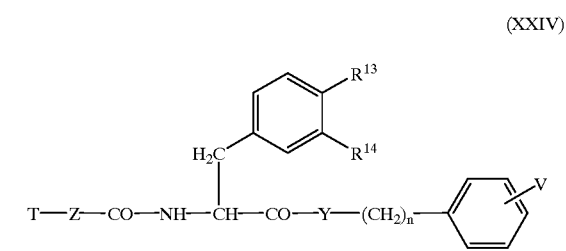

(XXIV)

wherein n, T, V, Y and Z are as hereinbefore defined, $R^{13}$ and $R^{14}$ independently of each other denote a nitro, nitroso or amino group, with the proviso that $R^{13}$ and $R^{14}$ cannot simultaneously represent amino groups.

The reduction of a compound of general formula XXIV is preferably carried out by catalytic hydrogenation in excess formic acid as solvent, possibly with the addition of other suitable solvents such as water or dimethylformamide, in the presence of noble metal catalysts, preferably palladium black, at temperatures between 15 and 100° C., preferably between 20 and 70° C., under a hydrogen pressure of 0.5 to 200 bar, preferably 1 to 5 bar.

o) In order to prepare compounds of general formula I wherein B denotes a 2-amino-1H-benzimidazol-5-yl or 2-amino-1H-benzimidazol-6-yl group:

Reacting diamines of general formula XXIII,

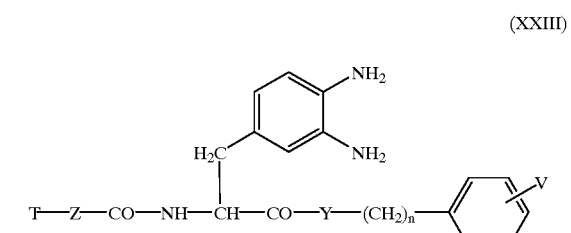

(XXIII)

wherein n, T, V, Y and Z are as hereinbefore defined, with chlorocyanogen, bromocyanogen, cyanamide or with alkylcyanates having 1 to 5 carbon atoms in the alkyl moiety.

The reaction is carried out at temperatures between 90 and 200° C., preferably between 100 and 180° C. The reaction with cyanamide is carried out in the presence of medium-strong to strong acids as catalysts, e.g. in the presence of hydrochloric acid, hydrobromic acid, phosphoric acid, sulphuric acid, methanesulphonic acid or p-toluenesulphonic acid; however, alternatively, the compounds of general formula I may also be introduced into the reaction with cyanamide in the form of their salts, e.g. in the form of hydrochlorides or p-toluenesulphonates. If bromo- or chlorocyanogen is used as the cyclocondensing electrophile, these reagents may also be produced in situ from alkali metal cyanides, e.g. sodium cyanide, and bromine or chlorine (see also the surveys in: R. Rastogi and S. Sharma, Synthesis 1983: 861–882; A. M. Simonov et al., Chem. Het. Comp. USSR 15: 705 (1979)). Methanol, water or mixtures thereof may be used as solvents, if necessary.

p) In order to prepare compounds of general formula I, wherein Z denotes an oxygen atom, an —NH— group or an ethylene group in which the methylene group bound to the carbonyl group is replaced by an oxygen atom or an —NH— group:
Reacting isocyanates of general formula XXV,

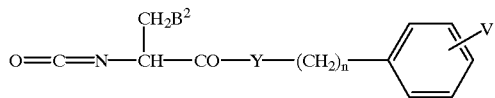

(XXV)

wherein n, V and Y are as hereinbefore defined and $B^2$ has the meanings given for B hereinbefore or denotes a group B substituted by the above-mentioned protecting groups, or a precursor group for the group B, e.g. a cyanophenyl or a cyanopropyl group, with compounds of general formula XXVI,

T—$Z^2$—H      (XXVI)

wherein

T is as hereinbefore defined and $Z^2$ denotes an oxygen atom, a —NH— group or a methyleneoxy group connected to the group T via the carbon atom, and, if necessary, subsequently cleaving any protecting groups or treating precursor functions using the methods described hereinbefore.

The reaction is carried out at temperatures between 0° C. and 150° C., preferably between 20° C. and 100° C., and optionally in the presence of an anhydrous solvents, e.g. tetrahydrofuran, 1,4-dioxane, dimethylformamide, dimethylacetamide, N-methyl-2-pyrrolidone or 1,3-dimethyl-2-imidazolidinone or mixtures thereof.

q) In order to prepare compounds of general formula I, wherein Z denotes an —NH— group or an ethylene group in which the methylene group connected to the carbonyl group is replaced by an —NH— group:
Reacting isocyanates of general formula XXVII,

T—$Z^3$—N=C=O      (XXVII)

wherein

T is as hereinbefore defined and $Z^3$ denotes a bond or a methylene group, with compounds of general formula V,

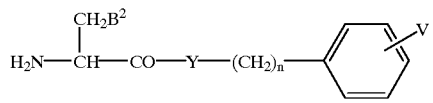

(V)

wherein n, V and Y are as hereinbefore defined and $B^2$ has the meanings given for B hereinbefore or denotes a group B substituted by the above-mentioned protecting groups or denotes a precursor group for the group B, e.g. a cyanophenyl or cyanopropyl group, and if necessary subsequent cleaving of protecting groups or modification of the precursor functions according to the processes described above.

The reaction is carried out at temperatures between 0 and 150° C., preferably at temperatures between 20 and 100° C., and optionally in the presence of anhydrous solvents, e.g. tetrahydrofuran, 1,4-dioxane, dimethylformamide, dimethylacetamide, N-methyl-2-pyrrolidone or 1,3-dimethyl-2-imidazolidinone.

r) In order to prepare compounds of general formula I, wherein V denotes a group —$(CH_2)_m$—$Y^1$—W—$Y^2$, wherein m and W are as hereinbefore defined, $Y^1$ denotes an oxygen atom or a group —$NR^2$—, wherein $R^2$ is a hydrogen atom or a straight-chain or branched $C_{1-6}$-alkyl group, and $Y^2$ denotes a straight-chain or branched $C_{1-10}$-alkyl group optionally substituted by a hydroxy, alkoxycarbonyl or aminocarbonyl group, a $C_{4-10}$-cycloalkyl group, a straight-chain or branched $C_{1-5}$-alkoxy group, an aminoalkyl, alkylaminoalkyl, dialkylaminoalkyl, phenylmethoxy or 2-phenylethoxy group, a phenyl or phenylalkyl group having 1 to 3 carbon atoms in the alkyl moiety and optionally mono-, di- or trisubstituted in the phenyl moiety by fluorine, chlorine or bromine atoms or by methyl, trifluoromethyl, cyano, amino, hydroxy, methoxy, acetyl, acetylamino, aminocarbonyl, methylaminocarbonyl or dimethylaminocarbonyl groups or an —$NR^3R^4$— group wherein $R^3$ denotes a hydrogen atom, a straight-chain or branched $C_{1-6}$alkyl group optionally substituted by a hydroxy, carboxy, alkoxycarbonyl or dialkylamino group, with the proviso that the hydroxy group is not bound in the 1-position of the alkyl group, a $C_{4-8}$-cycloalkyl group or a phenyl, phenylmethyl, 2-phenylethyl or 3-phenylpropyl group optionally mono-, di- or trisubstituted in the phenyl moiety by fluorine, chlorine or bromine atoms or by methyl, trifluoromethyl, hydroxy, methoxy, amino, acetylamino, aminocarbonyl, methylaminocarbonyl, dimethylaminocarbonyl or cyano groups, wherein the substituents may be identical or different, or $R^3$ denotes an alkanoyl, benzoyl, phenylalkanoyl, alkoxycarbonyl or aminocarbonyl group and $R^4$ has the meanings given for $R^3$ with the exception of phenyl, alkanoyl, benzoyl, phenylalkanoyl, alkoxycarbonyl and aminocarbonyl groups or W—$Y^2$ together may also represent a 5-amino-1H-1,2,4-triazol-3-yl-, or 1H-2-imidazolyl group:

Modifying compounds of general formula XXVIII,

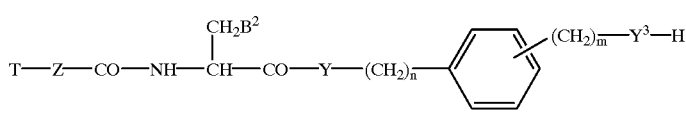

(XXVIII)

wherein n, m, T, Y and Z are as hereinbefore defined, $B^2$ has the meanings given for B hereinbefore or represents a group B substituted by the above-mentioned protecting groups, or a precursor group for the group B, e.g. a cyanophenyl or a cyanopropyl group, and $Y^3$ denotes an oxygen atom or a —$NR^2$— group, wherein $R^2$ denotes a hydrogen atom or a straight-chain or branched $C_{1-6}$-alkyl group, at the ($Y^3$—H) function and, if necessary, subsequently cleaving any protecting groups or modifying precursor functions and/or further modifying the primary group V obtained.

The modification at the ($Y^3$—H) function may be carried out, irrespective of the reagent used, either without a solvent or in a suitable solvent, e.g. in water, alcohols such as methanol, ethanol or propanol, in N-methylpyrrolidinone, dimethylformamide or dimethylacetamide or mixtures thereof, optionally in the presence of inorganic acids, e.g. hydrochloric acid or sulphuric acid, organic or inorganic bases such as triethylamine, Hunig-Base or sodium carbonate, and optionally with subsequent treatment with ammonia, with inorganic acids such as hydrochloric acid or sulphuric acid or with organic acids such as trifluoroacetic acid at temperatures between 0 and 150° C., preferably between 20 and 100° C..

Preferably, by reacting compounds of general formula XXVIII, wherein $Y^3$ is an —$NR^2$— group and $R^2$ denotes a hydrogen atom or a straight-chain or branched $C_{1-6}$-alkyl group, with alkali metal cyanates, e.g. sodium cyanate, in the presence of inorganic acids, e.g. hydrochloric acid, compounds of general formula I are obtained wherein V denotes the group —$(CH_2)_m$—$NR^2$—CO—$NH_2$, in which m is as hereinbefore defined and $R^2$ denotes a hydrogen atom or a straight-chain or branched $C_{1-6}$-alkyl group (see also: Org. Synth., Coll. Vol. IV, p. 515), by reacting with acetic acid anhydride in alcohols, e.g. in ethanol, compounds of general formula I are obtained wherein V denotes the group —$(CH_2)_m$—$NR^2$—CO—$CH_3$, where m is as hereinbefore defined and $R^2$ denotes a hydrogen atom or a straight-chain or branched $C_{1-6}$-alkyl group, by reacting with ethylchlorocarbonate in the presence of triethylamine, compounds of general formula I are obtained wherein V denotes the group —$(CH_2)_m$—$NR^2$—CO—$OC_2H_5$, where m is as hereinbefore defined and $R^2$ denotes a hydrogen atom or a straight-chain or branched $C_{1-6}$-alkyl group, by reacting with N-(tert.butyl)-chlorosulphonic acid amide, compounds of general formula I are obtained wherein V denotes the group —$(CH_2)_m$—$NR^2$—$SO_2$—NH—$C(CH_3)_3$ and by subsequent treatment with trifluoroacetic acid compounds of general formula I are obtained wherein V denotes the group —$(CH_2)_m$—$NR^2$—$SO_2$—$NH_2$, wherein m is as hereinbefore defined and $R^2$ denotes a hydrogen atom or a straight-chain or branched $C_{1-6}$-alkyl group, whilst it should be noted that any Pmc protecting group present in the group $B^2$ will also be removed, by reacting with benzoylchloride, compounds of general formula I are obtained wherein V denotes the group —$(CH_2)_m$—$NR^2$—CO—$C_6H_5$, wherein m is as hereinbefore defined and $R^2$ denotes a hydrogen atom or a straight-chain or branched $C_{1-6}$-alkyl group, by reacting with methylisocyanate compounds of general formula I are obtained wherein V denotes the group —$(CH_2)_m$—$NR^2$—CO—NH—$CH_3$, where m is as hereinbefore defined and $R^2$ denotes a hydrogen atom or a straight-chain or branched $C_{1-6}$-alkyl group, by reacting with dimethylcarbamoylchloride, compounds of general formula I are obtained, wherein V denotes the group —$(CH_2)_m$—$NR^2$—CO—$N(CH_3)_2$, where m is as hereinbefore defined and $R^2$ denotes a hydrogen atom or a straight-chain or branched $C_{1-6}$-alkyl group, by reacting with diphenylcyanocarbonimidate and subsequently with ammonia, compounds of general formula I are obtained wherein V denotes the group —$(CH_2)_m$—$NR^2$—C(=N—CN)—$NH_2$ and by subsequent treatment with dilute aqueous trifluoroacetic acid, compounds of general formula I are obtained wherein V denotes the group —$(CH_2)_m$—$NR^2$—C(=N—CO—$NH_2$)—$NH_2$, wherein m is as hereinbefore defined and $R^2$ denotes a hydrogen atom or a straight-chained or branched $C_{1-6}$-alkyl group (see also: R. L. Webb et al., J. Het. Chem. 24: 275 (1985), J. Rivier et al., J. Med. Chem. 34: 2395 (1991), J. Hirschfeld et al., J. Med. Chem. 35: 2231–2238 (1992), J. Rivier et al., J. Am. Chem. Soc. 112: 9624–9626 (1990)), by reacting with diphenylcyanocarbonimidate and subsequently with hydrazine, compounds of general formula I are obtained wherein V denotes the group —$(CH_2)_m$—$NR^2$—W—$Y^2$, where m is as hereinbefore defined and $R^2$ denotes a hydrogen atom or a straight-chain or branched $C_{1-6}$-alkyl group and W—$Y^2$ together denote 5-amino-1H-1,2,4-triazol-3-yl, by reacting with nitrobiuret, compounds of general formula I are obtained wherein V denotes the group —$(CH_2)_m$—$NR^2$—CO—NH—CO—$NH_2$ wherein m is as hereinbefore defined and $R^2$ denotes hydrogen atom or a straight-chain or branched $C_{1-6}$-alkyl group (see also: T. L. Davis et al., J. Am. Chem. Soc. 51: 1801–1806 (1929)), by reacting with N-(2,2-diethoxyethyl)-S-methyl-thiuronium salts and subsequently cyclising by reacting with aqueous inorganic acid, compounds of general formula I are obtained wherein V denotes the group —$(CH_2)_m$—$NR^2$—W—$Y^2$, wherein m is as hereinbefore defined and $R^2$ denotes a hydrogen atom or a straight-chain or branched $C_{1-6}$-alkyl group and W—$Y^2$ together denote a 1H-2-imidazolyl group (see also: B. T. Storey et al., J. Org. Chem. 29, 3118–3120 (1964)), and by reacting compounds of general formula XXVIII wherein $Y^3$ denotes an oxygen atom with phenylchlorocarbonate, with subsequent aminolysis, compounds of general formula I are obtained wherein V denotes the group —$(CH_2)_m$—O—CO—$NH_2$, wherein m is as hereinbefore defined (see also: G. R. Allen, Jr., J. F. Poletto and M. J. Weiss, J. Org. Chem. 30, 2897–2904 (1965)).

The amino acid derivatives of general formula I according to the invention contain at least one chiral centre. If in addition the group T is chiral, the compounds may occur in the form of two diastereomeric pairs of antipodes. The invention includes the individual isomers as well as the mixtures thereof.

The diastereomers may be separated on the basis of their different physico-chemical properties, e.g. by fractional crystallisation from suitable solvents, by high-pressure liquid or column chromatography using chiral or preferably achiral stationary phases.

Racemates falling into general formula I may be separated, for example, by HPLC on suitable chiral stationary phases (e.g. Chiral AGP, Chiralpak AD). Racemates which contain a basic function can be separated by means of the diastereomeric, optically active salts which are formed on reaction with an optically active acid such as (+)- or (−)-tartaric acid, (+)- or (−)-diacetyltartaric acid, (+)- or (−)-mono-methyltartrate or (+)-camphorsulphonic acid.

According to a conventional method of isomer separation, the racemate of a compound of general formula I is reacted with one of the above-mentioned optically active acids in an equimolar amount in a solvent and the crystalline, diastereomeric, optically active salts obtained are separated making use of their different solubilities. This reaction may be carried out in any kind of solvent provided that it exhibits a sufficient difference between the solubilities of the salts. Preferably, methanol, ethanol or mixtures thereof, e.g. in a ratio by volume of 50:50, are used. Then, each of the optically active salts is dissolved in water, neutralised with a base such as sodium carbonate or potassium carbonate, sodium hydroxide solution or potassium hydroxide solution and in this way the corresponding free compound is obtained in the (+)- or (−)-form.

Only the (R)-enantiomer or a mixture of two optically active diastereomeric compounds falling under general formula I is obtained if the methods of synthesis described above are carried out with a reaction component which contains the corresponding amino acid in the (R)-configuration.

The starting materials of general formulae III, IV, VI, VII, VIII, IX, X, XI, XII, XIII, XVI, XVII, XVIII, XXI, XXII, XXIII, XXIV, XXVI, XXVII required for synthesising the compounds of general formula I as well as the amino acids used are commercially available or are prepared by methods known from the literature. The acids II may be obtained, for example, under the conditions of Schotten-Baumann reaction from the corresponding α-amino acids and compounds of general formula II (see also: M. Bodanszky and A. Bodanszky, "The Practice of Peptide Synthesis" Springer Verlag 1984, p. 9 to 30).

The following procedure may be used, for example, in order to prepare the 4-[2-(aminocarbonyl)ethyl] phenylmethanamine of general formula III:

4-Cyanocinnamic is catalytically hydrogenated to form 4-(aminomethyl)-benzenepropanoic acid, the amino function is then protected by a tert.butoxycarbonyl group and the carboxylic acid function is converted into the primary carboxamide; the resulting 4-[[(2,2-dimethyl-1-oxopropyl) amino]methyl]benzenepropanamide when reacted with I,I-bis-(trifluoroacetoxy)iodobenzene, yields 4-[[(2,2-dimethyl-1-oxopropyl)amino]methyl]benzeneethanamine (see also: A. S. Radhakrishna, M. E. Parham, R. M. Riggs and G. M. Loudon, J. Org. Chem. 44: 1746–1747 (1979) and K. Seraminathan and N. Venkatasubramanian, J. Chem. Soc. Perkim Trans. II 1975, 1161), which may be converted into the corresponding urea in the usual way, e.g. by treating the hydrochloride with sodium cyanate; cleaving the tert.butoxycarbonyl group with suitable acids, e.g. trifluoroacetic acid, finally yields the desired 4-[2-(aminocarbonylamino) ethyl]phenylmethanamine.

The [2-(aminocarbonyl)-2,3-dihydro-1H-isoindol-5-yl] methanamine of general formula III may be prepared as follows, for example: The methyl 3,4-bis-(bromomethyl) benzoate obtainable in situ from methyl 3,4-dimethylbenzoate by photobromination, on being reacted with benzylamine, yields methyl 2,3-dihydro-2-(phenylmethyl)-1H-isoindol-5-carboxylate, the ester function of which is converted in the usual way into a carboxamide function and then, by reduction with lithium aluminium hydride, into an aminomethyl function; the primary amino group is protected with a tert.butoxycarbonyl group, the benzyl group in the 2-position is removed by hydrogenolysis and replaced by an aminocarbonyl group, e.g. by treating the hydrochloride of the resulting 5-[[(tert.butoxycarbonyl) amino]methyl]-2,3-dihydro-1H-isoindole with sodium cyanate; removal of the tert.butoxycarbonyl protecting group, e.g. with methanolic hydrogen chloride solution, then yields the desired 2-(amino-carbonyl)-2,3-dihydro-1H-isoindol-5-yl]methanamine in the form of the hydrochloride.

The 4-[(2-oxo-1-imidazolidinyl)methyl]benzenemethanamine which also comes under general formula III may be synthesised as follows, for example:

The 4-cyanobenzenemethanamine obtainable by modified Gabriel synthesis, when reacted with chloroethylisocyanate, yields 1-[(4-cyanophenyl)methyl]-3-(2-chloroethyl)urea which when treated with potassium tert.butoxide in dimethylformamide is easily cyclised into the 1-[(4-cyanophenyl) methyl]-2-imidazo-lidinone; catalytic hydrogenation then leads to the desired 4-[(2-oxo-1-imidazolidinyl)methyl] benzenemethanamine.

In order to synthesise the 4-[(3-methyl-1,2,4-oxadiazol-5-yl)methyl]benzenemethanamine which comes under general formula III, methyl 4-cyanobenzenepropanoate may for example be converted in the usual way into the methyl 4-[[(2,2-dimethyl-1-oxopropyl)amino]methyl]benzenepropanoate, which when reacted with acetamidoxime in the presence of sodium hydride is cyclised to form the 5-[[4-[[tert.butoxycarbonyl)amino]methyl]phenyl]methyl]-3-methyl-1,2,4-oxadiazole; subsequent cleaving of the protecting group with methanolic hydrogen chloride solution, for example, yields the desired 4-[(3-methyl-1,2,4-oxadiazol-5-yl)methyl]benzenemethanamine in the form of the hydrochloride.

The 4-[[(6-methyl-4(3H)-oxopyrimidin-2-yl)amino] methyl]-benzenemethanamine coming under general formula III may be obtained for example by reacting 4-cyanobenzenemethanamine with 6-methyl-2-methylthiopyrimidin-4(3H)-one and subsequent catalytic hydrogenation of the reaction product obtained; in the same way, 4-[[(5-methyl-4(3H)-oxopyrimidin-2-yl)amino]-methyl] benzenemethanamine can also be obtained.

Isocyanates of general formula XXV can easily be prepared from α-amino acid derivatives of general formula V, wherein $R^1$ denotes the hydrogen atom and the other groups are as herein-before defined, or from the hydrochlorides thereof by reacting with phosgene, diphosgene or triphosgene in the presence of pyridine (see also: J. S. Nowick, N. A. Powell, T. M. Nguyen and G. Noronha, J. Org. Chem. 57: 7364–7366 [1992]).

The starting compounds of general formula V in turn may be obtained from amino acids suitably protected at the α-amino group as described above and compounds of general formula III analogously to method b). The uronium salts of general formula XX required as starting compounds are most easily obtained by the addition of alcohols $R^{12}$-OH to the corresponding cyanamides, for example using potassium cyanide (see also: A. Donetti et al., Tetrah. Lett. 1969:

3327–3328; A. Donetti et al., J. Org. Chem. 37: 3352–3353 (1972); M. Okahara et al., Tetrah. Lett. 1981: 4105–4106) or sodium methoxide (see also: F. C. Schaefer et al., J. Org. Chem. 26: 412–418 (1961); R. M. Giuliano et al., J. Org. Chem. 51: 2304–2307 (1986); F.H.S. Hurd et al., J. Chem Soc. 1949: 1732–1738)) as catalysts. The starting compounds of general formula XXVIII may easily be obtained from precursors which, instead of having the terminal group -$(CH_2)_m$-$Y^3$-H of general formula XXVIII, have an end group -$(CH_2)_m$-$Y^3$-Pg, characterised by readily removable protecting groups Pg, such as tert.butoxycarbonyl or phenylmeth-oxycarbonyl, or precursor groups, such as -$(CH_2)_{m-1}$-C N or - $(CH_2)_m NO_2$.

The compounds of general formula I obtained may be converted into the physiologically acceptable salts thereof with in-organic or organic acids, particularly for pharmaceutical use.

Suitable acids for this purpose include, for example, hydrochloric acid, hydrobromic acid, phosphoric acid, nitric acid, sulphuric acid, methanesulphonic acid, p-toluenesulphonic acid, acetic acid, fumaric acid, succinic acid, lactic acid, mandelic acid, malic acid, citric acid, tartaric acid or maleic acid.

Moreover, the new compounds of formula I thus obtained, if they contain a carboxy group, may if desired subsequently be converted into the addition salts thereof with inorganic or organic bases, particularly for pharmaceutical use into the physiologically acceptable addition salts thereof. Suitable bases include, for example, sodium hydroxide, potassium hydroxide, ammonia, cyclohexylamine, dicyclohexylamine, ethanolamine, diethanolamine and triethanolamine.

Neuropeptide Y (NPY) is known as a powerful stimulant of feeding behavior acting through at least 6 pharmacologically defined receptor subtypes to elicit a wide variety of physiological functions.

WO 97/19682, WO 97/20820, WO 97/20821, WO 97/20822 and WO 97/20823 disclose methods of modifying feeding behavior, including increasing or decreasing food consumption, e.g. in connection with treating obesity, appetite disorders, bulimia or anorexia. These methods involve administration of selective antagonists to the Y5 receptor, based on the hypothesis that stimulation of feeding behavior occurs primarily through activation of the NPY-Y5 receptor subtype, considering this receptor subtype to be the putative "feeding" receptor.

Applicants have found that the new compounds of general formula I and the physiologically acceptable salts thereof have NPY antagonist properties and exhibit good affinities in NPY-receptor binding studies, especially binding highly selectively and with high affinity to the NPY-Y1 receptor subtype. Since the new compounds inhibit significantly food intake in rats the applicants are convinced that the NPY-Y1receptor is the relevant "feeding" receptor.

The new compounds exhibit NPY-antagonist properties both in vivo and in vitro in the pharmacological test systems described hereinafter.

In order to demonstrate the affinity of compounds of general formula I for human NPY-receptors and their antagonist properties, the following experiments were carried out:

A. Studies of binding with SK-N-MC cells
(expressing the human $Y_1$-receptor)

The cells are detached using a mixture of 0.02% EDTA in PBS and resuspended in 10 ml of incubation medium (MEM/25 mM Hepes +0.5% BSA, 50 µM PMSF, 0.1% bacitracin, 3.75 mM $CaCl_2$) per 40 million cells approx. After 5 minutes' centrifuging (150×g) the pellet is resuspended in the same volume and, after a further washing step in 10 ml of incubation medium, counted and diluted to 1.25 million cells/ml. Then 200 µl of a suspension of 1.25 million cells/ml is incubated for 3 hours at ambient temperature with 25 µl of a 300 pM solution of [$^{125}$I]-Bolton-Hunter-NPY and increasing concentrations ($10^{-11}$ to $10^{-6}$ M) of the test substances, whilst maintaining a total volume of 250 µl. Incubation is ended by centrifuging (10 minutes at 3000×g and 40°C.). After washing once with PBS, the radioactivity of the pellet is measured in a gamma counter. The radioactivity thus obtained represents the sum of specific and non-specific binding of [$^{125}$I]-Bolton-Hunter-NPY. The proportion of non-specific binding is defined as that radioactivity which is bound in the presence of 1 µM NPY. The $IC_{50}$ values of the unlabelled test substances are determined graphically. They represent the concentration of the test substance in question at which the specific binding of [$^{125}$I]-Bolton-Hunter-NPY to the NPY-$Y_1$ receptor is inhibited by 50%.

A=(R)-N-[[4-(Aminocarbonylaminomethyl)phenyl]methyl]-$N^2$-bis(4-hydroxyphenyl)acetyl]-argininamide-trifluoracetate B=(R)-N-[[4-(Aminocarbonylaminomethyl)phenyl]methyl]-$N^2$-[bis(4-chlorphenyl)acetyl]-argininamide-trifluoracetate C=(R)-N-[[4-Aminocarbonylaminomethyl)phenyl]methyl]-$N^2$-(diphenylacetyl)-argininamide-trifluoracetate D=(R)-$N^2$-(Diphenylacetyl)-N-[[4-(ethoxycarbonylmethylamino- carbonylaminomethyl)phenyl]methyl]-argininamide-trifluor-acetate E=(R,S)-$N^5$-(Aminoiminomethyl)-$N^2$-(diphenylacetyl)-N-[(4-hydroxyphenyl)methyl]-$N^5$-methyl-ornithinamide-hydrochloride F=(R)-N-[[4-(Aminocarbonylmethyl)phenyl]methyl]-$N^2$-(diphenyl-acetyl)-argininamide-diacetate G=(R)-$N^2$-(Diphenylacetyl)-N-[[4-(ethylaminocarbonylamino- methyl)-phenyl]methyl]-argininamide-bis-(trifluoracetate)

H=(R)-$N^2$-(Diphenylacetyl)-N-[[4-(ethoxycarbonylamino-carbonylaminomethyl)phenyl]methyl]-argininamide-trifluor-acetate I=(R)-N-[[4-(Dimethylaminocarbonylaminomethyl)phenyl]methyl]-$N^2$-(diphenylacetyl)-argininamide-bis-(trifluor-acetate)

K=(R)-N-[[4-(Aminocarbonylaminomethyl)phenyl]methyl]-$N^2$-[(3,4-dichlorphenyl)amino]carbonyl]-argininamide-tri-fluoracetate L=(R)-N-[[4-(Aminocarbonylaminomethyl)phenyl]methyl]-$N^2$-[α-(4-hydroxyphenyl)-α-[4-methoxycarbonylmethoxy)-phenyl]-acetyl]-argininamide-acetate M=(R)-$N^2$-(Diphenylacetyl)-arginine-[4-(aminocarbonylamino-methyl)phenyl]methylester-trifluoracetate N=(R)-N-[[4-(Aminocarbonylaminomethyl)phenyl]methyl]-$N^2$-(6-methoxy-2-naphthoyl)-argininamide-acetate O=(R)-N-[[4-(Aminocarbonylaminomethyl)phenyl]methyl]-$N^2$-(3,3-diphenyl-1-oxopropyl)-argininamide P=(R)-N-[[4-(Aminocarbonylaminomethyl)phenyl]methyl]-$N^2$-(diphenylacetyl)-N-methyl-argininamide-acetate Q=(R)-$N^2$-(Diphenylacetyl)-N-[[4-(ethoxycarbonylamino-methyl)phenyl]methyl]-argininamide-trifluoracetate R=(R)-N-[[4-(Aminocarbonylaminomethyl)phenyl]methyl]-N²-[(4-amino-3,5-dichlorphenyl)acetyl]-argininamide-tri-fluoracetate S=(R)-N-[[4-(Aminocarbonylmethyl)phenyl]methyl]-N²-(diphenylacetyl)-N⁵-(1H-imidazol-2-yl)-ornithinamide-hydroiodide The obtained values are shown in table 1:

TABLE 1

| Substance | IC$_{50}$ [nM] |
| --- | --- |
| A | 0.17 |
| B | 0.35 |
| C | 0.37 |
| D | 0.4 |
| E | 0.62 |
| F | 0.63 |
| G | 0.75 |
| H | 1.1 |
| I | 1.5 |
| K | 1.8 |
| L | 2.2 |
| M | 3.0 |
| N | 3.4 |
| O | 3.45 |
| P | 3.5 |
| Q | 4.25 |
| R | 4.5 |
| S | 28.3 |

B. Subtype and species selectivities of NPY receptor antagonists

Receptor binding studies have been performed with compound C as described below using the following cells and tissues endoge- nously expressing Y1 and Y2 receptors:

SK-N-MC (neuroblastoma) cells: Cells were grown and receptor binding assay performed as described hereinbefore under A and by Wieland et al. in Peptides 16, 1389–1394 (1995).

SMS-KAN (neuroblastoma) cells: Cells were grown and receptor binding assay performed analogously as described hereinbefore under A and by Wieland et al. in Peptides 16, 1389–1394 (1995).

BHK cells stably expressing the human Y1 receptor: Cells were grown in DMEM with 4.5 g/l glucose, 10% FCS, 1% PENStrep, 1 mg/ml G-418, 1 mg/ml hygromycin B. 96h before receptor binding assay 1mM IPTG was added in order to induce expression. Confluent cells were removed with 0.06% EDTA/PBS (1 min incubation) and resuspended in 15 ml incubation buffer (MEM/25 mM HEPES +1% BSA, 50 mM PMSF, 0.1% bacitracin, 3.75 mM CaCl$_2$). After 10 min centrifugation at RT (150×g), the pellet was resuspended in 50 ml incubation buffer, respun and resuspended in 30 ml incubation buffer. After counting, the cells were diluted to a final concentration of 2.5×10⁵ cells/ml. Two hundred microliters of this cell suspension was incubated 3 h at RT with 30 pM [$^{125}$I]NPY and increasing concentrations of test compounds in a total volume of 250 ml. The incubation was stopped by 10 min centrifugation, 3000×g at 4° C. The pellet was resuspended with 0.25 ml PBS recentrifuged and the pellet measured in a γ-counter.

HEK 293 cells expressing the rat Y1 receptor: Confluent cells (2) were removed with 0.02% EDTA / PBS and resuspended in 10 ml incubation buffer (MEM/25 mM Hepes+0.5% BSA, 50 μM PMSF, 0.1% bacitracin, 3.75 mM CaCl$_2$). After 5 min centrifugation (150×g) the pellet was resuspended in equal volume and after further centrifugation in 10 ml incubation buffer. After counting the cells were diluted to give a concentration of 1×10⁶ cells/ml. 100 μl of this cell suspension was incubated 3 hrs at RT with 30 pM [$^{125}$I]BH-NPY solutions and increasing concentrations of test compounds in a total volume of 250 μl. The incubation was stopped by centrifugation (5 min, 1500×g), the pellet washed with 0.25 ml of incubation buffer without resuspension, recentrifuged and membrane-bound radioactivity was counted. Non-specific binding was determined in presence of 100 nM NPY.

BHK cells stably expressing the human Y2 receptor: Assay was performed essentially as described for human Y1 expressing BHK cells.

BHK cells stably transfected with rat Y4 receptor: Cultivation and receptor binding was performed as described for hY1/BHK with exception of incubation medium (25 mM HEPES, 2.5 mM CaCl$_2$, 1.0 mM MgCl$_2$, pH 7.4) and final concentration of cell suspension 5×10⁵ cells/ml. 24 h before receptor binding assay 1.0 mM IPTG was added for induction of expression. Incubation time for binding assay: 2 h.

HEK 293 cells stably transfected with human Y5 receptor:

Centrifugated cells were cultivated as described for BHK/Y1 cells except that a concentration of 0.7 mg/ml G-418 was used, no hygromycin added and no IPTG induction was necessary. The incubation buffer, cell cultivation and receptor binding was performed as described. Final concentration was 1.5×10⁶ cells/ml and centrifugation stopped as described for Y1/BHK cells.

CHO cells transiently transfected with human Y4 and rat Y5 receptor: Transfection was performed using the lipofectamine method according to the manufacturer's protocol (GIBCO BRL Eggenstein, Germany) using expression plasmids encoding the rat Y5 or human Y4 receptor, respectively. Receptor binding was performed as described for rat Y1 expressing HEK 293 cells.

The results obtained are shown in table 2:

IC$_{50}$ values are given as means ±S.E.M. of the data obtained from 3 to 5 different experiments.

TABLE 2

| Receptor | Affinity IC$_{50}$ [nM] |
| --- | --- |
| humanY1/SK-N-MC | 0.38 ± 0.06 |
| rat Y1/293 | 0.72 ± 0.42 |
| humanY2/SMS-KAN | >10,000 |
| humanY2/BHK | >1,000 |
| humanY4/CHO | 12,300 ± 5,000 |
| ratY4/BHK | >10,000 |
| humanY5/293 | >10,000 |
| ratY5/CHO | 21,000 ± 4,500 |

C. Antagonism of NPY mediated Ca$^{2+}$ release and of NPY mediated inhibition of cAMP synthesis Ca$^{2+}$ mobilization: SK-N-MC cells were harvested from culture plates by gently scraping with a "rubber policeman" in Ca$^{2+}$/Mg$^{2+}$free phosphate buffered saline (PBS, pH 7.4). The cells were resuspended in loading buffer (phosphate buffer saline, 1mg/ml glucose, 0.1% BSA), adjusted to 3×10⁶ cells/ml and incubated with 1 mM Fura-2-acetoxymethylester (FURA-2/AM, SERVA, Heidelberg, Germany) for 60 min with shaking in the dark at RT. The cells were washed by centrifugation for 5 min at 150 ×g, resuspended in the same volume of PBS supplemented with 1 mg/ml glucose and allowed to recover by incubation at room temperature for 1 h. The cells were washed again by centrifugation and adjusted to 1×10⁶ cells/ml. The cells were incubated with NPY (1 nM - 1 mM) with or without prior incubation (30 s) of the antagonist. Fluorescence readings were performed on a Perkin Elmer spectrometer (LS50B) at 340/380 nm excitation and 510 emission over 2.5 min with a slit width of 7.5 nm. Calculation of cytoplasmic $Ca^{2+}$ concentration was performed according to Grynkiewicz et al., 1985 (3).

cAMP assay: SK-N-MC cells have been washed twice with 20 ml cAMP buffer (145 mM NaCl, 5mM KCl, 1mM MgSO4, 10mM Hepes pH 7.4, supplemented with 0.5% BSA, 10 mM glucose, 37° C). Cells were removed by a rubber policeman and resuspended in 50 ml cAMP buffer (37° C.), after 5 min at 150×g, the pellet is washed again and resuspended in 10 ml cell medium (37° C.) and the cell suspension is diluted to a final concentration of 1 million cells/ml. 1 ml of the cell suspension were pre-incubated 5 min at room temperature with 100 μM (final concentration) papaverine and buffer or different concentrations of the antagonist. 10 μl NPY solution of different concentrations and 10 μl Forskolin (1.5 mM) were added and incubated 1 h at 37° C. by shaking. The incubation was stopped by addition of 0.1 ml of 1M HCl (15 min incubation) and centrifugation at 4°C., 15 min, 2000×g. The supernatant was diluted with 0.05 M acetate buffer of the cAMP Kit (Amersham, RPA 509) and assayed. The sample (100 μl) was incubated with 100 μl [$^{125}$I]-cAMP, 100 μl anti-cAMP antiserum 3 h, 4° C., by shaking. The second antibody was added, the solution mixed and incubated 10 min at RT (shaking). After 10 min centrifugation at 3200×g at RT, the supernatant is removed and the pellet counted in a gamma-counter.

The results obtained are shown in table 3:

TABLE 3

|  | Antagonism of NPY mediated $Ca^{2+}$ release | Antagonism of NPY mediated inhibition of cAMP synthesis |
|---|---|---|
| Compound C | 8.9 ± 0.5 | 9.1 ± 0.4 |
| Compound E | 8.42 (n = 1) | 8.58 (n = 1) |

The compounds of the present invention antagonize the NPY induced intracellular calcium release in human Y1 receptor expressing SKN-MC cells. The compounds reduce the NPY induced inhibition of cAMP synthesis. The inhibition of the NPY mediated second messenger systems by the compounds of the present invention shows that the compounds are NPY Y1 receptor antagonists.

D. NPY-antagonism in vitro

Male rats (CHbb: THOM, 300 to 350 g) are given heparin (100 IU, i.v.) and the animals are then killed by a blow to the back of the neck. The abdomen is opened along the centre of the body and the left kidney is removed after the insertion of catheters in the renal artery, renal vein and ureter. The isolated kidney is immediately perfused with a modified Krebs-Ringer solution having the following composition (4 ml/minute):

| NaCl | 118.0 mmol/l |
|---|---|
| $KH_2PO_4$ | 1.2 mmol/l |
| KCl | 4.8 mmol/l |
| $HgSO_4$ | 1.2 mmol/l |
| $CaCl_2$ | 2.5 mmol/l |
| $NaHCO_3$ | 25.0 mmol/l |
| Glucose | 6.5 mmol/l |

A mixture of 95% $O_2$/5% $CO_2$ is passed through the solution which is kept at a temperature of 37° C. The perfusion pressure is measured continuously using a pressure gauge. After a 60 minute stabilisation period the perfusion rate is adjusted so as to obtain a perfusion pressure of approximately 100 mm Hg. After a further 30 minutes the experiment is started and NPY (1μM) is administered as a bolus (0.1 ml) at 15 minute intervals until the pressure increase observed reaches a constant value. The compounds to be tested are given in the form of a continuous infusion over a period of 5 minutes and then NPY is injected. After a 30 minute wash-out period the next highest concentration of test substance is investigated. 3 to 5 different concentrations of the particular compound are tested on each occasion. Concentration/activity curves can be obtained by plotting the percentage inhibition of the NPY activity against the logarithm of the concentration (mol/1) of the compound.

The obtained values are shown in table 4:

| Substance | $pIC_{50}$ (mol/l) |
|---|---|
| C | 8.12 |
| E | 8.41 |
| Q | 7.77 |

E. In vivo NPY-antagonism

Male rats of normal blood pressure (Chbb:THOM, 300 to 350 g) are anaesthetised with sodium hexobarbital (150 mg/kg, i.p.). After intubation of the trachea the animals are pithed by introducing a blunt needle through the eye into the spinal bone marrow channel. The animals are ventilated with oxygen-rich ambient air using a respiratory pump (20 strokes/minute). A cannula is inserted in the left carotid artery and the arterial blood pressure is measured using a pressure gauge (Braun Melsungen Combitrans) connected to a recording device. For injection purposes a catheter is placed in the left jugular vein through which heparin is administered (200 IU/kg, i.v.). After the blood pressure has been stabilised, the animals are given 2 bolus injections of NPY (10 μg/kg, i.v.) at intervals of 15 minutes. The average increase in diastolic blood pressure is taken as the reference value (=100%). The test substances are injected in increasing doses (4 to 6 doses) at intervals of 15 minutes. One minute after administration of the test substance, NPY is administered.

The antagonistic effect of the test substances is determined by plotting the percentage inhibition of the NPY-induced blood pressure effects against the logarithm of the concentration of active substance.

The obtained values are shown in table 5:

| Substance | pIC$_{50}$ (mol/kg) |
|---|---|
| C | 8.11 |
| E | 7.87 |
| Q | 6.79 |

F. In vivo Studies in rats: Food intake in satiated rats

For these determinations food intake was measured in normal satiated rats after application of NPY to the paraventricular nucleus (PVN) in the presence or absence of the test compound. Male Chbb: Thom rats weighing between 300 and 350 g were used for all experiments. The rats were individually housed in stainless steel cages where water and food were available ad libitum.

Rats under Pentobarbital anaesthesia were stereotactically implanted with a stainless steel double guide cannula targeted bilaterally at the PVNs. Stereotactic coordinates were: −1.8mm caudal, 0.5mm lateral to bregma and 7.0 mm below the skull surface. Injection cannulae extended the guide cannulae by 1 mm. Animals were allowed to recover from surgery for at least 10 days before being used in the experiments. Rats were handled and mock-injected during the one-week recovery period to habituate them to the injection procedure.

Animals treated with both test compounds and NPY were treated first with the test compound. Then, 15 min. after PVN infusion of the test compound or vehicle (control) 1 μg of NPY was administered by PVN infusion.

Food intake was measured by placing preweighed pellets into the cages at the time of NPY injection. Pellets were removed from the cage at 2 h post NPY injection. The food intake of animals treated with test compound was calculated as a percentage of the food intake of control animals, i.e., animals treated with vehicle.

G. Food intake in food-deprived rats

Food-deprivation experiments were conducted with male Chbb:Thom rats weighing between 300 and 350 g. The animals were individually housed for the duration of the study and allowed free access to normal food together with tap water. Food was removed from the animals for 24 hours starting at 8:00 a.m. At the end of the fasting period compound or vehicle was administered to the animals by infusion into the PVN. Food was returned to the animals and their food intake monitored at various time periods during the following 24 hour period. The food intake of animals treated with test compound was calculated as a percentage of the food intake of control animals (i.e., animals treated with vehicle).

RESULTS

NPY (1 μg) elicited a robust feeding response in satiated rats. The injection of NPY was found to significantly induce two hour food intake, namely 3.5 g versus 0.5 g in animals injected with vehicle. The NPY induced food intake was reduced in animals treated with test compound, e.g. with (R)-N-[[4-Aminocarbonyl-phenyl]methyl]-N$^2$-(diphenylacetyl)-argininamidetate-trifluoracetate (compound C).

The obtained values are shown in Table 6.

TABLE 6

| | Food intake following NPY application (g/animal) | % Inhibition of food intake |
|---|---|---|
| Vehicle | 3.53 | — |
| 15 μg of compound C | 2.62 | 25.9 |
| 30 μg of compound C | 1.67 | 52.8 |
| 60 μg of compound C | 1.07 | 69.8 |
| 30 μg of compound A | 2.40 | 32 |

It is obvious from the results of Table 6 that the compounds of the present invention produce a dose-dependent inhibition of the NPY-induced food intake. In 24 hour food deprived rats compound C injection (15 μg, bilaterally) resulted in a significant reduction in food intake for at least 4 h.

These experiments indicate that the compounds of the present invention bind with high affinity and selectivity to the Y1 receptor and inhibit significantly food intake in rats.

In view of their pharmacological properties the compounds of general formula I and the physiologically acceptable salts thereof are thus suitable for the treatment of disorders or diseases associated with the inhibition of the Y1 receptor subtype, especially diseases caused by eating disorders such as obesity, bulimia nervosa, diabetes and dyslipidemia. Furthermore, the compounds of general formula I and the physiologically acceptable salts thereof are suitable for the treatment of any disease states in which the Y1 receptor subtype is involved, for example for the treatment of memory loss, migraine, sleep disorders, pain, cardiovascular diseases, e.g. for treating of arterial hypertension, hypertensive crisis, stress-induced high blood pressure caused e.g. by environmental influence, physical exercise or cold stress, chronic heart insufficiency, coronary heart disease such as Angina pectoris, myocardial infarct and Syndrome X, and also for treating subarachnoidal bleeding, vascular-hypertrophic changes, e.g. restenosis after coronary angioplasty (PCTA), cerebral and coronary vasospasms, e.g. stroke, chronic kidney failure, hyperthyroidism, epileptic diseases as well as for the diagnosis, estimation of prognosis and treatment of tumor diseases such as phaeochromocytoma, neuro(fibro)-blastoma, ganglioneuroma, ganglioneuroblastoma, rhabdomyosarcoma, malignant ectomesenchymoma, anablastic astrocytoma or haemangioblastoma.

The dosage required to achieve these effects is appropriately 0.01 to 3 mg/kg of body weight, preferably 0.1 to 1 mg/kg of body weight for intravenous administration, and 0.1 to 10 mg/kg of body weight, preferably 1 to 10 mg/kg of body weight, for oral administration, in each case 1 to 3×a day.

For this purpose, the compounds of general formula I prepared according to the invention, optionally combined with other active substances such as hypotensive agents, ACE-inhibitors, diuretics and/or calcium antagonists, together with one or more inert conventional carriers and/or diluents, such as corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, cetylstearylalcohol, carboxymethylcellulose or fatty substances such as hard fat or suitable mixtures thereof, may be made into conventional galenic preparations such as plain or coated tablets, capsules, powders, suspensions or suppositories.

For the above-mentioned combinations, the other active substances may be, for example, bendroflumethiazide, chlorothiazide, hydrochlorothiazide, spironolactone, benzothiazide, cyclothiazide, ethacrinic acid, furosemide, metoprolol, prazosine, atenolol, propranolol, (di) hydralazine-hydrochloride, diltiazem, felodipine, nicardipine, nifedipine, nisoldipine, nitrendipine, captopril, enalapril, lisinopril, cilazapril, quinapril, fosinopril and ramipril. The dosage of these active substances is preferably ⅕ of the minimum dosage normally recommended up to ¹⁄₁ of the normal recommended dosage, eg. 15 to 200 mg of hydrochlorothiazide, 125 to 2000 mg of chlorothiazide, 15 to 200 mg of ethacrinic acid, 5 to 80 mg of furosemide, 20 to 480 mg of propranolol, 5 to 60 mg of felo- dipine, 5 to 60 mg of nifedipine or 5 to 60 mg of nitrendipine.

The invention further relates to the use of the compounds of general formula I as valuable excipients for the production and purification (by affinity chromatography) of antibodies and, after suitable radioactive labelling, for example by direct labelling with $^{125}$I or $^{131}$I or by tritiation of suitable precursors, for example by the replacement of halogen atoms with tritium, in RIA and ELISA assays and as a diagnostic or analytical aid in neutrotransmitter research.

The Examples which follow are intended to illustrate the invention:

PRELIMINARY REMARKS

"Mp." denotes "melting point", "D." denotes "decomposition". Satisfactory elementary analyses, IR-, UV-, $^1$H-NMR- and usually mass spectra have been obtained for all the compounds. Unless otherwise stated, $R_F$ values have been determined using ready-prepared silica gel 60 $F_{254}$ TLC plates (E. Merck, Darmstadt, Item No. 5729) and an eluant consisting of n-butanol/glacial acetic acid/water=4/1/1 (v/v/v), without chamber saturation. If there are no detailed data on the configuration, it is not specified whether it is the (R)-enantiomer or whether partial or even total racemisation has occurred.

EXAMPLE 1

(R)-N-[[4-Acetylaminomethyl)phenyl]methyl]-N$^2$-(diphenylacetyl)argininamide-trifluoroacetate a) (R)-N$^2$-(9-Fluorenylmethoxycarbonyl)-N$^G$-(2,2,5,7,8-pentamethylchroman-6-sulphonyl)-N-[[4-[[(phenylmethoxycarbonyl)-amino]methyl]phenyl]methyl]-argininamide To a solution of 15.0 g (20.14 mMol) Fmoc-D-Arg(Pmc)-OH (89 percent) in 250 ml of anhydrous tetrahydrofuran were added, under the protection of inert gas, at ambient temperature and with stirring, one after the other, 4.33 g (20.99 mMol) of dicyclohexylcarbodiimide, 2.83 g (20.94 mMol) of HOBT and 5.68 g (21.01 mMol) of 4-[[(phenylmethoxycarbonyl)amino]-methyl] benzenemethanamide (R. Epton et al., Polymer 21: 481–482 (1980)), the mixture was stirred for a further hour at ambient temperature then for 1 hour at 60° C. and finally overnight at ambient temperature. The insoluble matter was filtered off, the solvent was eliminated from the filtrate, the initially amorphous residue was intensively stirred with 200 ml of dichloromethane and after the addition of 600 ml of water to the resulting solution it was shaken for 30 minutes in a shaking machine. The resulting precipitate was suction filtered and purified by decocting with 300 ml of diethyl- ether and intensively washing several times with dichloromethane and ether. After drying in vacuo, 14.50 g (79% of theory) of colourless crystals were obtained, Mp. 132–136° C. (D.).

IR (KBr): 1693.3 (Urethane-CO),
1652.9, 1625.9 (Amide-CO, C=N) cm$^{-1}$
ESI-MS: (M+H)$^+$=915
(M+Na)$^+$=937 b) (R)-N$^G$-(2,2,5,7,8-Pentamethylchroman-6-sulphonyl)-N-[[4-[[(phenylmethoxycarbonyl)amino]methyl]phenyl] methyl)-argininamide A solution of 13.5 g (14.75 mMol) of (R)-N$^2$-(9-fluorenylmeth-oxycarbonyl)-N$^G$-(2,2,5,7,8-pentamethylchroman-6-sulphonyl)-N-[[4-[[(phenylmethoxycarbonyl)amino]methyl]phenyl]methyl]-argininamide in 80 ml of dimethylformamide was mixed with 18 ml (175 mMol) of diethylamine, shaken thoroughly and left to stand for 4 hours at ambient temperature. The solvent was eliminated in an oil pump vacuum at slightly elevated temperature, the residue was distributed between ethyl acetate and water, the combined ethyl acetate phases were dried over sodium sulphate and evaporated down in vacuo. The amorphous, glassy residue remaining was purified by column chromatography on silica gel (Macherey-Nagel, 35–70 mesh ASTM) using initially dichloromethane/methanol/conc. aqueous ammonia=90/10/0.25 and subsequently dichloromethane/methanol/conc. aqueous ammonia=80/20/0.5 (v/v/v) as eluant. By evaporating the appropriate fractions down, 9.8 g (96% of theory) of the desired compound were obtained as a colourless, amorphous/ glassy substance.

IR (KBr): 1714.6 (Urethane-CO),
1620.1 cm$^{-1}$ (C=N)

c) (R)-N$^2$-(Diphenylacetyl)-N$^G$-(2,2,5,7,8-pentamethylchroman-6-sulphonyl)-N-[[4-[[(phenylmethoxycarbonyl)amino]methyl]-phenyl]methyl]-argininamide Prepared analogously to Example 1a) from diphenylacetic acid and (R)-N$^G$-(2,2,5,7,8-pentamethylchroman-6-sulphonyl)-N-[[4-[[(phenylmethoxycarbonyl)amino] methyl]phenyl]methyl]-argininamide in the presence of dicyclohexylcarbodiimide and hydroxybenzotriazole in a yield of 96% of theory. Colourless crystals, Mp. 118–121° C. (D.).

IR (KBr): 3442.7, 3307.7 (NH),
1693.4 (Urethane-CO),
1643.3 (Amide-CO) cm$^{-1}$ d) (R)-N-[[4-(Aminomethyl)phenyl]methyl]-N$^2$-(diphenylacetyl)-N$^G$-(2,2,5,7,8-pentamethylchroman-6-sulphonyl)-argininamide A mixture of 11.75 g (13.25 mMol) of (R)-N$^2$-(diphenylacetyl)-N$^G$-(2,2,5,7,8-pentamethylchroman-6-sulphonyl)-N-[[4-[[(phenyl-oxycarbonyl)amino]methyl] phenyl]methyl]argininamide, 300 ml methanol and 2.0 g of 10 percent palladium on animal charcoal was hydrogenated at ambient temperature under 5 bars of hydrogen pressure until the uptake of hydrogen had ceased. The catalyst was filtered off, the filtrate was evaporated down in vacuo, the amorphous/glassy residue remaining was purified on silica gel (Macherey-Nagel, 0.063 to 0.2 mm) by column chromatography, using dichloromethane/methanol/conc. aqueous ammonia =80/20/0.25 (v/v/v) as eluant. By evaporating the appropriate fractions down, 7.88 g (79% of theory) of the desired compound were obtained as a colourless, glassy/amorphous substance. IR(KBr): 1652.9 (Amide-CO) cm$^{-1}$ e) (R)-N-[[4-(Acetylaminomethyl)phenyl]methyl]-N$^2$-(diphenyl-acetyl)-N$^G$-(2,2,5,7,8-pentamethylchroman-6-sulphonyl)-argininamide To a solution of 1.0 g (1.328 mMol) of (R)-N-[[4-(aminomethyl)phenyl]methyl]-N$^2$-(diphenylacetyl)-N$^G$-(2,2,5,7,8-pentamethylchroman-6-sulphonyl)-argininamide in 10 ml of ethanol was added dropwise within 10 minutes a solution of 0.15 g (1.469 mMol) of acetic anhydride in 3 ml of diethylether. The mixture was evaporated down in vacuo, the residue was distributed between dichloromethane and saturated aqueous potassium carbonate solution. The dichloromethane phase was dried over sodium sulphate and freed from solvent, the residue was digested again with a little dichloromethane and suction filtered after crystallising out. After drying in vacuo, 0.91 g (86% of theory) of colourless crystals were obtained, Mp. 128–132° C. IR(KBr): 1643.3 (Amide-CO) cm$^{-1}$ f) (R)-N-[[4-(Acetylaminomethyl)phenyl]methyl]-N$^2$-(diphenyl-acetyl)-argininamide-trifluoroacetate Into a mixture of 18.6 ml of trifluoroacetic acid, 0.6 ml of anisole, 0.4 ml of 1,2-ethanedithiol and 0.4 ml of water which is externally cooled with ice/methanol, were added within 20 minutes and with stirring 0.85 g (1.069 mMol) of (R)-N-[[4- (acetylaminomethyl)phenyl]methyl]-N$^2$-(diphenylacetyl)-N$^G$-(2,2,5,7,8-pentamethylchroman-6-sulphonyl)-argininamide. After the cooling was removed the mixture was stirred for a further 14 hours at ambient temperature. It was filtered, the filtrate was diluted with the same volume of diethylether and filtered again. The filtrate thus obtained was evaporated down in vacuo and the residue was digested intensively several times with diethylether. The crystals obtained were finally suction filtered, washed with diethylether and dried over phosphorus pentoxide in vacuo. 0.67 g (98% of theory) of colourless crystals were obtained.

R$_f$ value: 0.57

IR (KBr): 1652.9 (Amide-CO), 1203.5, 1185.8, 1136.0 (Trifluoroacetate) cm$^{-1}$

ESI-MS: (M+H)$^+$=529

(2M+H)$^+$=1057

EXAMPLE 2

(R)-N$^2$-(Diphenylacetyl)-N-[[4-(ethoxycarbonylaminomethyl)-phenyl]methyl]-argininamide-trifluoroacetate a) (R)-N$^2$-(Diphenylacetyl)-N-[[4-(ethoxycarbonylaminomethyl)-phenyl)methyl]-N$^G$-(2,2,5,7,8-pentamethylchroman-6-sulphonyl)argininamide To a solution of 1.0 g (1.328 mMol) of (R)-N-[[4-(aminomethyl)phenyl]methyl]-N$^2$-(diphenylacetyl)-N$^G$-(2,2,5,7,8-pentamethylchroman-6-sulphonyl)-argininamide in 10 ml of anhydrous tetrahydrofuran were added dropwise first 0.2 g (1.976 mMol) of triethylamine, then a solution of 0.16 g (1.474 mMol) of ethylchlorocarbonate in 2 ml of anhydrous tetrahydrofuran. After 10 minutes' stirring at ambient temperature the mixture was evaporated down in vacuo, the residue was distributed between water and dichloromethane, the dichloromethane phase was dried over sodium sulphate and freed from solvent in vacuo. The residue remaining was intensively triturated with ether and suction filtered. 1.0 g (91% of theory) of a colourless product were obtained, Mp. 117–120° C.

IR (KBr): 1689.5 (Carbonate-C=O),
1643.3 (Amide-C=O) cm$^{-1}$ b) (R)-N$^2$-(Diphenylacetyl-N-[[4-(ethoxycarbonylaminomethyl)phenyl]methyl]-argininamide-trifluoroacetate Prepared analogously to Example 1f) from (R)-N$^2$-(diphenylacetyl-N-[[4-(ethoxycarbonylaminomethyl)phenyl]methyl]-N$^6$-(2,2,5,7,8-pentamethylchroman-6-sulphonyl)-argininamide and trifluoroacetic acid in a yield of 86% of theory.

R$_f$ value: 0.72; colourless substance, Mp. 76–80° C. (D.).

IR (KBr): 1668.3 (Amide-C=O) cm$^{-1}$

ESI-MS: (M+H)$^+$=559

(2M+H)$^+$=1117

EXAMPLE 3

(R)-N-[[4-(Aminosulphonylaminomethyl)phenyl]methyl]-N$^2$-(diphenylacetyl)-argininamide-trifluoroacetate a) (R)-N-[[4-[[[[(1,1-Dimethylethyl)amino]sulphonyl]amino]- methyl]phenyl]methyl]-N$^2$-(diphenylacetyl)-N$^G$-(2,2,5,7,8-pentamethylchroman-6-sulphonyl)-argininamide To a solution, cooled to −50° C., of 1.0 g (1.328 mMol) of (R)-N-[[4-(aminomethyl)phenyl]methyl]-N$^2$-(diphenylacetyl)-N$^G$-(2,2,5,7,8-pentamethylchroman-6-sulphonyl)-argininamide in a mixture of 10 ml of anhydrous tetrahydrofuran and 0.2 g (1.976 mMol) of triethylamine was added dropwise a solution of 0.26 g (1.515 mMol) of N-(1,1-dimethylethyl)-chlorosulphonamide (W. L. Matier et al., J. Med. Chem. 15, 538–541 (1972)) in 2 ml of anhydrous tetrahydrofuran. The mixture was allowed to warm up to ambient temperature, 1 ½% times the above-mentioned quantity of triethylamine and N-(1,1-dimethylethyl)chlorosulphonamide were added once more and the mixture was stirred for 14 hours at ambient temperature. The mixture was evaporated down in vacuo, the residue was distributed between dichloromethane and water, the organic phase was dried over sodium sulphate and again freed from solvent. The residue remaining was thoroughly triturated with diethylether, then decocted with ether and suction filtered and finally purified further by column chromatography on silica gel (Macherey-Nagel, 35–70 mesh ASTM) using dichloromethane/methanol/conc. aqueous ammonia=90/10/0.25 (v/v/v) as eluant. After the appropriate fractions had been worked up in the usual way 0.65 g (55% of theory) of colourless crystals were obtained, Mp. 112–117° C. IR (KBr): 1656.8 (Amide-C=O) cm$^{-1}$ b) (R)-N-[[4-(Aminosulphonylaminomethyl)phenyl] methyl]-N$^2$-diphenylacetyl)-argininamide-trifluoroacetate Prepared analogously to Example 1f) from (R)-N-[[4-[[[[1,1-dimethyl)amino]sulphonyl]amino]methyl]phenyl] methyl]-N$^2$-diphenylacetyl)-N$^G$-(2,2,5,7,8-pentamethylchroman-6-sulphonyl)-argininamide and trifluoroacetic acid in a yield of 79% of theory.

R$_f$ value: 0.68; colourless amorphous substance.

IR (KBr): 1662.5 (Amide-C=O),
1330.8, 1137.9 (SO$_2$-N) cm$^{-1}$

ESI-MS: (M+H)$^+$566

EXAMPLE 4

(R)-N-[[4-Aminocarbonylaminomethyl)phenyl]methyl]-N$^2$- (diphenylacetyl)-argininamide-trifluoroacetate a) (R)-N$^5$-[Amino(nitroimino)methyl]-N$^2$-(diphenylacetyl)-ornithine To a suspension of 50 g (0.228 Mol) H-D-Arg(NO$_2$)-OH in 400 ml of tetrahydrofuran was added a solution of 9.12 g (0.228 Mol) of sodium hydroxide in 100 ml of water. To this mixture was then added dropwise, within 30 minutes, a solution of 52.6 g (0.228 Mol) of diphenylacetylchloride in 400 ml of tetrahydrofuran and, simultaneously, a solution of 9.12 g (0.228 Mol) of sodium hydroxide in water without external cooling, the mixture was stirred for a further 12 hours at ambient temperature and then the solvents were distilled off in a water jet vacuum. The oily residue remaining was dissolved in 600 ml of water and the aqueous solution obtained was then acidified with 230 ml of 1N aqueous hydrochloric acid. The precipitate formed was taken up in 500 ml of ethyl acetate, the ethyl acetate solution was then washed thoroughly with water, dried over sodium sulphate and freed from solvent in vacuo. After recrystallisation from acetone, 80.0 g (85% of theory) of colourless crystals were obtained, Mp. 80° C.

IR (KBr): 1710, 1655 (C=O) cm$^{-1}$
ESI-MS: (M-H)$^-$=412 (calculated: 412)

b) (R)-N-[[4-(Aminocarbonylaminomethyl)phenyl]methyl]-N$^5$-[amino(nitroimino)methyl]-N$^2$-(diphenylacetyl)-ornithinamide To a mixture of 5.79 g (14.0 mMol) of (R)-N$^5$-[amino(nitro- imino)methyl]-N$^2$-(diphenylacetyl)-ornithine, 2.51 g (14.01 mMol) of 4-(aminocarbonylaminomethyl)-benzenemethanamine, 1.81 g (14.0 mMol) of diisopropylethylamine, 50 ml of anhydrous dimethylformamide and 25 ml of anhydrous tetrahydrofuran were added, with stirring and external cooling with ice water, 4.48 g (13.95 mmol) of TBTU. The resulting mixture was then stirred for 20 hours at ambient temperature and for 1 hour at a reaction temperature of 70° C. The solvents were distilled off in an oil pump vacuum and the residue was carefully stirred with 100 ml each of dichloromethane and water. The crystals precipitated at the interface between the two phases were suction filtered, washed with water, dichloromethane, isopropanol and diethylether and dried in vacuo. 7.72 g (96% of theory) of a colourless crystalline substance were obtained.

IR (KBr): 1635.5 (Amide-C=O) cm$^{-1}$ c) R-N-[[-4-(Aminocarbonylaminomethyl)phenyl]methyl]-N$^2$- (diphenylacetyl)-argininamide-trifluoroacetate A solution of 7.6 g (13.23 mmol) of (R)-N-[[4-(aminocarbonyl-aminomethyl)phenyl]methyl]-N$^5$-[amino(nitroimino)methyl]-N$^2$-(diphenylacetyl)-ornithinamide in 200 ml of 80 percent aqueous acetic acid was hydrogenated in the presence of 4.0 g of palladium black at 40° C. under 5 bar of hydrogen pressure until the uptake of hydrogen had ceased. The catalyst was filtered off, the filtrate was evaporated down in vacuo, mixed twice with 10 ml of water and once each with 10 ml of ethanol and isopropanol and evaporated down once more. The glassy residue was taken up in 200 ml of hot isopropanol, evaporated down to a volume of about 20 ml and left to stand at ambient temperature. The crystalline suspension obtained after some time was diluted with the same volume of diethylether, stirred thoroughly and suction filtered. After decoction with dichloromethane and washing with isopropanol/diethylether=1/1 (v/v) and diethylether, 7.15 g (92% of theory) of colourless crystals were obtained, Mp. 124–128° C., which are the acetate of the desired compound.

IR (KBr): 1649.9 (Amide-C=O) cm$^{-1}$
ESI-MS: (M+H)$^+$=530
(M+Na)$^+$=552
(M+K)$^+$=568

If the above crystals are dissolved in 70 ml of trifluoroacetic acid and evaporated down under mild conditions in vacuo, after this process has been repeated several times, an initially oily substance is obtained which crystallises when stirred with diethylether and this is the desired trifluoroacetate. R$_f$ value: 0.56; colourless crystals, Mp. 100–105° C. (D.).

IR (KBr): 1656.8 (Amide-C=O) cm$^{-1}$
ESI-MS: (M+H)$^+$=530

EXAMPLE 5

(R,S)-N$^5$-(Aminoiminomethyl)-N$^2$-(diphenylacetyl)-N-[(4-hydroxyphenyl)methyl]-N$^5$-methyl]ornithinamide-hydrochloride a) Diethyl (α-(acetylamino)-α-[3-[(phenylmethyl)methylamino]- propyl]malonate A sodium ethoxide solution freshly prepared from 5.8 g (0.252 Mol) of sodium and 250 ml of anhydrous ethanol was added dropwise at ambient temperature and within about 15 minutes to a mixture obtained from 49.4 g (0.25 Mol) of 3-chloro-N-methyl- N-(phenylmethyl)-propanamine, 60 g (0.268 Mol) of 97% diethyl acetamido-malonate, 11.3 g (0.075 Mol) of sodium iodide and 800 ml of dry dioxane. The mixture was stirred for 30 minutes at ambient temperature and then refluxed for 5 hours. It was left to stand overnight at ambient temperature, the insoluble matter was filtered off, the filtrate was freed from solvent and the residue remaining was distributed between ethyl acetate and water. The ethyl acetate phase was dried over sodium sulphate and evaporated down, the oil obtained was finally purified by column chromatography (Kieselgel MN 60, Macherey-Nagel, 70–230 mesh ASTM; mobile phase: dichloromethane/methanol/conc. aqueous ammonia=90/10/0.25 (v/v/v)). 53 g (56% of theory) of a colourless viscous oil were obtained.

IR (KBr): 1741.6 (Ester-C=O), 1683.8 (Amide-C=O) cm$^{-1}$ b) (R,S)-N$^5$-ethyl-N$^5$-(phenylmethyl)-ornithine-dihydrochloride 20.4 g (0.0539 Mol) of diethyl α-(acetylamino)-α-[3-[(phe- nylmethyl)methylamino]propyl]-malonate was dissolved in 50 ml of glacial acetic acid and after the addition of 100 ml of 3N aqueous hydrochloric acid the mixture was refluxed for 6 hours. The highly viscous, slightly yellowish mass remaining after evaporation of the solvent and obtained in quantitative yield was further reacted without any further purification.

c) (R,S)-N$^2$-(Diphenylacetyl)-N$^5$-methyl-N$^5$-(phenylmethyl)-ornithine-hydrochloride Diphenylacetylchloride and (R,S)-N$^5$-methyl-N$^5$-(phenylmethyl)-ornithine-dihydrochloride were reacted analogously to Example 4a). The mixture obtained was evaporated down in a water jet vacuum until the tetrahydrofuran used as solvent had been eliminated, then acidified with 3N aqueous hydrochloric acid and extracted carefully with diethylether. The aqueous phase was then evaporated down under reduced pressure at a maximum bath temperature of ±40° C. The yield of colourless crystals of Mp. 125–130° C., which were used in the next stage without purification, was 27% of theory.

IR (KBr): 1715 (Carboxylic acid-C=O), 1664 (Amide-C=O) cm$^{-1}$ d) (R,S)-N$^2$-(Diphenylacetyl)-N-[(4-hydroxyphenyl)methyl]-N$^5$-methyl-N$^5$-(Phenylmethyl)-ornithinamide Prepared analogously to Example 4b) from (R,S)-N$^2$-(diphenyl-acetyl)-N$^5$-methyl-N$^5$-(phenylmethyl)-ornithine-hydrochloride, (4-hydroxy-phenyl)methanamine and TBTU in a yield of 28% of theory.

R$_f$ value: 0.75; colourless crystals, Mp. 160–162° C. (ethyl acetate).

IR (KBr): 1679.9 and 1633.6 (Amide-C=O)cm$^{-1}$ e) (R,S)-N²-(Diphenylacetyl)-N-[(4-hydroxyphenyl) methyl]-N⁵-methyl-ornithinamide Prepared analogously to Example 1d) from (R,S)-N²-(diphenyl-acetyl)-N-(4-hydroxyphenyl)methyl]-N⁵-methyl-N⁵-(phenylmethyl)-ornithinamide by catalytic hydrogenation in the presence of palladium hydroxide/activated charcoal (Pearlman's catalyst) in a yield of 75% of theory.

$R_f$ value: 0.52; colourless crystals, Mp. 118–130° C. (dichloromethane).

IR (KBr): 3290 (N-H, O-H), 1635.5 (Amide-C=O)cm$^{-1}$

MS: M⁺=445 f) (R,S)-N⁵-(Amininoiminomethyl)-N²-(diphenylacetyl)-N-[[4-hydroxyphenyl)methyl]-N⁵-methyl-ornithinamide-hydrochloride A mixture of 0.45 g (1.01 mMol) of (R,S)-N²-(diphenylacetyl)-N-[(4-hydroxyphenyl)methyl]-N⁵-methyl-ornithinamide, 10 ml of 1N ethanolic hydrochloric acid solution and 0.45 g (10.7 mMol) of cyanamide (97–98 percent) was refluxed for 3 days. By the addition of a little 0.1 N ethanolic hydrochloric acid solution a pH of about 5.0 was adjusted, then a further 0.15 g of cyanamide were added and the mixture was refluxed for a further 2 days. The reaction mixture was freed from solvent and the residue remaining was distributed between water and dichloromethane. The dichloromethane phase was discarded and the aqueous phase was evaporated down in vacuo. The residue was suspended in about 5 ml of water and acidified slightly with 2N aqueous hydrochloric acid to give a pH of about 3. After standing for several days, fine colourless crystals are precipitated from the aqueous solution thus obtained and these crystals are suction filtered and washed with a little water. After decoction with tetrahydrofuran and washing with acetone and diethylether, 138 mg (26% of theory) of colourless crystals were obtained, Mp. 130–135° C. (D.).

$R_f$ value: 0.61

IR (KBr): 1647.1 (Amide-C=O) cm$^{-1}$

ESI-MS: (M+H)⁺=488

(2M+H)⁺=976

EXAMPLE 6

(R)-N-[[4-(Aminocarbonylmethyl)phenyl]methyl]-N²-(diphenyl-acetyl)-argininamide-diacetate a) 4-Cyanophenylacetic acid 1 g (7.03 mMol) of 4-cyanophenylacetonitrile was added to conc. hydrochloric acid preheated to 105° C. and kept at this temperature for 5 minutes. It was cooled to 0° C., the precipi- tate formed was collected and washed thoroughly with ice water. After purification by column chromatography on silica gel (Macherey-Nagel, 35–70 mesh ASTM) using ethyl acetate/methanol/glacial acetic acid=95/5/0.5 (v/v/v) as eluant, 0.5 g (44% of theory) of colourless crystals were obtained Mp. 152.154° C.

IR (KBr): 2229.6 (C N)

1697.2 (Carboxylic acid-C=O) cm$^{-1}$ b) 4-Cyanophenylacetamide

To a solution of 1.6 g (9.93 mMol) of 4-cyanophenylacetic acid in 20 ml of anhydrous tetrahydrofuran were added, with stirring, 1.8 g (11.1 mMol) of N,N'-carbonyldiimidazole and then dry ammonia gas was introduced until a slightly alkaline reaction was obtained. The mixture was stirred for a further hour at ambient temperature, after which the solvent was distilled off in vacuo. After purification on silica gel (Baker, 0.03 to 0.06 mm) using ethyl acetate/methanol=¹⁄₁ (v/v) as eluant and working up in the usual way, 0.7 g (44% of theory) of colourless crystals were obtained Mp. 196–197° C. (diethylether).

IR (KBr): 3447.2, 3309.0, 3203.7 (N-H), 2242.8 (C N), 1663.6 (Amide-C=O) cm$^{-1}$ c) 4-(Aminocarbonylmethyl)benzenemethanamine 0.65 g (4.057 mMol) of 4-cyanophenylacetamide were dissolved in 50 ml of methanol which was saturated with ammonia at+10° C. After the addition of 0.3 g of Raney nickel the mixture was hydrogenated in an autoclave at 40° C. under 5 bar of hydrogen pressure. After the uptake of hydrogen had ended the catalyst was filtered off and excess ammonia was distilled off with the solvent. The residue was acidified with 20 percent hydrochloric acid against Congo red and the non-basic impurities were removed by etherification. The ether extract was discarded, the aqueous solution was made alkaline with sodium hydroxide with external cooling and exhaustively extracted with ether. The ether solution was dried over caustic potash and freed from solvent, the residue was triturated with a few drops of ether and suction filtered. 610 mg (100% of theory) of colourless crystals were obtained, Mp. 138–140° C. IR (KBr): 1660.6, 1637.5 (Amide-C=O) cm$^{-1}$ d) (R)-N-[[4-(Aminocarbonylmethyl)phenyl]methyl]-N⁵-[amino-(nitroimino)methyl]-N²-(diphenylacetyl)-ornithinamide Prepared analogously to Example 4b) but using dimethylformamide as solvent instead of dimethylformamide/tetrahydrofuran mixture and 4-methylmorpholine instead of diisopropylethylamine as auxiliary base, from (R)-N⁵-[amino(nitroimino)methyl]-N²-(diphenylacetyl)-ornithine, 4-(aminocarbonylmethyl)-benzenemethanamine and TBTU in a yield of 73% of theory.

Colourless amorphous substance.

IR (KBr): 1658.7 (Amide-CO) cm$^{-1}$

ESI-MS: (M+H)⁺=560

(M+Na)⁺=582 e) (R)-N-[[4-(Aminocarbonylmethyl)phenyl]methyl]-N²-(diphenylacetyl)-argininamide-diacetate Prepared analogously to Example 4c) from (R)-N-[[4-(aminocarbonylmethyl)phenyl]methyl]-N⁵-[amino (nitroimino)methyl]-N²-(diphenylacetyl)-ornithine by catalytic hydrogenation in the presence of palladium black and 80 percent aqueous acetic acid in a yield of 33% of theory.

$R_f$ value: 0.58; colourless crystals, Mp. 115–117° C. (acetone).

IR (KBr): 1662.5 (Amide-C=O) cm$^{-1}$

ESI-MS: (M+H)⁺=515

EXAMPLE 7

(R)-N²-(Diphenylacetyl)-N-[[4-(methylaminosulphonylmethyl)-phenyl]methyl]-argininamide-diacetate a) Sodium salt of 4-cyanobenzenemethanesulphonic acid 8.3 g (32.9 mMol) of sodium sulphite-heptahydrate dissolved in 35 ml of water were added to a solution of 5.88 g (29.98 mMol) of 4-(bromomethyl)benzonitrile in 35 ml of acetone and then refluxed for 30 minutes. The acetone was distilled off, the aqueous solution remaining was filtered while boiling hot and the filtrate was then cooled to +10° C. The crystals precipitated after standing for 2 hours were suction filtered, thoroughly washed with ethanol and dried over diphosphorus pentoxide in vacuo. 5.35 g (81% of theory) of colourless crystals were obtained, Mp. >250° C.

IR (KBr) 2233.4 (C N), 1211.2, 1055.0, 979.8 ($SO_3$-) $cm^{-1}$ b) 4-Cyanobenzenemethanesulphonic acid chloride A suspension of 1.1 g (5.02 mMol) of the sodium salt of 4-cyanobenzenemethanesulphonic acid in 20 ml of acetonitrile was mixed with 1.2 g (5.76 mMol) of phosphorus-(V)-chloride and then refluxed for 24 hours. The insoluble matter was filtered off and the filtrate was evaporated down in vacuo. Yield; 0.8 g (74% of theory). The product was used in the next step without purification.

c) 4-Cyano-N-methyl-benzenemethanesulphonamide

Gaseous methylamine was introduced into a solution of 0.8 g (3.71 mMol) of 4-cyanobenzenemethanesulphonic acid chloride in 20 ml of tetrahydrofuran until a distinctly alkaline reaction was obtained. The mixture was stirred for a further hour at ambient temperature, the excess methylamine together with the solvent was distilled off in vacuo and the residue was triturated with diethylether. The crystals formed were suction filtered and dried. 420 mg (54% of theory) of colourless crystals were obtained, Mp. 151–152° C.

IR (KEr) : 2227.7 (C N), 1313.4, 1126.4 ($SO_2$-N) $cm^{-1}$

MS: $M^+$=210 d) 4-(Methylaminosulphonylmethyl)benzenemethanamine

Prepared analogously to Example 6c) from 4-cyano-N-methyl-benzenemethanesulphonamide by catalytic hydrogenation in the presence of ammonia and Raney nickel in a yield of 60% of theory. Colourless crystals, Mp. 128–130° C. (diethylether/methanol).

IR (KBr): 1319.2, 1122.5 ($SO_2$-N)$cm^{-1}$

MS: $M^+$=214 e) (R)-$N^5$-[Amino(nitroimino)methyl]-$N^2$-(diphenylacetyl)-N- [[4-(methylaminosulphonylmethyl)phenyl]methyl]-ornithinamide Prepared analogously to Example 6d) from (R)-$N^5$-[amino(nitroimino)methyl]-$N^2$-(diphenylacetyl)-ornithine, 4-(methylamino-sulphonylmethyl)benzenemethanamine and TBTU in a yield of 70% of theory. Colourless amorphous substance.

IR(KBr): 1649.0 (Amide-C=O), 1315.4, 1155.3 ($SO_2$-N) $cm^{-1}$

ESI-MS: $(M+H)^+$=610

$(M+Na)^+$=632

$(M+K)^+$=648 f) R)-$N^2$-(Diphenylacetyl)-N-[[4-(methylaminosulphonylmethyl)-phenyl]methyl]-argininamide-diacetate Prepared analogously to Example 4c) from (R)-$N^5$-[amino(nitroimino)methyl]-$N^2$-(diphenylacetyl)-N-[[4-(methylaminosulphonyl-methyl)phenyl)methyl]-ornithinamide by catalytic hydrogenation in the presence of palladium black and 80 percent acetic acid in a yield of 30% of theory.

$R_f$ value: 0.62; colourless amorphous substance.

IR(KBr): 1637.5 (Amide-C=O) $cm^{-1}$

ESI-MS: $(M+H)^+$=565

EXAMPLE 8

(R)-N-[[3-(Aminocarbonylaminomethyl)phenyl]methyl]-$N^2$-(diphenylacetyl)argininamide-acetate a) 3-(Aminocarbonylaminomethyl)benzenemethanamine A mixture of 4.08 g (29.96 mMol) of 3-(aminomethyl)benzene-methanamine, 30 ml tetrahydrofuran and 30 ml 1N aqueous hydrochloric acid were mixed with 1.95 g (29.58 mMol) of sodium cyanate added in batches. After stirring for 6 hours at ambient temperature the solvents were largely distilled off in vacuo, the residue was distributed between water and dichloromethane, the dichloromethane phase was dried over sodium sulphate and evaporated down. The residue was purified by column chromatography on silica gel (Macherey-Nagel, 35–70 mesh ASTM) using dichloromethane/methanol/cyclohexane/conc. aqueous ammonia=68/15/15/2 (v/v/v/v) as eluant. By working up the corresponding fractions, 0.9 g (17% of theory) of colourless crystals were obtained, Mp. 127–129° C. (diethylether).

IR (KBr): 3379.3, 3311.6 (N-H), 1658.7 (Urea-C=O) $cm^{-1}$ b) (R)-N-[[3-(Aminocarbonylaminomethyl)phenyl]methyl]-$N^5$-[amino(nitroimino)methyl]-$N^2$-(diphenylacetyl)-ornithinamide Prepared analogously to Example 4b) from (R)-$N^5$-[amino(nitroimino]methyl]-$N^2$-(diphenylacetyl)-ornithine, 3-(amino-carbonylaminomethyl)benzenemethanamine and TBTU in a yield of 50% of theory. Colourless amorphous substance.

IR (KBr): 1651.0 (Amide-/Urea-C=O) $cm^{-1}$

ESI-MS: $(M+H)^+$=575

$(M+Na)^+$=597

$(M+K)^+$=613 c) (R)-N-[[3-(Aminocarbonylaminomethyl)phenyl]methyl]-$N^2$-(diphenylacetyl)-argininamide-acetate Prepared analogously to Example 4c) from (R)N-[[3-(aminocarbonylaminomethyl)phenyl]methyl]-$N^5$-[amino(nitroimino]methyl]-$N^2$-(diphenylacetyl)-ornithinamide by catalytic hydrogenation in the presence of palladium black and 80% acetic acid in a yield of 42% of theory.

$R_f$ value: 0.61; colourless crystals, Mp. 98–103° C.

IR (KBr): 1641.3 (Amide-/Urea-C=O) $cm^{-1}$

ESI-MS: $(M+H)^+$=530

$(M+Na)^+$=5552.

EXAMPLE 9

(R,S)-N-[[4-(Aminocarbonylaminomethyl)phenyl]methyl]-$N^5$-(aminoiminomethyl)-$N^2$(diphenylacetyl)-$N^5$-methyl-ornithinamide hydrochloride a) (R,S)-N-[[4-(Aminocarbonylaminomethyl)phenyl]methyl]-$N^2$-(diphenylacetyl)-$N^5$-methyl-$N^5$-(phenylmethyl)-ornithinamide Prepared analogously to Example 4b) but using triethylamine instead of diisopropylethylamine from (R,S)-$N^2$-(diphenyl-acetyl)-$N^5$-methyl-$N^5$-(phenylmethyl)-ornithine, 4-(aminocarbonylaminomethyl)benzenemethanamine and TBTU in a yield of 81% of theory. Colourless crystals, Mp. 180–185° C.

IR (KBr): 3435.0, 3350.2, 3257.6 (N-H), 1639.4 (Amide-C=O) $cm^1$

ESI-MS: $(M+H)^+$=492

$(M+Na)^+$=614

$(M+K)^+$=630 b) (R,S)-N-[[4-(Aminocarbonylaminomethyl)phenyl]methyl]-$N^2$-(diphenyl-acetyl)-$N^5$-methyl-ornithinamide Prepared analogously to Example 5e) from (R,S)-N-[[4-(amino-carbonylaminomethyl)phenyl]methyl]-$N^2$-

(diphenylacetyl)-$N^5$-methyl-$N^5$-(phenylmethyl)-ornithinamide by catalytic hydrogenation in the presence of palladium hydroxide/activated charcoal in a yield of 88% of theory. Colourless crystals, Mp. 175–180° C. (D., ethanol).

IR (KBr): 3481.3, 3429.2, 3390.7, 3278.8 (N-H), 1656.8 (Amide-C=O) cm$^{-1}$

ESI-MS: (M+H)$^+$=502 c) (R,S)-N-[[4-(Aminocarbonylaminomethyl)phenyl]methyl]-$N^5$-(aminoimino-methyl)-$N^2$-(diphenylacetyl)-$N^5$-methyl-ornithinamide-hydrochloride Prepared analogously to Example 5f) from (R,S)-N-[[4-(aminocarbonylaminomethyl)phenyl]methyl]-$N^2$-(diphenylacetyl)-$N^5$-methyl-ornithinamide, cyanamide and hydrogen chloride in a yield of 9% of theory.

$R_f$ value: 0.48; colourless substance.

IR (KBr): 1652.9 (Amide-C=O) cm$^{-1}$

ESI-MS: (M+H)$^+$=544

EXAMPLE 10

(R)-$N^2$-(Diphenylacetyl)-N-[[4-(ethoxycarbonylaminomethyl)-phenyl]methyl]-argininamide-trifluoroacetate a) (R)-$N^2$-(Diphenylacetyl)-N-[[4-(methoxycarbonylamino-methyl)phenyl]methyl]-$N^G$-(2,2,5,7,8-pentamethylchroman-6-sulphonyl)-argininamide Prepared analogously to Example 2a) from (R)-N-[[4-(aminomethyl)phenyl]methyl]-$N^2$-(diphenylacetyl)-$N^G$-(2,2,5,7,8-pentamethyl-chroman-6-sulphonyl)-argininamide and methylchlorocarbonate in a yield of 83% of theory. Colourless crystals.

Mp. 122–126° C.

IR (KBr): 3438.9, 3307.7 (N-H), 1695.3 (Carbamate-C=O), 1643.3 (Amide-C=O), 1298.0, 1166.9 (SO$_2$-N) cm$^-$ b) (R)-$N^2$-(Diphenylacetyl)-N-[[4-(methoxycarbonylamino-methyl)phenyl]methyl]-argininamide-trifluoroacetate Prepared analogously to Example 1f) from (R)-$N^2$-(diphenylacetyl)-N-[[4-(methoxycarbonylaminomethyl)-phenyl]methyl]-$N^G$-(2,2,5,7,8-pentamethylchroman-6-sulphonyl)-argininamide and trifluoroacetic acid in a yield of 83% of theory.

$R_f$ value: 0.68; colourless crystals, Mp. 87–95° C.

IR (KBr): 1662.5 (Amide-C=O), 1203.5, 1179.8, 1134.1 (trifluoroacetate) cm$^1$

ESI-MS: (M+H)$^+$=545

(M+Na)$^+$=567

(M+K)$^+$=583

EXAMPLE 11

(R)-$N^2$-(Diphenylacetyl)-N-[[4-(methylaminocarbonylaminomethyl)-phenyl]methyl]-argininamide-trifluoroacetate a) (R)-$N^2$-(Diphenylacetyl)-N-[[4-(methylaminocarbonylamino-methyl)phenyl]methyl]-$N^G$-(2,2,5,7,8-pentamethylchroman-6-sulphonyl)-argininamide To a solution of 0.75 g (0.996 mMol) of (R)-N-[[4-(aminomethyl)-phenyl]methyl]-$N^2$-(diphenylacetyl)-$N^G$-(2,2,5,7,8-pentamethyl-chroman-6-sulphonyl)-argininamide and 0.3 ml (3,17 mMol) of triethylamine in 5 ml of anhydrous tetrahydrofuran was added a solution of 0.063 g (1.104 mMol) methylisocyanate in 1 ml of dry tetrahydrofuran. The mixture was diluted with 20 ml of diethylether, the precipitate formed was suction filtered, washed thoroughly with ether, dried, then washed with water, after which it was dried again. 0.57 g (71% of theory) of colourless crystals were obtained, Mp. 105–120° C.

IR (KBr): 1643.3 (Amide-C=O), 1298.0, 1166.9 (SO$_2$-N) cm$^{-1}$

ESI-MS: (M+H)$^+$=810

(M+Na)$^+$=832

(M+K)$^+$=848 b) (R)-$N^2$-(Diphenylacetyl)-N-[[4-(methylaminocarbonylamino-methyl)phenyl]methyl]-argininamide-trifluoroacetate Prepared analogously to Example 1f) from (R)-$N^2$-(diphenyl-acetyl)-N-[[4-(methylaminocarbonylaminomethyl)phenyl]methyl]-$N_G$-(2,2,5,7,8-pentamethylchroman-6-sulphonyl)-argininamide and trifluoroacetic acid in a yield of 89% of theory. $R_f$ value: 0.56; colourless crystals, Mp. 94–97° C.

IR (KBr): 1658.7 (Amide-C=O) cm$^{-1}$

ESI-MS: (M+H)$^+$=544

(M+Na)$^+$=566

EXAMPLE 12

(R)-N-[[4-(Benzoylaminomethyl)phenyl]methyl]-$N^2$-(diphenylacetyl)-argininamide-trifluoroacetate a) (R)-N-[[4-(Benzoylaminomethyl)phenyl]methyl]-$N^2$-(diphenyl-acetyl)-$N^G$-(2,2,5,7,8-pentamethylchroman-6-sulphonyl)-argininamide Prepared analogously to Example 2a) from (R)-N-[[4-(aminomethyl)phenyl]methyl]-$N^2$-(diphenylacetyl)-$N^G$-(2,2,5,7,8-pentamethyl-chroman-6-sulphonyl)-argininamide and benzoylchloride in a yield of 89% of theory. Colourless crystals, Mp. 120–124° C.

IR (KBr): 1652.9 (Amide-C=O), 1298.0, 1166.9 (SO$_2$-N)cm$^{-1}$

ESI-MS: (M+H)$^+$=857

(M+Na)$^+$=879 b) (R)-N-[[4-(Benzoylaminomethyl)phenyl]methyl]-$N^2$-(diphenyl-acetyl)-argininamide-trifluoroacetate Prepared analogously to Example 1f) from (R)-N-[[4-(benzoyl-aminomethyl)phenyl]methyl]-$N^2$-(diphenylacetyl)-$N^G$-(2,2,5,7,8-pentamethylchroman-6-sulphonyl)-argininamide and trifluoroacetic acid in a yield of 95% of theory.

$R_f$ value: 0.71; colourless crystals, Mp. 96–102° C.

IR (KBr): 1658.7 (Amide-C=O) cm$^{-1}$

ESI-MS: (M+H)$^+$=591

(M+Na)$^+$=613

EXAMPLE 13

(R)-$N^2$-(Diphenylacetyl)-N-[[4-(phenylaminocarbonylamino-methyl)phenyl]methyl]-argininamide-trifluorocetate a) (R)-$N^2$-(Diphenylacetyl)-$N^G$-(2,2,5,7,8-pentamethylchroman-6-sulphonyl)-N-[[4-(phenylaminocarbonylaminomethyl)phenyl]-methyl]-argininamide Prepared analogously to Example 11a) from (R)-N-[[4-(aminomethyl)phenyl]methyl]-$N^2$-(diphenylacetyl)-$N^G$-(2, 2,5,7,8-pentamethylchroman-6-sulfonyl)-argininamide and phenylisocyanate in a yield of 70% of theory. Colourless crystals, Mp. 141–144° C.

IR (KBr): 1643.3 (Amide-C=O), 1299.9, 1166.9 ($SO_2$-N) $cm^{-1}$ b) (R)-$N^2$-(Diphenylacetyl)-N-[[4-(phenylaminocarbonylamino-methyl)phenyl]methyl]-argininamide-trifluoroacetate Prepared analogously to Example 1f) from (R)-$N^2$-(diphenyl-acetyl)-$N^G$-(2,2,5,7,8-pentamethylchroman-6-sulphonyl)-N-[[4-(phenylaminocarbonylaminomethyl)phenyl]methyl]-argininamide and trifluoroacetic acid in a yield of 91% of theory.

$R_f$ value: 0.73; colourless crystals, Mp. 102–106° C.

IR (KBr): 1660.6 (Amide-C=O) $cm^{-1}$

ESI-MS: $(M+H)^+$=606

EXAMPLE 14

(R,S)-N-[[[4-(Aminocarbonylaminomethyl)phenyl]methyl]-3-[3-(aminoiminomethyl)phenyl]-$N^2$-(diphenylacetyl)-alaninamide acetate a) (R,S)-3-(3-Cyanophenyl)alanine-hydrochloride Prepared analogously to Example 5b) from diethyl α-(acetamido)-α-[(3-cyanophenyl)methyl]malonate (Mp. 139–141° C.; prepared analogously to Example 5a) from diethyl α-acetamido-malonate and 3-(bromomethyl) benzonitrile in the presence of sodium methoxide), hydrochloric acid and glacial acetic acid in a yield of 69% of theory.

Colourless crystals, Mp. 206° C. (D.).

b) (R,S)-3-(3-Cyanophenyl)-$N^2$-(diphenylacetyl)-alanine

Prepared analogously to Example 4a) from (R,S)-3-(3-cyanophenyl)-alanine-hydrochloride and diphenylacetylchloride in the presence of sodium hydroxide solution in a yield of 58% of theory.

Colourless crystals, Mp. 145–147° C. (ethyl acetate).

IR (KBr): 3380 (N-H), 2230 (C N), 1725 (Carboxylic acid-C=O), 1665 (Amide-C=O), 1515 (Amide-II) $cm^{-1}$ c) (R,S)-N-[[4-(Aminocarbonylaminomethyl)phenyl]methyl]-3-(3-cyanophenyl)-$N^2$-(diphenylacetyl)-alaninamide Prepared analogously to Example 4b) but using dimethylformamide instead of dimethylformamide/tetrahydrofuran mixture, from (R,S)-3-(3-cyanophenyl)-$N^2$-(diphenylacetyl)-alanine, 4-(amino-carbonylaminomethyl)benzenemethanamine and TBTU in a yield of 59% of theory. Colourless crystals, Mp. 210–212° C. (ethanol).

IR (KBr): 2229.6 (C N), 1641.3 (Amide/Urea-C=O) $cm^{-1}$ d) (R,S)-N-[[4-(Aminocarbonylaminomethyl)phenyl]methyl]-3-[3-[amino(hydroxyimino)methyl]phenyl]-$N^2$-(diphenylacetyl)-alaninamide A mixture of 273 mg (0.5 mMol) of (R,S)-N-[[4-(aminocarbonyl-aminomethyl)phenyl]methyl]-3-(3-cyanophenyl)-$N^2$-(diphenylacetyl)-alaninamide, 69.5 mg (1.0 mMol) of hydroxylaminohydrochloride, 30 ml of methanol and 0.17 ml (0.126 g; 1 mMol) of diisopropyl-ethylamine were refluxed for 24 hours. The same amounts of hydroxylaminehydrochloride and diisopropylethylamine were added again and the mixture was refluxed for a further 24 hours. It was filtered hot and the solvent was eliminated from the filtrate. The residue was stirred with water and suction filtered. The colourless crystals obtained were decocted with acetone, washed with ether and dried.

Yield: 190 mg (66% of theory).

IR (KBr): 1641.3 (Amide/Urea-C=O)

ESI-MS: $(M+H)^+$=579

$(M+Na)^+$=601 e) (R, S)-N-[[4-(Aminocarbonylaminomethyl)phenyl]methyl]-3-[3-aminoiminomethyl)phenyl]-$N^2$-(diphenylacetyl)-alanine-amide-acetate Prepared analogously to Example 4c), but using palladium on animal charcoal (10%) as catalyst and using glacial acetic acid as solvent, from (R, S)-N-[[4-(aminocarbonylaminomethyl)phenyl]methyl]-3-[3-[amino (hydroxyimino)methyl]phenyl]-$N^2$-(diphenylacetyl)-alaninamide in a yield of 38% of theory.

$R_f$ value: 0.66; colourless crystals, Mp. 188–190° C.

IR (KBr): 1643.3 (Amide-/Urea-C=O) $cm^{-1}$,

Bands of salt

ESI-MS: $(M+H)^+$=563

EXAMPLE 15

(R)-N-[[4-(Aminocarbonylaminomethyl)phenyl]methyl]-$N^2$-(diphenylacetyl)-$N^5$-(1H-imidazol-2-yl)-ornithinamide-hydroiodide a) (R)-$N^2$-(Diphenylacetyl)-$N^5$-(phenylmethoxycarbonyl)-ornithine Prepared analogously to Example 4a) from diphenylacetylchloride and (R)-$N^5$-(phenylmethoxycarbonyl)ornithine in a yield of 81% of theory.

Colourless crystals, Mp. 127–128° C. (ethyl acetate).

IR (KBr): 3400.3, 3313.5 (N-H), 1708.8, 1679.9, 1662.5, 1645.2 (C=O) $cm^{-1}$ b) (R)-N-[[4-(Aminocarbonylaminomethyl)phenyl]methyl]-$N^2$-(diphenylacetyl)-$N^5$-(phenylmethoxycarbonyl)-ornithine-amide Prepared analogously to Example 14c) from (R)-$N^2$-(diphenylacetyl)-$N^5$-(phenylmethoxycarbonyl)-ornithine, 4-(aminocarbonylaminomethyl)benzenemethanamine and TBTU in a yield of 92% of theory.

Colourless crystals, Mp. 188–190° C.

IR (KBr): 1696.5 (Urethane-CO), 1663.6 (Amide-C=O), 1637.3 (Urea-C=O) $cm^{-1}$ c) (R)-N-[[4-(Aminocarbonylaminomethyl)phenyl]methyl]-$N^2$-(diphenylacetyl)-ornithinamide Prepared analogously to Example 1d) from (R)-N-[[4-(aminocarbonylaminomethyl)phenyl]methyl]-$N^2$-(diphenylacetyl)-$N^5$-(phenyl-methoxycarbonyl)-ornithinamide by catalytic hydrogenation in the presence of palladium on activated charcoal in a yield of 33% theory. Colourless, highly viscous oil.

IR (KBr): 3429.2, 3278.8 (N-H), 1637.5 (Amide-/Urea-C=O) $cm^{-1}$

ESI-MS: $(M+H)^+$=488 d) (R)-N-[[4-(Aminocarbonylaminomethyl)phenyl]methyl]-$N^2$-(diphenylacetyl)-$N^5$-(1H-imidazol-2-yl)-ornithinamide-hydroiodide A mixture of 1.47 g (3.015 mMol) of (R)-N-[[4-(aminocarbonyl-aminomethyl)phenyl]methyl]-$N^2$-

(diphenylacetyl)-ornithinamide, 3.0 g (8.977 mMol) of N-(2,2-diethoxyethyl)-S-methylthiouroniumiodide, 0.91 g (8.993 mMol) of triethylamine and 25 ml dimethylformamide were stirred for 4 hours at a reaction temperature of 75 to 80° C., during which time methanethiol was released. The dimethylformamide was distilled off in vacuo, the residue remaining was dissolved in 25 ml of ethanol and after the addition of 5 ml of 2N aqueous hydrochloric acid it was stirred overnight at ambient temperature. The reaction mixture was evaporated down in vacuo, the residue was taken up in 50 ml of water and extracted with ethyl acetate. The ethyl acetate extract was discarded, the aqueous phase was made alkaline with potassium carbonate and extracted once more with 50 ml of ethyl acetate. The unextractable oily substance was left to stand, the aqueous layer was decanted off, the oily part was dissolved in ethanol to purified by column chromatography on silica gel (Baker, 0.03 to 0.06 mm) using ethyl acetate/methanol/conc. ammonia=70/30/1 (v/v/v) as eluant. From the appropriate eluates were obtained 220 mg (11% of theory) of colourless crystals, Mp. 192–194° C.

$R_f$ value: 0.60.

IR (KBr): 3510.2 (Amide-N-H), 1672.2 (Amide-C=O)

1649.0 (Urea-C=O) cm$^{-1}$

ESI-MS: (M+H)$^+$=554

(M+Na)$^+$=576

(M+K)$^+$=592

EXAMPLE 16

(R)-N-[[4-(Aminosulphonylmethyl)phenyl]methyl]-N$^2$-(diphenyl-acetyl)-argininamide-diacetate a) 4-Cyanobenzenemethanesulphonic Prepared analogously to Example 7c) from 4-cyanobenzene-methanesulphonic acid chloride and ammonia gas in a yield of 67% of theory.

Colourless crystals.

b) 4-(Aminosulphonylmethyl)benzenemethanamine

Prepared analogously to Example 6c) from 4-cyanobenzene-methanesulphonamide by catalytic hydrogenation in the presence of ammonia and Raney nickel in a yield of 92% of theory.

Colourless crystals, Mp. 150–153° C.

IR (KBr): 3375.2, 3319.3 (N-H), 1319.2, 1132.1 (SO$_2$N) cm$^{-1}$ c) (R)-N$^5$-[Amino(nitroimino)methyl]-N-[[4-(aminosulphonyl-methyl)phenyl]methyl]-N$^2$-(diphenylacetyl)-ornithinamide Prepared analogously to Example 4b) from (R)-N$^5$-[amino(nitroimino)methyl]-N$^2$-(diphenylacetyl)-ornithine, 4-(aminosulphonylmethyl)-benzenemethanamine and TBTU in a yield of 98% of theory.

IR (KBr): 1637.5 (Amide-C=O), 1330.8, 1128.3 (SO$_2$-N) cm$^{-1}$

ESI-MS: (M+H)$^+$=596

(M+Na)$^+$=618

(M+K)$^+$=634 d) (R)-N-[[4-(Aminosulphonylmethyl)phenyl]methyl]-N$^2$-(diphenyl-acetyl)argininamide-diacetate Prepared analogously to Example 4c) from (R)-N$^5$-[amino(nitroimino)methyl]-N-[[4-(aminosulphonylmethyl) phenyl]methyl]-N$^2$-(diphenylacetyl)-ornithinamide by catalytic hydrogenation in the presence of palladium black and 80% acetic acid in a yield of 96% of theory.

$R_f$ value: 0.59; colourless amorphous substance.

IR (KBr): 1652.9 (Amide-C=O), 1328.9, 1128.3 (SO$_2$-N) cm$^{-1}$,

Bands of salt

ESI-MS: (M+H)$^+$=551.

EXAMPLE 17

(R)-N-[[4-[[(5-Amino-1H-1,2,4-triazol-3-yl)amino] methyl]-phenyl]methyl]-N$^2$-(diphenylacetyl)argininamide-bis-(trifluoroacetate)

a) (R)-N-[[4-[[[(Cyanoimino)phenoxymethyl]amino] methyl]-phenyl]methyl]-N$^2$-(diphenylacetyl)-N$^G$-(2,2,5,7,8-pentamethyl-chroman-6-sulphonyl)-argininamide A mixture of 2.5 g (3.32 mMol) of (R)-N-[[4-(aminomethyl)-phenyl]methyl]-N$^2$-(diphenylacetyl)-N$^G$-(2,2,5,7,8-pentamethyl-chroman-6-sulphonyl)-argininamide, 0.80 g (3.36 mMol) of N-cyanodiphenoxyimidocarbonate and 50 ml of isopropanol was stirred for 15 hours at ambient temperature. The crystal slurry formed was suction filtered, washed twice with 5 ml of isopropanol and once with 50 ml of diethylether and dried in vacuo. 2.3 g (72% of theory) of colourless crystals were obtained, Mp. 127–133° C. (D.)

IR (KBr): 3440.8, 3288.4 cm$^{-1}$ (N-H), 2192.9 (C N), 1643.3 (Amide-C=O) cm$^{-1}$ b) (R)-N-[[4-[[(5-Amino-1H-1,2,4-triazol-3-yl)amino] methyl]-phenyl]methyl]-N$^2$-(diphenylacetyl)-N$^G$-(2,2,5,7,8-pentamethylchroman-6-sulphonyl)-argininamide To a suspension of 0.7 g (0.7314 mMol) of (R)-N-[[4-[[[(cyanoimino)-phenoxymethyl]amino]methyl]phenyl] methyl]-N$^2$-(diphenylacetyl)-N$^G$-(2,2,5,7,8-pentamethylchroman-6-sulphonyl)-argininamide in 20 ml methanol were added 0.05 ml (1.03 mMol) of hydrazine hydrate and the mixture was then stirred for 60 hours at ambient temperature. The colourless precipitate formed was suction filtered and washed with diethylether. 0.49 g (82% of theory) of colourless crystals were obtained, Mp. 163–166° C.

IR (KBr): 1639.4 (Amide-C=O, C=N) cm$^{-1}$

ESI-MS: (M+H)$^+$=835

(M+Na)$^+$=857 c) (R)-N-[[4-[[(5-Amino-1H-1,2,4-triazol-3-yl)amino] methyl]-phenyl]methyl]-N$^2$-(diphenylacetyl)argininamide-bis-(trifluoroacetate)

Prepared analogously to Example 1f) from (R)-N-[[4-[[(5-amino-1H-1,2,4-triazol-3-yl)amino]methyl]phenyl] methyl]-N$^2$-(diphenylacetyl)-N$^G$-(2,2,5,7,8-pentamethylchroman-6-sulphonyl)argininamide and trifluoroacetic acid in a yield of 87% of theory. $R_f$ value: 0.48; colourless crystals.

ESI-MS: (M+H)$^+$=569

(M+2H)$^{++}$=285

EXAMPLE 18

(R)-N$^2$-(Diphenylacetyl)-N-[[4-[[(1H-imidazol-2-yl) amino]-methyl]phenyl]methyl]-argininamide-trifluoroacetate a) (R)-N-[[4-[[[[(2,2-Diethoxyethyl)amino]iminomethyl] amino]-methyl]phenyl]methyl]-N$^2$-(diphenylacetyl)-N$^G$-(2,2,5,7,8-pentamethylchroman-6-sulphonyl)-argininamide A mixture of 0.75 g (0.996 mMol) of (R)-N-[[4-(aminomethyl)-phenyl]methyl]-N$^2$-(diphenylacetyl)-N$^G$-(2, 2,5,7,8-pentamethyl-chroman-6-sulphonyl)-argininamide, 1.0 g (2.992 mMol) of N-(2,2-diethoxymethyl)-S-methylthiouronium iodide, 0.50 g (4.94 mMol) of triethylamine and 10 ml of ethanol was stirred for 16 hours at a reaction temperature of 60 to 70° C., during which methanethiol was released. The solvent was distilled off in vacuo, the residue remaining was distributed between dichloromethane and water, the dichloromethane phase was dried over sodium sulphate and evaporated down again. The remaining product, when purified by column chromatography on silica gel (Macherey-Nagel, 35–70 mesh ASTM) using dichloromethane/methanol/conc. aqueous ammonia= 80/20/0.25 (v/v/v) as eluant, yielded 0.70 g (77% of theory) of a lemon-yellow, glassy, amorphous substance.

IR (KBr): 1652.9, 1635.5 (Amide-C=O, C=N) cm$^{-1}$

ESI-MS: (M+H)$^+$=911

(M+Na)$^+$=933 b) (R)-N$^2$-(Diphenylacetyl)-N-[[4-[[(1H-imidazol-2-yl)amino]-methyl]phenyl]methyl]-N$^G$-(2,2,5,7,8-pentamethylchroman-6-sulphonyl)argininamide 0.6 g (0.658 mMol) of (R)-N-[[4-[[[[(2,2-diethoxyethyl)amino]-iminomethyl]amino]methyl]phenyl]methyl]-N$^2$-(diphenylacetyl)-N$^G$-(2,2,5,7,8-pentamethylchroman-6-sulphonyl)-argininamide were dissolved in 5 ml of methanol and mixed with 5 ml of conc. aqueous hydrochloric acid whilst being externally cooled with ice, the mixture was taken out of the ice bath and left to stand at ambient temperature for 40 hours. The solvent was removed in vacuo, the residue was taken up in dichloromethane and washed once with water and once with saturated saline solution. The combined dichloromethane phases were dried over sodium sulphate and evaporated down in vacuo and the residue remaining was further purified by column chromatography on silica gel (Macherey-Nagel, 35–70 mesh ASTM) using dichloromethane/methanol/conc. aqueous ammonia=90/10/0.3 (v/v/v). 0.16 g (30% of theory) of a colourless, glassy-amorphous substance were obtained.

ESI-MS: (M+H)$^+$=819

(M+Na)$^+$=841 c) (R)-N$^2$-(Diphenylacetyl)-N- [[4-[[(1H-imidazol-2-yl)amino]-methyl]phenyl]methyl]-argininamide-trifluoroacetate Prepared analogously to Example 1f) from (R)-N$^2$-(diphenylacetyl)-N-[[4-[[(1H-imidazol-2-yl)amino]methyl]phenyl]methyl]-N$^G$-(2,2,5,7,8-pentamethylchroman-6-sulphonyl)-argininamide and trifluoroacetic acid in a yield of 68% of theory.

R$_f$ value: 0.43; colourless crystals.

IR (KBr): 1670.3 (Amide-C=O, Guanidinium) cm$^{-1}$

ESI-MS: (M+H)$^+$=553

(M+2H)$^{++}$=277

EXAMPLE 19

(R)-N-[[4-(Aminocarbonylaminomethyl)phenyl]methyl]-N$^2$-[(3,4-dichlorophenyl)acetyl]-argininamide-trifluoroacetate a) (R)-N-[[4-(Aminocarbonylaminomethyl)phenyl]methyl]-N$^2$-(9-fluorenylmethoxycarbonyl)-N$^G$-(4-methoxy-2,3,6-trimethyl-phenylsulphonyl)-argininamide Prepared analogously to Example 1a) but using dimethylformamide as solvent instead of tetrahydrofuran, from (R)-N$^2$-(9-fluorenylmethoxycarbonyl)-N$^G$-(4-methoxy-2,3,6-trimethylphenylsulphonyl)-arginine, 4-(aminocarbonylaminomethyl)benzenemethanamine and dicyclohexylcarbodiimide. The product was used in the next step without purification.

ESI-MS: (M+H)$^+$=770

(M+Na)$^+$=792 b) (R)-N-[[[4-(Aminocarbonylaminomethyl)phenyl]methyl]-N$^G$-(4-methoxy-2,3,6-trimethylphenylsulphonyl)-argininamide Prepared analogously to Example 1b) from (R)-N-[[4-(aminocarbonylaminomethyl)phenyl]methyl]-N$^2$-(9-fluorenylmethoxycarbonyl)-N$^G$-(4-methoxy-2,3,6-trimethylphenylsulphonyl)-argininamide and diethylamine in a yield of 32% of theory.

Colourless amorphous substance.

IR (KBr): 3431.2, 3344.4 (N-H), 1656.8 (Amide-C=O), 1620.1 (Urea-C=O/C=N) cm$^{-1}$ c) (R)-N-[[4-(Aminocarbonylaminomethyl)phenyl]methyl]-N$^2$-[(3,4-dichlorophenyl)acetyl]-N$^G$-(4-methoxy-2,3,6-trimethyl-phenylsulphonyl)-argininamide Prepared analogously to Example 4b) from 3,4-dichlorophenyl-acetic acid, (R)-N-[[4-(aminocarbonylaminomethyl)phenyl]methyl]-N$^G$-(4-methoxy-2,3,6-trimethylphenylsulphonyl)-argininamide and TBETU in a yield of 65% of theory.

Colourless amorphous substance.

IR (KBr): 1652.9 (Amide-C=O), 1629.8 (Urea-C=O) cm$^{-1}$ d) (R)-N-[[4-(Aminocarbonylaminomethyl)phenyl]methyl]-N$^2$-[(3 4-dichlorophenyl)acetyl]-argininamide-trifluoroacetate Prepared analogously to Example 1f) from (R)-N-[[4-(aminocarbonylaminomethyl)phenyl]methyl]-N$^2$-[(3,4-dichlorophenyl)acetyl]-N$^G$-(4-methoxy-2,3,6-trimethylphenylsulphonyl)-argininamide and trifluoroacetic acid in a yield of 75% of theory.

R$_f$ value: 0.55; colourless crystals, Mp. 100–104° C.

IR (KBr): 1660.6 (Amide-C=O), 1203.5, 1136.0 (Trifluoroacetate) cm$^{-1}$

ESI-MS: (M+H)$^+$522/524/526 (Cl$_2$).

EXAMPLE 20

(R)-N-[4-(Aminocarbonylaminomethyl)phenyl]methyl]-N$^2$-[(2-naphthyl)acetyl]-argininamide-trifluoroacetate a) (R)-N-[[4-(Aminocarbonylaminomethyl)phenyl]methyl]-N$^G$-(4-methoxy-2,3,6-trimethylphenylsulphonyl)-N$^2$-[(2-naphthyl)-acetyl]-argininamide Prepared analogously to Example 4b) from 2-naphthylacetic acid, (R)-N-[[4-(aminocarbonylaminomethyl)phenyl]methyl]-N$^G$-(4-methoxy-2,3,6-trimethylphenylsulphonyl)-argininamide and TBTU in a yield of 65% of theory.

Colourless amorphous substance.

IR (KBr): 1652.9 (Amide-/Urea-C=O), 1307.7, 1118.6 (SO$_2$-N) cm$^{-1}$ b) (R)-N-[[4-(Aminocarbonylaminomethyl)phenyl]methyl]-N$^2$-[(2-naphthyl)acetyl]-argininamide-trifluoroacetate Prepared analogously to Example 1f) from (R)-N-[4-(aminocarbonylaminomethyl)phenyl]methyl]-N$^G$-(4-methoxy-2,3,6-trimethyl-phenylsulphonyl)-N$^2$-[(2-naphthyl)acetyl]-argininamide and trifluoroacetic acid in a yield of 73% of theory.

R$_f$ value: 0.56; colourless crystals, Mp. 158–163° C.

IR (KBr): 1652.9 (Amide-/Urea-C=O), 1205.4, 1182.3, 1128.3 (Trifluoroacetate) cm$^{-1}$

ESI-MS: (M+H)$^+$=504

(M-Na)$^+$=526

EXAMPLE 21

(R)-N-[[4-(Aminocarbonylaminomethyl)phenyl]methyl]-N$^2$-[(5-bromo-1H-indol-$^3$-yl)acetyl]-argininamide-trifluoroacetate a) (R)-N-[[4-(Aminocarbonylaminomethyl)phenyl]methyl]-N$^2$-[(5-bromo-1H-indol-3-yl)acetyl]-N$^G$-(4-methoxy-2,3,6-trimethyl-phenylsulphonyl)-argininamide Prepared analogously to Example 4b) from 5-bromo-1H-indole-3-acetic acid, (R)-N-[[4-(aminocarbonylaminomethyl)phenyl]methyl]-N$^G$-(4-methoxy-2,3,6-trimethylphenylsulphonyl)-arginin-amide and TBTU in a yield of 94% of theory.

Colourless amorphous substance.

IR (KBr): 1652.9 (Amide-/Urea-C=O), 1307.7, 1120.6 (SO$_2$-N)

b) (R)-N-[[4-(Aminocarbonylaminomethyl)phenyl]methyl]-N$^2$-[(5-bromo-1H-indol-3-yl)acetyl]argininamide-trifluoroacetate Prepared analogously to Example 1f) from (R)-N-[[4-(aminocarbonylaminomethyl)phenyl]methyl]-N$^2$-[(5-bromo-1H-indol-3-yl)-acetyl]-N$^G$-(4-methoxy-2,3,6-trimethylphenylsulphonyl)-argininamide and trifluoroacetic acid in a yield of 80% of theory.

R$_f$ value: 0.54; colourless crystals, Mp. 120–124° C.

IR (KBr): 1654.8 (Amide-/Urea-C=O) cm$^{-1}$

ESI-MS: (M+H)$^+$=571/573 (Br.).

EXAMPLE 22

(R)-N-[[4-(Aminocarbonylaminomethyl)phenyl]methyl]-N$^2$-(3,3-di-phenyl-1-oxopropyl)-argininamide-trifluoroacetate a) (R)-N-[[4-(Aminocarbonylaminomethyl)phenyl]methyl]-N$^2$-(3,3-diphenyl-1-oxopropyl)-N$^G$-(4-methoxy-2,3,6-trimethylphenylsulphonyl)argininamide Prepared analogously to Example 4b) from 3,3-diphenylpropionic acid, (R)-N-[[4-(aminocarbonylaminomethyl)phenyl]methyl]-N$^G$-(4-methoxy-2,3,6-trimethylphenylsulphonyl)-argininamide and TBTU in a yield of 100% of theory.

Colourless amorphous foamy substance.

IR (KBr): 1654.8 (Amide-/Urea-C=O), 1307.7, 1120.6 (SO$_2$-N) cm$^{-1}$ b) (R)-N-[[4-(Aminocarbonylaminomethyl)phenyl]methyl]-N$^2$-(3,3-diphenyl-1-oxopropyl)-argininamide-trifluoroacetate Prepared analogously to Example 1f) from (R)-N-[[4-(aminocarbonylaminomethyl)phenyl]methyl]-N$^2$-(3,3-diphenyl-1-oxopropyl)-N$^G$-(4-methoxy-2,3,6-trimethylphenylsulphonyl)-argininamide and trifluoroacetic acid in a yield of 56% of theory.

R$_f$ value: 0.59; colourless crystals, Mp. 104–108° C.

By treating a methanolic solution of the above salt with 1N sodium hydroxide solution and working up in the usual way the free base is obtained, Mp. 129–132° C.

IR (KBr): 1652.9 (Amide-C=O), 1624.0 (Urea-C=O, C=N) cm$^{-1}$

ESI-MS: (M+H)$^+$=544

(M+Na)$^+$=566

EXAMPLE 23

(R)-N$^2$-(Diphenylacetyl)-N-[[4-(ethylaminocarbonylaminomethyl)-phenyl]methyl]-argininamide-bis-(trifluoroacetate)

a) (R)-N$^2$-(Diphenylacetyl)-N-[[4-(ethylaminocarbonylaminomethyl)phenyl]methyl]-N$^6$-(2,2,5,7,8-pentamethylchroman-6-sulphonyl)-argininamide Prepared analogously to Example 11a) from (R)-N-[[4-(amino-methyl)phenyl]methyl]-N$^2$-(diphenylacetyl)-N$^G$-(2,2,5,7,8-pentamethylchroman-6-sulphonyl)-argininamide and ethylisocyanate in a yield of 93% of theory.

Colourless crystals.

IR (KBr): 1637.5 (Amide-/Urea-C=O) cm$^{-1}$

ESI-MS: (M+H)$^+$=824

(M+Na)$^+$=846

(M+K)$^+$=862 b) (R)-N$^2$-(Diphenylacetyl)-N-[[4-(ethylaminocarbonylaminomethyl)-phenyl]methyl]-argininamide-bis-(trifluoroacetate)

Prepared analogously to Example 1f) from (R)-N$^2$-(diphenylacetyl)-N-[[-4-(ethylaminocarbonylaminomethyl)phenyl]methyl]-N$^G$-(2,2,5,7,8-pentamethylchroman-6-sulphonyl)-argininamide and trifluoroacetic acid in a yield of 87% of theory.

R$_f$ value: 0.68; colourless crystals.

IR (KBr): 1652.9 (Amide-/Urea-C=O),

ESI-MS: (M+H)$^+$=558

(M+Na)$^+$=580

(M+H+Na)$^{++}$=290.5

EXAMPLE 24

(R)-N$^2$-(Diphenylacetyl)-N-[[4-[(1-methylethyl)aminocarbonyl-aminomethyl]phenyl]methyl]-argininamide a) (R)-N$^2$-(Diphenylacetyl)-N-[[4-[(1-methylethyl)aminocarbonylaminomethyl]phenyl]methyl]-N$^G$-(2,2,5,7,8-pentamethyl-chroman-6-sulphonyl)-argininamide Prepared analogously to Example 11a) from (R)-N-[[4-(aminomethyl)phenyl]methyl]-N$^2$-(diphenylacetyl)-N$^G$-(2,2,5,7,8-pentamethylchroman-6-sulphonyl)-argininamide and isopropylisocyanate in a yield of 93% of theory.

Colourless crystals.

IR (KBr): 1649.9 (Amide-/Urea-C=O) cm$^{-1}$

Bands of salt

ESI-MS: (M+H)$^+$=572

(M+H−Na)$^{++}$=297.5 b) (R)-N$^2$-(Diphenylacetyl)-N-[[4-[(1-methylethyl)aminocarbonylaminomethyl]phenyl]methyl]-argininamide-bis-(trifluoroacetate)

Prepared analogously to Example 1f) from (R)-N$^2$-(diphenylacetyl)-N-[[4-[(1-methylethyl)aminocarbonylaminomethyl]phenyl]methyl]-N$^G$-(2,2,5,7,8-pentamethylchroman-6-sulphonyl)-argininamide and trifluoroacetic acid in a yield of 71% of theory.

R$_f$ value: 0.70; colourless crystals.

IR (KBr): 1649.9 (Amide-/Urea-C=O) cm$^{-1}$,

Bands of salt

ESI-MS: (M+H)$^+$=572

(M+H+Na)$^{++}$=297.5

EXAMPLE 25

(R)-N-[[4-[[[Amino(aminocarbonylimino)methyl]amino]methyl]-phenyl]methyl]-N$^2$-(diphenylacetyl)-argininamide-bis-trifluoroacetate a) (R)-N-[[4-[[[Amino(cyanimino)methyl]amino]methyl]phenyl]-methyl]-N$^2$-(diphenylacetyl)-N$^G$-(2,2,5,7,8-pentamethyl-chroman-6-sulphonyl)argininamide To a solution of 1.8 g (1.881 mmol) of (R)-N-[[4-[[[(cyanoimino)-phenoxymethyl]amino]methyl]phenyl]methyl]-N$^2$-(diphenylacetyl)-N$^G$-(2,2,5,7,8-pentamethylchroman-6-sulphonyl)-argininamide in 30 ml of a mixture of methanol and tetrahydrofuran (1/1; v/v), gaseous ammonia was piped in for 1 hour at ambient temperature and then for 4 hours at a reaction temperature of 48° C. and the mixture was then left to stand overnight at ambient temperature. The excess ammonia was distilled off at reduced pressure together with the solvent, the residue was triturated with diethylether and suction filtered. After drying, 1.54 g (100% of theory) of colourless crystals were obtained, Mp. 113–133° C.

IR (KBr): 2177.5 (C N),
1629.8 (Amide-/Urea-C=O, C=N),
1298.0, 1166.9 (SO$_2$-N) cm$^{-1}$
ESI-MS: (M+H)$^+$=820
(M+Na)$^+$=842 b) (R)-N-[[4-[[[Amino(aminocarbonylimino)methyl]amino]-methyl]phenyl]methyl]-N$^2$-(diphenylacetyl)-N$^G$-(2,2,5,7,8-pentamethylchroman-6-sulphonyl)-argininamide-trifluoroacetate To a solution of 0.33 g (0.402 mMol) of (R)-N-[[4-[[[amino(cyanoimino)methyl]amino]methyl]phenyl]methyl]-N$^2$-(diphenylacetyl)-N$^G$-(2,2,5,7,8-pentamethylchroman-6-sulphonyl)-argininamide in 2.4 ml of tetrahydrofuran were added successively 0.264 g (2.32 mMol) of trifluoroacetic acid and 0.04 g (2.22 mMol) of water and the mixture was kept for 18 hours at ambient temperature and then for 6 hours at reflux temperature. It was evaporated down in vacuo and the residue was digested several times with fresh diethylether. After drying, 0.34 g (89% of theory) of colourless crystals were obtained, Mp. 126–146° C.

IR (KBr): 1672.2 (Amide-C=O),
1168.8 (SO$_2$-N),
1203.5, 1136.0, 1109.0 (Trifluoroacetate) cm$^{-1}$
ESI-MS: (M+H)$^+$=838
(M+Na)$^+$=860 c) (R)-N-[[4-[[[Amino(aminocarbonylimino)methyl]amino]-methyl]phenyl]methyl]-N$^2$-(diphenylacetyl)-argininamide-bis-(trifluoroacetate)

Prepared analogously to Example 1f) from (R)-N-[[4-[[[amino(aminocarbonylimino)methyl]amino]methyl]phenyl]methyl]-N$^2$-(diphenyl-acetyl)-N$^G$-(2,2,5,7,8-pentamethylchroman-6-sulphonyl)-argininamide-trifluoroacetate and trifluoroacetic acid in a yield of 75% of theory.

R$_f$ value: 0.45; colourless crystals, Mp. 75–85° C.
IR (KBr): 1666.4 (Amide-/Urea-C=O)
ESI-MS: (M+H)$^+$=572
(M+Na)$^+$=594
(M+2H)+=286.5

EXAMPLE 26

(R)-N-[[4-(Aminocarbonylaminomethyl)phenyl]methyl]-N$^2$-[(4-amino-3,5-dichlorophenyl)acetyl]-argininamide-trifluoroacetate a) (R)-N-[[4-(Aminocarbonylaminomethyl)phenyl]methyl]-N$^2$-9-(fluorenylmethoxycarbonyl)-N$^G$-(2,2,5,7,8-pentamethyl-chroman-6-sulphonyl)-argininamide Prepared analogously to Example 19a) from (R)-N$^2$-(9-fluorenyl-methoxycarbonyl)-N$^G$-(2,2,5,7,8-pentamethylchroman-6-sulphonyl)-arginine, 4-(aminocarbonylaminomethyl)benzenemethanamine and dicyclohexylcarbodiimide in a quantitative yield. Colourless crystals, Mp. 127–133° C. (acetonitrile).

IR (KBr): 1643.3 (Amide-/Urea-C=O),
1298.0 (SO$_2$-N) cm$^{-1}$ b) (R)-N-[[4-(Aminocarbonylaminomethyl)phenyl]methyl]-N$^G$-(2,2,5,7,8-pentamethylchroman-6-sulphonyl)argininamide Prepared analogously to Example 1b) from (R)-N-[[4-(aminocarbonylaminomethyl)phenyl]methyl]-N$^2$-(9-fluorenylmethoxycarbonyl)-N$^G$-(2,2,5,7,8-pentamethylchroman-6-sulphonyl)argininamide and diethylamine in a yield of 79% of theory. Colourless amorphous substance.

IR (KBr): 1652.9 (Amide-/Urea-C=O) cm$^{-1}$,
ESI-MS: (M+H)$^+$=602
(M+Na)$^+$=624
(M+K)$^+$=640 c) (R)-N-[[4-(Aminocarbonylaminomethyl)phenyl]methyl]-N$^2$-[(4-amino-3,5-dichlorophenyl)acetyl]-N$^G$-(2,2,5,7,8-pentamethylchroman-6-sulphonyl)-argininamide Prepared analogously to Example 4b) from 4-amino-3,5-dichlorobenzeneacetic acid, (R)-N-[[4-(aminocarbonylaminomethyl)phenyl]methyl]-N$^G$-(2,2,5,7,8-pentamethylchroman-6-sulphonyl)-argininamide and TBTU in a yield of 26% of theory.

Colourless crystals, Mp. 162–164° C.
IR (KBr): 1643.3 (Amide-/Urea-C=O) cm$^{-1}$ d) (R)-N-[[4-(Aminocarbonylaminomethyl)phenyl]methyl]-N$^2$-[(4-amino-3,5-dichlorophenyl)acetyl]-argininamide-trifluoroacetate Prepared analogously to Example 1f from (R)-N-[[4-(aminocarbonylaminomethyl)phenyl]methyl]-N$^2$-[(4-amino-3,5-dichlorophenyl)-acetyl]-N$^G$-(2,2,5,7,8-pentamethylchroman-6-sulphonyl)-argininamide and trifluoroacetic acid in a yield of 83% of theory.

R$_f$ value: 0.55; colourless crystals, Mp. 116–119° C.
IR (KBr) 3341.8, 3282.6 (N-H),
1650.0 (Amide-/Urea-C=O),
1557.8 (Amide-II),
1208.9, 1136.5 (Trifluoroacetate) cm$^{-1}$
ESI-MS: (M+H)$^+$=537/539/541 (Cl$_2$)

EXAMPLE 27

(R)-N-[[4-(Aminocarbonylaminomethyl)phenyl]methyl]-N$^2$-[(3-methyl-5-phenyl-1H-indol-2-yl)carbonyl]-argininamide-trifluoroacetate a) (R)-N-[[4-(Aminocarbonylaminomethyl)phenyl]methyl]-N$^2$-[(3-methyl-5-phenyl-1H-indol-2-yl)carbonyl]-N$^G$-(2,2,5,7,8-pentamethylchroman-6-sulphonyl)-argininamide Prepared analogously to Example 4b) from 3-methyl-5-phenyl-1H-indole-2-carboxylic acid, (R)-N-[[4-(aminocarbonylaminomethyl)-phenyl]methyl]-N$^G$-(2,2,5,7,8-pentamethylchroman-6-sulphonyl)-argininamide and TBTU in a yield of 72% of theory. Colourless crystals, Mp. 135–138° C.

IR (KEr): 1656.3 (Amide-C=O),
1627.2 (Urea-C=O),
1299.0 (SO$_2$-N) cm$^{-1}$
ESI-MS: (M+H)$^+$=835
(M+Na)$^+$=857 b) (R)-N-[[4-(Aminocarbonylaminomethyl)phenyl]methyl]-N$^2$-[(3-methyl-5-phenyl-1H-indol-2-yl)carbonyl]-argininamide-trifluoroacetate Prepared analogously to Example 1f) from (R)-N-[[4-(aminocarbonylaminomethyl)phenyl]methyl]-N$^2$-[(3-methyl-5-phenyl-1H-indol-2-yl)carbonyl]-N$^G$-(2,2,5,7,8-pentamethylchroman-6-sulphonyl)-argininamide and trifluoroacetic acid in a yield of 87% of theory.

R$_f$ value: 0.59; colourless crystals, Mp. 125–130° C.
IR (KBr): 1668.3 (Amide-/Urea-C=O) cm$^{-1}$
ESI-MS: (M+H)$^+$=569

EXAMPLE 28
(R)-N-[[4-(Aminocarbonylaminomethyl)phenyl]methyl]-N$^2$-[[4-(benzoylamino)phenyl]acetyl]-argininamide-trifluorocetate a) 4-(Benzoylamino)benzeneacetic Acid Prepared analogously to Example 4a) from benzoylchloride and 4-aminobenzene acetic acid in a yield of 52% of theory. Colourless crystals, Mp. 207–208° C. (ethanol).

b) (R)-N-[[4-(Aminocarbonylaminomethyl)phenyl]methyl]-N$^2$-[[4-(benzoylamino)phenyl]acetyl]-N$^G$-(2,2,5,7,8-pentamethylchroman-6-sulphonyl)-argininamide Prepared analogously to Example 4b) from 4-(benzoylamino)benzeneacetic acid, (R)-N-[[4-(aminocarbonylaminomethyl)phenyl]methyl]-N$^G$-(2,2,5,7,8-pentamethylchroman-6-sulphonyl)-argininamide and TBTU in a yield of 65% of theory. Colourless crystals, Mp. 166–170° C.

IR (KBr): 1641.3 (Amide-/Urea-C=O) cm$^{-1}$ c) (R)-N-[[4-(Aminocarbonylaminomethyl)phenyl]methyl]-N$^2$-[[4-(benzoylamino)phenyl]acetyl]-argininamidetrifluoroacetate Prepared analogously to Example 1f) from (R)-N-[[4-(aminocarbonylaminomethyl)phenyl]methyl]-N$^2$-[[4-(benzoylamino)phenyl]-acetyl]-N$^G$-(2,2,5,7,8-pentamethylchroman-6-sulphonyl)-argininamide and trifluoroacetic acid in a yield of 88% of theory.

R$_f$ value: 0.53; colourless crystal, Mp. 125–130° C.
IR (KBr): 1654.8 (Amide-/Urea-C=O) cm$^{-1}$
ESI-MS: (M+H)$^+$=573 (M+Na)$^+$=595

EXAMPLE 29
(R) -N-[[4-(Aminocarbonylaminomethyl)phenyl]methyl]-N$^2$-[[5-(2-phenylethoxy)-1H-indol-2-yl]carbonyl]-argininamidetrifluoroacetate a) 2-Nitro-5-(2-phenylethoxy)-toluene To a sodium ethoxide solution prepared from 15 g (0.652 Mol) of sodium and 500 ml of anhydrous ethanol were added, successively, 100 g (0.653 Mol) of 5-hydroxy-2-nitrotoluene and 90 ml (121.95 g=0.659 Mol) of 2-phenylethylbromide and the mixture was refluxed for 5 hours. A further 50 ml (0.366 Mol) of 2-phenylethylbromide were added and again the mixture was refluxed for 10 hours. The solvent was distilled off in vacuo, the residue was taken up in ether and extracted several times with dilute sodium hydroxide solution. The ethereal phase was evaporated down, the residue was stirred thoroughly with 400 ml of petroleum ether 35/60. The resulting crystals were suction filtered and washed with petroleum ether. Yield: 95.2 g (57% of theory) of slightly yellowish crystals, Mp. 70–72° C. IR (CH$_2$Cl$_2$): 1340, 1515 (NO$_2$) cm$^{-1}$ b) [2-Nitro-5-(2-phenylethoxy)phenyl]pyroracemic Acid To a clear solution obtained by adding 43.7 g (0.389 Mol) of potassium-tert.butoxide to a mixture of 420 ml of anhydrous ether and 162 ml of anhydrous ethanol were added 50.6 ml (54.4 g=0.373 Mol) of diethyl oxalate followed 30 minutes later by a solution of 95 g (0.369 Mol) of 2-nitro-5-(2-phenylethoxy)toluene in 100 ml of anhydrous ether. The mixture was then refluxed for 4 hours and kept at ambient temperature for a further 36 hours. The precipitate was filtered off, washed thoroughly with dry ether and dried in the air. Yield of the potassium salt of ethyl [2-nitro-5-(2-phenylethoxy)phenyl]pyroracemate: 101.5 g (70% of theory).

98.0 g (0.248 Mol) of this potassium salt was stirred with 800 ml of water, adjusted to pH 8–9 using dilute sodium hydroxide solution and stirred overnight at ambient temperature. The solution was filtered, the filtrate was carefully mixed with concentrated hydrochloric acid until the precipitation reaction had ended. The acid precipitated was taken up in dichloromethane, the solution was washed with water, dried over sodium sulphate and evaporated down in vacuo. 87.0 g (74% of theory) of slightly yellowish crystals were obtained, Mp. 100–105° C.

IR (CH$_2$Cl$_2$): 1738, 1790 (C=O) cm$^{-1}$
ESI-MS: M$^+$=329 c) 5-(2-Phenylethoxy)-1H-indole-2-carboxylic Acid 15.0 g (0.0456 Mol) of [2-nitro-5-(2-phenylethoxy)phenyl]-pyroracemic acid were dissolved in a solution of 65 ml of conc. ammonia and 28 ml of water. To this was added rapidly a solution of 85 g (0.306 Mol) of iron(II)-sulphate-heptahydrate in 93 ml of water, the mixture was heated for 1 hour over a steam bath and refluxed for 30 minutes. It was filtered whilst still hot and the precipitate was washed thoroughly with 75 ml of 5% aqueous ammonia. The combined, still hot filtrates were acidified with conc. hydrochloric acid against Congo red. After cooling, they were extracted exhaustively with ethyl acetate and worked up in the usual way. 9.0 g (70% of theory) of colourless crystals were obtained, Mp. 184–187° C. (aqueous ethanol).

IR (KBr): 1685 (C=O) cm$^{-1}$
MS: M$^+$=281 d) (R)-N-[[4-(Aminocarbonylaminomethyl)phenyl]methyl]-N$^2$-[[5-(2-phenylethoxy)-1H-indol-2-yl]carbonyl]-N$^G$-(2,2,5,7,8-pentamethylchroman-6-sulphonyl)-argininamide Prepared analogously to Example 4b) from 5-(2-phenylethoxy)-1H-indole-2-carboxylic acid, (R)-N-[[4-(aminocarbonylaminomethyl)phenyl]methyl]-N$^G$-(2,2,5,7,8-pentamethylchroman-6-sulphonyl)-argininamide and TBTU in a yield of 70% of theory. Colourless crystals, Mp. 138–142° C.

IR (KBr): 1638.2 (Amide-/Urea-C=O), 1546 (Amide-II), 1297.6, 1167.0 (SO$_2$-N) cm$^{-1}$
ESI-MS: (M+H)$^+$=865 (M+Na)$^+$=887 (M+K)$^+$=903 e) (R)-N-[[4-(Aminocarbonylaminomethyl)phenyl]methyl]-N$^2$-[[5-(2-phenylethoxy)-1H-indol-2-yl]carbonyl]-argininamidetrifluoroacetate Prepared analogously to Example 1f) from (R)-N-[[4-(aminocarbonylaminomethyl)phenyl]methyl]-N$^2$-[[5-(2-phenylethoxy)-1H-indol-2-yl]carbonyl]-N$^G$-(2,2,5,7,8-pentamethylchroman-6-sulphonyl)-argininamide and trifluoroacetic acid in a yield of 90% of theory.

R$_f$ value: 0.60; colourless crystals, Mp. 106–111° C.
IR (KBr): 1662.5 (Amide-/Urea-C=O) cm$^{-1}$
ESI-MS: (M+H)$^+$=599 (M+Na)$^+$=621 (M+H+Na)$^{++}$=311 (M+2Na)$^{++}$=322

EXAMPLE 30
(R)-N-[[4-(Aminocarbonylaminomethyl)phenyl]methyl]-N$^2$-[(4-amino-3,5-dibromophenyl)acetyl]-argininamidetrifluoroacetate a) (R)-N-[[4-(Aminocarbonylaminomethyl)phenyl]methyl]-N²-[(4-amino-3,5-dibromophenyl)acetyl]-N^G-(2,2,5,7,8-pentamethylchroman-6-sulphonyl)argininamide Prepared analogously to Example 4b) from 4-amino-3,5-dibromobenzeneacetic acid, (R)-N-[[4-(aminocarbonylaminomethyl)phenyl]methyl]-N^G-(2,2,5,7,8-pentamethylchroman-6-sulphonyl)-argininamide and TBTU in a yield of 71% of theory. Colourless crystals, Mp. 172–176° C. (methanol).

IR (KBr): 1641.3 (Amide-/Urea-C=O) cm⁻¹ b) (R)-N-[[4-(Aminocarbonylaminomethyl)phenyl]methyl]-N²-[(4-amino-3.5-dibromophenyl)acetyl]-argininamidetrifluoroacetate Prepared analogously to Example 1f) from (R)-N-[[4-(aminocarbonylaminomethyl)phenyl]methyl]-N²-[(4-amino-3,5-dibromophenyl)acetyl]-N^G-(2,2,5,7,8-pentamethylchroman-6-sulphonyl)-argininamide and trifluoroacetic acid in a yield of 97% of theory.

$R_f$ value: 0.55; colourless crystals, Mp. 159–161° C.
IR (KBr): 1639.4 (Amide-/Urea-C=O), 1545.2 (Amide-II), 1205.6, 1133.7 (Trifluoroacetate cm⁻¹)
ESI-MS: (M+H)⁺=625/627/629 (Br₂).

EXAMPLE 31

(R)-N-[[4-(Aminocarbonylaminomethyl)phenyl]methyl]-N²-[(5-bromo-3-methyl-1H-indol-2-yl)carbonyl]-argininamidetrifluoroacetate a) (R)-N-[[4-(Aminocarbonylaminomethyl)phenyl]methyl]-N²-[(5-bromo-3-methyl-1H-indol-2-yl)carbonyl]-N^G-(2,2,5,7,8-pentamethylchroman-6-sulphonyl)-argininamide Prepared analogously to Example 4b) from 5-bromo-3-methyl-1H-indole-2-carboxylic acid, (R)-N-[[4-(aminocarbonylaminomethyl)phenyl]methyl]-N^G-(2,2,5,7,8-pentamethylchroman-6-sulphonyl)-argininamide and TBTU in a yield of 84% of theory. Colourless crystals, Mp. 170–175° C.

IR (KBr): 1637.5 (Amide-/Urea-C=O) cm⁻¹ b) (R)-N-[[4-(Aminocarbonylaminomethyl)phenyl]methyl]-N²-[(5-bromo-3-methyl-1H-indol-2-yl)carbonyl]-argininamidetrifluoroacetate Prepared analogously to Example 1f) from (R)-N-[[4-(aminocarbonylaminomethyl)phenyl]methyl]-N²-[(5-bromo-3-methyl-1H-indol-2-yl)-carbonyl]-N^G-(2,2,5,7,8-pentamethylchroman-6-sulphonyl)-argininamide and trifluoroacetic acid in a yield of 100% of theory.

$R_f$ value: 0.58; colourless crystals, Mp. 130–133° C.
IR (KBr): 1662.2 (Amide-/Urea-C=O), 1559.0 (Amide-II), 1205.2, 1137.8 (Trifluoroacetate) cm⁻¹
ESI-MS: (M+H)⁺=571/573 (Br)

EXAMPLE 32

(R) -N-[[4-(Aminocarbonylmethyl)phenyl]methyl]-N²-[(2-naphthyl)carbonyl]-argininamide a) (R)-N²-[(2-Naphthyl)carbonyl]-N⁵-(phenylmethoxycarbonyl)-ornithine Prepared analogously to Example 4a) from 2-naphthalene carboxylic acid and (R)-N⁵-(phenylmethoxycarbonyl)-ornithine in a yield of 73% of theory. Colourless crystals, Mp. 155–157° C.

b) (R)-N-[[4-(Aminocarbonylmethyl)phenyl]methyl]-N²-[(2-naphthyl)carbonyl-N⁵-(phenylmethoxycarbonyl)-ornithinamide Prepared analogously to Example 6d) from (R)-N²-[(2-naphthyl)carbonyl]-N⁵-(phenylmethoxycarbonyl)-ornithine, 4-aminocarbonylmethyl)benzenemethanamine and TBTU in a yield of 61% of theory. Colourless crystals, Mp. 182–184° C.

IR (KBr): 1685.7 (Carbamate-C=O), 1664.5, 1633.6 (Amide-C=O) cm⁻¹ c) (R)-N-[[4-(Aminocarbonylmethyl)phenyl]methyl]-N²-[(2-naphthyl)-carbonyl]-ornithinamide Prepared analogously to Example 1d) but using glacial acetic acid/methanol=1/1 (v/v) as solvent instead of methanol, from (R)-N-[[4-(aminocarbonylmethyl)phenyl]methyl]-N²-[(2-naphthyl)carbonyl]-N⁵-(phenylmethoxycarbonyl)-ornithinamide by catalytic hydrogenation in the presence of palladium on activated charcoal in a yield of 86% of theory. Colourless, highly viscous oil which was used without any further purification.

d) (R)[[4-(Aminocarbonylmethyl)phenyl]methyl]-N²-[(2-naphthyl)carbonyl]-argininamide A mixture of 0.4 g (0.812 mMol) of (R)-N-[[4-(aminocarbonylmethyl)phenyl]methyl]-N²-[(2-naphthyl)carbonyl]-ornithinamide, 0.33 g (1.64 mMol) of 3,5-dimethylpyrazol-1-carboxylic acid amidinium nitrate, 0.5 ml (3.57 mMol) of triethylamine and 25 ml of dimethylformamide was stirred overnight at a reaction temperature of 50° C. The solvent was distilled off in vacuo and the residue was purified by column chromatography (silica gel Baker 30–60 μm) using ethyl acetate/methanol/glacial acetic acid =70/30/1 (v/v/v) as eluant. The appropriate eluates were combined and freed from solvent, the residue was dissolved in a little water and made alkaline with 1N sodium hydroxide solution. The precipitated amorphous substance obtained was suction filtered and dried in vacuo over diphosphorus pentoxide. Yield: 110 mg (29% of theory).

$R_f$ value: 0.56; colourless amorphous substance.
IR (KBr): 1664.5, 1622.0 (Amide-C=O) cm⁻¹
ESI-MS: (M+H)⁺475 (M+Na)⁺=497.

EXAMPLE 33

(R)-N-[[4-(Aminocarbonylmethyl)phenyl]methyl]-N²-(diphenylacetyl)-N⁵-(1H-imidazol-2-yl)-ornithinamide-hydroiodide a) (R)-N-[[4-(Aminocarbonylmethyl)phenyl]methyl]-N²-(diphenylacetyl)-N⁵-(phenylmethoxycarbonyl)-ornithinamide Prepared analogously to Example 6d) from (R)-N²-diphenylacetyl-N⁵-(phenylmethoxycarbonyl)-ornithine, 4-(aminocarbonylmethyl)-benzenemethanamine and TBTU in a yield of 89% of theory. Colourless crystals, Mp. 203–205° C.

IR (KBr): 1689.5 (Carbamate-C=O), 1658.7, 1641.3 (Amide-C=O) cm⁻¹ b) (R)-N-[[4-(Aminocarbonylmethyl)phenyl]methyl]-N²-(diphenylacetyl)-ornithinamide Prepared analogously to Example 1d) but using a mixture of glacial acetic acid and ethanol (1/1, v/v) as solvent instead of methanol, from (R)-N-[[4-(aminocarbonylmethyl)phenyl]methyl]-N²-(diphenylacetyl)-N⁵-(phenylmethoxycarbonyl)-ornithinamide by catalytic hydrogenation in the presence of palladium on animal charcoal in a yield of 82% of theory. Colourless amorphous substance.

c) (R)-N-[[4-(Aminocarbonylmethyl)phenyl]methyl]-N²-(diphenylacetyl)-N⁵-(1H-imidazol-2-yl)-ornithinamide-hydroiodide Prepared analogously to Example 15d) from (R)-N-[[4-(aminocarbonylmethyl)phenyl]methyl]-N²-(diphenylacetyl)-ornithinamide and N-(2,2-diethoxyethyl)-S-methylthiouroniumiodide in a yield of 7% of theory.

$R_f$ value: 0.59; colourless amorphous substance.
IR (KBr): 1662.5 (Amide-C=O) cm⁻¹
ESI-MS: (M+H)⁺=539 (M+Na)+=561

EXAMPLE 34

(R)-N²-(Diphenylacetyl)-N-(ethoxycarbonylaminocarbonylaminomethyl)-[[4-phenyl]methyl]-argininamidetrifluoroacetate a) (R)-N²-(Diphenylacetyl)-N-[[4-(ethoxycarbonylaminocarbonylaminomethyl)phenyl]methyl]-N^G-(2,2,5,7,8-pentamethylchroman-6-sulphonyl)-argininamide Prepared analogously to Example 11a) from (R)-N-[[4-(aminomethyl)-phenyl]methyl]-N²-(diphenylacetyl)-N^G-(2,2,5,7,8-pentamethylchroman-6-sulphonyl)-argininamide and ethoxycarbonyl-isocyanate in a yield of 78% of theory. Colourless, glassy-amorphous substance.

IR (KBr): 1726.2 (Urethane-C=O), 1656.8 (Amide-/Urea-C=O) cm⁻¹ b) (R)-N²-(Diphenylacetyl)-N-[[4-(ethoxycarbonylaminocarbonylaminomethyl)phenyl]methyl]-argininamidetrifluoroacetate Prepared analogously to Example 1f) from (R)-N²-(diphenylacetyl)-N-[[4-(ethoxycarbonylaminocarbonylaminomethyl)phenyl]methyl]-N^G-(2,2,5,7,8-pentamethylchroman-6-sulphonyl)-argininamide and trifluoroacetic acid in a yield of 75% of theory.

$R_f$ value: 0.69; colourless crystals.
IR (KBr): 1668.3 (broad, C=O) cm⁻¹
ESI-MS: (M+H)⁺=602

EXAMPLE 35

(R) -N-[[4-(Dimethylaminocarbonylaminomethyl)phenyl]methyl]-N²-(diphenylacetyl)-argininamide-bis-(trifluoroacetate)

a) (R)-N-[[4-(Dimethylaminocarbonylaminomethyl)phenyl]methyl]-N²-(diphenylacetyl)-N^G-(2,2,5,7,8-pentamethylchroman-6-sulphonyl)-argininamide Prepared analogously to Example 2a) from (R)-N-[[4-(aminomethyl)-phenyl]methyl]-N²-(diphenylacetyl)-N^G-(2,2,5,7,8-pentamethylchroman-6-sulphonyl)-argininamide and dimethylcarbamoylchloride in a yield of 93% of theory. Colourless crystals.

IR (KBr): 1639.4 (Amide-/Urea-C=O) cm⁻¹ b) (R)-N-[[4-(Dimethylaminocarbonylaminomethyl)phenyl]methyl]-N²-(diphenylacetyl)-argininamide-bis-(trifluoroacetate)

Prepared analogously to Example 1f) from (R)-N-[[4-(dimethylaminocarbonylaminomethyl)phenyl]methyl]-N²-(diphenylacetyl)-N^G-(2,2,5,7,8-pentamethylchroman-6-sulphonyl)-argininamide and trifluoroacetic acid in a yield of 84% of theory.

$R_f$ value: 0.55; colourless crystals.
IR (KBr): 1666.5 (Amide-/Urea-C=O), 1541.5 (Amide-II), 1206.3, 1137.6 (Trifluoroacetate) cm⁻¹
ESI-MS: (M+H)⁺=558 (M+Na)⁺=580 (M+K)⁺=596

EXAMPLE 36

(R,S)-N-[[4-(Aminocarbonylmethyl)phenyl]methyl]-N⁵-(aminoiminomethyl)-N²-(diphenylacetyl)-N⁵-methyl-ornithinamidehydrochloride a) (R,S)-N-[[4-(Aminocarbonylmethyl)phenyl]methyl]-N⁵-methyl-N⁵-(phenylmethyl)-ornithinamide Prepared analogously to Example 4b) from (R,S)-N²-(diphenylacetyl)-N⁵-methyl-N⁵-(phenylmethyl)-ornithine, 4-(aminocarbonylmethyl)-benzenemethanamine and TBTU in a yield of 52% of theory. Colourless, amorphous substance.

IR (KBr): 1664.5, 1633.6 (Amide-C=O) cm⁻¹ b) (R,S)-N-[[4-(Aminocarbonylmethyl)phenyl]methyl]-N²-(diphenylacetyl)-N⁵-methyl-ornithinamide Prepared analogously to Example 5e) from (R,S)-N-[[4-(aminocarbonylmethyl)phenyl]methyl]-N²-(diphenylacetyl)-N⁵-methyl-N⁵-(phenylmethyl)-ornithinamide by catalytic hydrogenation in the presence of palladium hydroxide/activated charcoal (Pearlman's catalyst) in a yield of 80% of theory. Colourless crystals, Mp. 203–206° C.

IR (KBr): 1668.3, 1635.5 (Amide-C=O) cm⁻¹
MS: (M+H)⁺=486 c) (R,S)-N-[[4-(Aminocarbonylmethyl)phenyl]methyl]-N⁵-(aminoiminomethyl)-N²-(diphenylacetyl)-N⁵-methyl-ornithinamidehydrochloride Prepared analogously to Example 5f) from (R,S)-N-[[4-(aminocarbonylmethyl)phenyl]methyl]-N²-(diphenylacetyl)-N⁵-methyl-ornithinamide, cyanamide and hydrogen chloride in a yield of 63% of theory.

$R_f$ value: 0.47; colourless, porous-amorphous substance.
IR (KBr): 1652.9, (Amide-C=O) cm⁻¹
ESI-MS: (M+H)⁺=529

EXAMPLE 37

(R)-N-[[4-(Aminocarbonylaminomethyl)phenyl]methyl]-N²-(2,2-diphenyl-1-oxo-2-phenoxyethyl)-argininamidetrifluoroacetate a) (R)-N-[[4-(Aminocarbonylaminomethyl)phenyl]methyl]-N²-(2,2-diphenyl-2-hydroxy-1-oxoethyl)-N⁵-(2,2,5,7,8-pentamethylchroman-6-sulphonyl)-argininamide To a solution of 0.63 g (1.047 mMol) of (R)-N-[[4-(aminocarbonylaminomethyl)phenyl]methyl]-N⁵-(2,2,5,7,8-pentamethylchroman-6-sulphonyl)-argininamide and 0.207 ml (1.188 mMol) of diisopropylethylamine in 10 ml of anhydrous dimethylformamide were added, in batches, 0.32 g (1.207 mMol) of 2-chloro-2,2-diphenylacetylchloride and the mixture was stirred for 2¼ hours at ambient temperature. It was stirred with 25 ml of water and filtered. The crystalline precipitate obtained was dissolved in 7 ml of 80% aqueous acetic acid and heated to 80 C. for 1½ hours after the addition of 0.7 g (8.53 mMol) of sodium acetate. It was digested once more with 25 ml of water, the precipitate formed was suction filtered and dried in vacuo. After purifying by column chromatography on silica gel (Macherey-Nagel, 35–70 mesh ASTM) using dichloromethane/methanol/cyclohexane/conc. aqueous ammonia=68/15/15/2 as eluant and working up the appropriate fractions, 0.48 g (56% of theory) of a colourless amorphous substance were obtained.

IR (KBr): 1658.7 (Amide-C=O) cm⁻¹
ESI-MS: (M+H)⁺=812 (M+Na)⁺=834 b) (R)-N-[[4-(Aminocarbonylaminomethyl)phenyl]methyl]-N²-(2,2-diphenyl-1-oxo-2-phenoxyethyl)-argininamidetrifluoroacetate Prepared analogously to Example 1f) from (R)-N-[[4-(aminocarbonylaminomethyl)phenyl]methyl]-N²-(2,2-diphenyl-2-hydroxy-1-oxo-ethyl)-N⁵-(2,2,5,7,8-pentamethylchroman-6-sulphonyl)-argininamide, anisole and trifluoroacetic acid in a yield of 60% of theory.

$R_f$ value: 0.63; colourless crystals, Mp. 98–100° C.
IR (KBr): 1656.8 (Amide-C=O) cm⁻¹
ESI-MS: (M+H)⁺=622

EXAMPLE 38

(R)-N-[[4-(Aminocarbonyloxymethyl)phenyl]methyl]-N²-(diphenylacetyl)-argininamide-acetate a) (R)-N⁵-[Amino(nitroimino)methyl]-N²-(diphenylacetyl)-N-[[4-(hydroxymethyl)phenyl]methyl]-ornithinamide Prepared analogously to Example 12a) from (R)-N⁵-[amino(nitroimino)methyl]-N²-(diphenylacetyl)-ornithine, [4-(hydroxymethyl)phenyl]methanamine (Mp.: 75–77° C., prepared from 4-cyano-benzaldehyde by reduction with lithium aluminium hydride) and isobutylchlorocarbonate in a yield of 77% of theory. Colourless, amorphous substance.

IR (KBr): 1620–1690 (C=O, C=N) cm$^{-1}$
EI-MS: (M+H)$^+$=533 (M+Na)$^+$=555 b) (R)-N$^5$-[Amino(nitroimino)methyl]-N$^2$-(diphenylacetyl)-N-[[4-(phenoxycarbonyloxymethyl)phenyl]methyl]-ornithinamide To a solution of 1.15 g (2.158 mMol) of (R)-N$^5$-[amino(nitroimino)methyl]-N$^2$-(diphenylacetyl)-N-[[4-(hydroxymethyl)phenyl]methyl]-ornithinamide in 20 ml of pyridine were added 0.42 g (2.683 mMol) of phenylchloroformate, whilst externally cooling with ice, and the mixture was then stirred for a further 2 hours at ambient temperature. The pyridine was distilled off in vacuo, the residue was stirred with water, the crystals precipitated were suction filtered and recrystallised from ethanol. After drying in vacuo, 0.9 g (64% of theory) of colourless crystals were obtained, Mp. 186–187° C.

IR (KBr): 1759.0 (Carbonate-C=O), 1639.4 (Amide-C=O) cm$^{-1}$ c) (R)-N-[[4-(Aminocarbonyloxymethyl)phenyl]methyl]-N$^5$-[amino(nitroimino)methyl]-N$^2$-(diphenylacetyl)-ornithinamide A solution of 0.9 g (1.379 mMol) of (R)-N$^5$-[amino(nitroimino)-methyl]-N$^2$-(diphenylacetyl)-N-[[4-(phenoxycarbonyloxymethyl)-phenyl]methyl]-ornithinamide in 20 ml of dimethylformamide was diluted with 80 ml of dichloromethane and cooled to –50 to –60° C., after which about 50 ml of liquid ammonia were condensed into the mixture. The temperature of the mixture was allowed to come up to ambient temperature within about 6 hours and the ammonia was largely distilled off overnight. Residual ammonia together with the solvents was distilled off in vacuo. The residue was thoroughly triturated with 10 ml of diisopropylether/acetone (1:1, v/v), the precipitate formed was suction filtered and washed with diethylether. After drying, 0.7 g of colourless crystals were obtained, Mp. 130–132° C.

IR (KBr): 1703.0 (Urethane-C=O), 1641.3 (Amide-C=O) cm$^{-1}$ d) (R)-N-[[4-(Aminocarbonyloxymethyl)phenyl]methyl]-N$^2$-(diphenylacetyl)-argininamide-acetate 0.7 g (1.216 mMol) of (R)-N-[[4-(Aminocarbonyloxymethyl)-phenyl]methyl]-N$^5$-[amino(nitroimino)methyl]-N$^2$-(diphenylacetyl)ornithinamide were dissolved in 50 ml of 60% aqueous formic acid, mixed with 2.7 g (11.97 mMol) of tin(II)-chloride-dihydrate and heated to +50° C. for 10 minutes. 20 ml of formic acid were added and the mixture was maintained at +50° C. for a further 72 hours. It was evaporated down in vacuo. the residue was taken up in methanol and filtered to remove the insoluble matter. It was evaporated down once more, the residue remaining was taken up in saturated aqueous soda solution and suction filtered. The crystals were treated once more with methanol, then filtered, the filtrate was evaporated down and carefully freed from any accompanying matter by column chromatography on silica gel (Baker; 0.03–0.06 mm) using ethyl acetate/methanol/glacial acetic acid=70/30/1 (v/v/v) as eluant. 40 mg (5.6% of theory) of a colourless, glassy-amorphous substance were obtained.

R$_f$ value: 0.66.

EXAMPLE 39

(R)-N-[[4-[[[(1,1-Dimethylethoxy)carbonyl]amino]methyl]phenyl]methyl]-N$^2$-(diphenylacetyl)-argininamide-acetate a) (R)-N$^5$-[Amino(nitroimino)methyl]-N-[[4[[[(1,1-dimethylethoxy)carbonyl]amino]methyl]phenyl]methyl]-N$^2$-(diphenylacetyl)-ornithinamide Prepared analogously to Example 4b) from (R)-N$^5$-[amino(nitroimino)-methyl]-N$^2$-(diphenylacetyl)-ornithine and 4-[[[(1,1-dimethylethoxy)carbonyl]amino]methyl]benzenemethanamine in a yield of 66% of theory. Colourless crystals, Mp. 198° C.

IR (KBr): 3477.5, 3294.2 (N-H), 1689.5 (Carbamate-C=O), 1641.3 (Amide-C=O) cm$^{-1}$ b) (R)-N-[[4-[[[(1,1-Dimethylethoxy)carbonyl]amino]methyl]-phenyl]methyl]-N$^2$-(diphenylacetyl)-argininamide-acetate Prepared analogously to Example 4c) from (R)-N$^5$-[amino(nitroimino)-methyl]-N-[[4-[[[(1,1-dimethylethoxy)carbonyl]amino]methyl]phenyl]methyl]-N$^2$-(diphenylacetyl)-ornithinamide by catalytic hydrogenation in the presence of palladium black and 80% aqueous acetic acid in a yield of 75% of theory.

R$_f$ value: 0.69; colourless crystals, Mp. 95–100° C.

IR (KBr): 1682.4 (Carbamate-C=O), 1645.2 (Amide-C=O) cm$^{-1}$

ESI-MS: (M+H)$^+$=587 (M+Na)$^+$=609

EXAMPLE 40

(R,S)-N-[[4-(Aminocarbonylmethyl)phenyl]methyl]-3-[3-(aminoiminomethyl)phenyl]-N$^2$-(diphenylacetyl)-alaninamide-diacetate a) (R,S)-N-[[4-(Aminocarbonylmethyl)phenyl]methyl]-3-(3-cyanophenyl)-N$^2$-(diphenylacetyl)-alaninamide Prepared analogously to Example 6d) from (R,S)-3-(3-cyanophenyl)-N$^2$-(diphenylacetyl)-alanine and 4-(aminocarbonylmethyl)-benzenemethanamine in a yield of 90% of theory. Colourless crystals, Mp. 242–244° C.

IR (KBr): 2231.5 (C N), 1656.8, 1643.3 (Amide-C=O) cm$^{-1}$ b) (R,S)-N-[[4-(Aminocarbonylmethyl)phenyl]methyl]-3-[3-[amino-(hydroxyimino)methyl)phenyl]-N$^2$-(diphenylacetyl)-alaninamide Prepared analogously to Example 14d), but using triethylamine instead of diisopropylamine, from (R,S)-N-[[4-(aminocarbonylmethyl)phenyl]methyl]-3-(3-cyanophenyl)-N$^2$-(diphenylacetyl)-alaninamide and hydroxylamine-hydrochloride in a yield of 81% of theory. Colourless crystals, Mp. 224° C.

IR (KBr): 3485.2, 3408.0, 3348.2, 3263.4 (O-H, N-H), 1651.0 (Amide-C=O) cm$^{-1}$ c) (R,S)-N-[[4-(Aminocarbonylmethyl)phenyl]methyl]-3-[3-(aminoiminomethyl)phenyl]-N$^2$-(diphenylacetyl)-alaninamide-diacetate Prepared analogously to Example 14e) from (R,S)-N-[[4-(aminocarbonylmethyl)phenyl]methyl]-3-[3-[amino(hydroxyimino)-methylphenyl]-N$^2$-(diphenylacetyl)-alaninamide by catalytic hydrogenation in the presence of palladium/activated charcoal and glacial acetic acid in a yield of 21% of theory.

R$_f$ value: 0.63; colourless, amorphous substance.

IR (KBr): 1656.8 (Amide-C=O) cm$^{-1}$

ESI-MS: (M+H)$^+$=548 (M+Na)$^+$=570

EXAMPLE 41

(R)-N-[[4-(Aminocarbonylaminocarbonylaminomethyl)phenyl]-methyl]-N$^2$-(diphenylacetyl)-argininamide-acetate a) (R)-N$^5$-[Amino(nitroimino)methyl]-N-[[4-(aminomethyl)phenyl]methyl]-N$^2$-(diphenylacetyl)-ornithinamide Prepared analogously to Example 1f) from (R)-N$^5$-[amino(nitroimino)methyl]-N-[[4[[[(1,1-dimethylethoxy)-carbonyl]amino]methyl]phenyl]methyl]-N$^2$-(diphenylacetyl)-ornithinamide and trifluoroacetic acid in a yield of 90% of theory. Colourless crystals, Mp. 198–199° C.

IR (KBr): 1645.2 (Amide-C=O) cm$^{-1}$

ESI-MS: (M+H)⁺=532 (M+Na)⁺=554 b) (R)-N-[[4-(Aminocarbonylaminocarbonylaminomethyl)phenyl]-methyl]-N⁵-[amino(nitroimino)methyl]-N²-(diphenylacetyl)-ornithinamide A mixture of 0.53 g (0.997 mMol) of (R)-N⁵-[amino(nitroimino)-methyl]-N-[[4-(aminomethyl)phenyl]methyl]-N²-(diphenylacetyl)-ornithinamide, 0.16 g (1.08 mMol) of nitrobiuret, 50 ml of methanol and 0.2 ml of diisopropylethylamine was refluxed for 5 hours with stirring. The same amount of nitrobiuret and diisopropylethylamine was added again and the mixture was refluxed for a further 3 hours. The crystals obtained after leaving the mixture to stand for 14 hours at ambient temperature were suction filtered, washed thoroughly with methanol and diethylether and dried in vacuo. 0.51 g (83% of theory) of colourless crystals were obtained, Mp. 214–218° C.

ESI-MS: (M+H)⁺=618 (M+Na)⁺=640 c) (R)-N-[[4-(Aminocarbonylaminocarbonylaminomethyl)-phenyl]methyl]-N²-(diphenylacetyl)-argininamide-acetate Prepared analogously to Example 4c) from (R)-N-[[4-(aminocarbonylaminocarbonylaminomethyl)phenyl]methyl]-N⁵-[amino(nitroimino)methyl]-N²-(diphenylacetyl)-ornithinamide by catalytic hydrogenation in the presence of palladium black and 80% aqueous acetic acid in a yield of 76% of theory.

$R_f$ value: 0.59; colourless, glassy-amorphous substance.
IR (KBr): 1662.5 (Amide-C=O) cm⁻¹
ESI-MS: (M+H)⁺=573

EXAMPLE 42
(R)-N-[[4-[[[Amino(cyanimino)methyl]amino]methyl]phenyl]-methyl]-N²-(diphenylacetyl)-argininamide-acetate a) (R)-N⁵-[Amino(nitroimino)methyl]-N-[[4-[[[(cyanimino)phenoxymethyl]amino]methyl]phenyl]methyl]-N²-(diphenylacetyl)ornithinamide Prepared analogously to Example 17a), but using dimethylformamide instead of isopropanol, from (R)-N⁵-[amino(nitroimino)methyl]-N-[[4-(aminomethyl)phenyl]methyl]-N²-(diphenylacetyl)-ornithinamide and N-cyanodiphenoxyimidocarbonate in a yield of 99% of theory. Colourless crystals, Mp. 182–186° C.

IR (KBr): 3377.2, 3300.0, 3211.3 (N-H), 2191.0 (C N), 1641.3 (Amide-C=O) cm⁻¹
ESI-MS: (M+H)⁺=676 (M+Na)⁺=698 (M+K)⁺=714 b) (R)-N-[[4-[[[Amino(cyanimino)methyl]amino]methyl]phenyl]-methyl]-N⁵-[amino(nitroimino)methyl]-N²-(diphenylacetyl)-ornithinamide Prepared analogously to Example 25a), but using dimethylformamide instead of the methanol/tetrahydrofuran mixture from (R)-N⁵-[amino(nitroimino)methyl]-N-[[4-[[[(cyanoimino)phenoxymethyl]amino]methyl]phenyl]methyl]-N²-(diphenylacetyl)-ornithinamide and ammonia in a yield of 96% of theory. Colourless crystals, Mp. 135–140° C. (ethyl acetate).

IR (KBr): 2175.6 (C N), 1641.3 (Amide-C=O) cm⁻¹
ESI-MS: (M+H)⁺=599 (M+Na)⁺=621 (M+K)⁺=637 c) (R)-N-[[4-[[[Amino(cyanoimino)methyl]amino]methyl]phenyl]-methyl]-N²-(diphenylacetyl)-argininamide-acetate Prepared analogously to Example 1d) from (R)-N-[[4-[[[amino-(cyanoimino)methyl]amino]methyl]phenyl]methyl]-N⁵-[amino(nitroimino)methyl]-N²-(diphenylacetyl)-ornithinamide by catalytic hydrogenation in the presence of palladium/activated charcoal and using methanol as solvent. After final purification by column chromatography on silica gel (Macherey-Nagel, 0.063–0.2 mm) using n-butanol/glacial acetic acid/water=4/1/1 (v/v/v) as eluant, the desired compound is obtained as a colourless, amorphous-glassy substance in a yield of 5.9% of theory.

$R_f$ value: 0.60.
IR (KBr): 2175.6 (C N), 1652.9 (Amide-C=O) cm¹
ESI-MS: (M+H)⁺=554 (M+H+Na)²⁺=288.65

EXAMPLE 43
(R)-N²-(Diphenylacetyl)-N-[[4-(methoxycarbonylmethyl)phenyl]-methyl]-argininamide-diacetate a) Methyl 4-cyanobenzeneacetate 20.1 g (0.125 Mol) of 4-cyanobenzeneacetate were dissolved in 400 ml of dichloromethane and, after the addition of 59.5 g (0.5 Mol) of thionylchloride, refluxed for 4 hours. The excess thionylchloride was distilled off together with the solvent, finally in vacuo, the residue was taken up in 400 ml of dry methanol and refluxed for 1 hour. The crude product remaining after the excess methanol had been distilled off was purified by column chromatography on silica gel (Macherey-Nagel, 0.2–0.5 mm) using petroleum ether/ethyl acetate=8/2 (v/v) as eluant and, after the usual working up of the suitable fractions, yielded 9.5 g (43% of theory) of colourless needles, Mp. 40–41° C. (petroleum ether/diisopropylether 1/1, (v/v)).

IR (KBr): 2227.7 (C N), 1735.8 (Carboxylate-C=O) cm⁻¹ b) 4-(Methoxycarbonylmethyl)benzenemethanamine-hydrochloride

A solution of 8.8 g (0.05 Mol) of methyl 4-cyanobenzene acetate in 200 ml of methanol was hydrogenated, after the addition of 50 ml of 1 N aqueous hydrochloric acid and 3 g of palladium on activated charcoal (10%), at ambient temperature under a hydrogen pressure of 3 bar until the uptake of hydrogen had ended. The solution freed from catalyst was evaporated down, the residue was combined with two batches of 50 ml of toluene and evaporated down again. 10.7 g (99% of theory) of a crude crystalline material was obtained which was used without further purification in the next step.

c) (R)-N⁵-[Amino(nitroimino)methyl]-N²-(diphenylacetyl)-N-[[4-(methoxycarbonylmethyl)phenyl]methyl]-ornithinamide Prepared analogously to Example 6d) from (R)-N⁵-[amino(nitroimino)-methyl]-N²-(diphenylacetyl)-ornithinamide and 4-(methoxycarbonylmethyl)benzenemethanamine-hydrochloride in a yield of 21% of theory. Colourless crystals, Mp. 158–160° C.

IR (KBr): 1739.7 (Carboxylate-C=O), 1641.3 (Amide-C=O) cm⁻¹ d) (R)-N²-(Diphenylacetyl)-N-[[4-(methoxycarbonylmethyl)-phenyl]methyl]-argininamide-diacetate Prepared analogously to Example 4c) from (R)-N⁵-[amino(nitroimino)methyl]-N²-(diphenylacetyl)-N-[[4-(methoxycarbonylmethyl)phenyl]methyl]-ornithinamide by catalytic hydrogenation in the presence of palladium black and 80% aqueous acetic acid in a yield of 44% of theory.

$R_f$ value: 0.67; colourless, amorphous substance.
IR (KBr): 1737.8 (Carboxylate-C=O), 1652.9 (Amide-C=O) cm⁻¹
ESI-MS: (M+H)⁺=530 (M+Na)⁺=552

EXAMPLE 44
(R)-N²-(Diphenylacetyl)-N-[[4-(methylaminocarbonylmethyl)-phenyl]methyl]-argininamidetrifluoroacetate a) 4-(Methylaminocarbonylmethyl)benzenemethanamine
Prepared analogously to Example 6c) from 4-cyano-N-methylbenzeneacetamide by catalytic hydrogenation in the presence of Raney nickel and ammonia in a quantitative yield. Colourless oil, which was used in the next step without further purification.

IR (KBr): 3382.9, 3290.4 (N-H), 1658.7 (Amide-C=O) cm$^{-1}$ b) (R)-N$^2$-(Diphenylacetyl)-N$^G$-(2,2,5,7,8-pentamethylchroman-6-sulphonyl)-arginine Prepared analogously to Example 4a) from diphenylacetylchloride, (R)-N$^G$-(2,2,5,7,8-pentamethylchroman-6-sulphonyl)-arginine and sodium hydroxide solution in a quantitative yield. Colourless, amorphous substance.

IR (KBr): 1737.8, (Carboxylic acid-C=O), 1627.8 (Amide-C=O), 1384.8, 1109.0 (SO$_2$-N) cm$^{-1}$ c) (R)-N$^2$-(Diphenylacetyl)-N-[[4-(methylaminocarbonylmethyl)phenyl]methyl]-N$^G$-(2,2,5,7,8-pentamethylchroman-6-sulphonyl)-argininamide Prepared analogously to Example 14c) from (R)-N$^2$-(diphenylacetyl)-N$^G$-(2,2,5,7,8-pentamethylchroman-6-sulphonyl)-arginine, 4-(methylaminocarbonylmethyl)benzenemethanamine and TBTU in a yield of 80% of theory. Colourless, amorphous substance.

IR (KBr): 1652.9 (Amide-C=O), 1298.0, 1166.9 (SO$_2$-N) cm$^{-1}$

ESI-MS: (M+H)$^+$=795 (M+Na)$^+$=817 (M+K)$^+$=833 d) (R)-N$^2$-(Diphenylacetyl)-N-[[4-(methylaminocarbonylmethyl)phenyl]methyl]-argininamidetrifluoroacetate Prepared analogously to Example 1f) from (R)-N$^2$-(diphenylacetyl)-N-[[4-(methylaminocarbonylmethyl)phenyl]methyl]-N$^G$-(2,2,5,7,8-pentamethylchroman-6-sulphonyl)-argininamide and trifluoroacetic acid in a yield of 84% of theory.

R$_f$ value: 0.58; colourless, amorphous-glassy substance.

IR (KBr): 1647.1 (Amide-C=O), 1204.0, 1180.4, 1134.2 (Trifluoroacetate) cm$^{-1}$ ESI-MS: (M+H)$^+$=529 (M+Na)$^+$=551

EXAMPLE 45

(R)-[[4-[[[(Dimethylamino)carbonyl]methylamino]methyl]phenyl]-methyl]-N$^2$-(diphenylacetyl)-argininamidetrifluoroacetate a) 4-Cyano-N-methyl-N-(phenylmethyl)benzenemethanamine To a solution of 12.9 ml (0.1 Mol) of benzylmethylamine in 50 ml of tetrahydrofuran were added, in batches 9.8 g (0.05 Mol) of 4-(bromomethyl)benzonitrile and the mixture was then stirred for 6 hours at ambient temperature and 3 hours at a reaction temperature of 30° C. The mixture was filtered, the filtrate was evaporated down in vacuo, the residue was taken up in 50 ml of diethylether, filtered again and the filtrate was evaporated down once more. A quantitative yield of an oil was obtained which was used in the next step without further purification.

IR (KBr): 2227.7 (C N) cm$^{-1}$ b) 4-[[(Phenylmethyl)methylamino]methyl]benzenemethanamine To a suspension of 1.9 g (0.05 Mol) of lithium aluminium hydride in 70 ml of anhydrous tetrahydrofuran was added dropwise, at ambient temperature, a solution of 12.1 g (0.051 Mol) of 4-cyano-N-methyl-N-(phenylmethyl)benzenemethanamine in 30 ml of dry tetrahydrofuran and the mixture was then heated to 60° C. for 3 hours and refluxed for 2 hours. A further 0.5 g of lithium aluminium hydride were added and the mixture was refluxed for another 3 hours. After working up in the usual way and purification by column chromatography (Baker; 0.03–0.06 mm; dichloromethane/methanol/cyclohexane/conc. aqueous ammonia=68/15/15/2 (v/v/v/v)) 10.2 g (83% of theory) of a colourless oil were obtained.

c) (R)-N$^2$-(Fmoc)-N$^G$-(2,2,5,7,8-pentamethylchroman-6-sulphonyl)-N-[[4-[[(phenylmethyl)methylamino]methyl]phenyl]methyl]-argininamide Prepared analogously to Example 1a) from (R)-N$^2$-(Fmoc)-N$^G$-(2,2,5,7,8-pentamethylchroman-6-sulphonyl)-arginine, 4-[[(phenylmethyl)methylamino]methyl]benzenemethanamine and dicyclohexylcarbodiimide in a quantitative yield. Colourless, amorphous substance.

IR (KBr): 1724.3 (Carbamate-C=O), 1662.5, 1618.2 (Amide-C=O, C=N), 1369.4, 1107.1 (SO$_2$-N) cm$^{-1}$ ESI-MS: (M+H)$^+$=885 (M+Na)$^+$=907 d) (R)-N$^G$-(2,2,5,7,8-pentamethylchroman-6-sulphonyl)-N-[[4-[[(phenylmethyl)methylamino]methyl]phenyl]methyl]-argininamide Prepared analogously to Example 1b), but using tetrahydrofuran as solvent instead of dimethylformamide, from (R)-N$^2$-(Fmoc)-N$^G$-(2,2,5,7,8-pentamethylchroman-6-sulphonyl)-N-[[4-[[(phenylmethyl)methylamino]methyl]phenyl]methyl]-argininamide and diethylamine in a yield of 88% of theory. Colourless, amorphous substance.

IR (KBr): 3435.0, 3336.7 (N-H), 1618.2 (Amide-C=O, C=N), 1298.0, 1166.9 (SO$_2$-N) cm$^{-1}$ e) (R)-N$^2$-(Diphenylacetyl)-N$^G$-(2,2,5,7,8-pentamethylchroman-6-sulphonyl)-N-[[4-[[(phenylmethyl)methylamino]methyl]phenyl]methyl]-argininamide Prepared analogously to Example 1b), but using tetrahydrofuran as solvent instead of dimethylformamide/tetrahydrofuran mixture, from diphenylacetic acid, (R)-N$^G$-(2,2,5,7,8-pentamethylchroman-6-sulphonyl)-N-[[4-[[(phenylmethyl)methylamino]methyl]phenyl]methyl]-argininamide and TBTU in a yield of 99% of theory.

Colourless, amorphous substance.

IR (KBr): 3433.1, 3323.2 (N-H), 1620.1, 1651.0 (Amide-C=O, C=N), 1382.9, 1166.9 (SO$_2$-N) cm$^{-1}$ f) (R)-N$^2$-(Diphenylacetyl)-N-[[4-[(methylamino)methyl]phenyl]methyl]-N$^G$-(2,2,5,7,8-pentamethylchroman-6-sulphonyl)-argininamide Prepared analogously to Example 1d), but using ethanol as solvent instead of methanol, from (R)-N$^2$-(diphenylacetyl)-N$^G$-(2,2,5,7,8-pentamethylchroman-6-sulphonyl)-N-[[4-[[(phenylmethyl)methylamino]methyl]phenyl]methyl]-argininamide by catalytic hydrogenation in the presence of palladium/activated charcoal in a yield of 34% of theory. Colourless, amorphous substance.

IR (KBr): 3431.2, 3321.2 (N-H), 1651.0 (Amide-C=O, C=N), 1298.0, 1166.9 (SO$_2$-N) cm$^{-1}$ g) (R)-N-[[4-[[[(Dimethylamino)carbonyl]methylamino]methyl]-phenyl]methyl]-N$^2$-(diphenylacetyl)-N$^G$-(2,2,5,7,8-pentamethylchroman-6-sulphonyl)-argininamide Prepared analogously to Example 2a) from (R)-N$^2$-(diphenylacetyl)-N-[[4-[(methylamino)methyl]phenyl]methyl]-N$^G$-(2,2,5,7,8-pentamethylchroman-6-sulphonyl)-argininamide and dimethylcarbamoylchloride in a yield of 84% of theory. Colourless, crystalline substance.

IR (KBr): 1622.0 (Amide-C=O, C=N) cm$^{-1}$ h) (R)-N-[[4-[[[(Dimethylamino)carbonyl]methylamino]methyl]phenyl]methyl]-N$^2$-(diphenylacetyl)-argininamidetrifluoroacetate Prepared analogously to Example 1f) from (R)-N-[[4-[[[(dimethylamino)carbonyl]methylamino]methyl]phenyl]methyl]-N$^2$-(diphenylacetyl)-N$^G$-(2,2,5,7,8-pentamethylchroman-6-sulphonyl)-argininamide and trifluoroacetic acid in a yield of 89% of theory.

$R_f$ value: 0.64; colourless crystals.
IR (KBr): 1668.3 (Amide-C=O), 1203.5, 1176.5, 1130.2 (Trifluoroacetate) cm$^{-1}$
ESI-MS: (M+H)$^+$=572 (M+Na)$^+$=594

EXAMPLE 46
(R)-N-[[4-[[[(Amino)carbonyl]methylamino]methyl] phenyl]-methyl]-N$^2$-(diphenylacetyl)-argininamidetrifluoroacetate a) (R)-N-[[4-[[[(Amino)carbonyl]methylamino]methyl] phenyl]methyl]-N$^2$-(diphenylacetyl)-N$^G$-(2,2,5,7,8-pentamethylchroman-6-sulphonyl)-argininamide Prepared analogously to Example 8a) from (R)-N$^2$-(diphenylacetyl)-N-[[4-[(methylamino)methyl]phenyl]methyl]-N$^G$-(2,2,5,7,8-pentamethylchroman-6-sulphonyl)-argininamide-hydrochloride and sodium cyanate in a quantitative yield. Colourless crystals.

IR (KBr): 3429–2, 3350.2 (N-H), 1651.0 (Amide-C=O), 1298.0, 1166.9 (SO$_2$-N) cm$^{-1}$ b) (R)-N-[[4-[[[(Amino)carbonyl]methylamino]methyl] phenyl]-methyl]-N$^2$-(diphenylacetyl)-argininamidetrifluoroacetate Prepared analogously to Example 1f) from (R)-N-[[4-[[[(amino)carbonyl]methylamino]methyl]phenyl]methyl]-N$^2$-(diphenylacetyl)-N$^G$-(2,2,5,7,8-pentamethylchroman-6-sulphonyl)-argininamide and trifluoroacetic acid in a yield of 65% of theory.

$R_f$ value: 0.59; colourless, amorphous substance.
IR (KBr): 1652.9 (Amide-C=O),
ESI-MS: (M+H)$^+$=544 (M+Na)$^+$=566

EXAMPLE 47
(R)-N$^2$-(Diphenylacetyl)-N-[[4-[[[(methylamino)carbonyl] methylamino]methyl]phenyl]methyl]-argininamidetrifluoroacetate a) (R)-N$^2$-(Diphenylacetyl)-N-[[4-[[[(methylamino) carbonyl]-methylamino]methyl]phenyl]methyl]-N$^G$-(2,2,5, 7,8-pentamethylchroman-6-sulphonyl)-argininamide Prepared analogously to Example 11a) from (R)-N$^2$-(diphenylacetyl)-N-[[4-[(methylamino)methyl]phenyl] methyl]-N$^G$-(2,2,5,7,8-pentaethylchroman-6-sulphonyl)-argininamide and methylisocyanate in quantitative yield. Colourless crystals.

IR (KBr): 3409.9, 3336.7 (N-H), 1629.8 (Amide-C=O, C=N), 1298.0, 1166.9 (SO$_2$-N) cm$^{-1}$ b) (R)-N$^2$-(Diphenylacetyl)-N-[[4-[[[(methylamino) carbonyl]-methylamino]methyl]phenyl]methyl]-argininamidetrifluoroacetate Prepared analogously to Example 1f) from (R)-N$^2$-(diphenylacetyl)-N-[[4-[[[(methylamino)carbonyl] methylamino]methyl]phenyl]methyl]-N$^G$-(2,2,5,7,8-pentamethylchroman-6-sulphonyl)-argininamide and trifluoroacetic acid in a yield of 69% of theory.

$R_f$ value: 0.61; colourless, amorphous substance.
IR (KBr): 1660.6 (Amide-C=O) cm$^{-1}$
ESI-MS: (M+H)$^+$=558 (M+Na)$^+$=580

EXAMPLE 48
(R)-N$^2$-(Diphenylacetyl)-N-[[4-[[(methoxycarbonyl) methylamino]methyl]phenyl]methyl]-argininamidetrifluoroacetate a) (R)-N$^2$-(Diphenylacetyl)-N-[[4-[[(methoxycarbonyl) methylamino]methyl]phenyl]methyl]-N$^G$-(2,2,5,7,8-pentamethylchroman-6-sulphonyl)-argininamide Prepared analogously to Example 2a) from (R)-N$^2$-(diphenylacetyl)-N-[[4-[[[(methylamino)carbonyl] methylamino]methyl]phenyl]methyl]-N$^G$-(2,2,5,7,8-pentamethylchroman-6-sulphonyl)-argininamide and methylchlorocarbonate in a yield of 92% of theory. Colourless, amorphous substance.

IR (KBr): 3433.1, 3325.1 (N-H), 1705.0 (Carbamate-C=O), 1654.8, 1620.1 (Amide-C=O, C=N), 1298.0, 1166.9 (SO$_2$-N) cm$^{-1}$ b) (R)-N$^2$-(Diphenylacetyl)-N-[[4-[[(methoxycarbonyl) methylamino]methyl]phenyl]methyl]-argininamidetrifluoroacetate Prepared analogously to Example 1f) from (R)-N$^2$-(diphenylacetyl)-N-[[4-[[(methoxycarbonyl)methylamino] methyl]phenyl]methyl]-N$^G$-(2,2,5,7,8-pentamethylchroman-6-sulphonyl)-argininamide and trifluoroacetic acid in a yield of 83% of theory.

$R_f$ value: 0.74; colourless, amorphous substance.
IR (KBr): 3292 (N-H), 1716.5 (Carbamate-C=O), 1676.0, 1654.8, 1635.5 (Amide-C=O, C=N), 1201.6, 1134.1 (Trifluoroacetate) cm$^{-1}$
ESI-MS: (M+H)$^+$=559 (M+Na)$^+$=581

EXAMPLE 49
(R)-N-[[4-[[[(Carboxymethyl)amino]carbonyl]methyl] phenyl]methyl]-N$^2$-(diphenylacetyl)-argininamide-diacetate a) (R)-N$^5$-[Amino(nitroimino)methyl]-N-[[4-(carboxymethyl)-phenyl]methyl]-N$^2$-(diphenylacetyl)-ornithinamide 440 mg (0.766 mMol) of (R)-N$^5$-[Amino(nitroimino) methyl]-N$^2$-(diphenylacetyl)-N-[[4-(methoxycarbonylmethyl)phenyl]methyl]-ornithinamide were dissolved in 50 ml of methanol and after the addition of 2.4 ml (2.4 mMol) of 1N sodium hydroxide solution the mixture was refluxed for 3 hours. The methanol was distilled off under reduced pressure, the residue was diluted with 5 ml of water and carefully acidified with 1N hydrochloric acid. It was exhaustively extracted with ethyl acetate, the combined ethyl acetate extracts were dried over sodium sulphate and evaporated down. The residue was stirred several times with a little diisopropylether/diethylether and after drying yielded 400 mg (93% of theory) of a colourless, amorphous substance.

IR (KBr): 1710.8 (Carboxylic acid-C=O), 1641.3 (Amide-C=O) cm$^{-1}$ b) (R)-N$^5$-[Amino(nitroimino)methyl]-N$^2$-(diphenylacetyl)-N-[[4-[[(methoxycarbonylmethyl)amino] carbonyl]methyl]phenyl]methyl]-ornithinamide Prepared analogously to Example 6d) from (R)-N$^5$-[amino(nitroimino)-methyl]-N-[[4-(carboxymethyl)phenyl] methyl]-N$^2$-(diphenylacetyl)-ornithinamide, glycinemethylester hydrochloride and TBTU in a yield of 52% of theory. Colourless crystals, Mp. 168–170° C.

IR (KBr): 1757.0 (Carboxylate-C=O), 1645.2 (Amide-C=O) cm$^{-1}$ c) (R)-N$^5$-[Amino(nitroimino)methyl]-N-[[4-[[[(carboxymethyl)amino]carbonyl]methyl]phenyl]methyl]-N$^2$-(diphenylacetyl)-ornithinamide Prepared analogously to Example 49a) by saponification of (R)-N$^5$-[amino(nitroimino)methyl]-N$^2$-(diphenylacetyl)-N-[[4-[[[(methoxycarbonylmethyl)amino]carbonyl]methyl] phenyl]methy]-ornithinamide in a yield of 80% of theory. Colourless crystals,
Mp. 160–162° C.

IR (KBr): 3377.2, 3311.6, 3274.9 (N-H, O-H), 1637.5 (Amide-C=O) cm$^{-1}$ d) (R)-N-[[4-[[[(Carboxymethyl)amino]carbonyl]methyl] phenyl]methyl]-N$^2$-(diphenylacetyl)-argininamide-diacetate Prepared analogously to Example 4c) from N$^5$-[amino (nitroimino)methyl]-N-[[4-[[[(carboxymethyl)amino] carbonyl]methyl]phenyl]methyl]-N$^2$-(diphenylacetyl)-ornithinamide by catalytic hydrogenation in the presence of palladium black and 80% aqueous acetic acid in a yield of 65% $N^2$ of theory.

$R_f$ value: 0.49; amorphous-glassy substance.
IR (KBr): 1652.9 (Amide-C=O) cm$^{-1}$
ESI-MS: (M+H)$^+$=573 (M+Na)$^+$=595

EXAMPLE 50

(R)-N-[[4-[[[Bis-(carboxymethyl)amino]carbonyl]methyl] phenyl]methyl]-N$^2$-(diphenylacetyl)-argininamide a) (R)-N$^5$-[Amino(nitroimino)methyl]-N-[[4-[[[bis-(methoxy-carbonylmethyl)amino]carbonyl]methyl]phenyl] methyl]-N$^2$-(diphenylacetyl)-ornithinamide Prepared analogously to Example 6d) from (R)-N$^5$-[amino(nitroimino)-methyl]-N-[[4-[[[(carboxymethyl) amino]carbonyl]methyl]phenyl]methyl]-N$^2$-(diphenylacetyl)-ornithinamide and methyl iminodiacetate in a yield of 35% of theory. Colourless, amorphous substance.

IR (KBr): 1749.3 (Carboxylate-C=O), 1652.9 (Amide-C=O, C=N) cm$^{-1}$ b) (R)-N$^5$-[Amino(nitroimino)methyl]-N-[[4-[[[bis-(carboxymethyl)amino]carbonyl]methyl]phenyl]methyl]-N$^2$-(diphenylacetyl)-ornithinamide Prepared analogously to Example 6d) by alkaline saponification of (R)-N$^5$-[amino(nitroimino)methyl]-N-[[4-[[[bis-(methoxycarbonylmethyl)amino]carbonyl]methyl]phenyl] methyl]-N$^2$-(diphenylacetyl)-ornithinamide in a yield of 83% of theory. Colourless, amorphous-glassy substance.

IR (KBr): 1733.9 (Carboxylic acid-C=O), 1635.5 (Amide-C=O, C=N) cm$^{-1}$ c) (R)-N-[[4-[[[Bis-(carboxymethyl)amino]carbonyl] methyl]-phenyl]methyl]-N$^2$-(diphenylacetyl)-argininamide Prepared analogously to Example 4c) from (R)-N$^5$-[amino(nitroimino)methyl]-N-[[4-[[[bis-(carboxymethyl) amino]carbonyl]methyl]phenyl]methyl]-N$^2$-(diphenylacetyl)-ornithinamide by catalytic hydrogenation in the presence of palladium black and 80% aqueous acetic acid in a yield of 92% of theory.

$R_f$ value: 0.44; glassy-amorphous substance.
IR (KBr): 1652.9 (Amide-C=O) cm$^{-1}$
ESI-MS: (M+H)$^+$=631 (M+Na)$^+$=653 (M–H)$^-$=629

EXAMPLE 51

(R)-N-[[4-[[[Bis-(methoxycarbonylmethyl)amino]carbonyl] methyl]phenyl]methyl]-N$^2$-(diphenylacetyl)-argininamidediacetate Prepared analogously to Example 4c) from (R)-N$^5$-(amino(nitroimino)-methyl]-N-[[4-[[[bis-(methoxycarbonylmethyl)amino]carbonyl]methyl]phenyl] methyl]-N$^2$-(diphenylacetyl)-ornithinamide by catalytic hydrogenation in the presence of palladium black and 80% aqueous acetic acid in a yield of 63% of theory.

$R_f$ value: 0.56; glassy-amorphous substance.
ESI-MS: (M+H)$^+$=659 (M+Na)$^+$=681 (M–H)$^-$=657

EXAMPLE 52

(R)-N$^2$-(Diphenylacetyl)-N-[(4-[[[[(ethoxycarbonyl) amino]-carbonyl]methylamino]methyl]phenyl]methyl]-argininamidetrifluoroacetate a) (R)-N$^2$-(Diphenylacetyl)-N-[[4-[[[[(ethoxycarbonyl) amino]-carbonyl]methylamino]methyl]phenyl]methyl]-N$^G$-(2,2,5,7,8-pentamethylchroman-6-sulphonyl)-argininamide Prepared analogously to Example 11a) from (R)-N$^2$-(diphenylacetyl)-N-[[4-[(methylamino)methyl]phenyl] methyl]-N$^G$-(2,2,5,7,8-pentamethylchroman-6-sulphonyl)-argininamide and ethoxycarbonyl-isocyanate in a yield of 70% of theory. Colourless, glassy-amorphous substance.

IR (KBr): 3435.0, 3342.4 (N-H), 1760.9 (Acylurethane-C=O), 1662.5 (Amide-C=O), 1298.0, 1166.9 (SO$_2$-N) cm$^{-1}$ b) (R)-N$^2$-(Diphenylacetyl)-N-[[4-[[[[(ethoxycarbonyl) amino]carbonyl]methylamino]methyl]phenyl]methyl]-argininamidetrifluoroacetate Prepared analogously to Example 1f) from (R)-N$^2$-(diphenylacetyl)-N-[[4-[[[[(ethoxycarbonyl)amino] carbonyl]methylamino]methyl]phenyl]methyl]-N$^G$-(2,2,5,7, 8-pentamethylchroman-6-sulphonyl)-argininamide and trifluoroacetic acid in a yield of 98% of theory.

$R_f$ value: 0.61; glassy-amorphous substance.
IR (KBr): 1759.0 (Carbamate-C=O), 1662.5 (Amide-C=O) cm$^{-1}$
ESI-MS: (M+H)$^+$=616 (M+Na)$^+$=638 (M+H+Na)$^{++}$=319.5

EXAMPLE 53

(R)-N$^2$-(Diphenylacetyl)-arginine-[4-(aminocarbonylaminomethyl)phenyl]methylester-trifluoroacetate a) Ethyl 4-(aminocarbonylaminomethyl)benzoate 38.0 g (0.196 Mol) of 4-(aminocarbonylaminomethyl) benzoic acid were dissolved in 1.5 l of anhydrous ethanol and refluxed for 5 hours while dry hydrogen chloride was introduced. The small amount of insoluble matter was filtered off, the filtrate was concentrated down to a volume of about 100 ml, diluted with 1 l of water and treated with solid potash until the development of carbon dioxide had ended and a distinctly alkaline reaction was obtained. The mixture was left to stand for 2 hours, the crystals formed were suction filtered, washed thoroughly with water, then with diisopropylether and diethylether and dried in vacuo. 32.8 g (75% of theory) of colourless crystals were obtained, Mp. 173–175° C.

b) 4-(Aminocarbonylaminomethyl)benzenemethanol 13.0 g (0.058 Mol) of ethyl 4-(aminocarbonylaminomethyl)-benzoate were dissolved in 1 l of tetrahydrofuran and after the addition of 6.0 g (0.275 Mol) of lithium borohydride the mixture was stirred for 18 hours at a temperature of 75° C. A further 1.5 g of lithium borohydride were added and heated for a further 4 hours to 75° C. The mixture was left to cool, stirred with a mixture of 80 ml of methanol and 20 ml of water, adjusted to pH 3 by the addition of 3N hydrochloric acid and stirred overnight at ambient temperature. The crystals formed were suction filtered, washed thoroughly with water and dried in vacuo. 0.55 g (5.3% of theory) of colourless crystals were obtained.

IR (KBr): 3440.8, 3336.7 (O-H, N-H), 1654.8 (Urea-C=O) cm$^{-1}$ c) (R)-N$^2$-(Diphenylacetyl)-N$^G$-(2,2,5,7,8-pentamethylchroman-6-sulphonyl)-arginine-[4-(aminocarbonylaminomethyl)phenyl]-methylester Prepared analogously to Example 1a), but in the absence of HOBt and with the addition of 4-(1-pyrrolidinyl)pyridine, from (R)-N$^2$-(diphenylacetyl)-N$^G$-(2,2,5,7,8-pentamethylchroman-6-sulphonyl)-arginine, 4-(aminocarbonylaminomethyl)benzene-methanol and dicyclohexylcarbodiimide in a yield of 82% of theory. Colourless, amorphous substance.

IR (KBr): 3438.9, 3344.4 (N-H), 1741.6 (Carboxylate-C=O), 1658.7 (Amide-/Urea-C=O), 1298.0, 1166.9 (SO$_2$-N) cm$^{-1}$ d) (R)-N$^2$-(Diphenylacetyl)-arginine-[4-(aminocarbonylaminomethyl)phenyl]methylester-trifluoroacetate Prepared analogously to Example 1f) from (R)-N$^2$-(diphenylacetyl)-N$^G$-(2,2,5,7,8-pentamethylchroman-6-sulphonyl)-arginine-[4-(aminocarbonylaminomethyl) phenyl]methylester and trifluoroacetic acid in a yield of 78% of theory.

$R_f$ value: 0.66; colourless, amorphous substance.
IR (KBr): 1739.7 (Carboxylate-C=O), 1658.7 (Amide-/Urea-C=O) cm$^{-1}$
ESI-MS: (M+H)$^+$=531 (M+Na)$^+$=553

EXAMPLE 54
(R)-N-[[4-(Aminocarbonylaminomethyl)phenyl]methyl]-N$^2$-[(2,4-dichlorophenyl)acetyl]-argininamidetrifluoroacetate a) (R)-N-[[4-(Aminocarbonylaminomethyl)phenyl]methyl]-N$^2$-[(2,4-dichlorophenyl)acetyl]-N$^G$-(2,2,5,7,8-pentamethylchroman-6-sulphonyl)-argininamide Prepared analogously to Example 4b) from 2,4-dichlorobenzene acetic acid and (R)-N-[[4-(aminocarbonylaminomethyl)phenyl]methyl]-N$^G$-(2,2,5,7,8-pentamethylchroman-6-sulphonyl)-argininamide in a yield of 78% of theory. Colourless, amorphous-glassy substance.

IR (KBr): 3436.9, 3342.4 (N-H), 1654.8 (Amide-/Urea-C=O) cm$^{-1}$ b) (R)-N-[[4-(Aminocarbonylaminomethyl)phenyl]methyl]-N$^2$-[(2,4-dichlorophenyl)acetyl]-argininamidetrifluoroacetate Prepared analogously to Example 1f) from (R)-N-[[4-(aminocarbonylaminomethyl)phenyl]methyl]-N$^2$-[(2,4-dichlorophenyl)acetyl]-N$^G$-(2,2,5,7,8-pentamethylchroman-6-sulfonyl)-argininamide and trifluoroacetic acid in a yield of 82% of theory.

$R_f$ value: 0.56; glassy-amorphous substance.
IR (KBr): 1654.8 (Amide-/Urea-C=O), 1203.5, 1182.3, 1134.1 (Trifluoroacetate) cm$^{-1}$
ESI-MS: (M+H)$^+$=522/524/526 (Cl$_2$)

EXAMPLE 55
(R)-N-[[4-(Aminocarbonylaminomethyl)phenyl]methyl]-N$^2$-[(2,6-dichlorophenyl)acetyl]-argininamidetrifluoroacetate a) (R)-N-[[4-(Aminocarbonylaminomethyl)phenyl]methyl]-N$^2$-[(2,6-dichlorophenyl)acetyl]-N$^G$-(2,2,5,7,8-pentamethylchroman-6-sulphonyl)-argininamide Prepared analogously to Example 4b) from 2,6-dichlorobenzene acetic acid, (R)-N-[[4-(aminocarbonylaminomethyl)phenyl]methyl]-N$^G$-(2,2,5,7,8-pentamethylchroman-6-sulphonyl)-argininamide and TBTU in a quantitative yield. Colourless, amorphous-glassy substance.

IR (KBr): 1652.9 (Amide-/Urea-C=O), 1299.9, 1166.9 (SO$_2$-N) cm$^{-1}$
ESI-MS: (M+H)$^+$=788/790/792 (Cl$_2$)

b) (R)-N-[[4-(Aminocarbonylaminomethyl)phenyl]methyl]-N$^2$-[(2,6-dichlorophenyl)acetyl]-argininamidetrifluoroacetate Prepared analogously to Example 1f) from (R)-N-[[4-(aminocarbonylaminomethyl)phenyl]methyl]-N$^2$-[(2,6-dichlorophenyl)acetyl]-N$^G$-(2,2,5,7,8-pentamethylchroman-6-sulphonyl)-argininamide and trifluoroacetic acid in a yield of 57% of theory.

$R_f$ value: 0.57; glassy-amorphous substance.
IR (KBr): 1654.8 (Amide-/Urea-C=O), 1203.5, 1182.3, 1134.1 (Trifluoroacetate) cm$^{-1}$
ESI-MS: (M+H)$^+$=522/524/526 (Cl$_2$)

EXAMPLE 56
(R)-N-[[4-(Aminocarbonylaminomethyl)phenyl]methyl]-N$^2$-[bis-(4-methoxyphenyl)acetyl]-argininamide-acetate a) (R)-N-[[4-(Aminocarbonylaminomethyl)phenyl]methyl]-N$^5$-[amino(nitroimino)methyl]-N$^2$-[bis-(4-methoxyphenyl)acetyl]-ornithinamide Prepared analogously to Example 14c) from bis-(4-methoxyphenyl)-acetic acid, (R)-N-[[4-(aminocarbonylaminomethyl)phenyl]methyl]-N$^5$-[amino(nitroimino)methyl]-ornithinamidehydrochloride and TBTU in a yield of 48% of theory. Colourless crystals, Mp. 149–151° C. (Acetonitrile).

IR (KBr): 1635.5 (Amide-/Urea-C=O, C=N) cm$^{-1}$ b) (R)-N-[[4-(Aminocarbonylaminomethyl)phenyl]methyl]-N$^2$-[bis-(4-methoxyphenyl)acetyl]-argininamide-acetate Prepared analogously to Example 4c) from (R)-N-[[4-(aminocarbonylaminomethyl)phenyl]methyl]-N$^5$-[amino(nitroimino)methyl]-N$^2$-[bis-(4-methoxyphenyl)acetyl]-ornithinamide by catalytic hydrogenation in the presence of palladium black and 80% aqueous acetic acid in a yield of 68% of theory.

$R_f$ value: 0.58; colourless crystals.
IR (KBr): 3415.7 (N-H), 1635.5 (Amide-/Urea-C=O) cm$^{-1}$
ESI-MS: (M+H)$^+$=590

EXAMPLE 57
(R)-N-[[4-(Aminocarbonylaminomethyl)phenyl]methyl]-N$^2$-[(4-hydroxyphenyl)acetyl]-argininamide acetate a) (R)-N-[[4-(Aminocarbonylaminomethyl)phenyl]methyl]-N$^5$-[amino(nitroimino)methyl]-N$^2$-[(4-hydroxyphenyl)acetyl]-ornithinamide Prepared analogously to Example 14c) from 4-hydroxybenzene acetic acid, (R)-N-[[4-(aminocarbonylaminomethyl)phenyl]methyl]-N$^5$-[amino(nitroimino)methyl]-ornithinamidehydrochloride and TBTU in a yield of 90% of theory. Colourless crystals, Mp. 168–170° C.

IR (KBr): 1637.5 (Amide-/Urea-C=O, C=N) cm$^{-1}$ b) (R)-N-[[4-(Aminocarbonylaminomethyl)phenyl]methyl]-N$^2$-[(4-hydroxyphenyl)acetyl]-argininamide-acetate Prepared analogously to Example 4c) from (R)-N-[[4-(aminocarbonylaminomethyl)phenyl]methyl]-N$^5$-[amino(nitroimino)methyl]-N$^2$-[(4-hydroxyphenyl)acetyl]-ornithinamide by catalytic hydrogenation in the presence of palladium black and 80% aqueous acetic acid in a yield of 85% of theory.

$R_f$ value: 0.49; colourless crystals.
IR (KBr): 1647.1 (Amide-/Urea-C=O) cm$^{-1}$
ESI-MS: (M+H)$^+$=470 (M+Na)$^+$=492

EXAMPLE 58
(R)-N$^2$-(Diphenylacetyl)-N-[[4-(ethoxycarbonylmethylaminocarbonylaminomethyl)phenyl]methyl]-argininamidetrifluoroacetate a) (R)-N$^2$-(Diphenylacetyl)-N-[[4-(ethoxycarbonylmethylaminocarbonylaminomethyl)phenyl]methyl]-N$^G$-(2,2,5,7,8-pentamethylchroman-6-sulphonyl)-argininamide Prepared analogously to Example 11a) from (R)-N-[[4-(aminomethyl)phenyl]methyl]-N$^2$-(diphenylacetyl)-N$^G$-(2,2,5,7,8-pentamethylchroman-6-sulphonyl)-argininamide and ethyl isocyanatoacetate in a yield of 80% of theory. Colourless, amorphous, jelly-like substance.

IR (KBr): 1739.7 (Carboxylate-C=O), 1652.9 (Amide-C=O), 1298.0, 1166.9 (SO$_2$-N) cm$^{-1}$
ESI-MS: (M+H)$^+$=882.4 (M+Na)$^+$=904.3 (M+2Na)$^{++}$=463.5 b) (R)-N$^2$-(Diphenylacetyl)-N-[[4-(ethoxycarbonylmethylaminocarbonylaminomethyl)phenyl]methyl]-argininamidetrifluoroacetate Prepared analogously to Example 1f) from (R)-N$^2$-(diphenylacetyl)-N-[[4-

(ethoxycarbonylmethylaminocarbonylaminomethyl)phenyl]methyl]-N$^G$-(2,2,5,7,8-pentamethylchroman-6-sulphonyl)-argininamide and trifluoroacetic acid in a yield of 80% of theory.

R$_f$ value: 0.73; colourless crystals.

IR (KBr): 1733.9 (Carboxylate-C=O), 1654.8 (Amide-/Urea-C=O), 1203.5, 1179.1, 1134.1 (Trifluoroacetate) cm$^{-1}$

ESI-MS: (M+H)$^+$=616

EXAMPLE 59

(R)-N-[[4-(Carboxymethylaminocarbonylaminomethyl)phenyl]-methyl]-N$^2$-(diphenylacetyl)-argininamidetrifluoroacetate a) (R)-N-[[4-(Carboxymethylaminocarbonylaminomethyl)phenyl]-methyl]-N$^2$-(diphenylacetyl)-N$^G$-(2,2,5,7,8-pentamethylchroman-6-sulphonyl)-argininamide 0.6 g (0.68 mMol) of (R)-N$^2$-(diphenylacetyl)-N-[[4-(ethoxycarbonylmethylaminocarbonylaminomethyl)phenyl]methyl]-N$^G$-(2,2,5,7,8-pentamethylchroman-6-sulphonyl)-argininamide were dissolved in 200 ml of tetrahydrofuran, mixed with a solution of 0.11 g (4.59 mMol) of lithium hydroxide in 61 ml of water and stirred for 3 hours at ambient temperature. The tetrahydrofuran was eliminated by distillation in vacuo, the residue was carefully acidified with 1N hydrochloric acid and the precipitate formed was suction filtered after being left to stand for several hours at ambient temperature. It was washed thoroughly with water, dried in vacuo and 0.51 g (88% of theory) colourless crystals were obtained, Mp. 120–125° C.

IR (KBr): 1730.0 (Carboxylate-C=O), 1647.1 (Amide-/Urea-C=O) cm$^{-1}$ b) (R)-N-[[4-(Carboxymethylaminocarbonylaminomethyl)phenyl]methyl]-N$^2$-(diphenylacetyl)-argininamidetrifluoroacetate Prepared analogously to Example 1f) from (R)-N-[[4-(carboxymethylaminocarbonylaminomethyl)phenyl]methyl]-N$^2$-(diphenylacetyl)-N$^G$-(2,2,5,7,8-pentamethylchroman-6-sulphonyl)-argininamide and trifluoroacetic acid in a yield of 85% of theory.

R$_f$ value: 0.55; colourless crystals.

IR (KBr): 1660.6 (Amide-/Urea-C=O), 1558.4 (Amide-II), 1201.6, 1184.0, 1136.0 (Trifluoroacetate) cm$^{-1}$ ESI-MS: (M+H)$^+$=588 (M−H)−=586 (M+Na)$^+$=610

EXAMPLE 60

(R)-N-[[4-(Dimethylaminocarbonylmethyl)phenyl]methyl]-N$^2$-(diphenylacetyl)-argininamide-diacetate a) 4-(Dimethylaminocarbonylmethyl)benzenemethanamine Prepared analogously to Example 6c) from N,N-dimethyl-4-cyanobenzene acetamide (from 4-cyanobenzeneacetic acid and dimethylamine in the presence of N,N'-carbonyldiimidazole) by catalytic hydrogenation in the presence of Raney nickel and ammonia in a quantitative yield. Colourless oil which was used in the following step without any further purification.

IR (KBr): 1637.5 (Amide-C=O) cm$^{-1}$

MS: M$^+$=192 b) (R)-N$^5$-[Amino(nitroimino)methyl]-N-[[4-(dimethylaminocarbonylmethyl)phenyl]methyl]-N$^2$-(diphenylacetyl)-ornithinamide Prepared analogously to Example 6d) from (R)-N$^2$-(diphenylacetyl)-N$^G$-(2,2,5,7,8-pentamethylchroman-6-sulphonyl)-arginine, 4-(dimethylaminocarbonylmethyl)benzenemethanamine and TBTU in a yield of 76% of theory. Colourless crystal, Mp. 198–200° C. (Ethyl acetate).

IR (KBr): 3390.7, 3357.9, 3309–7 (N-H), 1639.4 (Amide-C=O) cm$^{-1}$

ESI-MS: (M+H)$^+$=588 (M+Na)$^+$=610 (2M+H)$^+$=1175 (2M+Na)$^+$=1197 c) (R)-N-[[4-(Dimethylaminocarbonylmethyl)phenyl]methyl]-N$^2$-(diphenylacetyl)-argininamide-diacetate Prepared analogously to Example 4c) from (R)-N$^5$-[amino(nitroimino)methyl]-N-[[4-(dimethylaminocarbonylmethyl)phenyl]methyl]-N$^2$-(diphenylacetyl)-ornithinamide by catalytic hydrogenation in the presence of palladium black and 80% aqueous acetic acid in a yield of 55% of theory.

R$_f$ value: 0.54; colourless, glassy-amorphous substance.

IR (KBr): 1649.0 (Amide-C=O) cm$^{-1}$

ESI-MS: (M+H)$^+$=543 (M+Na)$^+$=565

EXAMPLE 61

(R)-N-[[4-(Aminocarbonylaminomethyl)phenyl]methyl]-N$^2$-(diphenylacetyl)-N-(ethoxycarbonylmethyl)-argininamide-diacetate a) Ethyl [[(4-cyanophenyl)methyl]amino]acetate A mixture of 27.9 g (0.2 Mol) of glycine ethylester-hydrochloride, 350 ml of methanol, 3.9 g (0.062 Mol) of sodium cyanoborohydride and 13.1 g (0.1 Mol) of 4-cyanobenzaldehyde was stirred for 26 hours at ambient temperature, then evaporated to dryness in vacuo. The residue was distributed between ethyl acetate and saturated potash solution, the organic phase was dried over sodium sulphate and evaporated down in vacuo. The residue was purified on silica gel (Macherey-Nagel, 35–70 mesh ASTM) using petroleum ether/ethyl acetate=1/1 (v/v) as eluant and after the appropriate fractions have been worked up 11.7 g (54% of theory) of a colourless oil were obtained.

IR (KBr): 3340 (N-H), 2230 (C N), 1735 (Carboxylate-C=O) cm$^{-1}$ b) N$^2$-[(4-Cyanophenyl)methyl]-N$^2$-[(1,1-dimethylethoxy)-carbonyl]-glycineethylester A solution of 11.7 g (0.054 Mol) of ethyl [[(4-cyanophenyl)methyl]amino]acetate in 200 ml of anhydrous tetrahydrofuran was mixed with 13.1 g (0.06 Mol) di-tert.butyl-pyrocarbonate. The mixture was stirred for 3 hours at ambient temperature, then evaporated down in vacuo and 16.8 g (98% of theory) of a slightly yellowish oil were obtained which were used in the following step without any further purification.

IR (KBr): 2229.6 (C N), 1749.3 (Carboxylate-C=O), 1703.0 (Urethane-C=O) cm$^{-1}$ c) N$^2$-[[4-(Aminomethyl)phenyl]methyl]-N$^2$-[(1,1-dimethyl-ethoxy)carbonyl]-glycineethylester-hydrochloride Prepared analogously to Example 43b) from N$^2$-[(4-cyanophenyl)methyl]-N$^2$-[(1,1-dimethylethoxy)carbonyl]-glycineethylester by catalytic hydrogenation in the presence of palladium/activated charcoal and 1 equivalent of 1N hydrochloric acid in a yield of 88% of theory. Colourless, amorphous substance which was used in the next step without any further purification.

IR (KBr): 1749.3 (Carboxylate-C=O), 1701.1 (Urethane-C=O) cm$^{-1}$ d) N$^2$-[[4-(Aminocarbonylaminomethyl)phenyl]methyl]-N$^2$-[(1,1-dimethylethoxy)carbonyl]-glycineethylester Prepared analogously to Example 8a) from N$^2$-[[4-(aminomethyl)-phenyl]methyl]-N$^2$-[(1,1-dimethylethoxy)carbonyl]-glycineethyl-ester-hydrochloride and sodium cyanate in a yield of 93% of theory. Colourless, amorphous substance which was used in the next step without any further purification.

IR (KBr): 1749.3 (Carboxylate-C=O), 1697.3 (Urethane-C=O), 1664.5 (Urea-C=O) cm$^{-1}$ e) N$^2$-[[4-(Aminocarbonylaminomethyl)phenyl]methyl]-glycineethylester-trifluoracetate A solution of 1.8 g (4.93 mMol) of $N^2$-[[4-(aminocarbonylaminomethyl)phenyl]methyl]-$N^2$-[(1,1-dimethylethoxy)carbonyl]-glycineethylester in 56 ml of dichloromethane was mixed with a total of 3.4 ml of trifluoroacetic acid, which was added dropwise thereto whilst externally cooling with ice, and the resulting mixture was then stirred overnight at room temperature. The excess trifluoroacetic acid was removed together with the solvent by vacuum distillation, the residue was taken up several times in a little dichloromethane and evaporated down again and finally 0.7 g (37% of theory) of colourless crystals were obtained, Mp. 90–91° C.

IR (KBr): 3440.8, 3336.7 (N-H), 1739.7 (Carboxylate-C=O), 1652.9 (Urea-C=O) cm$^{-1}$, Trifluoroacetate bands f) (R)-N-[[4-(Aminocarbonylaminomethyl)phenyl]methyl]-$N^5$-[amino(nitroimino)methyl]-$N^2$-(diphenylacetyl)-N-(ethoxycarbonylmethyl)-ornithinamide Prepared analogously to Example 14c) from (R)-$N^5$-[amino[nitroimino)methyl]-$N^2$-(diphenylacetyl)-ornithine, $N^2$-[[4-(aminocarbonylaminomethyl)phenyl]methyl]-glycineethylester-trifluoroacetate and TBTU in a yield of 42% of theory. Colourless, amorphous substance.

IR (KBr): 1741.6 (Carboxylate-C=O), 1645.2 (Amide-/Urea-C=O) cm$^{-1}$

ESI-MS: (M+H)$^+$=661 (M+Na)$^+$=683 (M+K)$^+$=699 g) (R)-N-[[4-(Aminocarbonylaminomethyl)phenyl]methyl]-$N^2$-(diphenylacetyl)-N-(ethoxycarbonylmethyl)-argininamide-diacetate Prepared analogously to Example 4c) from (R)-N-[[4-(aminocarbonylaminomethyl)phenyl]methyl]-$N^5$-[amino(nitroimino)methyl]-$N^2$-(diphenylacetyl)-N-(ethoxycarbonylmethyl)-ornithinamide by catalytic hydrogenation in the presence of palladium black and 80% aqueous acetic acid in a yield of 90% of theory.

$R_f$ value: 0.64; glassy-amorphous substance.

IR (KBr): 1745.5 (Carboxylate-C=O), 1656.8 (Amide-/Urea-C=O) cm$^{-1}$

ESI-MS: (M+H)$^+$=616

EXAMPLE 62

(R)-N-[[4-(Aminocarbonylaminomethyl)phenyl]methyl]-N-(carboxymethyl)-$N^2$-(diphenylacetyl)-argininamide-acetate a) (R)-N-[[4-(Aminocarbonylaminomethyl)phenyl]methyl]-$N^5$-[amino(nitroimino)methyl]-N-(carboxymethyl)-$N^2$-(diphenylacetyl)-ornithinamide Prepared analogously to Example 59a) by saponification of (R)-N-[[4-(aminocarbonylaminomethyl)phenyl]methyl]-$N^5$-[amino(nitroimino)methyl]-$N^2$-(diphenylacetyl)-N-(ethoxycarbonylmethyl)-ornithinamide in a yield of 70% of theory. Colourless crystals, Mp. 78–81° C.

IR (KBr): 1728.1 (Carboxylic acid-C=O), 1635.5 (Amide-/Urea-C=O, C=N) cm$^{-1}$

ESI-MS: (M+H)$^+$=633 (M+Na)$^+$=655 (M+K)$^+$=671 (M-H+2Na)$^+$=677 b) (R)-N-[[4-(Aminocarbonylaminomethyl)phenyl]methyl]-N-(carboxymethyl)-$N^2$-(diphenylacetyl)-argininamide-acetate Prepared analogously to Example 4c) from (R)-N-[[4-(aminocarbonylaminomethyl)phenyl]methyl]-$N^5$-[amino(nitroimino)methyl]-N-(carboxymethyl)-$N^2$-(diphenylacetyl)-ornithinamide by catalytic hydrogenation in the presence of palladium black and 80% aqueous acetic acid in a yield of 79% of theory. Colourless crystals, Mp. 148–151° C. (Ethanol) and $R_f$ 0.51.

IR (KBr): 1639.4 (Amide-/Urea-C=O) cm$^{-1}$

ESI-MS: (M+H)$^+$=588 (M+Na)$^+$=610 (M-H+2Na)$^+$=632 (M-H)-=586

EXAMPLE 63

(R)-N-[[4-[2-(Aminocarbonyl)ethyl]phenyl]methyl]-$N^2$-(diphenylacetyl)-argininamide a) 4-Cyanobenzenepropanamide To a solution of 2.17 g (12.39 mMol) of 4-cyanobenzenepropanoic acid in 2 ml of anhydrous tetrahydrofuran were added, at a reaction temperature of about +40° C., 2.21 g (13.63 mMol) of N,N'-carbonyldiimidazole, the mixture was stirred for 30 minutes at the temperature specified, a further 0.5 g of N,N'-carbonyldiimidazole were added and the mixture was again stirred at an internal temperature of 40° C. The solution cooled to ambient temperature was mixed with 5.0 g (52 mMol) of ammonium carbonate, diluted with 25 ml of tetrahydrofuran and stirred for 90 minutes at ambient temperature. The mixture was stirred with 200 ml of water and the crystalline precipitate formed was suction filtered. The filtrate was saturated with common salt and extracted exhaustively with ethyl acetate. The combined ethyl acetate extracts dried over sodium sulphate and evaporated down yielded a residue which was suction filtered after trituration with tert.butyl-methylether. Together with the above crystals, 1.95 g (90% of theory) of colourless crystals were obtained, Mp. 220° C.

IR (KBr): 3419.6, 3311.6 (N-H), 2229.6 (C N), 1664.5 (Amide-C=O) cm$^{-1}$ b) 4-(2-(Aminocarbonyl)ethyl]benzenemethanamine Prepared analogously to Example 43b) from 4-cyanobenzenepropanamide by catalytic hydrogenation using palladium/activated charcoal and in the presence of 1 equivalent of 2N hydrochloric acid in a yield of 88% of theory. Colourless crystals (diethylether).

MS: M$^+$=178 c) (R)-N-[[4-[2-(Aminocarbonyl)ethyl]phenyl]methyl]-$N^5$-[amino(nitroimino)methyl]-$N^2$-(diphenylacetyl)-ornithinamide Prepared analogously to Example 4b) from (R)-$N^5$-[amino[nitroimino)methyl]-$N^2$-(diphenylacetyl)-ornithine, 4-[2-(aminocarbonyl)ethyl]benzenemethanamine and TBTU in a yield of 60% of theory. Colourless crystals, Mp. 139–140° C. (Acetonitrile).

ESI-MS: (M+H)$^+$=574 (M+Na)$^+$=596 (M+K)$^+$=612 d) (R)-N-[[4-[2-(Aminocarbonyl)ethyl]phenyl]methyl]-$N^2$-(diphenylacetyl)-argininamide Prepared analogously to Example 4c) from (R)-N-[[4-[2-(aminocarbonyl)ethyl]phenyl]methyl]-$N^5$-[amino(nitroimino)methyl]-$N^2$-(diphenylacetyl)-ornithinamide by catalytic hydrogenation in the presence of palladium black and 80% aqueous acetic acid in a yield of 38% of theory. Colourless crystals, Mp. 207–208° C.

$R_f$ value: 0.38.

IR (KBr): 1658.7, 1635.5 (Amide-C=O) cm$^{-1}$

ESI-MS: (M+H)$^+$=529 (M+Na)$^+$=551 (2M+H)$^+$=1057

EXAMPLE 64

(R)-N-[[4-(Aminocarbonylaminomethyl)phenyl]methyl]-$N^2$-[(2-naphthyl)carbonyl]-argininamide-acetate a) (R)-$N^5$-[Amino(nitroimino)methyl]-$N^2$-[(2-naphthyl)carbonyl]-ornithine Prepared analogously to Example 4a) from (R)-$N^5$-[amino(nitroimino)methyl]-ornithine and 2-naphthoylchloride in a yield of 64% of theory. Colourless crystals which were used in the next step without further purification.

b) (R)-N-[[4-(Aminocarbonylaminomethyl)phenyl]methyl]-$N^5$-[amino(nitroimino)methyl]-$N^2$-[(2-naphthyl)carbonyl]-ornithinamide Prepared analogously to Example 14c) from (R)-$N^5$-[amino(nitroimino)methyl]-$N^2$-[(2-naphthyl)carbonyl]-ornithine, 4-(aminocarbonylaminomethyl)benzenemethanamine and TBTU in a yield of 30% of theory. Colourless crystals which were further processed without being purified.

IR (KBr): 3492.9, 3368.2, 3298.1 (N-H), 1649.0, 1639.4 (Amide-/Urea-C=O), 1625.2 (C=N) cm$^{-1}$ c) (R)-N-[[4-(Aminocarbonylaminomethyl)phenyl]methyl]-N$^2$-[(2-naphthyl)carbonyl]-argininamide-acetate Prepared analogously to Example 4c) from (R)-N-[[4-(aminocarbonylaminomethyl)phenyl]methyl]-N$^5$-[amino(nitroimino)methyl]-N$^2$-[(2-naphthyl)carbonyl]-ornithinamide by catalytic hydrogenation in the presence of palladium black and 80% aqueous acetic acid in a yield of 72% of theory.

R$_f$ value: 0.32; colourless, amorphous substance.
IR (KBr): 1652.9 (Amide-/Urea-C=O) cm$^{-1}$
ESI-MS: (M+H)$^+$=490 (M+Na)$^+$=512

EXAMPLE 65

(R)-N-[[2-(Aminocarbonyl)-2,3-dihydro-1H-isoindol-5-yl]methyl]-N$^2$-(diphenylacetyl)-argininamide a) Methyl 2,3-dihydro-2-(phenylmethyl)-1H-isoindole-5-carboxylate A mixture of 77.0 g (0.469 Mol) of methyl 3,4-dimethylbenzoate, 178.0 g (1.0 Mol) of N-bromosuccinimide, 0.5 g of azoisobutyronitrile and 800 ml of tetrachloromethane was refluxed for 1 hour whilst simultaneously being subjected to intensive illumination with a 1000-Watt daylight bulb. The mixture was allowed to cool to about 40° C., then filtered and the filter residue was washed thoroughly with 200 ml of tetrachloromethane. Within about 30 minutes, at a reaction temperature of +30° C., a mixture of 53.6 g ( 0.575 Mol) of benzenemethanamine, 101.2 g (1.0 Mol) of triethylamine and 150 ml of toluene was added to the combined filtrates. The resulting mixture was refluxed for 3 hours, then left overnight at ambient temperature and filtered to remove the precipitate formed. The filtrate was freed from the solvent in vacuo, the residue remaining was distributed between tert.butyl-methyl-ether and 20% aqueous citric acid, then the aqueous phase was extracted thoroughly with tert.butylmethylether and ethyl acetate. Batches of sodium hydrogen carbonate were added to the aqueous phase until the development of carbon dioxide ceased, then the mixture was exhaustively extracted with a tert.butyl-methylether/ethyl acetate mixture (1:1 v/v). The combined extracts were worked up in the usual way and yielded 48.1 g (38% of theory) of colourless crystals, Mp. 72° C.

IR (CH$_2$Cl$_2$): 1735 (Carboxylate-C=O) cm$^{-1}$ b) 2,3-Dihydro-2-(phenylmethyl)-1H-isoindole-5-carboxylic acid-hydrochloride Prepared analogously to Example 49a) by saponification of methyl 2,3-dihydro-2-(phenylmethyl)-1H-isoindole-5-carboxylate in a quantitative yield. By treating with conc. hydrochloric acid the compound was converted into its hydrochloride, which was used in the following step without any further purification.

IR (KBr): 1710, 1695 (Carboxylic acid-C=O) cm$^{-1}$ c) 2,3-Dihydro-2-(phenylmethyl)-1H-isoindole-5-carboxylic Acid Chloride-hydrochloride 40.0 g (0.138 Mol) of 2,3-Dihydro-2-(phenylmethyl)-1H-isoindole-5-carboxylic acid-hydrochloride were suspended in 400 ml of anhydrous tetrahydrofuran and at a reaction temperature of 50 to 55° C. 100 g (0.84 Mol) of thionylchloride were added dropwise. The temperature was maintained at 50 to 60° C. until the development of gas had ceased completely and then the cooled solution was filtered to remove the insoluble matter. The filtrate was evaporated down in vacuo, the residue was triturated with 5 ml of dry tetrahydrofuran, suction filtered and dried over diphosphorus pentoxide in a desiccator. 34.8 g (82% of theory) of colourless crystals were obtained, Mp. 226–228° C. (D.).

IR (KBr): 1793, 1755 (Carboxylic acid chloride-C=O) cm$^{-1}$ d) 2,3-Dihydro-2-(phenylmethyl)-1H-isoindole-5-carboxamide To a mixture of 200 ml of conc. aqueous ammonia and 50 ml of tetrahydrofuran were added, in batches, 20.0 g (64.9 mMol) of 2,3-dihydro-2-(phenylmethyl)-1H-isoindole-5-carboxylic acid chloride-hydrochloride and the mixture was stirred overnight at ambient temperature. The precipitate formed was suction filtered, washed thoroughly with water and dried at 50° C. in a circulating air dryer. The desired compound was obtained in a quantitative yield in the form of colourless crystals.

IR (KBr): 3370, 3170 (N-H), 1650 (Amide-C=O) cm$^{-1}$ e) 2,3-Dihydro-2-(phenylmethyl)-1H-isoindole-5-ylmethanamine Prepared analogously to Example 45b) from 2,3-dihydro-2-(phenylmethyl)-1H-isoindole-5-carboxamide by reduction with lithium aluminium hydride. The desired compound was obtained as a colourless oil in a yield of 74% of theory.

f) 2,3-Dihydro-5-[[[(1,1-dimethylethoxy)carbonyl]amino]-methyl]-2-(phenylmethyl)-1H-isoindole Prepared analogously to Example 61b) from 2-(phenylmethyl)-2,3-dihydro-1H-isoindol-5-ylmethanamine and di-tert.butylpyrocarbonate in a yield of 34% of theory. The product was used in the following step without further purification.

g) 2,3-Dihydro-5-[[[(1,1-dimethylethoxy)carbonyl]amino]-methyl]-1H-isoindole

Prepared analogously to Example 1d), but using tetrahydrofuran as solvent instead of methanol and with the addition of 1 equivalent of 1N aqueous hydrochloric acid, from 2,3-di-hydro-5-[[[((1,1-dimethylethoxy)carbonyl]amino]methyl]-2-(phenylmethyl)-1H-isoindole by catalytic hydrogenation in the presence of palladium/activated charcoal in a yield of 97% of theory. Colourless crystals, Mp. 114–115° C.

IR (KBr): 3450 (N-H), 1710 (Carbamate-C=O) cm$^{-1}$ h) 2-(Aminocarbonyl)-2,3-dihydro-5-[[[(1,1-dimethylethoxy)-carbonyl]amino]methyl]-1H-isoindole Prepared analogously to Example 8a) from 2,3-dihydro-5-[[[(1,1-dimethylethoxy)carbonyl]amino]methyl]-1H-isoindole, 1 equivalent of 1N hydrochloric acid and sodium cyanate in a quantitative yield. Colourless crystals.

IR (KBr): 3392.6 (N-H), 1647.1, 1606.6 (C=O) cm$^{-1}$
MS: M$^+$=291 i) 2-(Aminocarbonyl)-2,3-dihydro-1H-isoindol-5-yl-methanamine Hydrochloride

A solution of 2.2 g (7.55 mMol) of 2-(aminocarbonyl)-2,3-dihydro-5-[[[(1,1-dimethylethoxy)carbonyl]amino]methyl]-1H-isoindole in 20 ml of saturated methanolic hydrogen chloride solution was stirred for 1 hour at ambient temperature, then freed in vacuo from excess hydrogen chloride and the solvent. The residue was triturated with tetrahydrofuran and suction filtered and finally dried overnight in the desiccator. Yield: 94% of theory; colourless crystals, Mp. 222–223° C.

IR (KBr): 1662.5 (Amide-C=O) cm$^{-1}$ j) (R)-N-[[2-(Aminocarbonyl)-2,3-dihydro-1H-isoindol-5-yl]-methyl]-N$^5$-[amino(nitroimino)methyl]-N$^2$-(diphenylacetyl)-ornithinamide Prepared analogously to Example 4b), but using dimethylsulphoxide as solvent instead of dimethylformamide/tetrahydrofuran mixture and with the addition of HOBt, from (R)-N$^5$-[amino[nitroimino)methyl]-N$^2$-(diphenylacetyl)-ornithinine and 2-(aminocarbonyl)-2,3-dihydro-1H-isoindol-5-yl-methanamine-hydrochloride in a yield of 21% of theory. Colourless crystals.

IR (KBr): 3288.4 (N-H), 1641.3 (Amide-C=O) cm$^{-1}$ k) (R)-N-[[2-(Aminocarbonyl)-2,3-dihydro-1H-isoindol-5-yl]-methyl]-N$^2$-(diphenylacetyl)-argininamide Prepared analogously to Example 4c) from (R)-N-[[2-(aminocarbonyl)-2,3-dihydro-1H-isoindol-5-yl]methyl]-N$^5$-[amino(nitroimino)methyl]-N$^2$-(diphenylacetyl)-ornithinamide by catalytic hydrogenation in the presence of palladium black and 80% aqueous acetic acid in a yield of 65% of theory.

R$_f$ value: 0.30; amorphous-foamy substance.
IR (KBr): 1641.3 (Amide-C=O) cm$^{-1}$
ESI-MS: (M+H)$^+$=542 (M+Na)$^+$=564

EXAMPLE 66

(R,S)-N-[[4-(Aminocarbonylaminomethyl)phenyl]methyl]-N$^2$-[[[(2-naphthyl)methyl]amino]carbonyl]-argininamide a) (R,S)-N$^5$-(Phenylmethoxycarbonyl)-ornithinemethylester-hydrochloride Prepared analogously to Example 53a) from (R,S)-N$^2$-carboxy-N$^5$-(phenylmethoxycarbonyl)-ornithinanhydride and saturated methanolic hydrogen chloride solution in a quantitative yield. Highly viscous oil which was reacted without further purification.

b) Methyl (R,S)-2-(isocyanato)-5-[(phenylmethoxycarbonyl)amino]-pentanoate

To a mixture of 10.7 g (33.8 mMol) of (R,S)-N$^5$-(phenyl-methoxycarbonyl)-ornithinemethylester-hydrochloride, 150 ml of anhydrous dichloromethane and 11 ml (136.2 mMol) of pyridine were added, dropwise and at a reaction temperature of 0 to 5° C., with stirring, 25.6 ml (49.4 mMol) of a 1.93 M solution of phosgene in toluene. The mixture was stirred for a further 2 hours at 0° C., filtered to remove the salt-like precipitate and the filtrate was evaporated down in vacuo. The oily residue remaining was dissolved in 150 ml of dry dichloromethane. Aliquot amounts thereof were used in the following reactions without purification.

c) (R,S)-N$^2$-[[[(2-Naphthyl)methyl]amino]carbonyl]-N$^5$-(phenylmethoxycarbonyl)-ornithinemethylester Prepared analogously to Example 11a) from 2-naphthalenemethanamine and methyl (R,S)-2-(isocyanato)-5-[(phenylmethoxycarbonyl)amino]pentanoate in a quantitative yield. The colourless, amorphous product was used in the following step without any further purification.

d) (R,S)-N$^2$-[[[(2-naphthyl)methyl]amino]carbonyl]-N$^5$-(phenylmethoxycarbonyl)-ornithine Prepared analogously to Example 49a), but using ethanol as solvent instead of methanol, by alkaline saponification of (R,S)-N$^2$-[[[(2-naphthyl)methyl]amino]carbonyl]-N$^5$-(phenylmethoxycarbonyl)-ornithinemethylester in a yield of 43% of theory. Colourless crystals, Mp. 148° C. (ethyl acetate).

IR (KBr): 3311.6 (N-H), 1689.5, 1627.8 (C=O) cm$^{-1}$ e) (R,S)-N-[[4-(Aminocarbonylaminomethyl)phenyl]methyl]-N$^2$-[[[(2-naphthyl)methyl]amino]carbonyl]-N$^5$-(phenylmethoxycarbonyl)-ornithinamide Prepared analogously to Example 14c) from (R,S)-N$^2$-[[[(2-naphthyl)methyl]amino]carbonyl]-N$^5$-(phenylmethoxycarbonyl)-ornithine, 4-(aminocarbonylaminomethyl)benzenemethanamine and TBTU in a yield of 93% of theory. Colourless crystals, Mp. 202–204° C.

IR (KBr): 1652.9 (Amide-/Urea-C=O) cm$^{-1}$ f) (R,S)-N-[[4-(Aminocarbonylaminomethyl)phenyl]methyl]-N$^2$-[[[(2-naphthyl)methyl]amino]carbonyl]-ornithinamide-acetate Prepared analogously to Example 1d), but using a mixture of methanol, water, glacial acetic acid and dimethylformamide (14/6/2/10; v/v/v/v/) as solvent instead of pure methanol, from (R,S)-N-[[4-(aminocarbonylaminomethyl)phenyl]-ethyl]-N$^2$-[[[(2-naphthyl)methyl]amino]carbonyl]-N$^5$-(phenyl-methoxycarbonyl)-ornithinamide by catalytic hydrogenation in the presence of palladium/activated charcoal in a yield of 94% of theory. Colourless crystals, Mp. 176° C. (Acetonitrile).

IR (KBr): 1645.2, 1618.2 (Amide-/Urea-C=O) cm$^{-1}$ g) (R,S)-N-[[4-(Aminocarbonylaminomethyl)phenyl]methyl]-N$^2$-[[[(2-naphthyl)methyl]amino]carbonyl]-argininamide Prepared analogously to Example 32d) from (R,S)-N-[[4-(aminocarbonylaminomethyl)phenyl]methyl]-N$^2$-[[[(2-naphthyl)methyl]amino]carbonyl]-ornithinamide-acetate and 3,5-dimethylpyrazole-1-carboxylic acid amidinium nitrate in a yield of 27% of theory. Colourless crystals, Mp. 178° C. (Methanol).

R$_f$ value: 0.31.
IR (KBr): 1652.9 (Amide-/Urea-C=O) cm$^{-1}$
ESI-MS: (M+H)$^+$=519

EXAMPLE 67

(R)-N$^2$-(Diphenylacetyl)-N-[[4-[(2-oxo-1-imidazolidinyl)-methyl]phenyl]methyl]-argininamide-acetate a) 1-(2-Chloroethyl)-3-[(4-cyanophenyl)methyl]-urea Prepared analogously to Example 11a), but using dioxane as solvent instead of tetrahydrofuran, from 4-cyanobenzenemethanamine and 2-chloroethylisocyanate in a yield of 84% of theory. Colourless crystals, Mp.-179–180° C.

IR (KBr): 3328.9 (N-H), 2229.6 (C N), 1622.0 (Urea-C=O) cm$^{-1}$ b) 1-[(4-Cyanophenyl)methyl]-imidazolidin-2-one To a solution of 20.0 g (84.1 mMol) of 1-(2-chloroethyl)-3-[(4-cyanophenyl)methyl]-urea in 200 ml of anhydrous dimethylformamide were added, in batches and at ambient temperature, 11.2 g (99.8 mMol) of potassium-tert.butoxide and the mixture was then stirred for 2 hours at +40° C. The reaction mixture was evaporated down in vacuo, the residue remaining was distributed between water and ethyl acetate, the organic phase was dried over sodium sulphate, clarified over activated charcoal and evaporated down in vacuo once more. The residue was triturated with tert.butyl-methylether, suction filtered and dried in a vacuum dryer. 3.0 g (18% of theory) of colourless crystals were obtained, Mp. 117–118° C.

IR (KBr): 3232.5 (N-H), 2231.5 (C N), 1697.3 (Five-membered ring-C=O) cm$^{-1}$
MS: M$^+$=201 c) 4-[(2-Oxo-1-imidazolidinyl)methyl]benzenemethanamine-hydrochloride

Prepared analogously to Example 43b) from 1-[(4-cyanophenyl)methyl]imidazolidin-2-one by catalytic hydrogenation using palladium/activated charcoal and in the presence of 1 equivalent of 1N hydrochloric acid in a yield of 81% of theory. Colourless crystals, Mp. >250° C. (Tetrahydrofuran).

IR (KBr): 3261.4 (N-H), 1676.0 (Five-membered ring-C=O)cm$^{-1}$ d) (R)-N$^5$-[Amino(nitroimino)methyl]-N$^2$-(diphenylacetyl)-N-[[4-[(2-oxo-1-imidazolidinyl)methyl]phenyl]methyl]-ornithinamide Prepared analogously to Example 4b), but with the addition of HOBt and using acetonitrile as solvent instead of the dimethylformamide/tetrahydrofuran mixture, from (R)-N$^5$-[aminonitroimino)methyl]-N$^2$-(diphenylacetyl)-ornithine, 4-[(2-oxo-1-imidazolidinyl)methyl]benzenemethanamine-hydrochloride and TBTU in a yield of 21% of theory. Colourless, amorphous substance.

IR (KBr): 3379.1, 3307.7 (N-H), 1693.4 (Five-membered ring-C=O), 1641.3 (Amide-C=O) cm$^{-1}$ ESI-MS: (M+H)$^+$=601 (M+Na)$^+$=623 e) (R)-N$^2$-(Diphenylacetyl)-N-[[4-[(2-oxo-1-imidazolidinyl)-methyl]phenyl]methyl]-argininamide-acetate Prepared analogously to Example 4c) from (R)-N$^5$-[amino(nitroimino)methyl]-N$^2$-(diphenylacetyl)-N-[[4-[(2-oxo-1-imidazolidinyl)methyl]phenyl]methyl]-ornithinamide by catalytic hydrogenation in the presence of palladium black and 80% aqueous acetic acid in a yield of 32% of theory.

R$_f$ value: 0.33; colourless, amorphous substance.

IR (KBr): 1660.6 (Amide-/Urea-C=O) cm$^{-1}$

ESI-MS: (M+H)$^+$=556 (M+Na)$^+$=578

EXAMPLE 68

(R,S)-N-[[4-(Aminocarbonylaminomethyl)phenyl]methyl]-3-[3-(aminoiminomethyl)phenyl]-N$^2$-[[(2-butyl-1H-benzimidazol-5-yl)amino]carbonyl]-alaninamide-acetate a) (R,S)-3-(3-Cyanophenyl)-alanine-methylester-hydrochloride A mixture of 33.0 g (145.6 mMol) of (R,S)-3-(3-cyanophenyl)-alanine-hydrochloride, 1 l of anhydrous methanol and 37.5 g (345.2 mMol) of chlorotrimethylsilane was stirred for 3 days at ambient temperature. The solvent was distilled off in vacuo, the residue was taken up in 300 ml of dichloromethane and washed successively with water, saturated aqueous sodium hydrogen carbonate solution and with water, dried over magnesium sulphate and freed from solvent once more. The oily residue remaining was dissolved in ethyl acetate and converted into the hydrochloride by means of ethereal hydrogen chloride solution. After drying, 23.0 g (66% of theory) of colourless crystals were obtained, Mp. 157–159° C.

b) Methyl (R,S)-3-cyano-α-(isocyanato)benzene-propanoate

Prepared analogously to Example 66b) from (R,S)-3-(3-cyanophenyl)-alanine methylester-hydrochloride and phosgene. Subsequently, aliquot amounts of a dichloromethane solution having a defined content of the resulting isocyanate were used.

c) (R,S)-N$^2$-[[(2-Butyl-1H-benzimidazol-5-yl)amino]carbonyl]-3-(3-cyanophenyl)-alanine Methylester Prepared analogously to Example 11a), but using anhydrous dichloromethane as solvent instead of tetrahydrofuran, from 5-amino-2-butyl-1H-benzimidazole and methyl (R,S)-3-cyano-α-(isocyanato)benzene-propanoate in a quantitative yield. The amorphous, resin-like crude product obtained was used in the following step without any further purification.

d) (R,S)-N$^2$-[[(2-Butyl-1H-benzimidazol-5-yl)amino]carbonyl]-3-(3-cyanophenyl)-alanine Prepared analogously to Example 59a) by saponifying (R,S)-N$^2$-[[(2-butyl-1H-benzimidazol-5-yl)amino]carbonyl]-3-(3-cyanophenyl)-alanine methylester with aqueous lithium hydroxide in a yield of 39% of theory. Colourless crystals, which were used in the following step without total purification.

e) (R,S)-N-[[4-(Aminocarbonylaminomethyl)phenyl]methyl]-N$^2$-[[(2-butyl-1H-benzimidazol-5-yl)amino]carbonyl]-3-(3-cyanophenyl)-alaninamide Prepared analogously to Example 14c) from (R,S)-N$^2$-[[(2-butyl-1H-benzimidazol-5-yl)amino]carbonyl]-3-(3-cyanophenyl)-alanine, 4-(aminocarbonylaminomethyl)benzenemethanamine and TBTU in a yield of 72% of theory. Colourless crystals.

f) (R,S)-N-[[4-(Aminocarbonylaminomethyl)phenyl]methyl]-3-[3-[amino(hydroxyimino)methyl]phenyl]-N$^2$-[[(2-butyl-1H-benzimidazol-5-yl)amino]carbonyl]-alaninamide Prepared analogously to Example 14d), but using sodium carbonate instead of diisopropylethylamine, from (R,S)-N-[[4-(aminocarbonylaminomethyl)phenyl]methyl]-N$^2$-[[(2-butyl-1H-benzimidazol-5-yl)amino]carbonyl]-3-(3-cyanophenyl)-alaninamide and hydroxylamine-hydrochloride in a yield of 76% of theory.

IR (KBr): 1647.1 (Amide-/Urea-C=O) cm$^{-1}$

ESI-MS: (M+H)$^+$=600 (M+2H)$^{++}$=300.6 g) (R,S)-N-[[4-(Aminocarbonylaminomethyl)phenyl]methyl]-3-[3-(aminoiminomethyl)phenyl]-N$^2$-[[(2-butyl-1H-benzimidazol-5-yl)amino]carbonyl-alaninamide-acetate Prepared analogously to Example 14e) from (R,S)-N-[[4-(aminocarbonylaminomethyl)phenyl]methyl]-3-[3-[amino(hydroxyimino)methyl]phenyl]-N$^2$-[[(2-butyl-1H-benzimidazol-5-yl)amino]carbonyl]-alaninamide by catalytic hydrogenation in the presence of palladium/activated charcoal and glacial acetic acid as solvent in a yield of 55% of theory.

R$_f$ value: 0.18; colourless, amorphous substance.

IR (KBr): 1664.2 (Amide-/Urea-C=O), 1562.2 (Amide-II) cm$^{-1}$

ESI-MS: (M+H)$^+$=584.2 (M+2H)$^{++}$=292.6 (M+Na)$^+$=606.4

EXAMPLE 69

(R)-N-[[4-(Aminocarbonylaminomethyl)phenyl]methyl]-N$^2$-[[(1-naphthyl)]amino]carbonyl]-argininamide-acetate a) (R)-N-[[4-(Aminocarbonylaminomethyl)phenyl]methyl]-N$^5$-[amino(nitroimino)methyl]-N$^2$-[(1,1-dimethylethoxy)-carbonyl]-ornithinamide Prepared analogously to Example 14c), but with the addition of HOBt, from (R)-N$^5$-[amino(nitroimino)methyl]-N$^2$-[(1,1-dimethylethoxy)-carbonyl]-ornithine, 4-(aminocarbonylaminomethyl)-benzenemethanamine and TBTU in a yield of 80% of theory. Colourless crystals, Mp. 172° C.

(KBr): 3454.3, 3419.6, 3332.8 (N-H), 1681.8 (Carbamate-C=O), 1660.6 (Amide-/Urea-C=O) cm$^{-1}$ b) (R)-N-[[4-(Aminocarbonylaminomethyl)phenyl]methyl]-N$^5$-[amino(nitroimino)methyl]-ornithinamidehydrochloride Prepared analogously to Example 65i) from (R)-N-[[4-(aminocarbonylaminomethyl)phenyl]methyl]-N$^5$-[amino(nitroimino)methyl]-N$^2$-[(1,1-dimethylethoxy)carbonyl]-ornithinamide and methanolic hydrogen chloride solution in a quantitative yield. Colourless crystals.

IR (KBr): 1676.0, 1635.5 (Amide-/Urea-C=O) cm$^{-1}$

ESI-MS: (M+H)$^+$=381 (M+Na)$^+$=403 c) (R)-N-[[4-(Aminocarbonylaminomethyl)phenyl]methyl]-N$^5$-[amino(nitroimino)methyl]-N$^2$-[[(1-naphthyl)amino]carbonyl]-ornithinamide Prepared analogously to Example 11a), but using dimethylformamide as solvent instead of tetrahydrofuran and diisopropylethylamine as auxiliary base instead of triethylamine, from 1-naphthylisocyanate and (R)-N-[[4-(aminocarbonylaminomethyl)phenyl]methyl]-N$^5$-[amino(nitroimino)methyl]-ornithinamidehydrochloride in a yield of 71% of theory. Colourless crystals, Mp. 210° C.

IR (KBr): 1625.9 (Amide-/Urea-C=O) cm$^{-1}$

ESI-MS: (M+H)$^+$=550 (M+Na)$^+$=572 (M+K)$^+$=588 d) (R)-N-[[4-(Aminocarbonylaminomethyl)phenyl]methyl]-N$^2$-[[(1-naphthyl)amino]carbonyl]-argininamide-acetate Prepared analogously to Example 4c) from (R)-N-[[4-(aminocarbonylaminomethyl)phenyl]methyl]-N$^5$-[amino (nitroimino)methyl]-N²-[[(1-naphthyl)amino]carbonyl]-ornithinamide by catalytic hydrogenation in the presence of palladium black and 80% aqueous acetic acid in a yield of 58% of theory.

$R_f$ value: 0.31; colourless crystals.

IR (KBr): 3333.2 (N-H), 1648.1, 1628.9 (Amide-/Urea-C=O), 1546.4 (Amide-II) cm$^{-1}$ ESI-MS: (M+H)$^+$=505 (M+Na)$^+$=527

EXAMPLE 70

(R,S)-N²-(Diphenylacetyl)-N-[[4-[2-(3-methyl-1,2,4-oxadiazol-5-yl)ethyl]phenyl]methyl]-argininamide-acetate a) 3-Methyl-5-[2-[4-(aminomethyl)phenyl]ethyl]-1,2,4-oxadiazole-hydrochloride A solution of 3.0 g (40.5 mMol) of acetamidoxime in 100 ml of anhydrous tetrahydrofuran was mixed with 1.96 g (44.9 mMol) of a 55% sodium hydride dispersion and stirred for 1 hour at a reaction temperature of 50° C. The mixture was left to cool, 6.0 g (20.45 mMol) of methyl 4-[[[(1,1-dimethylethoxy)carbonyl]amino]methyl]benzenepropanoate were added and the resulting mixture was refluxed for 2 hours. After cooling the mixture was filtered, the filtrate was evaporated down in a water jet vacuum and the residue was stirred overnight at ambient temperature with 100 ml of a saturated methanolic hydrogen chloride solution. After working up in the conventional manner, 1.2 g (23% of theory) of colourless crystals were obtained.

IR (KBr): 3292.3 (N-H) cm$^{-1}$

MS: M$^+$=217 b) (R,S)-N⁵-[(1,1-Dimethylethoxy)carbonyl]-N²-(diphenylacetyl)-N-[[4-[2-(3-methyl-1,2,4-oxadiazol-5-yl)ethyl]-phenyl]methyl]-ornithinamide Prepared analogously to Example 67d) from (R,S)-N⁵-[(1,1-dimethylethoxy)carbonyl]-N²-(diphenylacetyl)-ornithine, 3-methyl-5-[2-[4-(aminomethyl)phenyl]ethyl]-1,2,4-oxadiazole-hydrochloride and TBTU in a yield of 49% of theory. Colourless crystals.

IR (KBr): 3350.2 (N-H), 1678.0, 1647.1 (Carbamate-/Amide-C=O) cm$^{-1}$ c) (R,S)-N²-(Diphenylacetyl)-N-[[4-[2-(3-methyl-1,2,4-oxadiazol-5-yl)ethyl]phenyl]methyl]-ornithinamidehydrochloride Prepared analogously to Example 65i) from (R,S)-N⁵-[(1,1-dimethylethoxy)carbonyl]-N²-(diphenylacetyl)-N-[[4-[2-(3-methyl-1,2,4-oxadiazol-5-yl)ethyl]phenyl]methyl]-ornithinamide by treating with methanolic hydrogen chloride solution in a yield of 97% of theory. Colourless crystals, which were used without purification in the next stage.

d) (R,S)-N²-(Diphenylacetyl)-N-[[4-[2-(3-methyl-1,2,4-oxadiazol-5-yl)ethyl]phenyl]methyl]-argininamide-acetate Prepared analogously to Example 32d), but using tetrahydrofuran as solvent instead of dimethylformamide, from (R,S)-N²- (diphenylacetyl)-N-[[4-[2-(3-methyl-1,2,4-oxadiazol-5-yl)ethyl]phenyl]methyl]-ornithinamide-hydrochloride and 3,5-dimethylpyrazole-1-carboxylic acid amidinium nitrate in a yield of 23% of theory.

$R_f$ value: 0.49; colourless, amorphous substance. IR (KBr): 3398.3, 3287.6 (N—H), 1642.9 (Amide-C=O), 1580.1, 1559.2, 1540.3 (C=N, Amide-II) cm$^{-1}$ ESI-MS: (M+H)$^+$=568 (M+Na)$^+$=590

Example 71

(R)-N-[[4-(Aminocarbonylaminomethyl)phenyl]methyl]-N²-[(1H-indol-2-yl)carbonyl]-argininamide-hydrochloride a) (R)-N-[[4-(Aminocarbonylaminomethyl)phenyl]methyl]-N⁵-[amino(nitroimino)methyl]-N²-[(1H-indol-2-yl)carbonyl]ornithinamide Prepared analogously to Example 69a) from 1H-indole-2-carboxylic acid, (R)-N-[[4-(aminocarbonylaminomethyl)phenyl]methyl]-N⁵-[amino(nitroimino)methyl]-ornithinamide-hydrochloride and TBTU in a yield of 20% of theory.

Colourless crystals, Mp. 220° C. ESI-MS: (M+Na)$^+$=546 (M+K)$^+$=562 b) (R)-N-[[4-(Aminocarbonylaminomethyl)phenyl]methyl]-N²-[(1H-indol-2-yl)carbonyl]-argininamide-hydrochloride Prepared analogously to Example 4c) from (R)-N-[[4-(aminocarbonylaminomethyl)phenyl]methyl]-N⁵-[amino(nitroimino)methyl]-N²-[(1H-indol-2-yl)carbonyl]-ornithinamide by catalytic hydrogenation in the presence of palladium black and 80% aqueous acetic acid and subsequent treatment with hydrochloric acid in a yield of 72% of theory.

$R_f$ value: 0.32; colourless, amorphous substance. IR (KBr): 1649.0 (Amide-/Urea-C=O) cm$^{-1}$ ESI-MS: (M+H)$^+$=479

Example 72

(R)-N-[[4-(Aminocarbonylaminomethyl)phenyl]methyl]-N²-[(1H-indol-3-yl)acetyl]-argininamide-acetate a) (R)-N-[[4-(Aminocarbonylaminomethyl)phenyl]methyl]-N⁵-[amino(nitroimino)methyl]-N²-[(1H-indol-3-yl)acetyl]ornithinamide Prepared analogously to Example 69a) from 1H-indole-3-acetic acid, (R)-N-[[4-(aminocarbonylaminomethyl)phenyl]methyl]-N⁵-[amino(nitroimino)methyl]-ornithinamide-hydrochloride and TBTU in a yield of 50% of theory.

Colourless crystals (Isopropanol). ESI-MS: (M+Na)$^+$=560 (M+K)$^+$=576 b) (R)-N-[[4-(Aminocarbonylaminomethyl)phenyl]methyl]-N²-[(1H-indol-3-yl)acetyl]-argininamide-acetate Prepared analogously to Example 4c) from (R)-N-[[4-(aminocarbonylaminomethyl)phenyl]methyl]-N⁵-[amino(nitroimino)methyl]-N²-[(1H-indol-3-yl)acetyl]-ornithinamide by catalytic hydrogenation in the presence of palladium black and 80% aqueous acetic acid in a yield of 60% of theory.

$R_f$ value: 0.25; colourless, amorphous substance. IR (KBr): 1652.9 (Amide-/Urea-C=O) cm$^{-1}$ ESI-MS: (M+H)$^+$=493

Example 73

(R)-N-[[4-(Aminocarbonylaminomethyl)phenyl]methyl]-N²-[[(3,4-dichlorophenyl)]amino]carbonyl]-argininamide-trifluoroacetate a) (R)-N-[[4-(Aminocarbonylaminomethyl)phenyl]methyl]-N²-[[(3,4-dichlorophenyl)]amino]carbonyl]-N$^G$-(2,2,5,7,8-pentamethylchroman-6-sulphonyl)-argininamide Prepared analogously to Example 69c) from 3,4-dichlorophenylisocyanate and (R)-N-[[4-(aminocarbonylaminomethyl)phenyl]methyl]-N$^G$-(2,2,5,7,8-pentamethylchroman-6-sulphonyl)-argininamide in a yield of 90% of theory.

Colourless crystals, Mp. 160–162° C. IR (KBr): 1635.5 (Amide-/Urea-C=O) cm$^{-1}$ b) (R)-N-[[4-(Aminocarbonylaminomethyl)phenyl]methyl]-N²-[[(3,4-dichlorophenyl)amino]carbonyl]-argininamide-trifluoroacetate Prepared analogously to Example 1f) from (R)-N-[[4-(aminocarbonylaminomethyl)phenyl]methyl]-N²-[[(3,4-dichlorophenyl)amino]carbonyl]-N$^G$-(2,2,5,7,8-pentamethylchroman-6-sulphonyl)-argininamide and trifluoroacetic acid in a yield of 68% of theory.

$R_f$ value: 0.31; colourless crystals, Mp. 205–206° C. IR (KBr): 1635.5 (Amide-/Urea-C=O) cm$^{-1}$ ESI-MS: (M+H)$^+$=523/525/527 (Cl$_2$)

Example 74
(R)-N-[[4-(Aminocarbonylaminomethyl)phenyl]methyl]-N²-[(1H-indol-4-yl)carbonyl]-argininamide-acetate a) (R)-N-[[4-(Aminocarbonylaminomethyl)phenyl]methyl]-N⁵-[amino(nitroimino)methyl]-N²-[(1H-indol-4-yl)carbonyl]ornithinamide Prepared analogously to Example 69a) from 1H-indole-4-carboxylic acid, (R)-N-[[4-(aminocarbonylaminomethyl)phenyl]methyl]-N⁵-[amino(nitroimino)methyl]-ornithinamide-hydrochloride and TBTU in a yield of 82% of theory.

Colourless crystals, Mp. 191° C. (D.). ESI-MS: (M+H)⁺=524 (M+Na)⁺=546 (M+K)⁺=562 b) (R)-N-[[4-(Aminocarbonylaminomethyl)phenyl]methyl]-N²-[(1H-indol-4-yl)carbonyl]-argininamide-acetate Prepared analogously to Example 4c) from (R)-N-[[4-(aminocarbonylaminomethyl)phenyl]methyl]-N⁵-[amino(nitroimino)methyl]-N²-[(1H-indol-4-yl)carbonyl]-ornithinamide by catalytic hydrogenation in the presence of palladium black and 80% aqueous acetic acid in a yield of 72% of theory.

$R_f$ value: 0.28; colourless crystals (ethyl acetate/diisopropylether 1/4; v/v). IR (KBr): 1652.9 (Amide-/Urea-C=O) cm⁻¹ ESI-MS: (M+H)⁺=479

Example 75
(R)-N-[[4-(Aminocarbonylaminomethyl)phenyl]methyl]-N²-[(1H-indol-3-yl)carbonyl]-argininamide-acetate a) (R)-N-[[4-(Aminocarbonylaminomethyl)phenyl]methyl]-N⁵-[amino(nitroimino)methyl]-N²-[(1H-indol-3-yl)carbonyl]ornithinamide Prepared analogously to Example 69a) from 1H-indole-3-carboxylic acid, (R)-N-[[4-(aminocarbonylaminomethyl)phenyl]methyl]-N⁵-[amino(nitroimino)methyl]-ornithinamide-hydrochloride and TBTU in a yield of 31% of theory.

Colourless crystals (Tetrahydrofuran). ESI-MS: (M+H)⁺=524 (M+Na)⁺=546 (M+K)⁺=562 (M+NH₄)⁺=541 b) (R)-N-[[4-(Aminocarbonylaminomethyl)phenyl]methyl]-N²-[(1H-indol-3-yl)carbonyl]-argininamide-acetate Prepared analogously to Example 4c) from (R)-N-[[4-(aminocarbonylaminomethyl)phenyl]methyl]-N⁵-[amino(nitroimino)methyl]-N²-[(1H-indol-3-yl)carbonyl]-ornithinamide by catalytic hydrogenation in the presence of palladium black and 80% aqueous acetic acid in a yield of 24% of theory.

$R_f$ value: 0.27; colourless, amorphous substance. IR (KBr): 1658.7 (Amide-/Urea-C=O) cm⁻¹ ESI-MS: (M+H)⁺=479

Example 76
(R)-N-[[4-(Aminocarbonylaminomethyl)phenyl]methyl]-N²-[(1H-indol-5-yl)carbonyl]-argininamide-acetate a) (R)-N-[[4-(Aminocarbonylaminomethyl)phenyl]methyl]-N⁵-[amino(nitroimino)methyl]-N²-[(1H-indol-5-yl)carbonyl]-ornithinamide Prepared analogously to Example 69a) from 1H-indole-5-carboxylic acid, (R)-N-[[4-(aminocarbonylaminomethyl)phenyl]methyl]-N⁵-[amino-(nitroimino)methyl]-ornithinamide-hydrochloride and TBTU in a yield of 48% of theory.

Colourless crystals, Mp. 195–197° C. (D.) (Methanol). ESI-MS: (M+H)⁺=524 (M+Na)⁺=546 (M+K)⁺=562 b) (R)-N-[[4-(Aminocarbonylaminomethyl)phenyl]methyl]-N²-[(1H-indol-5-yl)carbonyl]-argininamide-acetate Prepared analogously to Example 4c) from (R)-N-[[4-(aminocarbonylaminomethyl)phenyl]methyl]-N⁵-[amino(nitroimino)methyl]-N²-[(1H-indol-5-yl)carbonyl]-ornithinamide by catalytic hydrogenation in the presence of palladium black and 80% aqueous acetic acid in a yield of 66% of theory.

$R_f$ value: 0.30; colourless, amorphous substance. IR (KBr): 1652.9 (Amide-/Urea-C=O) cm⁻¹ ESI-MS: (M+H)⁺=479

Example 77
(R)-N-[[4-(Aminocarbonylaminomethyl)phenyl]methyl]-N²-[3,5-bis-(trifluoromethyl)benzoyl]-argininamide-acetate a) (R)-N-[[4-(Aminocarbonylaminomethyl)phenyl]methyl]-N⁵-[amino(nitroimino)methyl]-N²-[3,5-bis-(trifluoromethyl)-benzoyl]-ornithinamide Prepared analogously to Example 69a) from 3,5-bis-(trifluoromethyl)-benzoic acid, (R)-N-[[4-(aminocarbonylaminomethyl)phenyl]methyl]-N⁵-[amino(nitroimino)methyl]-ornithinamide-hydrochloride and TBTU in a yield of 55% of theory.

Colourless crystal (diisopropylether/ethyl acetate 9/1, v/v). ESI-MS: (M+H)⁺=621 (M+Na)⁺=643 (M+K)⁺=659 b) (R)-N-[[4-(Aminocarbonylaminomethyl)phenyl]methyl]-N²-[3,5-bis-(trifluoromethyl)benzoyl]-argininamide-acetate Prepared analogously to Example 4c) from (R)-N-[[4-(aminocarbonylaminomethyl)phenyl]methyl]-N⁵-[amino(nitroimino)methyl]-N²-[3,5-bis-(trifluoromethyl)benzoyl]-ornithinamide by catalytic hydrogenation in the presence of palladium charcoal and 80% aqueous acetic acid in a yield of 52% of theory.

$R_f$ value: 0.37; colourless, amorphous substance. IR (KBr): 1652.9 (Amide-/Urea-C=O) cm⁻¹ ESI-MS: (M+H)⁺=576 (M+Na)⁺=598

Example 78
(R)-N-[[4-(Aminocarbonylaminomethyl)phenyl]methyl]-N²-(4-butylbenzoyl)-argininamide-acetate a) (R)-N-[[4-(Aminocarbonylaminomethyl)phenyl]methyl]-N⁵-[amino(nitroimino)methyl]-N²-(4-butylbenzoyl)-ornithinamide Prepared analogously to Example 69a) from 4-butylbenzoic acid, (R)-N-[[4-(aminocarbonylaminomethyl)phenyl]methyl]-N⁵-[amino(nitroimino)methyl]-ornithinamide-hydrochloride and TBTU in a yield of 33% of theory.

Colourless crystals, Mp. 217° C. ESI-MS: (M+H)⁺=541 (M+Na)⁺=563 (M+K)⁺=579 b) (R)-N-[[4-(Aminocarbonylaminomethyl)phenyl]methyl]-N²-(4-butylbenzoyl)-argininamide-acetate Prepared analogously to Example 4c) from (R)-N-[[4-(aminocarbonylaminomethyl)phenyl]methyl]-N⁵-[amino(nitroimino)methyl]-N²-(4-butylbenzoyl)-ornithinamide by catalytic hydrogenation in the presence of palladium black and 80% aqueous acetic acid in a yield of 39% of theory.

$R_f$ value: 0.33; colourless, amorphous substance. IR (KBr): 1658.7, 1631.7 (Amide-/Urea-C=O; C=N) cm⁻¹ ESI-MS: (M+H)⁺=496 (M+Na)⁺=518

Example 79
(R)-N-[[4-(Aminocarbonylaminomethyl)phenyl]methyl]-N²-(3,5-dimethylbenzoyl)-argininamide-acetate a) (R)-N-[[4-(Aminocarbonylaminomethyl)phenyl]methyl]-N⁵-[amino(nitroimino)methyl]-N²-(3,5-dimethylbenzoyl)-ornithinamide Prepared analogously to Example 69a) from 3,5-dimethylbenzoic acid, (R)-N-[[4-(aminocarbonylaminomethyl)phenyl]methyl]-N⁵-[amino(nitroimino)methyl]-ornithinamide-hydrochloride and TBTU in a yield of 49% of theory.

Colourless crystals, Mp. 204° C. (ethyl acetate). ESI-MS: (M+H)⁺=513 (M+Na)⁺=535 (M+K)⁺=551 b) (R)-N-[[4-(Aminocarbonylaminomethyl)phenyl]methyl]-$N^2$-(3,5-dimethylbenzoyl)-argininamide-acetate Prepared analogously to Example 4c) from (R)-N-[[4-(aminocarbonylaminomethyl)phenyl]methyl]-$N^5$-[amino(nitroimino)methyl]-$N^2$-(3,5-dimethylbenzoyl)-ornithinamide by catalytic hydrogenation in the presence of palladium black and 80% aqueous acetic acid in a yield of 62% of theory.

$R_f$ value: 0.30; colourless, amorphous substance. IR (KBr): 1654.8 (Amide-/Urea-C=O) cm$^{-1}$ ESI-MS: (M+H)$^+$=468 (M+Na)$^+$=490

Example 80
(R)-N-[[4-(Aminocarbonylaminomethyl)phenyl]methyl]-$N^2$-[(benzo[b]furan-2-yl)carbonyl]-argininamide-acetate a) (R)-N-[[4-(Aminocarbonylaminomethyl)phenyl]methyl]-$N^5$-[amino(nitroimino)methyl]-$N^2$-[(benzo[b]furan-2-yl)carbonyl]ornithinamide Prepared analogously to Example 69a) from benzo[b]furan-2-carboxylic acid, (R)-N-[[4-(aminocarbonylaminomethyl)phenyl]methyl]-$N^5$-[amino(nitroimino)methyl]-ornithinamidehydrochloride and TBTU in a yield of 56% of theory.

Colourless crystals, Mp. 214° C. (ethyl acetate). ESI-MS: (M+H)$^+$=525 (M+Na)$^+$=547 (M+K)$^+$=563 b) (R)-N-[[4-(Aminocarbonylaminomethyl)phenyl]methyl]-$N^2$-[(benzo[b]furan-2-yl)carbonyl]-argininamide-acetate Prepared analogously to Example 4c) from (R)-N-[[4-(aminocarbonylaminomethyl)phenyl]methyl]-$N^5$-[amino(nitroimino)methyl]-$N^2$-[(benzo[b]furan-2-yl)carbonyl]-ornithinamide by catalytic hydrogenation in the presence of palladium black and 80% aqueous acetic acid in a yield of 66% of theory.

$R_f$ value: 0.30; colourless, amorphous substance. IR (KBr): 1654.7 (Amide-/Urea-C=O), 1562.6 (Amide-II) cm$^{-1}$ ESI-MS: (M+H)$^+$=480 (M+Na)$^+$=502

Example 81
(R)-N-[[4-(Aminocarbonylaminomethyl)phenyl]methyl]-$N^2$-(6-methoxy-2-naphthoyl)-argininamide-acetate a) (R)-N-[[4-(Aminocarbonylaminomethyl)phenyl]methyl]-$N^5$-[amino(nitroimino)methyl]-$N^2$-(6-methoxy-2-naphthoyl)-ornithinamide Prepared analogously to Example 69a) from 6-methoxy-2-naphthoic acid, (R)-N-[[4-(aminocarbonylaminomethyl)phenyl]methyl]-$N^5$-[amino(nitroimino)methyl]-ornithinamide-hydrochloride and TBTU in a yield of 70% of theory.

Colourless crystals (Ethyl acetate). ESI-MS: (M+H)$^+$=565 (M+Na)$^+$=587 (M+K)$^+$=603 b) (R)-N-[[4-(Aminocarbonylaminomethyl)phenyl]methyl]-$N^2$-(6-methoxy-2-naphthoyl)-argininamide-acetate Prepared analogously to Example 4c) from (R)-N-[[4-(aminocarbonylaminomethyl)phenyl]methyl]-$N^5$-[amino(nitroimino)methyl]-$N^2$-(6-methoxy-2-naphthoyl)-ornithinamide by catalytic hydrogenation in the presence of palladium black and 80% aqueous acetic acid in a yield of 70% of theory.

$R_f$ value: 0.31; colourless, amorphous substance. IR (KBr): 1631.7 (Amide-/Urea-C=O) cm$^{-1}$ ESI-MS: (M+H)$^+$=520

Example 82
(R)-N-[[4-(Aminocarbonylaminomethyl)phenyl]methyl]-$N^2$-[(7-methyl-2-propyl-1H-benzimidazol-5-yl)carbonyl]-argininamide-diacetate a) (R)-N-[[4-(Aminocarbonylaminomethyl)phenyl]methyl]-$N^5$-[amino(nitroimino)methyl]-$N^2$-[(7-methyl-2-propyl-1H-benzimidazol-5-yl)carbonyl]-ornithinamide Prepared analogously to Example 69a) from 7-methyl-2-propyl-1H-benzimidazole-5-carboxylic acid, (R)-N-[[4-(aminocarbonylaminomethyl)phenyl]methyl]-$N^5$-[amino(nitroimino)methyl]-ornithinamide-hydrochloride and TBTU in a yield of 70% of theory.

Colourless, amorphous substance. IR (KBr): 1658.7 (Amide-/Urea-C=O), 1546.8 (Amide-II) cm$^{-1}$ ESI-MS: (M+H)$^+$=536.0 (M+Na)$^+$=558.1 (M+2H)$^{++}$=268.5 b) (R)-N-[[4-(Aminocarbonylaminomethyl)phenyl]methyl]-$N^2$-[(7-methyl-2-propyl-1H-benzimidazol-5-yl)carbonyl]-argininamide-diacetate Prepared analogously to Example 4c) from (R)-N-[[4-(aminocarbonylaminomethyl)phenyl]methyl]-$N^5$-[amino(nitroimino)methyl]-$N^2$-[(7-methyl-2-propyl-1H-benzimidazol-5-yl)carbonyl]-ornithinamide by catalytic hydrogenation in the presence of palladium black and 80% aqueous acetic acid in a yield of 54% of theory.

$R_f$ value: 0.13; colourless, amorphous substance. ESI-MS: (M+H)$^+$=581 (M+Na)$^+$=603 (M+H+Na)$^{++}$=302

Example 83
(R)-N-[[4-(Aminocarbonylaminomethyl)phenyl]methyl]-$N^2$-[(2-cyclopropyl-1,4-dimethyl-1H-benzimidazol-6-yl)carbonyl]argininamide-acetate a) (R)-N-[[4-(Aminocarbonylaminomethyl)phenyl]methyl]-$N^5$-[amino(nitroimino)methyl]-$N^2$-[(2-cyclopropyl-1,4-dimethyl-1H-benzimidazol-6-yl)carbonyl]-ornithinamide Prepared analogously to Example 69a) from 2-cyclopropyl-1,4-dimethyl-1H-benzimidazole-6-carboxylic acid, (R)-N-[[4-(aminocarbonylaminomethyl)phenyl]methyl]-$N^5$-[amino(nitroimino)methyl]-ornithinamide-hydrochloride and TBTU in a yield of 51% of theory.

Colourless, amorphous substance. ESI-MS: (M+H)$^+$=593 (M+Na)$^+$=615 (M+H+Na)$^{++}$=308 b) (R)-N-[[4-(Aminocarbonylaminomethyl)phenyl]methyl]-$N^2$-[(2-cyclopropyl-1,4-dimethyl-1H-benzimidazol-6-yl)carbonyl]-argininamide-acetate Prepared analogously to Example 4c) from (R)-N-[[4-(aminocarbonylaminomethyl)phenyl]methyl]-$N^5$-[amino(nitroimino)methyl]-$N^2$-[(2-cyclopropyl-1,4-dimethyl-1H-benzimidazol-6-yl)carbonyl]-ornithinamide by catalytic hydrogenation in the presence of palladium black and 80% aqueous acetic acid in a yield of 40% of theory.

$R_f$ value: 0.06; colourless, amorphous substance. IR (KBr): 1666.4 (Amide-/Urea-C=O) cm$^{-1}$ ESI-MS: (M+H)$^+$=548 (M+2H)$^{++}$=274.5

Example 84
(R)-$N^2$-(Diphenylacetyl)-N-[[4-[[(5-methyl-4(3H)-oxopyrimidin-2-yl)amino]methyl]phenyl]methyl]-argininamide acetate a) 5-Methyl-2-(methylthio)pyrimidin-4(3H)-one A solution of 10.0 g (70.3 mMol) of 5-methyl-4(3H)-oxopyrimidin-2-thiol in 100 ml of dimethylsulphoxide was mixed successively with 2.2 g (6.82 mMol) of tetrabutylammonium bromide, 3.8 g (67.7 mMol) of potassium hydroxide, dissolved in 10 ml of water, and 4.8 ml (80 mMol) of methyliodide and the mixture was then stirred for 2 hours at ambient temperature. The yellow precipitate formed was removed by suction filtering, washed with a little ethanol and with diethylether and dried in vacuo. 8.6 g (81% of theory) of yellow crystals were obtained, Mp. 238–239° C.

IR (KBr): 1645.2 (C=O) cm$^{-1}$ b) 4-[[(5-Methyl-4(3H)-oxopyrimidin-2-yl)amino]methyl]benzonitrile A mixture of 8.6 g (55.1 mMol) of 5-methyl-2-(methylthio)pyrimidin-4(3H)-one, 80 ml of anhydrous pyridine and 9.2 g (69.6 mMol) of 4-cyanobenzenemethanamine was refluxed for 24 hours. The cooled mixture was stirred into 300 ml of ice water, the precipitate formed was suction filtered and recrystallised from methanol. 8.0 g (60% of theory) of pale yellow crystals were obtained, Mp. 226–228° C.

IR (KBr): 3581.6 (O—H), 3485.2, 3348.2 (N—H), 2231.5 (C N), 1656.8 (C=O) cm$^{-1}$ c) 4-[[(5-Methyl-4(3H)-oxopyrimidin-2-yl)amino]methyl]-benzenemethanamine Prepared analogously to Example 6c) from 4-[[(5-methyl-4(3H)-oxopyrimidin-2-yl)amino]methyl]benzonitrile by catalytic hydrogenation in the presence of Raney nickel and ammonia in a quantitative yield. Pale yellow crystals, Mp. 215–216° C.

IR (KBr): 1643.3 (C=O) cm$^{-1}$ MS: M$^+$=244 d) (R)-N$^5$-[Amino(nitroimino)methyl]-N$^2$-(diphenylacetyl)-N-[[4-[[(5-methyl-4(3H)-oxopyrimidin-2-yl)amino]methyl]phenyl]methyl]-ornithinamide Prepared analogously to Example 69a) from (R)-N$^5$-[amino(nitroimino)methyl]-N$^2$-(diphenylacetyl)-ornithine, 4-[[(5-methyl-4(3H)-oxopyrimidin-2-yl)amino]methyl]benzenemethanamine and TBTU in a quantitative yield. The crude product was used in the next step without purification.

e) (R)-N$^2$-(Diphenylacetyl)-N-[[4-[[(5-methyl-4(3H)-oxopyrimidin-2-yl)amino]methyl]phenyl]methyl]-argininamide-acetate Prepared analogously to Example 4c) from (R)-N$^5$-[aminonitroimino)methyl]-N$^2$-(diphenylacetyl)-N-[[4-[[(5-methyl-4(3H)-oxopyrimidin-2-yl)amino]methyl]phenyl]methyl]-ornithinamide by catalytic hydrogenation in the presence of palladium black and 80% aqueous acetic acid in a yield of 34% of theory.

R$_f$ value: 0.35; crystals, Mp. 165–167° C. IR (KBr): 1639.4 (C=O) cm$^{-1}$ ESI-MS: (M+H)$^+$=595 (M+2H)$^{++}$=298

Example 85
(R)-N$^2$-(Diphenylacetyl)-N-[[4-[[(6-methyl-4(3H)-oxopyrimidin-2-yl)amino]methyl]phenyl]methyl]-argininamide-acetate a) 6-Methyl-2-(methylthio)pyrimidin-4(3H)-one Prepared analogously to Example 84a) from 5-methyl-4(3H)-oxopyrimidin-2-thiol and methyliodide in a yield of 47% of theory.

Yellow crystal, Mp. 218° C. (Methanol). IR (KBr): 1643.3 (C=O) cm$^{-1}$ b) 4-[[(6-Methyl-4(3H)-oxopyrimidin-2-yl)amino]methyl]-benzonitrile Prepared analogously to Example 84b) from 6-methyl-2-(methylthio)pyrimidin-4(3H)-one and 4-cyanobenzenemethanamine in a yield of 67% of theory.

Crystals, Mp. 222–224° C. (Methanol). IR (KBr): 3359.8 (N—H), 2227.7 (C N), 1664.5 (C=O) cm$^{-1}$ c) 4-[[(6-Methyl-4(3H)-oxopyrimidin-2-yl)amino]methyl]-benzenemethanamine Prepared analogously to Example 6c) from 4-[[(6-methyl-4(3H)-oxopyrimidin-2-yl)amino]methyl]benzonitrile by catalytic hydrogenation in the presence of Raney nickel and ammonia in a quantitative yield.

Pale yellow crystals, Mp. 106° C. IR (KBr): 1656.8 (C=O) cm$^{-1}$ d) (R)-N$^5$-[Amino(nitroimino)methyl]-N$^2$-(diphenylacetyl)-N-[[4-[[(6-methyl-4(3H)-oxopyrimidin-2-yl)amino]methyl]phenyl]methyl]-ornithinamide Prepared analogously to Example 69a) from (R)-N$^5$-[amino(nitroimino)methyl]-N$^2$-(diphenylacetyl)-ornithine, 4-[[(6-methyl- 4(3H)-oxopyrimidin-2-yl)amino]methyl]benzenemethanamine and TBTU in a yield of 61% of theory.

Crystals, Mp. 194–196° C. (Methanol). IR (KBr): 3290.4 (N—H), 1637.5 (Amide-C=O) cm$^{-1}$ ESI-MS: (M+H)$^+$=640 (M+Na)$^+$=662 e) (R)-N$^2$-(Diphenylacetyl)-N-[[4-[[(6-methyl-4(3H)-oxopyrimidin-2-yl)amino]methyl]phenyl]methyl]-argininamide-acetate Prepared analogously to Example 4c) from (R)-N$^5$-[amino(nitroimino)methyl]-N$^2$-(diphenylacetyl)-N-[[4-[[(6-methyl-4(3H)-oxopyrimidin-2-yl)amino]methyl]phenyl]methyl]-ornithinamide by catalytic hydrogenation in the presence of palladium black and 80% aqueous acetic acid in a yield of 77% of theory.

R$_f$ value: 0.34; crystals (Acetone). IR (KBr): 1641.3 (Amide-C=O) cm$^{-1}$ ESI-MS: (M+H)$^+$=595 (M+Na)$^+$=617 (M+2H)$^{++}$=298

Example 86
(R,S)-N-[[4-(Aminocarbonylaminomethyl)phenyl]methyl]-3-(1H-benzimidazol-5-yl)-N$^2$-(diphenylacetyl)-alaninamide-hydrochloride a) (R,S)-3-(4-Amino-3-nitrophenyl)-N$^2$-(diphenylacetyl)-alanine Prepared analogously to Example 4a) from diphenylacetylchloride and (R,S)-3-[4-(acetylamino)-3-nitrophenyl]-N$^2$-(trifluoroacetyl)-alanine in a yield of 87% of theory.

Crystals. IR (KBr): 1726.2 (Carboxylic acid-C=O), 1637.5 (Amide-C=O), 1519.8 (Amide-II), 1342.4 (NO$_2$) cm$^{-1}$ b) (R,S)-N-[[4-(Aminocarbonylaminomethyl)phenyl]methyl]-3-(4-amino-3-nitrophenyl)-N$^2$-(diphenylacetyl)-alaninamide Prepared analogously to Example 69a) from (R,S)-3-(4-amino-3-nitrophenyl)-N$^2$-(diphenylacetyl)-alanine, 4-(aminocarbonylaminomethyl)benzenemethanamine and TBTU in a yield of 64% of theory.

Crystals, Mp. 190–193° C. (Methanol). IR (KBr): 1641.3 (Amide-/Urea-C=O), 1517.9 (Amide-II), 1340.4 (NO$_2$) cm$^{-1}$ c) (R,S)-N-[[4-(Aminocarbonylaminomethyl)phenyl]methyl]-3-(1-formyl-1H-benzimidazol-5-/-6-yl)-N$^2$-(diphenylacetyl)-alaninamide A solution of 3.7 g (6.372 mMol) of (R,S)-N-[[4-(aminocarbonylaminomethyl)phenyl]methyl]-3-(4-amino-3-nitrophenyl)-N$^2$-(diphenylacetyl)-alaninamide in 100 ml of formic acid was hydrogenated under a hydrogen pressure of 5 bar and at a temperature of 60° C. in the presence of 1.0 g of palladium black until the uptake of hydrogen had ceased. The catalyst was filtered off, the filtrate was stirred into 500 ml of water and made ammoniacal. It was extracted exhaustively with ethyl acetate, the combined extracts were dried over sodium sulphate and evaporated down in vacuo. The residue was purified by column chromatography on silica gel (Macherey-Nagel, 30–60 µm) using first of all ethyl acetate and later ethyl acetate/methanol/cyclohexane/conc. aqueous ammonia=8/1/1/0.1 (v/v/v/v) as eluant. From the appropriate eluates, 670 mg (18% of theory) of colourless crystals were isolated, Mp. 210–212° C. (Acetonitrile). IR (KBr): 3276.9 (N—H) 1728.1 (Formyl-C=O), 1660.6, 1641.3 (Amide-/Urea-C=O) cm$^{-1}$ ESI-MS: (M+H)$^+$=589 (M+Na)$^+$=611 d) (R,S)-N-[[4-(Aminocarbonylaminomethyl)phenyl]methyl]-3-(1H-benzimidazol-5-yl)-N$^2$-(diphenylacetyl)-alaninamide-hydrochloride A solution of 500 mg (0.849 mMol) of (R,S)-N-[[4-(aminocarbonylaminomethyl)phenyl]methyl]-3-(1-formyl-1H-benzimidazol-5-/-6-yl)-N$^2$-(diphenylacetyl)-alaninamide in 10 ml of methanol was mixed with 1 ml of conc. hydrochloric acid and the mixture was then stirred for 30 minutes at ambient temperature. The mixture was evaporated down in a water jet vacuum and the residue was triturated with diisopropylether and diethylether. After filtering and drying in vacuo, 420 mg (83% of theory) of colourless crystals were obtained, Mp. 135–137° C.

$R_f$ value: 0.51. IR (KBr): 1647.1 (Amide-/Urea-C=O) cm$^{-1}$ ESI-MS: (M+H)$^+$=561

Example 87

(R,S)-N$^2$-(Diphenylacetyl)-N-[[4-(3-methyl-1,2,4-oxadiazol-5-yl-methyl)phenyl]methyl]-argininamide-acetate a) Methyl 4-[[[(1,1-dimethylethoxy)carbonyl]amino]methyl]benzene acetate Prepared analogously to Example 61b), but with the addition of 2 equivalents of 1 N sodium hydroxide solution, from methyl 4-(aminomethyl)benzene acetate-hydrochloride and di-tert.butylpyrocarbonate in a yield of 50% of theory. Colourless crystals.

IR (KBr): 3382.9 (N—H) 1733.9 (Carboxylate-C=O), 1683.8 (Carbamate-C=O) cm$^{-1}$ b) 5-[[4-[[[(1,1-Dimethylethoxy)carbonyl]amino]methyl]phenyl]methyl]-3-methyl-1,2,4-oxadiazole 7.4 g (0.1 Mol) of acetamidoxime were dissolved in 250 ml of dry tetrahydrofuran, mixed with 2.64 g (0.108 Mol) of 98% sodium hydride and stirred at a reaction temperature of +50° C. until the development of hydrogen had ceased (about 1 hour). The mixture was allowed to cool to ambient temperature, 14.0 g (0.05 Mol) of methyl 4-[[[(1,1-dimethylethoxy)carbonyl]amino]methyl]benzene acetate were added and the resulting mixture was refluxed for one hour. After cooling, the mixture was diluted with ice water to a volume of 1 l and extracted exhaustively with ethyl acetate. The combined acetate extracts were washed twice with water, once with 20% aqueous citric acid solution and twice more with water, dried over sodium sulphate, filtered over activated charcoal and evaporated down in vacuo. 12.7 g (84% of theory) of a colourless oil were obtained which slowly crystallised out when left to stand.

]IR (KBr): 1716.5 (Carbamate-C=O) cm$^{-1}$ MS: M$^+$=303 c) 4-(3-Methyl-1,2,4-oxadiazol-5-ylmethyl) benzenemethanamine-hydrochloride

Prepared analogously to Example 65i) by treating 5-[[4-[[[(1,1-dimethylethoxy)carbonyl]amino]methyl]phenyl]methyl]-3-methyl-1,2,4-oxadiazole with methanolic hydrogen chloride solution in a yield of 56% of theory.

Colourless crystals, Mp. 227–228° C. MS: M$^+$=203 d) (R,S)-N$^5$-[(1,1-Dimethylethoxy)carbonyl]-N$^2$-(diphenylacetyl)-N-[[4-(3-methyl-1,2,4-oxadiazol-5-yl-methyl)phenyl]methyl]-ornithinamide Prepared analogously to Example 4b), but with the addition of HOBt, from (R,S)-N$^5$-[(1,1-dimethylethoxy)carbonyl]-N$^2$-(diphenylacetyl)-ornithine, 4-(3-methyl-1,2,4-oxadiazol-5 -ylmethyl)benzenemethanamine-hydrochloride and TBTU in a yield of 99% of theory.

Colourless crystals, Mp. 178–179° C.

e) (R,S)-N$^2$-(Diphenylacetyl)-N-[[4-(3-methyl-1,2,4-oxadiazol-5-ylmethyl)-phenyl]methyl]-ornithinamide-hydrochloride Prepared analogously to Example 65i) from (R,S)-N$^5$-[(1,1-dimethylethoxy)carbonyl]-N$^2$-(diphenylacetyl)-N-[[4-(3-methyl-1,2,4-oxadiazol-5-ylmethyl)phenyl]methyl]-ornithinamide by treating with methanolic hydrogen chloride solution in a yield of 75% of theory.

Colourless crystals, Mp. 195–196° C. IR (KBr): 3282.7 (N—H), 1639.4 (Amide-C=O) cm$^{-1}$ f) (R,S)-N$^2$-(Diphenylacetyl)-N-[[4-(3-methyl-1,2,4-oxadiazol-5-ylmethyl)phenyl]methyl]-argininamide-acetate Prepared analogously to Example 32d) from (R,S)-N$^2$-(diphenylacetyl)-N-[[4-(3-methyl-1,2,4-oxadiazol-5-ylmethyl)phenyl]methyl]-ornithinamide-hydrochloride and 3,5-dimethylpyrazole-1-carboxylic acid amidinium nitrate with subsequent chromatographic purification using acetic acid in a yield of 70% of theory.

$R_f$ value: 0.46; colourless crystals. IR (KBr): 1652 (Amide-C=O) cm$^{-1}$ ESI-MS: (M+H)$^+$=554 (M+Na)$^+$=576

Example 88

(R,S)-N-[[4-(Aminocarbonylmethyl)phenyl]methyl]-N$^2$-[[(3,4-dichlorophenyl)amino]carbonyl]-N$^5$-(1H-imidazol-2-yl)-ornithinamide a) 1-(3,4-Dichlorophenyl)-4-[3-[(phenylmethoxycarbonyl)amino]propyl]-imidazolidin-2,5-dione Prepared analogously to Example 11a), but using dimethylformamide as solvent instead of tetrahydrofuran, from 3,4-dichlorophenylisocyanate and (R,S)-N$^5$-(phenylmethoxycarbonyl)-ornithinemethylester-hydrochloride in the presence of triethylamine in a yield of 53% of theory.

Colourless crystals, Mp. 168° C. (Acetonitrile). IR (KBr): 1774.4, 1706.9 (Five-membered ring-C=O), 1683.8 (Carbamate-C=O) cm$^{-1}$ ESI-MS: (M+H)$^+$=436/438/440 (Cl$_2$) (M+NH$_4$)$^+$=453/455/457 (Cl$_2$) (M+Na)$^+$=458/460/462 (Cl$_2$)

b) (R,S)-N$^2$-[[(3,4-Dichlorophenyl)amino]carbonyl]-N$^5$-(phenylmethoxycarbonyl)-ornithine Prepared analogously to Example 59a) from 1-(3,4-dichlorophenyl)-4-[3-[(phenylmethoxycarbonyl)amino]propyl]-imidazolidin-2,5-dione by saponification with lithium hydroxide in a quantitative yield.

Colourless crystals. IR (KBr): 3361.7 (N—H), 1670.3 (C=O) cm$^{-1}$ ESI-MS: (M+H)$^+$=454/456/458 (Cl$_2$) (M+NH$_4$)$^+$=471/473/475 (Cl$_2$) (M+Na)$^+$=476/478/480 (Cl$_2$)

c) (R,S)-N-[[4-(Aminocarbonylmethyl)phenyl]methyl]-N$^2$-[[(3,4-dichlorophenyl)amino]carbonyl]-N$^5$-(phenylmethoxycarbonyl)-ornithinamide Prepared analogously to Example 69a) from (R,S)-N$^2$-[[(3,4-dichlorophenyl)amino]carbonyl]-N$^5$-(phenylmethoxycarbonyl)-ornithine, 4-(aminocarbonylmethyl)benzenemethanamine and TBTU in a yield of 87% of theory. Colourless crystals, Mp. 220–223° C.

IR (KBr): 3413.8, 3300.0 (N—H), 1689.5 (Carbamate-C=O), 1649.0, 1629.8 (Amide-/Urea-C=O) cm$^{-1}$ d) (R,S)-N-[[4-(Aminocarbonylmethyl)phenyl]methyl]-N$^2$-[[(3,4-dichlorophenyl)amino]carbonyl]-ornithinamide 5.2 g (8.66 mMol) of (R,S)-N-[[4-(aminocarbonylmethyl)phenyl]methyl]-N$^2$-[[(3,4-dichlorophenyl)amino]carbonyl]-N$^5$-(phenylmethoxycarbonyl)-ornithinamide were added to 50 ml of a 33% solution of hydrogen bromide in glacial acetic acid and stirred for 4 hours at ambient temperature. The mixture was diluted with 500 ml of ice water, extracted once with 200 ml of ethyl acetate and the acidic aqueous phase was made alkaline with sodium hydroxide. The precipitate formed was suction filtered and dissolved in 300 ml of methanol. The methanol solution was clarified with activated charcoal and evaporated down in vacuo and the crystalline residue remaining was used in the subsequent step without further purification.

Yield: 3.8 g (94% of theory). IR (KBr): 1652.9 (Amide-/Urea-C=O) cm$^{-1}$ ESI-MS: (M+H)$^+$=466/468/470 (Cl$_2$) (M+Na)$^+$=488/490/492 (Cl$_2$)

e) (R,S)-N-[[4-(Aminocarbonylmethyl)phenyl]methyl]-N$^2$-[[(3,4-dichlorophenyl)amino]carbonyl]-N$^5$-(1H-imidazol-2-yl)-ornithinamide Prepared analogously to Example 15d), but using pyridine as solvent instead of dimethylformamide, from (R,S)-N-[[4-

(aminocarbonylmethyl)phenyl]methyl]-$N^2$-[[(3,4-dichlorophenyl)amino]carbonyl]-ornithinamide and N-(2,2-iethoxyethyl)-S-methylthiuronium chloride in a yield of 69% of theory.

$R_f$ value: 0.34; colourless crystals. IR (KBr): 3296.2 (N—H), 1664.5, 1629.8 (Amide-/Urea-C=O) cm$^{-1}$ ESI-MS: (M+H)$^+$=532/534/536 (Cl$_2$)

Example 89

(R)-N-[[4-(Aminocarbonylaminomethyl)phenyl]methyl]-$N^2$-[[1-(ethoxycarbonylmethyl)-1H-indol-3-yl]acetyl]-argininamide-acetate a) 1-(Ethoxycarbonylmethyl)-1H-indole-3-acetic acid Prepared analogously to Example 45f), but using tetrahydrofuran instead of ethanol as solvent, from phenylmethyl 1-(ethoxycarbonylmethyl)-1H-indole-3-acetate by catalytic hydrogenation in the presence of palladium/activated charcoal in a yield of 60% of theory. Colourless crystal, Mp. 138° C.

MS: M$^+$=261 b) (R)-N-[[4-(Aminocarbonylaminomethyl)phenyl]methyl]-$N^5$-[amino(nitroimino)methyl]-$N^2$-[[1-(ethoxycarbonylmethyl)-1H-indol-3-yl]acetyl]-ornithinamide Prepared analogously to Example 69a) from 1-(ethoxycarbonylmethyl)-1H-indole-3-acetic acid, (R)-N-[[4-(aminocarbonylaminomethyl)phenyl]methyl]-$N^5$-[amino(nitroimino)methyl]-ornithinamide-hydrochloride and TBTU in a yield of 56% of theory.

Colourless, amorphous substance, which was used in the next step without any further purification.

c) (R)-N-[[4-(Aminocarbonylaminomethyl)phenyl]methyl]-$N^2$-[[1-(ethoxycarbonylmethyl)-1H-indol-3-yl]acetyl]-argininamide-acetate Prepared analogously to Example 4c) from (R)-N-[[4-(aminocarbonylaminomethyl)phenyl]methyl]-$N^5$-[amino(nitroimino)methyl]-$N^2$-[[1-(ethoxycarbonylmethyl)-1H-indol-3-yl]acetyl]-ornithinamide by catalytic hydrogenation in the presence of palladium black and 80% aqueous acetic acid in a yield of 56% of theory.

$R_f$ value: 0.23; colourless, amorphous substance. IR (KBr): 1739.7 (Carboxylate-C=O), 1652.9 (Amide-/Urea-C=O) cm$^{-1}$ ESI-MS: (M+H)$^+$=579

Example 90

(R)-N-[[4-(Aminocarbonylaminomethyl)phenyl]methyl]-$N^2$-[[1-(carboxymethyl)-1H-indol-3-yl]acetyl]-argininamide Prepared analogously to Example 59a) from (R)-N-[[4-(aminocarbonylaminomethyl)phenyl]methyl]-$N^2$-[[1-(ethoxycarbonylmethyl)-1H-indol-3-yl]acetyl]-argininamide-acetate by saponification with lithium hydroxide in a yield of 59% of theory.

$R_f$ value: 0.16; colourless crystals. IR (KBr): 3398.4, 3300.0, (N—H), 1668.3, 1654.8, 1641.3, 1610.5 (Carboxylic acid/Amide/Urea-C=O, C=N) cm$^{-1}$ ESI-MS: (M+H)$^+$=551 (M+Na)$^+$=573 (M–H+2Na)$^+$=595

Example 91

(R)-N-[[4-(Aminocarbonylaminomethyl)phenyl]methyl]-$N^2$-[[1-[3-(diethylamino)propyl]-1H-indol-3-yl]acetyl]-argininamide-acetate a) Phenylmethyl 1-[3-(diethylamino)propyl]-1H-indole-3-acetate At a temperature of about +50° C., 6.2 g (44.9 mMol) of potassium carbonate were added to a solution of 4.0 g (15.1 mMol) of phenylmethyl 1H-indole-3-acetate in 40 ml of dimethylformamide and then at the same temperature a solution of 3.0 g (20.0 mMol) of 3-(diethylamino)propylchloride in 5 ml of dimethylformamid were added dropwise. The mixture was stirred for a further hour at 50° C. and overnight at ambient temperature, heated up to 100° C. again and once more 1.0 g of 3-(diethylamino)propylchloride were added. After stirring for 5 hours at ambient temperature, the mixture was stirred into 300 ml of ice water and extracted exhaustively with diisopropylether. The combined organic extracts were washed with saturated saline solution, dried over magnesium sulphate, clarified with activated charcoal and evaporated down under reduced pressure. A colourless oil was obtained in a yield of 5.37 g (94% of theory) and was used in the following step without further purification.

MS: M$^+$=378 b) 1-[3-(Diethylamino)propyl]-1H-indole-3-acetic acid

Prepared analogously to Example 45f), but using tetrahydrofuran instead of ethanol as solvent, from phenylmethyl 1-[3-(diethylamino)propyl]-1H-indole-3-acetate by catalytic hydrogenation in the presence of palladium/activated charcoal in a yield of 94% of theory.

Colourless crystalline substance. IR (KBr): 1706.9 cm-1 (Carboxylic acid-C=O)

c) (R)-N-[[4-(Aminocarbonylaminomethyl)phenyl]methyl]-$N^5$-[amino(nitroimino)methyl]-$N^2$-[[1-[3-(diethylamino)propyl]-1H-indol-3-yl]acetyl]-ornithinamide Prepared analogously to Example 69a) from 1-[3-(diethylamino)propyl]-1H-indole-3-acetic acid, (R)-N-[[4-(aminocarbonylaminomethyl)phenyl]methyl]-$N^5$-[amino(nitroimino)methyl]-ornithinamide-hydrochloride and TBTU in a yield of 27% of theory.

Colourless, amorphous substance, which was used in the following step without further purification. IR (KBr): 1651.0 (Amide-/Urea-C=O) cm$^{-1}$ ESI-MS: (M+H)$^+$=651 (M+Na)$^+$=673 (M+2H)$^{++}$=326 (M+H+Na)$^+$=337 d) (R)-N-[[4-(Aminocarbonylaminomethyl)phenyl]methyl]-$N^2$-[[1-[3-(diethylamino)propyl]-1H-indol-3-yl]acetyl]-argininamide-acetate Prepared analogously to Example 4c) from (R)-N-[[4-(aminocarbonylaminomethyl)phenyl]methyl]-$N^5$-[amino(nitroimino)methyl]-$N^2$-[[1-[3-(diethylamino)propyl]-1H-indol-3-yl]acetyl]-ornithinamide by catalytic hydrogenation in the presence of palladium black and 80% aqueous acetic acid in a yield of 52% of theory.

$R_f$ value: 0.02; colourless, amorphous substance. IR (KBr): 1652.9 (Amide-/Urea-C=O) cm$^{-1}$ ESI-MS: (M+H)$^+$=606.1 (M+Na)$^+$=628.0 (M+2H)$^{++}$=303.5

Example 92

(R)-N-[[4-(Aminocarbonylmethyl)phenyl]methyl]-$N^2$-[[(2,4-dichlorophenyl)amino]carbonyl]-$N^5$-(1H-imidazol-2-yl)-ornithinamide a) (R)-N-[[4-(Aminocarbonylmethyl)phenyl]methyl]-$N^2$-[(2,2-dimethylethoxy)carbonyl]-$N^5$-(phenylmethoxycarbonyl)-ornithinamide Prepared analogously to Example 69a) from (R)-$N^2$-[(2,2-dimethylethoxy)carbonyl]-$N^5$-(phenylmethoxycarbonyl)-ornithine, 4-(aminocarbonylmethyl)benzenemethanamine and TBTU in a yield of 84% of theory. Colourless crystals, Mp. 145° C. (Methanol).

IR (KBr): 3390.7, 3325.1, 3197.8 (N—H), 1681.8 (Carbamate-C=O), 1656.8 (Amide-C=O) cm$^{-1}$ b) (R)-N-[[4-(Aminocarbonylmethyl)phenyl]methyl]-$N^5$-(phenylmethoxycarbonyl)-ornithinamide-trifluoroacetate Prepared analogously to Example if) from (R)-N-[[4-(aminocarbonylmethyl)phenyl]methyl]-$N^2$-[(2,2-dimethylethoxy)carbonyl]-$N^5$-(phenylmethoxycarbonyl)-ornithinamide and trifluoroacetic acid in a quantitative yield.

Colourless, amorphous substance which was used in the following step without purification.

c) (R)-N-[[4-(Aminocarbonylmethyl)phenyl]methyl]-N²-[[(2,4-dichlorophenyl)amino]carbonyl]-N⁵-(phenylmethoxycarbonyl)-ornithinamide Prepared analogously to Example 88a) from (R)-N-[[4-(aminocarbonylmethyl)phenyl]methyl]-N⁵-(phenylmethoxycarbonyl)-ornithinamide-trifluoroacetate and 2,4-dichlorophenylisocyanate in a yield of 96% of theory.

Colourless crystals, Mp. 218° C. IR (KBr): 3309.7 (N—H), 1685.7 (Carbamate-C=O), 1658.7, 1635.5 (Amide-/Urea-C=O) cm⁻¹ d) (R)-N-[[4-(Aminocarbonylmethyl)phenyl]methyl]-N²-[[(2,4-dichlorophenyl)amino]carbonyl]-ornithinamide Prepared analogously to Example 88d) from (R)-N-[[4-(aminocarbonylmethyl)phenyl]methyl]-N²-[[(2,4-dichlorophenyl)amino]carbonyl]-N⁵-(phenylmethoxycarbonyl)-ornithinamide by the action of hydrogen bromide in glacial acetic acid in a yield of 92% of theory.

Colourless crystals, Mp. 205–207° C. IR (KBr): 1654.8, 1633.6 (Amide-/Urea-C=O) cm⁻¹ e) (R)-N-[[4-(Aminocarbonylmethyl)phenyl]methyl]-N²-[[(2,4-dichlorophenyl)amino]carbonyl]-N⁵-(1H-imidazol-2-yl)-ornithinamide Prepared analogously to Example 15d), but using pyridine as solvent instead of dimethylformamide, from (R)-N-[[4-(aminocarbonylmethyl)phenyl]methyl]-N²-[[(2,4-dichlorophenyl)amino]carbonyl]-ornithinamide and N-(2,2-diethoxyethyl)-S-methylthiuronium chloride in a yield of 2% of theory.

$R_f$ value: 0.34; colourless crystals. IR (KBr): 3286.5 (N—H), 1656.8, 1633.6 (Amide-/Urea-C=O) cm⁻¹ ESI-MS: (M+H)⁺=532/534/536 (Cl₂)

Example 93

(R)-N-[[4-(Aminocarbonylaminomethyl)phenyl]methyl]-N²-[(2-naphthyl)methoxycarbonyl]-argininamide-formiate a) (R)-N⁵-[Amino(nitroimino)methyl]-N²-[(2-naphthyl)methoxycarbonyl]-ornithine Prepared analogously to Example 4a) by reacting equimolar amounts of (R)-N⁵-[amino(nitroimino)methyl]-ornithine and 2-naphthylmethylchlorocarbonate in the presence of 2 equivalents of sodium hydroxide solution in a yield of 74% of theory.

Colourless crystals, Mp.153–154° C. IR (KBr): ca. 3380, 3330 (N—H), 1743.5, 1716.5, 1652.9 (Urethane-/Carboxylic acid-C=O) cm⁻¹ ESI-MS: (M-H)-=402 (M+Na)⁺=426 (M-H+2Na)⁺=448 b) (R)-N-[[4-(Aminocarbonylaminomethyl)phenyl]methyl]-N⁵-[amino(nitroimino)methyl]-N²-[(2-naphthyl)methoxycarbonyl]-ornithinamide Prepared analogously to Example 69a) from (R)-N⁵-[amino(nitroimino)methyl]-N²-[(2-naphthyl)methoxycarbonyl]-ornithine, 4-(aminocarbonylaminomethyl)benzenemethanamine and TBTU in a yield of 32% of theory. Colourless crystals, Mp. 155–160° C. (Methanol/glacial acetic acid 20/1, v/v).

ESI-MS: (M+H)⁺=565 (M+Na)⁺=587 c) (R)-N-[[4-(Aminocarbonylaminomethyl)phenyl]methyl]-N²-[(2-naphthyl)methoxycarbonyl]-argininamide-formiate Prepared analogously to Example 38d) from (R)-N-[[4-(aminocarbonylaminomethyl)phenyl]methyl]-N⁵-[amino(nitroimino)methyl]-N²-[(2-naphthyl)methoxycarbonyl]-ornithinamide by reduction with tin(II)-chloride-dihydrate in the presence of 60% aqueous formic acid in a yield of 31% of theory.

$R_f$ value: 0.30; colourless crystals. IR (KBr): 1639.4, broad (Urethane-/Amide-/Urea-C=O) ESI-MS: (M+H)⁺=520 (M+Na)⁺=540

Example 94

(R)-N-[[4-(Aminocarbonylaminomethyl)phenyl]methyl]-N²-[(1-methyl-1H-indol-3-yl)acetyl]-argininamide acetate a) (R)-N-[[4-(Aminocarbonylaminomethyl)phenyl]methyl]-N⁵-[amino(nitroimino)methyl]-N²-[(1-methyl-1H-indol-3-yl)acetyl]-ornithinamide Prepared analogously to Example 69a) from 1-methyl-1H-indole-3-acetic acid, (R)-N-[[4-(aminocarbonylaminomethyl)phenyl]methyl]-N⁵-[amino(nitroimino)methyl]-ornithinamide-hydrochloride and TBTU in a yield of 34% of theory. Colourless, amorphous substance, which was used in the following step without purification.

b) (R)-N-[[4-(Aminocarbonylaminomethyl)phenyl]methyl]-N²-[(1-methyl-1H-indol-3-yl)acetyl]-argininamide-acetate Prepared analogously to Example 4c) from (R)-N-[[4-(aminocarbonylaminomethyl)phenyl]methyl]-N⁵-[amino(nitroimino)methyl]-N²-[(1-methyl-1H-indol-3-yl)acetyl]-ornithinamide by catalytic hydrogenation in the presence of palladium black and 80% aqueous acetic acid in a yield of 86% of theory.

$R_f$ value: 0.24; colourless crystals. IR (KBr): 1656.8 (Amide-/Urea-C=O) cm⁻¹ ESI-MS: (M+H)⁺=507 (M+Na)⁺=529

Example 95

(R)-N²-(Diphenylacetyl)-N-[[4-[2-(methoxycarbonyl)ethyl]phenyl]methyl]-argininamide-diacetate a) 4-[2-(Methoxycarbonyl)ethyl]benzenemethanamine-hydrochloride Prepared analogously to Example 53a) from 4-[[(1,1-dimethylethoxy) carbonyl]amino]methyl]benzene propanoic acid and methanolic hydrogen chloride solution in a yield of 99% of theory. Colourless crystals, Mp. 206° C.

IR (KBr): 1741.6 (Carboxylate-C=O) cm⁻¹ b) (R)-N⁵-[Amino(nitroimino)methyl]-N²-(diphenylacetyl)-N-[[4-[2-(methoxycarbonyl)ethyl]-phenyl]methyl]-ornithinamide Prepared analogously to Example 69a) from (R)-N⁵-[amino(nitroimino)methyl]-N²-(diphenylacetyl)-ornithine, 4-[2-(methoxycarbonyl)ethyl]benzenemethanamine-hydrochloride and TBTU in a yield of 25% of theory. Colourless crystals, Mp. 159–161° C.

IR (KBr): 3375.2, 3303.9 (N—H), 1735.8 (Carboxylate-C=O), 1641.3 (Amide-C=O) cm⁻¹ ESI-MS: (M+H)+=589 (M+Na)⁺=611 c) (R)-N²-(Diphenylacetyl)-N-[[4-[2-(methoxycarbonyl)ethyl]phenyl]methyl]-argininamide-diacetate Prepared analogously to Example 4c) from (R)-N⁵-[amino(nitroimino) methyl]-N²-(diphenylacetyl)-N-[[4-[2-(methoxycarbonyl)ethyl]phenyl]methyl]-ornithinamide by catalytic hydrogenation in the presence of palladium black and 80% aqueous acetic acid in a yield of 57% of theory.

$R_f$ value: 0.70; colourless crystals, Mp. 150° C. (D.). IR (KBr): 1732.0 (Carboxylate-C=O), 1635.5 (Amide-C=O) cm⁻¹ ESI-MS: (M+H)⁺=544

Example 96

(R)-N-[[3-[[(4-Amino-1,4-dioxobutyl)amino]methyl]phenyl]methyl]-N²-(diphenylacetyl)-argininamide-acetate a) (R)-N-[[3-[[(4-Amino-1,4-dioxobutyl)amino]methyl]phenyl]methyl]-N⁵-[amino(nitroimino)methyl]-N²-(diphenylacetyl)-ornithinamide Prepared analogously to Example 69a) from (R)-N⁵-[amino(nitroimino)methyl]-N²-(diphenylacetyl)-ornithine, 3-[[(4-amino-1,4-dioxobutyl)amino]methyl] benzenemethanamine and TBTU in a yield of 25% of theory.

IR (KBr): 1647.1 (Amide-C=O) cm$^{-1}$ ESI-MS: (M+H)$^+$=631 (M+Na)$^+$=653 (M+K)$^+$=669 b) (R)-N-[[3-[[(4-Amino-1,4-dioxobutyl)amino]methyl] phenyl]methyl]-N$^2$-(diphenylacetyl)-argininamide-acetate Prepared analogously to Example 4c) from (R)-N-[[3-[[(4-amino-1,4-dioxobutyl)amino]methyl]phenyl]methyl]-N$^2$-(diphenylacetyl)-N$^5$-[amino(nitroimino)methyl]-ornithinamide by catalytic hydrogenation in the presence of palladium black and 80% aqueous acetic acid in a yield of 31% of theory.

R$_f$ value: 0.48; colourless, amorphous substance. IR (KBr): 1656.8 (Amide-C=O) cm$^{-1}$ ESI-MS: (M+H)$^+$=586.1 (M+Na)$^+$=608.1 (M+H+Na)$^{++}$=304.5

Example 97

(R)-N-[[4-[2-(Aminocarbonylamino)ethyl]phenyl]methyl]-N$^2$-(diphenylacetyl)-argininamide a) 4-[[[(1,1-Dimethylethoxy)carbonyl]amino]methyl] benzene propanamide Prepared analogously to Example 63a) from 4-[[[(1,1-dimethylethoxy)carbonyl]amino]methyl]benzene propanoic acid, N,N'-carbonyldiimidazole and ammonium carbonate in a yield of 84% of theory. Colourless crystals, which were used in the following step without purification.

b) 4-[[[(1,1-Dimethylethoxy)carbonyl]amino]methyl] benzene-ethanamine

A mixture of 10.0 g (38.1 mMol) of 4-[[[(1,1-dimethylethoxy)carbonyl]amino]methyl]benzenepropanamide, 18.5 g (43 mMol) of I,I-bis-(trifluoroacetoxy)iodobenzene, 100 ml of acetonitrile and 20 ml of water was stirred for 8 hours at a reaction temperature of 40° C. A further 2.5 g of I,I-bis-(trifluoroacetoxy) iodobenzene were added and the mixture was again kept at 40° C. for 6 hours. The acetonitrile was distilled off in vacuo, the residue was taken up in 200 ml of water, then filtered, the filtrate was extracted once with 50 ml of diethylether and then made alkaline with sodium hydroxide. The alkaline aqueous phase was extracted three times with 100 ml of dichloromethane, the combined dichloromethane extracts were dried over sodium sulphate and freed from solvent in vacuo. The residue was purified by column chromatograph on silica gel (Macherey-Nagel, 35–70 mesh ASTM) using first of all tert.butyl-methylether and then tert.butylmethylether/methanol/conc. aqueous ammonia=9/1/0.3 (v/v/v) as eluant. 4.5 g (50% of theory) of a colourless oil were obtained.

c) 4-[2-(Aminocarbonylamino)ethyl]-N-[(1,1-dimethylethoxy)carbonyl]benzenemethanamine Prepared analogously to Example 8a) from 4-[[[(1,1-dimethylethoxy)carbonyl]amino]methyl]benzenethanamine and sodium cyanate in the presence of 1 equivalent of 1N hydrochloric acid in a yield of 63% of theory.

Colourless crystals, Mp. 172–175° C. IR (KBr): 3417.7, 3325.1, 3211.3 (N—H), 1681.8 (Carbamate-C=O), 1652.9 (Urea-C=O) cm$^{-1}$ d) 4-[2-(Aminocarbonylamino)ethyl]benzenemethanamine-trifluoroacetate Prepared analogously to Example 61e), but using tetrahydrofuran as solvent instead of dichloromethane, from 4-[2-(aminocarbonylamino)ethyl]-N-[(1,1-dimethylethoxy) carbonyl]benzenemethanamine and trifluoroacetic acid in a yield of 61% of theory. Colourless crystals, which were used in the following step without total purification.

e) (R)-N-[[4-[2-(Aminocarbonylamino)ethyl]phenyl] methyl]-N$^5$-[amino(nitroimino)methyl]-N$^2$-(diphenylacetyl)-ornithinamide Prepared analogously to Example 69a) from (R)-N$^5$-[amino(nitroimino)methyl]-N$^2$-(diphenylacetyl)-ornithine, 4-[2-(aminocarbonylamino)ethyl]benzenemethanamine-trifluoroacetate and TBTU in a yield of 59% of theory.

Colourless, amorphous substance. IR (KBr): 1651.0 (Amide-/Urea-C=O) cm$^{-1}$ f) (R)-N-[[4-[2-(Aminocarbonylamino)ethyl]phenyl] methyl]-N$^2$-(diphenylacetyl)-argininamide Prepared analogously to Example 4c) from (R)-N-[[4-[2-(aminocarbonylamino)ethyl]phenyl]methyl]-N$^5$-[amino (nitroimino)methyl]-N$^2$-(diphenylacetyl)-ornithinamide by catalytic hydrogenation in the presence of palladium black and 80% aqueous acetic acid in a yield of 39% of theory.

R$_f$ value: 0.58; colourless, amorphous substance. IR (KBr): 1649.0 (Amide-/Urea-C=O) cm$^{-1}$ ESI-MS: (M+H)$^+$=544

Example 98

(R,S)-N-[[4-(Aminocarbonylaminomethyl)phenyl]methyl]-6-(4,5-dihydro-1H-imidazol-2-yl)-N$^2$-(diphenylacetyl)-norleucinamide a) (R,S)-2-(4-Cyanobutyl)-N$^2$-(diphenylmethylene) glycinemethyl-ester To a solution of 35.0 g (138.2 mMol) of N$^2$-(diphenylmethylene)glycinemethylester in 300 ml of acetonitrile were added 4.45 g (13.8 mMol) of tetrabutylammonium bromide and 76.2 g (0.55 Mol) of potassium carbonate, then a solution of 26.9 g (166 mMol) of 5-bromovaleronitrile in 50 ml of acetonitrile was added dropwise and the resulting mixture was refluxed for 3 hours. It was left to stand at ambient temperature over the weekend, then a further 5.0 g of 5-bromovaleronitrile were added and the mixture was then refluxed for a further 5 hours. After cooling, the mixture was filtered and the filtrate was evaporated down under reduced pressure, finally in an oil pump vacuum and at elevated temperature. 46.0 g (100% of theory) of a colourless, highly viscous oil were obtained which was further processed without being purified.

b) (R,S)-2-(4-Cyanobutyl)-glycinemethylester-hydrochloride

A mixture of 41.9 g (0.1253 Mol) of (R,S)-2-(4-cyanobutyl)-N$^2$-(diphenylmethylene)-glycinemethylester and 125.3 ml of 1N hydrochloric acid was stirred for 4 hours at ambient temperature. The mixture was extracted twice with 100 ml of diethylether and the aqueous phase was evaporated down in a water jet vacuum at slightly elevated temperature. The residue was taken up in 100 ml of methanol and evaporated down in vacuo once more. This procedure was repeated twice more. Finally, the residue was carefully triturated with tetrahydrofuran and filtered. When the filtrate was evaporated down, 21 g (98% of theory) of a colourless, non-crystallising substance were obtained which was used in the following step without further purification.

c) (R,S)-2-(4-Cyanobutyl)-N$^2$-(diphenylacetyl)-glycine methylester

Prepared analogously to Example 4a), but using a saturated aqueous sodium carbonate solution instead of sodium hydroxide solution, from diphenylacetylchloride and (R,S)-2-(4-cyanobutyl)-glycine methylester-hydrochloride in a yield of 24% of theory.

Colourless, amorphous substance. IR (KBr): 3286.5 (N—H), 2246.9 (C N), 1755.1 (Carboxylate-C=O), 1647.1 (Amide-C=O) cm$^{-1}$ d) (R,S)-2-(4-Cyanobutyl)-N$^2$-(diphenylacetyl)-glycine Prepared analogously to Example 49a) by alkaline saponification of (R,S)-2-(4-cyanobutyl)-N$^2$-(diphenylacetyl)-glycine methylester in a yield of 91% of theory. Colourless crystals, Mp. 131–133° C. (Diisopropylether).

IR (KBr): 2245.0 (C N), 1716.5 (Carboxylic acid-C=O), 1649.0 (Amide-C=O) cm$^{-1}$ e) (R,S)-N-[[4-(Aminocarbonylaminomethyl)phenyl] methyl]-6-cyano-N$^2$-(diphenylacetyl)-norleucinamide Prepared analogously to Example 87d) from (R,S)-2-(4-cyanobutyl)-N$^2$-(diphenylacetyl)-glycine, 4-(aminocarbonylaminomethyl)benzenemethanamine and TBTU in a quantitative yield. Colourless crystals, Mp. 198–200° C.

IR (KBr): 3487.1 (N—H), 2245.0 (C N), 1647.1 (Amide-/Urea-C=O) cm$^{-1}$ ESI-MS: (M+H)$^+$=512 (M+Na)$^+$=534 (M+K)$^+$=550 f) (R,S)-N-[[4-(Aminocarbonylaminomethyl)phenyl] methyl]-6-(aminoiminomethyl)-N$^2$-(diphenylacetyl)-norleucinamidediacetate 1.0 g (1.955 mMol) of (R,S)-N-[[4-(aminocarbonylaminomethyl)phenyl]methyl]-6-cyano-N$^2$-(diphenylacetyl)-norleucinamide were stirred overnight with 20 ml of anhydrous methanolic hydrogen chloride solution at a reaction temperature of 0° C., whereupon the substance went into solution. The methanol was distilled off together with the excess hydrogen chloride under reduced pressure and at a bath temperature of not more than +40° C. The residue was taken up in 20 ml of anhydrous methanol and evaporated down once more; this procedure was repeated again. To the solution of the residue in 50 ml of dry methanol were added 1.87 g (19.5 mMol) of ammonium carbonate and the mixture was then stirred for 40 hours at ambient temperature. The solvent was eliminated in vacuo, the residue was purified by column chromatography on silica gel (Macherey-Nagel, 35–70 mesh ASTM) using first of all ethyl acetate/methanol/acetic acid/water 170/30/5/5 (v/v/v/v), and later methanol/acetic acid=8/2 (v/v) as eluant. Working up the appropriate fraction yielded 480 mg (38% of theory) of colourless crystals, Mp. 160° C. (D.).

R$_f$ value: 0.54. IR (KBr): 3514.1 (O—H, N—H), 1647.1 (Amide-/Urea-C=O) cm$^{-1}$ ESI-MS: (M+H)$^+$=529 g) (R,S)-N-[[4-(Aminocarbonylaminomethyl)phenyl] methyl]-6-(4,5-dihydro-1H-imidazol-2-yl)-N$^2$-(diphenylacetyl)-norleucinamide Prepared analogously to Example 98f), but using 1,2-ethanediamine instead of ammonium carbonate, from (R,S)-N-[[4-(aminocarbonylaminomethyl)phenyl]methyl]-6-cyano-N$^2$-(diphenylacetyl)-norleucinamide in a yield of 53% of theory.

R$_f$ value: 0.36; colourless crystals, Mp. 191–196° C. IR (KBr): 1652.9 (Amide-/Urea-C=O) cm$^{-1}$ ESI-MS: (M+H)$^+$=555

Example 99
(R)-N-[[4-(Aminocarbonylaminomethyl)phenyl]methyl]-N$^2$-(diphenylacetyl)-N-methyl-argininamide-acetate a) 4-Cyano-N-methylbenzenemethanamine-hydrochloride Prepared analogously to Example 61a) from 4-cyanobenzaldehyde, methylamine-hydrochloride and sodium cyanoborohydride. The resulting base was converted into the corresponding hydrochloride by treating the methanolic solution with ethereal hydrogen chloride. Yield: 52% of theory. Colourless crystals.

b) 4-Cyano-N-[(1,1-dimethylethoxy)carbonyl]-N-methylbenzenemethanamine

Prepared analogously to Example 61b), but with the addition of 1 equivalent of 1N sodium hydroxide solution, from 4-cyano-N-methylbenzenemethanamine-hydrochloride and di-tert.butyl-pyrocarbonate in a yield of 81% of theory. Colourless oil which was used in the following step without further purification.

IR (KBr): 2229.6 (C N), 1695.3 (Carbamate-C=O) cm$^{-1}$ c) 4-[[[(1,1-Dimethylethoxy)carbonyl]methylamino] methyl]benzenemethanamine Prepared analogously to Example 6c), but using palladium/activated charcoal as catalyst instead of Raney nickel, by catalytic hydrogenation of 4-cyano-N-[(1,1-dimethylethoxy)carbonyl]-N-methylbenzenemethanamine in the presence of ammonia in a yield of 99% of theory. Colourless, highly viscous oil, which was used in the following step without purification.

d) 4-(Aminocarbonylaminomethyl)-N-[(1,1-dimethylethoxy)carbonyl]-N-methylbenzenemethanamine Prepared analogously to Example 8a) from 4-[[[(1,1-dimethylethoxy)carbonyl]methylamino]methyl] benzenemethanamine, sodium cyanate and 1 equivalent of 1N hydrochloric acid in a quantitative yield. Colourless crystals, which were further processed without being purified.

e) 4-(Aminocarbonylaminomethyl)-N-methylbenzenemethanamine-hydrochloride

Prepared analogously to Example 65i) from 4-(aminocarbonylaminomethyl)-N-[(1,1-dimethylethoxy) carbonyl]-N-methylbenzenemethanamine and methanolic hydrogen chloride solution in a yield of 68% of theory. Colourless crystals.

IR (KBr): 3346.3, 3292.3, 3228.6 (N—H), 1705.0, 1631.7 (C=O) cm$^{-1}$ MS: M$^+$=193 f) (R)-N-[[4-(Aminocarbonylaminomethyl)phenyl]methyl]-N$^5$-[amino(nitroimino)methyl]-N$^2$-(diphenylacetyl)-N-methyl-ornithinamide Prepared analogously to Example 69a) from (R)-N$^5$-[amino(nitroimino)methyl]-N$^2$-(diphenylacetyl)-ornithine, 4-(aminocarbonylaminomethyl)-N-methylbenzenemethanamine-hydrochloride and TBTU in a yield of 39% of theory.

Colourless, amorphous substance. IR (KBr): 1633.6 (Amide-/Urea-C=O) cm$^{-1}$ g) (R)-N-[[4-(Aminocarbonylaminomethyl)phenyl]methyl]-N$^2$-(diphenylacetyl)-N-methyl-argininamide-acetate Prepared analogously to Example 4c) from (R)-N-[[4-(aminocarbonylaminomethyl)phenyl]methyl]-N$^5$-[amino (nitroimino)methyl]-N$^2$-(diphenylacetyl)-N-methyl-ornithinamide by catalytic hydrogenation in the presence of palladium black and 80% aqueous acetic acid in a yield of 69% of theory.

R$_f$ value: 0.55; colourless, amorphous substance. IR (KBr): 1649.0 (Amide-/Urea-C=O) cm$^{-1}$ ESI-MS: (M+H)$^+$=544

Example 100
N-[[4-(Aminocarbonylaminomethyl)phenyl]methyl]-N$^2$-[(D,L-5,11-dihydro-6(6H)-oxodibenz[b,e]azepin-11-yl) carbonyl]-D-argininamide-acetate (Isomer A)

a) (R)-N-[[4-(Aminocarbonylaminomethyl)phenyl]methyl]-N$^5$-[amino(nitroimino)methyl]-N$^2$-[(1,1-dimethylethoxy) carbonyl]-ornithinamide Prepared analogously to Example 69a) from (R)-N$^5$-[amino(nitroimino)methyl]-N$^2$-[(1,1-dimethylethoxy) carbonyl]-ornithine, 4-(amino-carbonylaminomethyl) benzenemethanamine and TBTU in a yield of 35% of theory.

Colourless crystals, which were further processed without purification. IR (KBr): 1656.8 (Amide-/Urea-C=O) cm$^{-1}$ ESI-MS: (M+H)$^+$=481 (M+Na)$^+$=503 b) (R)-N-[[4-(Aminocarbonylaminomethyl)phenyl]methyl]-N$^5$-[amino(nitroimino)methyl]-ornithinamide-hydrochloride Prepared analogously to Example 65i) by the action of methanolic hydrogen chloride solution on (R)-N-[[4-(aminocarbonylaminomethyl)phenyl]methyl]-N$^5$-[amino (nitroimino)methyl]-N²-[(1,1-dimethylethoxy)carbonyl]-ornithinamide in a yield of 99% of theory.

Colourless, amorphous substance, which was used in the next step without purification.

c) Diastereomere von N-[[4-(Aminocarbonylaminomethyl)phenyl]methyl]-N⁵-[amino(nitroimino)methyl]-N²-[(D,L-5,11-dihydro-6(6H)-oxodibenz[b,e]azepin-11-yl)carbonyl]-D-ornithinamide D,L-5,11-Dihydro-6(6H)-oxodibenz[b,e]azepin-11-carboxylic acid was reacted with (R)-N-[[4-(aminocarbonylaminomethyl)phenyl]methyl]-N⁵-[amino(nitroimino)methyl]-ornithinamide-hydrochloride and TBTU according to Example 69a). During chromatographic working up, 2 fractions were obtained consisting of diastereomer A with a higher $R_f$ value and diastereomer B with a lower $R_f$ value.

Diastereomer A: Yield 12% of theory; colourless, amorphous substance. IR (KBr): 1652.9 (Amide-/Urea-C=O) cm⁻¹ ESI-MS: (M+H)⁺=616 (M+Na)⁺=638

Diastereomer B: Yield 10% of theory; colourless, amorphous substance. IR (KBr): 1652.9 (Amide-/Urea-C=O) cm⁻¹ ESI-MS: (M+H)⁺=616 (M+Na)⁺=638 d) N-[[4-(Aminocarbonylaminomethyl)phenyl]methyl]-N²-[(D,L-5,11-dihydro-6(6H)-oxodibenz[b,e]azepin-11-yl)carbonyl]-D-argininamide-acetate (Isomer A)

Prepared analogously to Example 4c) from N-[[4-(aminocarbonylaminomethyl)phenyl]methyl]-N⁵-[amino(nitroimino)methyl]-N²-[(D,L-5,11-dihydro-6(6H)-oxodibenz[b,e]azepin-11-yl)carbonyl]-D-ornithinamide (Diastereomer A) by catalytic hydrogenation in the presence of palladium black and 80% aqueous acetic acid in a yield of 13% of theory.

$R_f$ value: 0.45; colourless, amorphous substance. ESI-MS: (M+H)⁺=571 (M+Na)⁺=593

Example 101

N-[[4-(Aminocarbonylaminomethyl)phenyl]methyl]-N²-[(D,L-5,11-dihydro-6(6H)-oxodibenz[b,e]azepin-11-yl)carbonyl]-D-argininamide-acetate (Isomer B)

Prepared analogously to Example 4c) from N-[[4-(aminocarbonylaminomethyl)phenyl]methyl]-N⁵-[amino(nitroimino)methyl]-N²-[(D,L-5,11-dihydro-6(6H)-oxodibenz[b,e]azepin-11-yl)carbonyl]-D-ornithinamide (Diastereomer B) by catalytic hydrogenation in the presence of palladium black and 80% aqueous acetic acid in a yield of 92% of theory.

$R_f$ value: 0.44; colourless, amorphous substance. IR (KBr): 1656.8 (Amide-/Urea-C=O) cm⁻¹ ESI-MS: (M+H)⁺=571 (M+Na)⁺=593

Example 102

(R)-N-[[4-(Aminocarbonylaminomethyl)phenyl]methyl]-N²-[bis-(4-fluorophenyl)acetyl]-argininamide-trifluoroacetate a) (R)-N-[[4-(Aminocarbonylaminomethyl)phenyl]methyl]-N²-[bis-(4-fluorophenyl)acetyl]-N^G-(2,2,5,7,8-pentamethylchroman-6-sulphonyl)-argininamide Prepared analogously to Example 69a) from bis-(4-fluorophenyl)acetic acid, (R)-N-[[4-(aminocarbonylaminomethyl)phenyl]methyl]-N^G-(2,2,5,7,8-pentamethylchroman-6-sulphonyl)-argininamide and TBTU in a yield of 60% of theory. Colourless crystals.

IR (KBr): 3435.0, 3348.2 (N—H), 1652.9 (Amide-/Urea-C=O) cm⁻¹ b) (R)-N-[[4-(Aminocarbonylaminomethyl)phenyl]methyl]-N²-[bis-(4-fluorophenyl)acetyl]-argininamide-trifluoroacetate Prepared analogously to Example 1f) from (R)-N-[[4-(aminocarbonylaminomethyl)phenyl]methyl]-N²-[bis-(4-fluorophenyl)acetyl]-N^G-(2,2,5,7,8-pentamethylchroman-6-sulphonyl)-argininamide and trifluoroacetic acid in a yield of 44% of theory.

$R_f$ value: 0.60; colourless crystals, Mp. 120° C. (D.). IR (KBr): 1654.8 (Amide-/Urea-C=O) cm⁻¹ ESI-MS: (M+H)⁺=566

Example 103

(R)-N-[[4-(Aminocarbonylaminomethyl)phenyl]methyl]-N²-[bis-(4-chlorophenyl)acetyl]-argininamide-trifluoroacetate a) (R)-N-[[4-(Aminocarbonylaminomethyl)phenyl]methyl]-N²-[bis-(4-chlorophenyl)acetyl]-N^G-(p)-argininamide Prepared analogously to Example 69a) from bis-(4-chlorophenyl)acetic acid, (R)-N-[[4-(aminocarbonylaminomethyl)phenyl]methyl]-N^G-(2,2,5,7,8-pentamethylchroman-6-sulphonyl)-argininamide and TBTU in a yield of 70% of theory. Colourless crystals, Mp. 180–183° C. (Ethyl acetate).

IR (KBr): 3436.9, 3344.4 (N—H), 1629.8 (Amide-/Urea-C=O), 1299.9, 1166.9 (SO₂—N) cm⁻¹ b) (R)-N-[[4-(Aminocarbonylaminomethyl)phenyl]methyl]-N²-[bis-(4-chlorophenyl)acetyl]-argininamide-trifluoroacetate Prepared analogously to Example 1f) from (R)-N-[[4-(aminocarbonylaminomethyl)phenyl]methyl]-N²-[bis-(4-chlorophenyl)acetyl]-N^G-(2,2,5,7,8-pentamethylchroman-6-sulphonyl)-argininamide and trifluoroacetic acid in a yield of 70% of theory.

$R_f$ value: 0.63; colourless crystal, Mp. 175–178° C. (D.). IR (KBr): 1652.9 (Amide-/Urea-C=O) cm⁻¹ ESI-MS: (M+H)⁺=598.1/600/602 (Cl₂)

Example 104

(R,S)-N-[[4-(Aminocarbonylmethyl)phenyl]methyl]-3-[4-(aminoiminomethyl)phenyl]-N²-(diphenylacetyl)-alaninamide a) (R S)-3-(4-Cyanophenyl)-alanine-hydrochloride A mixture of 235 g (0.707 Mol) of diethyl -(acetamido)-α-[(4-cyanophenyl)methyl]-malonate (Mp. 163–165° C.; prepared from diethyl α-(acetamido)-malonate and 4-(bromomethyl)-benzonitrile in the presence of sodium ethoxide), 1.28 l (3.84 Mol) of 3N aqueous hydrochloric acid and 0.64 l of glacial acetic acid were refluxed for 7 hours. The mixture cooled to +5° C. was filtered and the filtrate was evaporated down in vacuo. The residue was intensively washed with isopropanol and then dried in vacuo. 92.9 g (58% of theory) of colourless crystals were obtained, Mp. 219° C. (D.).

b) (R,S)-3-(4-Cyanophenyl)-N²-(diphenylacetyl)-alanine

Prepared analogously to Example 4a) from (R,S)-3-(4-cyanophenyl)alanine-hydrochloride and diphenylacetyl-chloride in the presence of sodium hydroxide solution in a yield of 82% of theory. Colourless crystals, Mp. 110° C. (D.).

IR (CH₂Cl₂): 2225 (C N), 1655 (Amide-C=O) cm⁻¹ c) (R,S)-N-[[4-(Aminocarbonylmethyl)phenyl]methyl]-3-(4-cyanophenyl)-N²-(diphenylacetyl)-alaninamide Prepared analogously to Example 87d) from (R,S)-3-(4-cyanophenyl)-N²-(diphenylacetyl)-alanine, 4-(aminocarbonylmethyl)benzenemethanamine and TBTU in a yield of 65% of theory. Colourless crystals, Mp. 234° C.

IR (KBr): 3286.5, 3195.9 (N—H), 2229.6 (C N), 1656.8 (Amide-C=O) cm⁻¹ ESI-MS: (M+H)⁺=531 (M+Na)⁺=553 (M+NH₄)⁺=548 d) (R,S)-N-[[4-(Aminocarbonylmethyl)phenyl]methyl]-3-[4-(aminoiminomethyl)phenyl]-N²-(diphenylacetyl)-alaninamide Prepared analogously to Example 98f) from (R,S)-N-[[4-(aminocarbonylmethyl)phenyl]methyl]-3-(4-cyanophenyl)-$N^2$-(diphenylacetyl)-alaninamide by the action of first of all methanolic hydrogen chloride solution and then ammonium carbonate in a yield of 39% of theory. Colourless crystals.

IR (KBr): 1645.2 (Amide-C=O) cm$^{-1}$ ESI-MS: (M+H)$^+$=548 (M+Na)$^+$=570

Example 105

(R)-N-[[4-[[[[3-(Dimethylamino)propyl]amino]carbonyl]methyl]phenyl]methyl]-$N^2$-(diphenylacetyl)-argininamide-acetate a) 4-[[[3-(Dimethylamino)propyl]amino]carbonyl]methyl]benzonitrile Prepared analogously to Example 67d) from 4-cyanobenzene acetic acid, 3-(dimethylamino) propanamine and TBTU in a yield of 60% of theory. Colourless, highly viscous oil.

IR (KBr): 3282.7 (N—H), 2229.6 (C N) 1643.3 (Amide-C=O) cm$^{-1}$ b) 4-[[[[3-(Dimethylamino)propyl]amino]carbonyl]methyl]benzenemethanamine Prepared analogously to Example 6c) from 4-[[[[3-(dimethylamino)propyl]amino]carbonyl]methyl] benzonitrile by catalytic hydrogenation in the presence of Raney nickel and ammonia in a quantitative yield. Colourless, highly viscous oil, which was used in the next step without purification.

c) (R)-$N^5$-[Amino(nitroimino)methyl]-N-[[4-[[[[3-(dimethylamino)propyl]amino]carbonyl]methyl]phenyl]methyl]-$N^2$-(diphenylacetyl)-ornithinamide Prepared analogously to Example 6d) from (R)-$N^5$-[amino(nitroimino)methyl]-$N^2$-(diphenylacetyl)-ornithine, 4-[[[[3-(dimethylamino)propyl]amino]carbonyl]methyl] benzenemethanamine and TBTU in a yield of 39% of theory. Colourless, amorphous substance.

IR (KBr): 1651.0 (Amide-C=O) cm$^{-1}$ ESI-MS: (M+H)$^+$=645 d) (R)-N-[[4-[[[[3-(Dimethylamino)propyl]amino]carbonyl]methyl]phenyl]methyl]-$N^2$-(diphenylacetyl)-argininamide-acetate Prepared analogously to Example 4c) from (R)-$N^5$-[amino(nitroimino)methyl]-N-[[4-[[[[3-(dimethylamino)propyl]amino]carbonyl]methyl]phenyl]methyl]-$N^2$-(diphenylacetyl)-ornithinamide by catalytic hydrogenation in the presence palladium black and 80% aqueous acetic acid in a quantitative yield.

$R_f$ value: 0.11; colourless, amorphous substance. IR (KBr): 1652.9 (Amide-C=O) cm$^{-1}$ ESI-MS: (M+H)$^+$= 600.3 (M+2H)$^{++}$=300.7

Example 106

(R)-N-[[4-[[[[2-(Dimethylamino)ethyl]amino]carbonyl]methyl]phenyl]methyl]-$N^2$-(diphenylacetyl)-argininamide-acetate a) 4-[[[[2-(Dimethylamino)ethyl]amino]carbonyl]methyl]benzonitrile Prepared analogously to Example 67d) from 4-cyanobenzene acetic acid, 2-(dimethylamino)ethanamine and TBTU in a yield of 69% of theory. Colourless, highly viscous oil.

IR (KBr): 2229. 6 (C N), 1664.5 (Amide-C=O) cm$^{-1}$ b) 4-[[[[2-(Dimethylamino)ethyl]amino]carbonyl]methyl]benzenemethanamine Prepared analogously to Example 6c) from 4-[[[[2-(dimethylamino)ethyl]amino]carbonyl]methyl]benzonitrile by catalytic hydrogenation in the presence of Raney nickel and ammonia in a yield of 92% of theory. Colourless, highly viscous oil, which was used in the next step without purification.

IR (KBr): 1666.4 (Amide-C=O) cm$^{-1}$ ESI-MS: (M+H)$^+$=236 (2M+H)$^+$=471 (2M+Na)$^+$=493 c) (R)-$N^5$-[Amino(nitroimino)methyl]-N-[[4-[[[[2-(dimethylamino)ethyl]amino]carbonyl]methyl]phenyl] methyl]-$N^2$-(diphenylacetyl)-ornithinamide Prepared analogously to Example 6d) from (R)-$N^5$-[amino(nitroimino)methyl]-$N^2$-(diphenylacetyl)-ornithine, 4-[[[[2-(dimethylamino)ethyl]amino]carbonyl]methyl] benzenemethanamine and TBTU in a yield 79% of theory. Colourless, amorphous substance.

IR (KBr): 1643.3 (Amide-C=O) cm$^{-1}$ d) (R)-N-[[4-[[[[2-(Dimethylamino)ethyl]amino]carbonyl]methyl]-phenyl]methyl]-$N^2$-(diphenylacetyl)-argininamide-acetate Prepared analogously to Example 4c) from (R)-$N^5$-[amino(nitroimino)methyl]-N-[[4-[[[[2-(dimethylamino)propyl]amino]carbonyl]methyl]phenyl]methyl]-$N^2$-(diphenylacetyl)-ornithinamide by catalytic hydrogenation in the presence of palladium black and 80% aqueous acetic acid in a yield of 98% of theory.

$R_f$ value: 0.13; colourless, amorphous substance. IR (KBr): 1652.9 (Amide-C=O) cm$^{-1}$ ESI-MS: (M+H)$^+$= 586.3 (M+2H)$^{++}$=293.8

Example 107

(R)-N-[[4-(Aminocarbonylaminomethyl)phenyl]methyl]-$N^2$-[bis-(4-hydroxyphenyl)acetyl]-argininamide-trifluoroacetate a) (R)-N-[[4-(Aminocarbonylaminomethyl)phenyl]methyl]-$N^2$-[bis-(4-hydroxyphenyl)acetyl]-$N^7$-(2,2,5,7,8-pentamethylchroman-6-sulphonyl)-argininamide Prepared analogously to Example 4b) from bis-(4-hydroxyphenyl)acetic acid (M. H. Hubacher, J. Org. Chem. 24, 1949–1951 (1959)), (R)-N-[[4-(aminocarbonylaminomethyl)phenyl]methyl]-$N^7$-(2,2,5,7, 8-pentamethylchroman-6-sulphonyl)-argininamide and TBTU in a yield of 63% of theory. Colourless amorphous substance.

IR (KBr): 1651.0 (Amide-, Urea-C=O), 1298.0, 1168.8 (SO$_2$—N) cm$^{-1}$ b) (R)-N-[[4-(Aminocarbonylaminomethyl)phenyl]methyl]-$N^2$-[bis-(4-hydroxyphenyl)acetyl]-argininamide-trifluoroacetate Prepared analogously to Example if) from (R)-N-[[4-(aminocarbonylaminomethyl)phenyl]methyl]-$N^2$-[bis-(4-hydroxyphenyl)acetyl]-$N^7$-(2,2,5,7,8-pentamethylchroman-6-sulphonyl)-argininamide and trifluoroacetic acid in a yield of 76% of theory.

$R_f$ value: 0.43; colourless, amorphous substance. IR (KBr): 1658.7 (Amide-, Urea-C=O), 1201.6, 1182.8, 1137.9 (Trifluoroacetate) cm$^{-1}$ ESI-MS: (M+H)$^+$=562 (M+Na)$^+$=584

Example 108

(R,S)-3-[3-(Aminoiminomethyl)phenyl]-$N^2$-(diphenylacetyl)-N-[[4-(ethoxycarbonylmethylaminocarbonylaminomethyl)phenyl] methyl]-alaninamide-hydrochloride a) 4-(Ethoxycarbonylmethylaminocarbonylaminomethyl) benzonitrile Prepared analogously to Example 1a), but using N,N-diisopropylethylamine instead of triethylamine, from 4-cyanobenzenemethanamine-hydrochloride and isocyanatoacetate in a yield of 84% of theory.

Colourless crystals, Mp. 150–152° C. IR (KBr) 2229.6 (C N), 1751.3 (Carboxylate-C=O), 1635.5 (Amide-C=O) cm$^{-1}$ b) 4-(Ethoxycarbonylmethylaminocarbonylaminomethyl) benzenemethanamine-hydrochloride Prepared analogously to Example 43b) from 4-(ethoxycarbonylmethylaminocarbonylaminomethyl) benzonitrile by catalytic hydrogenation in the presence of palladium on activated charcoal and 1% aqueous hydrochloric acid in a yield 87% of theory. Colourless crystals.

IR (KBr): 1751.3, 1728.1 (Carboxylate-C=O); 1629.8 (Amide-C=O) cm$^{-1}$ c) (R,S)-3-(3-Cyanophenyl)-N$^2$-(diphenylacetyl)-N-[[4-(ethoxycarbonylmethylaminocarbonylaminomethyl)phenyl]methyl]-alaninamide Prepared analogously to Example 14c) from (R,S)-3-(3-cyanophenyl)-N$^2$-(diphenylacetyl)-alanine and 4-(ethoxycarbonylmethylaminocarbonylaminomethyl) benzenemethanamine-hydrochloride in the presence of TBTU in a yield of 74% of theory.

Colourless crystals, Mp. 207–211° C. IR (KBr): 2229.6 (C N), 1743.5 (Carboxylate-C=O), 1641.3 (Amide-C=O) cm$^{-1}$ d) (R,S)-3-[3-(Aminoiminomethyl)phenyl]-N$^2$-(diphenylacetyl)-N-[[4-(ethoxycarbonylmethylaminocarbonylaminomethyl)-phenyl]methyl]-alaninamide-hydrochloride Prepared analogously to Example 98f), but using ethanol instead of methanol, from (R,S)-3-(3-cyanophenyl)-N$^2$-(diphenylacetyl)-N-[[4-(ethoxycarbonylmethylaminocarbonylaminomethyl)phenyl]methyl]-alaninamide by treating first with dry hydrogen chloride gas and later with ammonium carbonate in a yield of 45% of theory.

R$_f$ value: 0.65; colourless crystals, Mp. 160–163 C. IR (KBr): 1751.3 (Carboxylate-C=O), 1641.3 (Amide-C=O) cm$^{-1}$ ESI-MS: (M+H)$^+$=649

Example 109
(R,S)-N-[[4-(Aminocarbonylaminomethyl)phenyl]methyl]-3-[3-(aminoiminomethyl)phenyl]-N$^2$-[bis-(4-methoxyphenyl)acetyl]-alaninamide-acetate a) (R,S)-N-[[4-(Aminocarbonylaminomethyl)phenyl]methyl]-N$^2$-(tert. butoxycarbonyl)-3-(3-cyanophenyl)-alaninamide Prepared analogously to Example 14c) from (R,S)-N$^2$-(tert. butoxycarbonyl)-3-(3-cyanophenyl)-alanine, 4-(aminocarbonylaminomethyl)benzenemethanamine and TBTU in a yield of 64% of theory. Colourless, amorphous substance.

IR (KBr): 2233.4 (C N), 1679.9, 1654.8, 1641.3 (C=O) cm$^{-1}$ b) (R,S)-N-[[4-(Aminocarbonylaminomethyl)phenyl]methyl]-3-(3-cyanophenyl)-alaninamide-trifluoroacetate Prepared analogously to Example 61e) from (R,S)-N-[[4-(aminocarbonylaminomethyl)phenyl]methyl]-N$^2$-(tert.butoxycarbonyl)-3-(3-cyanophenyl)-alaninamide trifluoroacetic acid in a yield of 92% of theory.

Colourless crystals, Mp. 135–137° C. IR (KBr): 2229.6 (C N), 1676.0 (C=O), 1205.4, 1182.3, 1126.4 (Trifluoroacetate) cm$^{-1}$ c) (R,S)-N-[[4-(Aminocarbonylaminomethyl)phenyl]methyl]-N$^2$-[bis-(4-methoxyphenyl)acetyl]-3-(3-cyanophenyl)-alaninamide Prepared analogously to Example 4b) from bis-(4-methoxyphenyl)acetic acid and (R,S)-N-[[4-(aminocarbonylaminomethyl)phenyl]methyl]-3-(3-cyanophenyl)-alaninamide-trifluoroacetate in the presence of TBTU in a yield of 31% of theory.

Colourless crystals, Mp. 220–220° C. IR (KBr) 2227.7 (C N), 1641.3 (C=O) cm$^{-1}$ d) (R,S)-N-[[4-(Aminocarbonylaminomethyl)phenyl]methyl]-3-[3-[amino(hydroxyimino)methyl]phenyl]-N$^2$-[bis-(4-methoxyphenyl)acetyl]-alaninamide Prepared analogously to Example 14d), but using sodium carbonate instead of diisopropylethylamine and a methanol/water mixture (95/5; v/v) as solvent instead of pure methanol, from (R,S)-N-[[4-(aminocarbonylaminomethyl)phenyl]methyl]-N$^2$-[bis-(4-methoxyphenyl)acetyl]-3-(3-cyanophenyl)-alaninamide and hydroxylaminehydrochloride in a yield of 57% of theory.

Colourless crystals, Mp. 210 to 212° C. IR (KBr): 2830 (OCH$_3$), 1649.0 (Amide-C=O) cm$^{-1}$ ESI-MS: (M+H)$^+$=639 (M+Na)$^+$=661 e) (R,S)-N-[[4-(Aminocarbonylaminomethyl)phenyl]methyl]-3-[3-(aminoiminomethyl)phenyl]-N$^2$-[bis-(4-methoxyphenyl)acetyl]-alaninamide -acetate Prepared analogously to Example 14e) from (R,S)-N-[[4-(aminocarbonylaminomethyl)phenyl]methyl]-3-[3-[amino(hydroxyimino)methyl]phenyl]-N$^2$-[bis-(4-methoxyphenyl)acetyl]-alaninamide by catalytic hydrogenation in the presence of palladium/activated charcoal and glacial acetic acid as solvent in a quantitative yield.

R$_f$ value: 0.52; colourless crystals, Mp. 51–53 C. IR (KBr): 2830 (OCH$_3$), 1641.3 (Amide-C=O) cm$^{-1}$ ESI-MS: (M+H)$^+$=623 (M+Na)$^+$=645 (M+2H)$^{++}$=312 (M+H+Na)$^{++}$=323

Example 110
(R,S)-3-[3-3-(Aminoiminomethyl)phenyl]-N-[[4-[[[[3-(dimethylamino)propyl]amino]carbonyl]methyl]-N$^2$-(diphenylacetyl)-alaninamide a) (R,S)-3-(3-Cyanophenyl)-N$^2$-(diphenylacetyl)-N-[[4-(methoxycarbonylmethyl)phenyl]methyl]-alaninamide Prepared analogously to Example 6d) from (R,S)-3-(3-cyanophenyl)-N$^2$-(diphenylacetyl)-alanine and 4-(methoxycarbonylmethyl)benzenemethanamine-hydrochloride in the presence of TBTU in a yield of 34% of theory.

Colourless crystals, Mp. 194° C. IR (KBr): 2229.6 (C N), 1739.7 (Carboxylate-C=O), 1641.3 (Amide-C=O) cm$^{-1}$ b) (R,S)-N-[[4-(Carboxymethyl)phenyl]methyl]-3-(3-cyanophenyl)-N$^2$-(diphenylacetyl)-alaninamide Prepared analogously to Example 59a) from (R,S)-3-(3-cyanophenyl)-N$^2$-(diphenylacetyl)-N-[[4-(methoxycarbonylmethyl)phenyl]methyl]-alaninamide by saponification with lithium hydroxide in a yield of 89% of theory.

Colourless crystals, Mp. 222–223° C. IR (KBr): 2229.6 (C N), 1706.9 (Carboxylic acid-C=O), 1641.3 (Amide-C=O) cm$^{-1}$ c) (R,S)-3-(3-Cyanophenyl)-N-[[4-[[[[3-(dimethylamino)propyl]amino]carbonyl]methyl]-N$^2$-(diphenylacetyl)-alaninamide Prepared analogously to Example 9a) from (R,S)-N-[[4-(carboxymethyl)phenyl]methyl]-3-(3-cyanophenyl)-N$^2$-(diphenylacetyl)-alaninamide and N,N-dimethylpropanediamine in the presence of TBTU in a yield of 81% of theory.

Colourless crystals, Mp. 170–172° C. (Ethanol). IR (KBr): 2227.7 (C N), 1637.5 (Amide-C=O) cm$^{-1}$ d) (R,S)-3-[3-[Amino(hydroxyimino)methyl]phenyl]-N-[[4-[[[[3-(dimethylamino)propyl]amino]carbonyl]methyl]-N$^2$-(diphenylacetyl)-alaninamide Prepared analogously to Example 14d), but using ethanol as solvent instead of methanol, from (R,S)-3-(3-cyanophenyl)-N-[[4-[[[[3-(dimethylamino)propyl]amino]carbonyl]methyl]-N$^2$-(diphenylacetyl)-alaninamide and hydroxylaminehydrochloride in a yield of 76% of theory.

Colourless crystals, Mp. 184–186° C. IR (KBr): 1633.6 (Amide-C=O) cm$^{-1}$ ESI-MS: (M+H)$^+$=649 (M+2H)$^{++}$=325 (M+H+Na)$^{++}$=336 e) (R,S)-3-[3-(Aminoiminomethyl)phenyl]-N-[[4-[[[[3-dimethylmino)propyl]amino]carbonyl]methyl]-$N^2$-(diphenylacetyl)-alaninamide Prepared analogously to Example 14e) from (R,S)-3-[3-[amino(hydroxyimino)methyl]phenyl]-N-[[4-[[[[3-(dimethylamino)propyl]amino]carbonyl]methyl]-$N^2$-(diphenylacetyl)-alaninamide by catalytic hydrogenation in the presence palladium/activated charcoal and glacial acetic acid as solvent in a yield of 49% of theory.

$R_f$ value: 0.12; colourless, amorphous substance. IR (KBr): 1649.0 (Amide-C=O) cm$^{-1}$ ESI-MS: (M+H)$^+$= 633.4 (M+2H)$^{++}$=317.3

Example 111

(R,S)-3-[3-(Aminoiminomethyl)phenyl]-N-[[4-[(2,5-dioxo-1-imidazolidinyl)methyl]phenyl]methyl]-$N^2$-(diphenylacetyl)-alaninamide-hydrochloride Prepared analogously to Example 49a) from (R,S)-3-[3-(aminoiminomethyl)phenyl]-$N^2$-(diphenylacetyl)-N-[[4-(ethoxycarbonylmethylaminocarbonylaminomethyl)phenyl]methyl]-alaninamide-hydrochloride by treating with 1N aqueous sodium hydroxide solution and subsequently acidifying with 1N hydrochloric acid in a yield of 80% of theory.

$R_f$ value: 0.53; colourless crystals. IR (KBr): 1710.8 (Five-membered ring-C=O), 1679.9, 1658.7, 1641.3 (Amide-/Urea-C=O) cm$^{-1}$ ESI-MS: (M+H)$^+$=603 (M–H)–=601

Example 112

(R)-N-[[4-(Aminocarbonylaminomethyl)phenyl]methyl]-$N^2$-[bis-[4-(methoxycarbonylmethoxy)phenyl]acetyl]-argininamide-acetate a) (R)-N-[[4-(Aminocarbonylaminomethyl)phenyl]methyl]-$N^2$-[(1,1-dimethylethoxy)carbonyl]-$N^7$-nitroargininamide Prepared analogously to Example 45e) from (R)-$N^2$-[(1,1-dimethylethoxy)carbonyl]-$N^7$-nitroarginine and 4-(aminocarbonylaminomethyl)benzenemethanamine in the presence of TBTU in a yield of 54% of theory.

Colourless crystals, Mp. 173–175° C. (D.). IR (KBr): 1681.8 (Carbamate-C=O), 1660.6 (Amide-/Urea-C=O), 1525.6, 1315.4 (NNO$_2$) cm$^{-1}$ b) (R)-N-[[4-(Aminocarbonylaminomethyl)phenyl]methyl]-$N^7$-nitroargininamide Prepared analogously to Example 65i) from (R)-N-[[4-(aminocarbonylaminomethyl)phenyl]methyl]-$N^2$-[(1,1-dimethylethoxy)carbonyl]-$N^7$-nitroargininamide by treating with methanolic hydrogen chloride solution and subsequently converting into the base in a quantitative yield.

Colourless crystals (Isopropanol). IR (KBr): 1652.9 (Amide-/Urea-C=O) cm$^{-1}$ ESI-MS: (M+H)$^+$=381 (M+Na)$^+$=403 (M+K)$^+$=419 c) (R)-N-[[4-(Aminocarbonylaminomethyl)phenyl]methyl]-$N^2$-[bis-(4-hydroxyphenyl)acetyl]-$N^7$-nitroargininamide Prepared analogously to Example 14c) from bis(4-hydroxyphenyl)acetic acid and (R)-N-[[4-(aminocarbonylaminomethyl)phenyl]methyl]-$N^7$-nitroargininamide in the presence of TBTU in a yield of 29% of theory.

Colourless, amorphous substance.

d) (R)-N-[[4-(Aminocarbonylaminomethyl)phenyl]methyl]-$N^2$-[bis-[4-(methoxycarbonylmethoxy)phenyl]acetyl]-$N^7$-nitroargininamide To a solution of 91 mg (3.958 mMol) of sodium in 30 ml of anhydrous methanol were added, successively, 1.2 g (1.978 mMol) of (R)-N-[[4-(aminocarbonylaminomethyl)phenyl]methyl]-$N^2$-[bis-(4-hydroxyphenyl)acetyl]-$N^7$-nitroargininamide and 0.392 ml (0.633 g; 4.14 mMol) of methyl bromoacetate and the mixture was kept for 24 hours at a reaction temperature of 45° C. After working up the usual way and purifying by column chromatography (silica gel MN 60, Macherey-Nagel, 70–230 mesh ASTM; mobile phase: dichloromethane/methanol/cyclohexane/conc. aqueous ammonia=68/15/15/2 (v/v/v/v)) 0.11 g (7.4% of theory) of a colourless amorphous substance were obtained.

$R_f$ value: 0.43(Polygram® SIL G/UV$_{254}$ ready-made sheets for TLC made by Macherey-Nagel, Art.-No. 805021; eluant: dichloromethane/methanol/cyclohexane/conc. aqueous ammonia=68/15/15/2 (v/v/v/v)) MS: M$^+$=750 e) (R)-N-[[4-(Aminocarbonylaminomethyl)phenyl]methyl]-$N^2$-[bis-[4-(methoxycarbonylmethoxy)phenyl]acetyl]-argininamide-acetate Prepared analogously to Example 4c) from (R)-N-[[4-(aminocarbonylaminomethyl)phenyl]methyl]-$N^2$-[bis-[4-(methoxycarbonylmethoxy)phenyl]acetyl]-$N^7$-nitroargininamide by catalytic hydrogenation in the presence of palladium black and 80% aqueous acetic acid in a yield of 90% of theory.

$R_f$ value: 0.37; colourless, amorphous substance. IR (KBr): 1751.3 (Carboxylate-C=O), 1658.7 (Amide-/Urea-C=O) cm$^{-1}$ ESI-MS: (M+H)$^+$=706.3

Example 113

(R)-N-[[4-(Aminocarbonylaminomethyl)phenyl]methyl]-$N^2$-[α-(4-hydroxyphenyl)-α-[4-(methoxycarbonylmethoxy)phenyl]acetyl]-argininamide-acetate a) (R)-N-[[4-(Aminocarbonylaminomethyl)phenyl]methyl]-$N^2$-[α-(4-hydroxyphenyl)-α-[4-(methoxycarbonylmethoxy)phenyl]acetyl]-$N^7$-nitroargininamide As a by-product obtained in Example 112d) in a yield of 0.07 g (5.2% of theory).

$R_f$ value: 0.28; colourless, amorphous substance (conditions of investigation as in Example 112d). MS: M$^+$=678 b) (R)-N-[[4-(Aminocarbonylaminomethyl)phenyl]methyl]-$N^2$-[α-(4-hydroxyphenyl)-α-[4-(methoxycarbonylmethoxy)phenyl]acetyl]-argininamide-acetate Prepared analogously to Example 4c) from (R)-N-[[4-(aminocarbonylaminomethyl)phenyl]methyl]-$N^2$-[α-(4-hydroxyphenyl)-α-[4-(methoxycarbonylmethoxy)phenyl]acetyl]-$N^7$-nitroargininamide by catalytic hydrogenation in the presence of palladium black and 80% aqueous acetic acid in a yield of 99% of theory.

$R_f$ value: 0.40; colourless, amorphous substance. IR (KBr): 1741.6 (Carboxylate-C=O), 1652.9 (Amide-/Urea-C=O) cm$^{-1}$ ESI-MS: (M+H)$^+$=634.3

Example 114

(R)-N-[[4-(Aminocarbonylaminomethyl)phenyl]methyl]-$N^2$-[bis-[4-(hydroxycarbonylmethoxy)phenyl]acetyl]-argininamide-acetate a) (R)-N-[[4-(Aminocarbonylaminomethyl)phenyl]methyl]-$N^2$-[bis-[4-(hydroxycarbonylmethoxy)phenyl]acetyl]-$N^7$-nitroargininamide Prepared analogously to Example 49a) from (R)-N-[[4-(aminocarbonylaminomethyl)phenyl]methyl]-$N^2$-[bis-[4-(methoxycarbonylmethoxy)phenyl]acetyl]-$N^7$-nitroargininamide by saponification with 1N aqueous sodium hydroxide solution in a yield of 98% of theory.

Colourless, amorphous substance. ESI-MS: (M–H)–= 721.1 (M–2H)$^{2-}$=360.2 (M–2H+Na)–=743.1 b) (R)-N-[[4-(Aminocarbonylaminomethyl)phenyl]methyl]-$N^2$-[bis-[4-(hydroxycarbonylmethoxy)phenyl]acetyl]-argininamide-acetate Prepared analogously to Example 4c) from (R)-N-[[4-(aminocarbonylaminomethyl)phenyl]methyl]-$N^2$-[bis-[4-(hydroxycarbonylmethoxy)phenyl]acetyl]-$N^7$- nitroargininamide by catalytic hydrogenation in the presence of palladium black and 80% aqueous acetic acid in a yield of 79% of theory.

$R_f$ value: 0.18; colourless, amorphous substance. IR (KBr): 1718.5 (Carboxylic acid-C=O), 1654.8 (Amide-/Urea-C=O) cm$^{-1}$

ESI-MS: (M+H)$^+$=678 (M–H)–=676 (M–2H)$^{2-}$=337.7

What is claimed is:

1. A compound selected from the group consisting of:
   (A) (R)-N-[[4-(aminocarbonylaminomethyl)phenyl]methyl]-N$^2$-(diphenylacetyl)-argininamide;
   (B) (R,S)-N$^5$-(aminoiminomethyl)-N$^2$-(diphenylacetyl)-N-[(4-hydroxyphenyl)methyl]-N$^5$-methyl-ornithinamide;
   (C) (R)-N-[[4-(aminocarbonylmethyl)phenyl]methyl]-N$^2$-(diphenylacetyl)-argininamide;
   (D) (R)-N$^2$-(diphenylacetyl)-N-[[4-(methylaminocarbonylaminomethyl)phenyl]methyl]-argininamide;
   (E) (R)-N$^2$-(diphenylacetyl)-N-[[4-(ethylaminocarbonylaminomethyl)phenyl]methyl]-argininamide;
   (F) (R)-N-[[4-(aminocarbonylaminomethyl)phenyl]methyl]-N$^2$-[bis-(4-methoxyphenyl)acetyl]-argininamide;
   (G) (R)-N$^2$-(diphenylacetyl)-N-[[4-(ethoxycarbonylmethylaminocarbonylaminomethyl)phenyl]methyl]-argininamide;
   (H) (R)-N-[[4-(aminocarbonylaminomethyl)phenyl]methyl]-N$^2$-[bis-(4-fluorophenyl)acetyl]-argininamide;
   (I) (R)-N-[[4-(aminocarbonylaminomethyl)phenyl]methyl]-N$^2$-[bis-(4-chlorophenyl)acetyl]-argininamide;
   (J) (R)-N-[[4-(aminocarbonylaminomethyl)phenyl]methyl]-N$^2$-[bis-(4-hydroxyphenyl)acetyl]-argininamide;
   (K) (R)-N-[[4-(aminocarbonylaminomethyl)phenyl]methyl]-N$^2$-[bis-[4-(methoxycarbonylmethoxy)phenyl]acetyl]-argininamide; and,
   (L) (R)-N-[[4-(aminocarbonylaminomethyl)phenyl]methyl]-N$^2$-[bis-[4-(hydroxycarbonylmethoxy)phenyl]acetyl]-argininamide;

or a pharmaceutically acceptable salt thereof.

2. A compound selected from the group consisting of:
   (A) (R)-N-[[4-(aminocarbonylaminomethyl)phenyl]methyl]-N$^2$-(diphenylacetyl)-argininamide;
   (B) (R,S)-N$^5$-(aminoiminomethyl)-N$^2$-(diphenylacetyl)-N-[(4-hydroxyphenyl)methyl]-N$^5$-methyl-ornithinamide;
   (C) (R)-N-[[4-(aminocarbonylmethyl)phenyl]methyl]-N$^2$-(diphenylacetyl)-argininamide;
   (D) (R)-N$^2$-(diphenylacetyl)-N-[[4-(ethoxycarbonylmethylaminocarbonylaminomethyl)phenyl]methyl]-argininamide;
   (E) (R)-N-[[$^4$-(aminocarbonylaminomethyl)phenyl]methyl]-N$^2$-[bis-(4-fluorophenyl)acetyl]-argininamide;
   (F) (R)-N-[[4-(aminocarbonylaminomethyl)phenyl]methyl]-N$^2$-[bis-(4-chlorophenyl)acetyl]-argininamide;
   (G) (R)-N-[[4-(aminocarbonylaminomethyl)phenyl]methyl]-N$^2$-[bis-(4-hydroxyphenyl)acetyl]-argininamide; and,
   (H) (R)-N-[[4-(aminocarbonylaminomethyl)phenyl]methyl]-N$^2$-[bis-[4-(hydroxycarbonylmethoxy)phenyl]acetyl]-argininamide;

or a pharmaceutically acceptable salt thereof.

3. A compound selected from the group consisting of:
   (A) (R)-N$^2$-(diphenylacetyl)-N-[[4-(methylaminocarbonylaminomethyl)phenyl]methyl]-argininamide;
   (B) (R)-N$^2$-(diphenylacetyl)-N-[[4-(ethylaminocarbonylaminomethyl)phenyl]methyl]-argininamide;
   (C) (R)-N$^2$-(diphenylacetyl)-N-[[4-(ethoxycarbonylmethylaminocarbonylaminomethyl)phenyl]methyl]-argininamide;
   (D) (R)-N-[[4-(aminocarbonylaminomethyl)phenyl]methyl]-N$^2$-[bis-[4-(methoxycarbonylmethoxy)phenyl]acetyl]-argininamide; and,
   (E) (R)-N-[[4-(aminocarbonylaminomethyl)phenyl]methyl]-N$^2$-[bis-[4-(hydroxycarbonylmethoxy)phenyl]acetyl]-argininamide;

or a pharmaceutically acceptable salt thereof.

4. A pharmaceutical composition comprising a compound according to claim 1, 2 or 3, or a pharmaceutically acceptable salt thereof.

5. A method for treating a disease in which the Y1 receptor subtype is involved, which method comprises administering to a host in need of such treatment a therapeutically effective amount of a compound in accordance with claim 1, 2 or 3, or a pharmaceutically acceptable salt thereof.

6. A method for treating a disorder or disease associated with the inhibition of the Y1 receptor subtype, which method comprises administering to a host in need of such treatment a therapeutically effective amount of a compound in accordance with claim 1, 2 or 3, or a pharmaceutically acceptable salt thereof.

7. A method for treating obesity, bulimia nervosa, diabetes or dyslipidemia, which method comprises administering to a host in need of such treatment a therapeutically effective amount of a compound in accordance with claim 1, 2 or 3, or a pharmaceutically acceptable salt thereof.

8. A method for treating obesity, which method comprises administering to a host in need of such treatment a therapeutically effective amount of a compound in accordance with claim 1, 2 or 3, or a pharmaceutically acceptable salt thereof.

9. A method for treating memory loss, migraine, sleep disorders, pain, cardiovascular diseases, subarachnoidal bleeding, vascular-hypertrophic changes, cerebral and coronary vasospasms, chronic kidney failure, hyperthyroidism, epileptic diseases or tumor diseases, which method comprises administering to a host in need of such treatment a therapeutically effective amount of a compound in accordance with claim 1, 2 or 3, or a pharmaceutically acceptable salt thereof.

10. A method for treating hypertension, which method comprises administering to a host in need of such treatment a therapeutically effective amount of a compound in accordance with claim 1, 2 or 3, or a pharmaceutically acceptable salt thereof.

* * * * *